US008073627B2

(12) United States Patent
Ecker et al.

(10) Patent No.: US 8,073,627 B2
(45) Date of Patent: Dec. 6, 2011

(54) SYSTEM FOR INDENTIFICATION OF PATHOGENS

(75) Inventors: David J. Ecker, Encinitas, CA (US); Richard H. Griffey, Vista, CA (US); Rangarajan Sampath, San Diego, CA (US); Steven A. Hofstadler, Vista, CA (US); John McNeil, La Jolla, CA (US); Stanley T. Crooke, Carlsbad, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 0 days.

(21) Appl. No.: 10/754,415

(22) Filed: Jan. 9, 2004

(65) Prior Publication Data
US 2011/0238316 A1 Sep. 29, 2011

Related U.S. Application Data

(63) Continuation-in-part of application No. 09/891,793, filed on Jun. 26, 2001, now Pat. No. 7,217,510, and a continuation-in-part of application No. 10/728,486, filed on Dec. 5, 2003, now Pat. No. 7,718,354.

(60) Provisional application No. 60/509,911, filed on Oct. 9, 2003.

(51) Int. Cl.
*G01N 33/50* (2006.01)
(52) U.S. Cl. ............... 702/19; 702/23; 702/28; 436/173
(58) Field of Classification Search .................... None
See application file for complete search history.

(56) References Cited

U.S. PATENT DOCUMENTS

| | | |
|---|---|---|
| 4,075,475 A | 2/1978 | Risby et al. |
| 4,683,195 A | 7/1987 | Mullis et al. |
| 4,683,202 A | 7/1987 | Mullis |
| 4,965,188 A | 10/1990 | Mullis et al. |
| 5,015,845 A | 5/1991 | Allen et al. |
| 5,072,115 A | 12/1991 | Zhou |
| 5,143,905 A | 9/1992 | Sivasubramanian et al. |
| 5,213,961 A | 5/1993 | Bunn et al. |
| 5,219,727 A | 6/1993 | Wang et al. |
| 5,288,611 A | 2/1994 | Kohne |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,908 A | 1/1996 | Froehler et al. |
| 5,502,177 A | 3/1996 | Matteucci et al. |
| 5,503,980 A | 4/1996 | Cantor |
| 5,504,327 A | 4/1996 | Sproch et al. |
| 5,504,329 A | 4/1996 | Mann et al. |
| 5,523,217 A | 6/1996 | Lupski et al. |
| 5,527,669 A | 6/1996 | Resnick et al. |
| 5,527,675 A | 6/1996 | Coull et al. |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,641,632 A | 6/1997 | Kohne |
| 5,645,985 A | 7/1997 | Froehler et al. |
| 5,683,869 A | 11/1997 | Ramsay Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,707,802 A | 1/1998 | Sandhu et al. |
| 5,712,125 A | 1/1998 | Uhlen |
| 5,716,825 A | 2/1998 | Hancock et al. |
| 5,727,202 A | 3/1998 | Kucala |
| 5,745,751 A | 4/1998 | Nelson et al. |
| 5,747,246 A | 5/1998 | Pannetier et al. |
| 5,747,251 A | 5/1998 | Carson et al. |
| 5,753,467 A | 5/1998 | Jensen et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |
| 5,770,367 A | 6/1998 | Southern et al. |
| 5,777,324 A | 7/1998 | Hillenkamp |
| 5,814,442 A | 9/1998 | Natarajan et al. |
| 5,822,824 A | 10/1998 | Dion |
| 5,828,062 A | 10/1998 | Jarrell et al. |
| 5,830,653 A | 11/1998 | Froehler et al. |
| 5,830,655 A | 11/1998 | Monforte et al. |
| 5,830,853 A | 11/1998 | Backstrom et al. |
| 5,832,489 A | 11/1998 | Kucala |
| 5,834,255 A | 11/1998 | Van Gemen et al. |
| 5,845,174 A | 12/1998 | Yasui et al. |
| 5,849,492 A | 12/1998 | Rogan |
| 5,849,497 A | 12/1998 | Steinman |
| 5,849,901 A | 12/1998 | Mabilat et al. |
| 5,851,765 A | 12/1998 | Koster |
| 5,856,174 A | 1/1999 | Lipshutz et al. |

(Continued)

FOREIGN PATENT DOCUMENTS
DE 19732086 A1 1/1999
(Continued)

OTHER PUBLICATIONS

Widjojoatmodjo, J. Clin. Biol., 32(12):3002-3007 (1994).*

(Continued)

*Primary Examiner* — Karlheinz R Skowronek
(74) *Attorney, Agent, or Firm* — Casimir Jones S.C.; Christopher C. Sappenfield

(57) ABSTRACT

The present invention relates generally to the field of investigational bioinformatics and more particularly to secondary structure defining databases. The present invention further relates to methods for interrogating a database as a source of molecular masses of known bioagents for comparing against the molecular mass of an unknown or selected bioagent to determine either the identity of the selected bioagent, and/or to determine the origin of the selected bioagent. The identification of the bioagent is important for determining a proper course of treatment and/or irradication of the bioagent in such cases as biological warfare. Furthermore, the determination of the geographic origin of a selected bioagent will facilitate the identification of potential criminal identity.

25 Claims, 33 Drawing Sheets

U.S. PATENT DOCUMENTS

| | | | |
|---|---|---|---|
| 5,864,137 A | 1/1999 | Becker et al. | |
| 5,866,429 A | 2/1999 | Bloch | |
| 5,869,242 A | 2/1999 | Kamb | |
| 5,871,697 A | 2/1999 | Rothberg et al. | |
| 5,872,003 A | 2/1999 | Koster | |
| 5,876,936 A | 3/1999 | Ju | |
| 5,876,938 A | 3/1999 | Stolowitz et al. | |
| 5,885,775 A | 3/1999 | Haff et al. | |
| 5,900,481 A | 5/1999 | Lough et al. | |
| 5,928,905 A | 7/1999 | Stemmer et al. | |
| 5,928,906 A | 7/1999 | Koster | |
| 5,965,363 A | 10/1999 | Monforte et al. | |
| 5,965,383 A | 10/1999 | Vogel et al. | |
| 5,972,693 A | 10/1999 | Rothberg et al. | |
| 5,976,798 A | 11/1999 | Parker et al. | |
| 5,981,176 A | 11/1999 | Wallace | |
| 5,981,190 A | 11/1999 | Israel | |
| 5,994,066 A | 11/1999 | Bergeron et al. | |
| 6,001,564 A | 12/1999 | Bergeron et al. | |
| 6,005,096 A | 12/1999 | Matteucci et al. | |
| 6,007,690 A | 12/1999 | Nelson et al. | |
| 6,007,992 A | 12/1999 | Lin et al. | |
| 6,015,666 A | 1/2000 | Springer et al. | |
| 6,018,713 A | 1/2000 | Coli et al. | |
| 6,024,925 A | 2/2000 | Little et al. | |
| 6,028,183 A | 2/2000 | Lin et al. | |
| 6,043,031 A | 3/2000 | Koster et al. | |
| 6,046,005 A | 4/2000 | Ju | |
| 6,051,378 A | 4/2000 | Monforte et al. | |
| 6,054,278 A | 4/2000 | Dodge et al. | |
| 6,055,487 A | 4/2000 | Margery et al. | |
| 6,060,246 A | 5/2000 | Summerton et al. | |
| 6,061,686 A * | 5/2000 | Gauvin et al. | 707/10 |
| 6,063,031 A | 5/2000 | Cundari et al. | |
| 6,074,823 A | 6/2000 | Koster | |
| 6,074,831 A | 6/2000 | Yakhini et al. | |
| 6,090,558 A | 7/2000 | Butler et al. | |
| 6,104,028 A | 8/2000 | Hunter et al. | |
| 6,110,710 A | 8/2000 | Smith et al. | |
| 6,111,251 A | 8/2000 | Hillenkamp | |
| 6,133,436 A | 10/2000 | Koster et al. | |
| 6,140,053 A | 10/2000 | Koster | |
| 6,146,144 A | 11/2000 | Fowler et al. | |
| 6,146,854 A | 11/2000 | Koster et al. | |
| 6,153,389 A | 11/2000 | Haarer et al. | |
| 6,159,681 A | 12/2000 | Zebala | |
| 6,180,339 B1 | 1/2001 | Sandhu et al. | |
| 6,180,372 B1 | 1/2001 | Franzen | |
| 6,187,842 B1 | 2/2001 | Kobayashi et al. | |
| 6,194,144 B1 | 2/2001 | Koster | |
| 6,197,498 B1 | 3/2001 | Koster | |
| 6,214,555 B1 | 4/2001 | Leushner et al. | |
| 6,218,118 B1 | 4/2001 | Sampson et al. | |
| 6,221,587 B1 | 4/2001 | Ecker et al. | |
| 6,221,598 B1 | 4/2001 | Schumm et al. | |
| 6,221,601 B1 | 4/2001 | Koster et al. | |
| 6,221,605 B1 | 4/2001 | Koster | |
| 6,225,450 B1 | 5/2001 | Koster | |
| 6,235,476 B1 | 5/2001 | Bergmann et al. | |
| 6,235,478 B1 | 5/2001 | Koster | |
| 6,235,480 B1 | 5/2001 | Shultz et al. | |
| 6,238,871 B1 | 5/2001 | Koster | |
| 6,238,927 B1 | 5/2001 | Abrams et al. | |
| 6,239,159 B1 | 5/2001 | Brown et al. | |
| 6,258,538 B1 | 7/2001 | Koter et al. | |
| 6,261,769 B1 | 7/2001 | Everett et al. | |
| 6,265,716 B1 | 7/2001 | Hunter et al. | |
| 6,265,718 B1 | 7/2001 | Park et al. | |
| 6,266,131 B1 | 7/2001 | Hamada et al. | |
| 6,266,144 B1 | 7/2001 | Li | |
| 6,268,129 B1 | 7/2001 | Gut et al. | |
| 6,268,131 B1 | 7/2001 | Kang et al. | |
| 6,268,144 B1 | 7/2001 | Koster | |
| 6,268,146 B1 | 7/2001 | Shultz | |
| 6,270,973 B1 | 8/2001 | Lewis et al. | |
| 6,270,974 B1 | 8/2001 | Shultz et al. | |
| 6,274,726 B1 | 8/2001 | Laugharn, Jr. et al. | |
| 6,277,573 B1 | 8/2001 | Koster et al. | |
| 6,277,578 B1 | 8/2001 | Shultz et al. | |
| 6,277,634 B1 | 8/2001 | McCall et al. | |
| 6,300,076 B1 | 10/2001 | Koster | |
| 6,303,297 B1 | 10/2001 | Lincoln et al. | |
| 6,312,893 B1 | 11/2001 | Van Ness et al. | |
| 6,312,902 B1 | 11/2001 | Shultz et al. | |
| 6,322,970 B1 * | 11/2001 | Little et al. | 435/6 |
| 6,361,940 B1 | 3/2002 | Van Ness et al. | |
| 6,372,424 B1 | 4/2002 | Brow et al. | |
| 6,389,428 B1 | 5/2002 | Rigault et al. | |
| 6,391,551 B1 | 5/2002 | Shultz et al. | |
| 6,393,367 B1 * | 5/2002 | Tang et al. | 702/19 |
| 6,419,932 B1 | 7/2002 | Dale | |
| 6,423,966 B2 | 7/2002 | Hillenkamp et al. | |
| 6,428,955 B1 | 8/2002 | Koster et al. | |
| 6,428,956 B1 | 8/2002 | Crooke et al. | |
| 6,432,651 B1 | 8/2002 | Hughes et al. | |
| 6,436,635 B1 | 8/2002 | Fu et al. | |
| 6,436,640 B1 | 8/2002 | Simmons et al. | |
| 6,453,244 B1 | 9/2002 | Oefner et al. | |
| 6,458,533 B1 | 10/2002 | Felder et al. | |
| 6,468,743 B1 | 10/2002 | Romick et al. | |
| 6,468,748 B1 | 10/2002 | Monforte et al. | |
| 6,475,143 B2 | 11/2002 | Iliff | |
| 6,475,736 B1 | 11/2002 | Stanton, Jr. | |
| 6,475,738 B2 | 11/2002 | Shuber et al. | |
| 6,479,239 B1 | 11/2002 | Anderson et al. | |
| 6,500,621 B2 | 12/2002 | Koster | |
| 6,553,317 B1 | 4/2003 | Lincoln et al. | |
| 6,558,902 B1 | 5/2003 | Hillenkamp | |
| 6,563,025 B1 | 5/2003 | Song et al. | |
| 6,566,055 B1 | 5/2003 | Monforte et al. | |
| 6,568,055 B1 | 5/2003 | Tang et al. | |
| 6,582,916 B1 | 6/2003 | Schmidt et al. | |
| 6,586,584 B2 | 7/2003 | McMillian et al. | |
| 6,589,485 B2 | 7/2003 | Koster | |
| 6,602,662 B1 | 8/2003 | Koster et al. | |
| 6,605,433 B1 | 8/2003 | Fliss et al. | |
| 6,610,492 B1 | 8/2003 | Stanton, Jr. et al. | |
| 6,613,509 B1 | 9/2003 | Chen | |
| 6,613,520 B2 | 9/2003 | Ashby | |
| 6,623,928 B2 | 9/2003 | Van Ness et al. | |
| 6,638,714 B1 | 10/2003 | Linnen et al. | |
| 6,680,476 B1 | 1/2004 | Hidalgo et al. | |
| 6,682,889 B1 | 1/2004 | Wang et al. | |
| 6,705,530 B2 | 3/2004 | Kiekhaefer | |
| 6,706,530 B2 | 3/2004 | Hillenkamp | |
| 6,716,634 B1 | 4/2004 | Myerson | |
| 6,783,939 B2 | 8/2004 | Olmsted et al. | |
| 6,800,289 B2 | 10/2004 | Nagata et al. | |
| 6,813,615 B1 | 11/2004 | Colasanti et al. | |
| 6,836,742 B2 | 12/2004 | Brekenfeld | |
| 6,852,487 B1 | 2/2005 | Barany et al. | |
| 6,856,914 B1 | 2/2005 | Pelech | |
| 6,875,593 B2 | 4/2005 | Froehler et al. | |
| 6,906,316 B2 | 6/2005 | Sugiyama et al. | |
| 6,906,319 B2 | 6/2005 | Hoyes | |
| 6,914,137 B2 | 7/2005 | Baker | |
| 6,977,148 B2 | 12/2005 | Dean et al. | |
| 6,994,962 B1 | 2/2006 | Thilly | |
| 7,022,835 B1 | 4/2006 | Rauth et al. | |
| 7,024,370 B2 | 4/2006 | Epler et al. | |
| 7,108,974 B2 | 9/2006 | Ecker et al. | |
| 7,198,893 B1 | 4/2007 | Köster et al. | |
| 7,217,510 B2 | 5/2007 | Ecker et al. | |
| 7,226,739 B2 | 6/2007 | Ecker et al. | |
| 7,255,992 B2 | 8/2007 | Ecker et al. | |
| 7,285,422 B1 | 10/2007 | Little et al. | |
| 7,312,036 B2 | 12/2007 | Sampath et al. | |
| 7,321,828 B2 | 1/2008 | Cowsert et al. | |
| 7,349,808 B1 | 3/2008 | Kreiswirth et al. | |
| 7,390,458 B2 | 6/2008 | Burow et al. | |
| 7,419,787 B2 | 9/2008 | Köster | |
| 7,501,251 B2 | 3/2009 | Köster et al. | |
| 7,666,588 B2 | 2/2010 | Ecker et al. | |
| 7,718,354 B2 | 5/2010 | Ecker et al. | |
| 7,741,036 B2 | 6/2010 | Ecker et al. | |
| 7,781,162 B2 | 8/2010 | Ecker et al. | |
| 2001/0039263 A1 | 11/2001 | Matthes et al. | |

| | | | | | | |
|---|---|---|---|---|---|---|
| 2002/0006611 A1 | 1/2002 | Portugal et al. | | 2004/0122857 A1 | 6/2004 | Ecker et al. |
| 2002/0028923 A1 | 3/2002 | Cowsert et al. | | 2004/0126764 A1 | 7/2004 | Lasken et al. |
| 2002/0042112 A1 | 4/2002 | Koster et al. | | 2004/0137013 A1 | 7/2004 | Katinger et al. |
| 2002/0042506 A1 | 4/2002 | Kristyanne et al. | | 2004/0161770 A1 | 8/2004 | Ecker et al. |
| 2002/0045178 A1 | 4/2002 | Cantor et al. | | 2004/0180328 A1 | 9/2004 | Ecker et al. |
| 2002/0055101 A1 | 5/2002 | Bergeron et al. | | 2004/0185438 A1 | 9/2004 | Ecker |
| 2002/0090320 A1 | 7/2002 | Burow et al. | | 2004/0191769 A1 | 9/2004 | Marino et al. |
| 2002/0120408 A1 | 8/2002 | Kreiswirth et al. | | 2004/0202997 A1 | 10/2004 | Ecker et al. |
| 2002/0137057 A1 | 9/2002 | Wold et al. | | 2004/0209260 A1 | 10/2004 | Ecker et al. |
| 2002/0138210 A1* | 9/2002 | Wilkes et al. ............ 702/28 | | 2004/0253583 A1 | 12/2004 | Ecker et al. |
| 2002/0150903 A1 | 10/2002 | Koster et al. | | 2004/0253619 A1 | 12/2004 | Ecker et al. |
| 2002/0150927 A1 | 10/2002 | Matray et al. | | 2005/0026147 A1 | 2/2005 | Walker et al. |
| 2002/0168630 A1 | 11/2002 | Fleming et al. | | 2005/0026641 A1 | 2/2005 | Hokao |
| 2002/0187490 A1 | 12/2002 | Tiedje et al. | | 2005/0027459 A1 | 2/2005 | Ecker et al. |
| 2003/0017487 A1 | 1/2003 | Xue et al. | | 2005/0065813 A1 | 3/2005 | Mishelevich et al. |
| 2003/0027135 A1 | 2/2003 | Ecker et al. | | 2005/0130196 A1 | 6/2005 | Hofstadler et al. |
| 2003/0039976 A1 | 2/2003 | Haff et al. | | 2005/0130216 A1 | 6/2005 | Becker et al. |
| 2003/0050470 A1 | 3/2003 | An et al. | | 2005/0142584 A1 | 6/2005 | Willson et al. |
| 2003/0064483 A1 | 4/2003 | Shaw et al. | | 2005/0250125 A1 | 11/2005 | Novakoff |
| 2003/0073112 A1 | 4/2003 | Zhang et al. | | 2005/0266397 A1 | 12/2005 | Ecker et al. |
| 2003/0082539 A1 | 5/2003 | Ecker et al. | | 2005/0266411 A1 | 12/2005 | Hofstadler et al. |
| 2003/0084483 A1 | 5/2003 | Simpson et al. | | 2006/0020391 A1 | 1/2006 | Kreiswirth et al. |
| 2003/0101172 A1 | 5/2003 | De La Huerga | | 2006/0057605 A1 | 3/2006 | Sampath et al. |
| 2003/0104410 A1 | 6/2003 | Mittmann | | 2006/0121520 A1 | 6/2006 | Ecker et al. |
| 2003/0104699 A1 | 6/2003 | Minamihaba et al. | | 2006/0172330 A1 | 8/2006 | Osborn et al. |
| 2003/0113738 A1 | 6/2003 | Liu et al. | | 2006/0205040 A1 | 9/2006 | Sampath |
| 2003/0113745 A1 | 6/2003 | Monforte et al. | | 2006/0240412 A1 | 10/2006 | Hall et al. |
| 2003/0119018 A1 | 6/2003 | Omura et al. | | 2006/0259249 A1 | 11/2006 | Sampath et al. |
| 2003/0129589 A1 | 7/2003 | Koster et al. | | 2007/0218467 A1 | 9/2007 | Ecker et al. |
| 2003/0134312 A1 | 7/2003 | Burgoyne et al. | | 2008/0160512 A1 | 7/2008 | Ecker et al. |
| 2003/0148281 A1 | 8/2003 | Glucksmann | | 2008/0311558 A1 | 12/2008 | Ecker et al. |
| 2003/0148284 A1 | 8/2003 | Vision et al. | | 2009/0004643 A1 | 1/2009 | Ecker et al. |
| 2003/0167133 A1 | 9/2003 | Ecker et al. | | 2009/0023150 A1 | 1/2009 | Koster et al. |
| 2003/0167134 A1 | 9/2003 | Ecker et al. | | 2009/0042203 A1 | 2/2009 | Koster |
| 2003/0175695 A1 | 9/2003 | Ecker et al. | | 2009/0092977 A1 | 4/2009 | Koster |
| 2003/0175696 A1 | 9/2003 | Ecker et al. | | 2009/0125245 A1 | 5/2009 | Hofstadler et al. |
| 2003/0175697 A1 | 9/2003 | Ecker et al. | | 2009/0148829 A1 | 6/2009 | Ecker et al. |
| 2003/0175729 A1 | 9/2003 | Van Eijk et al. | | 2009/0148836 A1 | 6/2009 | Ecker et al. |
| 2003/0186247 A1 | 10/2003 | Smarason et al. | | 2009/0148837 A1 | 6/2009 | Ecker et al. |
| 2003/0187588 A1 | 10/2003 | Ecker et al. | | 2009/0182511 A1 | 7/2009 | Ecker et al. |
| 2003/0187593 A1 | 10/2003 | Ecker et al. | | 2009/0239224 A1 | 9/2009 | Ecker et al. |
| 2003/0187615 A1 | 10/2003 | Epler et al. | | 2009/0280471 A1 | 11/2009 | Ecker et al. |
| 2003/0190605 A1 | 10/2003 | Ecker et al. | | 2010/0070194 A1 | 3/2010 | Ecker et al. |
| 2003/0190635 A1 | 10/2003 | McSwiggen | | 2010/0145626 A1 | 6/2010 | Ecker et al. |
| 2003/0194699 A1 | 10/2003 | Lewis et al. | | 2010/0184035 A1 | 7/2010 | Hall et al. |
| 2003/0203398 A1 | 10/2003 | Bramucci et al. | | | | |
| 2003/0220844 A1 | 11/2003 | Marmellos et al. | | | FOREIGN PATENT DOCUMENTS | |
| 2003/0224377 A1 | 12/2003 | Wengel et al. | | DE | 19802905 A1 | 7/1999 |
| 2003/0225529 A1 | 12/2003 | Ecker et al. | | DE | 19824280 A1 | 12/1999 |
| 2003/0228571 A1 | 12/2003 | Ecker et al. | | DE | 19852167 A1 | 5/2000 |
| 2003/0228597 A1 | 12/2003 | Cowsert et al. | | DE | 19943374 A1 | 3/2001 |
| 2003/0228613 A1 | 12/2003 | Bornarth et al. | | DE | 10132147 A1 | 2/2003 |
| 2004/0005555 A1 | 1/2004 | Rothman et al. | | EP | 281390 A2 | 9/1988 |
| 2004/0013703 A1 | 1/2004 | Ralph et al. | | EP | 633321 A1 | 1/1995 |
| 2004/0014957 A1 | 1/2004 | Eldrup et al. | | EP | 620862 B1 | 4/1998 |
| 2004/0023207 A1 | 2/2004 | Polansky | | EP | 1035219 A1 | 9/2000 |
| 2004/0023209 A1 | 2/2004 | Jonasson | | EP | 1138782 A2 | 10/2001 |
| 2004/0029129 A1 | 2/2004 | Wang et al. | | EP | 1234888 A2 | 8/2002 |
| 2004/0038206 A1 | 2/2004 | Zhang et al. | | EP | 1308506 A1 | 5/2003 |
| 2004/0038208 A1 | 2/2004 | Fisher et al. | | EP | 1310571 A2 | 5/2003 |
| 2004/0038234 A1 | 2/2004 | Gut et al. | | EP | 1333101 A1 | 8/2003 |
| 2004/0038385 A1 | 2/2004 | Langlois et al. | | EP | 1365031 A1 | 11/2003 |
| 2004/0081993 A1 | 4/2004 | Cantor et al. | | EP | 1748072 A1 | 1/2007 |
| 2004/0101809 A1 | 5/2004 | Weiss et al. | | FR | 2811321 A1 | 1/2002 |
| 2004/0110169 A1 | 6/2004 | Ecker et al. | | GB | 2325002 A | 11/1998 |
| 2004/0111221 A1 | 6/2004 | Beattie et al. | | GB | 2339905 A | 2/2000 |
| 2004/0117129 A1 | 6/2004 | Ecker et al. | | JP | 5276999 A2 | 10/1993 |
| 2004/0117354 A1 | 6/2004 | Azzaro et al. | | JP | 11137259 A | 5/1999 |
| 2004/0121309 A1 | 6/2004 | Ecker et al. | | JP | 24024206 A2 | 1/2004 |
| 2004/0121310 A1 | 6/2004 | Ecker et al. | | JP | 2004000200 A2 | 1/2004 |
| 2004/0121311 A1 | 6/2004 | Ecker et al. | | JP | 24201641 A2 | 7/2004 |
| 2004/0121312 A1 | 6/2004 | Ecker et al. | | JP | 24201679 A2 | 7/2004 |
| 2004/0121313 A1 | 6/2004 | Ecker et al. | | WO | WO8803957 A1 | 6/1988 |
| 2004/0121314 A1 | 6/2004 | Ecker et al. | | WO | WO9015157 A1 | 12/1990 |
| 2004/0121315 A1 | 6/2004 | Ecker et al. | | WO | WO9205182 A1 | 4/1992 |
| 2004/0121329 A1 | 6/2004 | Ecker et al. | | WO | WO9208117 A1 | 5/1992 |
| 2004/0121335 A1 | 6/2004 | Ecker et al. | | WO | WO9209703 A1 | 6/1992 |
| 2004/0121340 A1 | 6/2004 | Ecker et al. | | WO | WO9219774 A1 | 11/1992 |
| 2004/0122598 A1 | 6/2004 | Ecker et al. | | WO | WO 93/03186 | 2/1993 |

| | | |
|---|---|---|
| WO | WO9305182 A1 | 3/1993 |
| WO | WO 93/08297 | 4/1993 |
| WO | WO 94/16101 | 7/1994 |
| WO | WO 94/21822 | 9/1994 |
| WO | WO9419490 A1 | 9/1994 |
| WO | WO 95/04161 | 2/1995 |
| WO | WO 95/13396 | 5/1995 |
| WO | WO9511996 A1 | 5/1995 |
| WO | WO9513395 A1 | 5/1995 |
| WO | WO9531997 A1 | 11/1995 |
| WO | WO9606187 A1 | 2/1996 |
| WO | WO9616186 A1 | 5/1996 |
| WO | WO 96/29431 | 9/1996 |
| WO | WO 96/32504 | 10/1996 |
| WO | WO 96/37630 | 11/1996 |
| WO | WO9635450 A1 | 11/1996 |
| WO | WO 97/33000 | 9/1997 |
| WO | WO9734909 A1 | 9/1997 |
| WO | WO 97/37041 | 10/1997 |
| WO | WO9747766 A1 | 12/1997 |
| WO | WO 98/03684 | 1/1998 |
| WO | WO 98/12355 | 3/1998 |
| WO | WO 98/14616 | 4/1998 |
| WO | WO 98/15652 | 4/1998 |
| WO | WO 98/20020 | 5/1998 |
| WO | WO 98/20157 | 5/1998 |
| WO | WO 98/20166 | 5/1998 |
| WO | WO 98/26095 | 6/1998 |
| WO | WO 98/31830 | 7/1998 |
| WO | WO9835057 A1 | 8/1998 |
| WO | WO9840520 A1 | 9/1998 |
| WO | WO 98/54751 | 12/1998 |
| WO | WO9854571 A1 | 12/1998 |
| WO | WO9905319 A2 | 2/1999 |
| WO | WO 99/12040 | 3/1999 |
| WO | WO 99/14375 | 3/1999 |
| WO | WO9913104 A1 | 3/1999 |
| WO | WO 99/31278 | 6/1999 |
| WO | WO9929898 A2 | 6/1999 |
| WO | WO9957318 A2 | 11/1999 |
| WO | WO9958713 A2 | 11/1999 |
| WO | WO9960183 A1 | 11/1999 |
| WO | WO0032750 A1 | 6/2000 |
| WO | WO0038636 A1 | 7/2000 |
| WO | WO0063362 A1 | 10/2000 |
| WO | WO0066762 A2 | 11/2000 |
| WO | WO0066789 A2 | 11/2000 |
| WO | WO0077260 A1 | 12/2000 |
| WO | WO0100828 A2 | 1/2001 |
| WO | WO0107648 A1 | 2/2001 |
| WO | WO0120018 A2 | 3/2001 |
| WO | WO0123604 A2 | 4/2001 |
| WO | WO0123608 A2 | 4/2001 |
| WO | WO0132930 A1 | 5/2001 |
| WO | WO0140497 A2 | 6/2001 |
| WO | WO0146404 A1 | 6/2001 |
| WO | WO0151661 A2 | 7/2001 |
| WO | WO0151662 A1 | 7/2001 |
| WO | WO0157263 A1 | 8/2001 |
| WO | WO0173119 A2 | 10/2001 |
| WO | WO0173199 A1 | 10/2001 |
| WO | WO0177392 A2 | 10/2001 |
| WO | WO0196388 A2 | 12/2001 |
| WO | WO0202811 A2 | 1/2002 |
| WO | WO0210186 A1 | 2/2002 |
| WO | WO0210444 A1 | 2/2002 |
| WO | WO 02/22873 | 3/2002 |
| WO | WO0218641 A2 | 3/2002 |
| WO | WO0221108 A2 | 3/2002 |
| WO | WO0224876 A2 | 3/2002 |
| WO | WO 02/50307 | 6/2002 |
| WO | WO 02/057491 | 7/2002 |
| WO | WO 02/070664 | 9/2002 |
| WO | WO02070728 A2 | 9/2002 |
| WO | WO02070737 A2 | 9/2002 |
| WO | WO 02/077278 | 10/2002 |
| WO | WO 02/099034 | 12/2002 |
| WO | WO02099095 A2 | 12/2002 |
| WO | WO02099129 A2 | 12/2002 |
| WO | WO02099130 A2 | 12/2002 |
| WO | WO 03/002750 | 1/2003 |
| WO | WO 03/008636 | 1/2003 |
| WO | WO03001976 A2 | 1/2003 |
| WO | WO 03/016546 | 2/2003 |
| WO | WO03012058 A2 | 2/2003 |
| WO | WO03012074 A2 | 2/2003 |
| WO | WO03014382 A2 | 2/2003 |
| WO | WO03018636 A2 | 3/2003 |
| WO | WO03020890 A2 | 3/2003 |
| WO | WO03033732 A2 | 4/2003 |
| WO | WO03054162 A2 | 7/2003 |
| WO | WO03054755 A2 | 7/2003 |
| WO | WO003060163 A2 | 7/2003 |
| WO | WO03075955 A1 | 9/2003 |
| WO | WO 03/088979 | 10/2003 |
| WO | WO 03/093506 | 11/2003 |
| WO | WO 03/097869 | 11/2003 |
| WO | WO0310219 A1 | 12/2003 |
| WO | WO03100035 A2 | 12/2003 |
| WO | WO03100068 A1 | 12/2003 |
| WO | WO03104410 A2 | 12/2003 |
| WO | WO03106635 A2 | 12/2003 |
| WO | WO2004003511 A2 | 1/2004 |
| WO | WO2004009849 A1 | 1/2004 |
| WO | WO2004011651 A1 | 2/2004 |
| WO | WO2004013357 A2 | 2/2004 |
| WO | WO2004040013 A1 | 5/2004 |
| WO | WO2004044123 A2 | 5/2004 |
| WO | WO20004044247 A2 | 5/2004 |
| WO | WO 2004/052175 | 6/2004 |
| WO | WO2004053076 A2 | 6/2004 |
| WO | WO2004053141 A2 | 6/2004 |
| WO | WO2004053164 A1 | 6/2004 |
| WO | WO2004060278 A2 | 7/2004 |
| WO | WO2004070001 A2 | 8/2004 |
| WO | WO2004072230 A2 | 8/2004 |
| WO | WO2004072231 A2 | 8/2004 |
| WO | WO2004101809 A2 | 11/2004 |
| WO | WO2005003384 A1 | 1/2005 |
| WO | WO2005009202 A2 | 2/2005 |
| WO | WO2005012572 A1 | 2/2005 |
| WO | WO2005024046 A2 | 3/2005 |
| WO | WO2005036369 A2 | 4/2005 |
| WO | WO 2005/053141 | 6/2005 |
| WO | WO2005054454 A1 | 6/2005 |
| WO | WO2005075686 A1 | 8/2005 |
| WO | WO2005086634 A2 | 9/2005 |
| WO | WO2005009197 A2 | 10/2005 |
| WO | WO2005098047 A2 | 10/2005 |
| WO | WO2005116263 A2 | 12/2005 |
| WO | WO2006089762 A1 | 8/2006 |
| WO | WO2006094238 A2 | 9/2006 |
| WO | WO2006135400 A2 | 12/2006 |
| WO | WO2007014045 A2 | 2/2007 |
| WO | WO2007086904 A2 | 8/2007 |
| WO | WO2008104002 A2 | 8/2008 |
| WO | WO2008118809 A1 | 10/2008 |

OTHER PUBLICATIONS

Schena, BioEssays, 18(5):427-431 (1996).*
Little et al. (Analytical Chemistry, vol. 69, p. 4540-4546, 1997).*
VanBaar (FEMS Microbiology Reviews, vol. 24, p. 193-219, 2000).*
Ke et al (Journal of Clinical Microbiology, vol. 37, No. 11, p. 3497-3503, Nov. 1999).*
Jackson et al. (Molecular Medicine Today, vol. 6, p. 271-276, Jul. 2000).*
Gendel (Food Microbiology, vol. 13, p. 1-15, 1996).*
Johnson et al. (Journal of microbiological methods, vol. 40, p. 241-254, 2000).*
Hannis et al. (Rapid Commun. Mass Spectrom. 13, 954-962, 1999).*
Bishop et al. (Chapter 4 Molecular sequence databases In Nucleic acid and protein sequence analysis: a practical approach, IRL Press, Oxford England, Ed. M.J. Bishop and C.J. Rawlings, 1987. p. 83-113).*
D. J. Aaserud et al., Accurate Base Composition of Double-Strand DNA by Mass Spectrometry, American Society for Mass Spectrometry, Sep. 1996; pp. 1266-1969.

R. T. Batey et al., Preparation of Isotopically Labeled Ribonucleotides for Multidimensional NMR Spectroscopy of RNA, Nucleic Acids Research, vol. 20, No. 17; pp. 4515-4523.

D. C. Muddiman et al., Characterization of PCR Products from Bacilli Using Electrospray Ionization FTICR Mass Spectrometry, Analytical Chemistry, vol. 68, No. 21, Nov. 1996; pp. 3705-3712.

C. M. Fraser et al., The Minimal Gene Complement of *Mycoplasma genitalium*, Science, vol. 270, Oct. 1995; pp. 397-403.

G. B. Hurst et al., Detection of Bacterial DNA Polymerase Chain Reaction Products by Matrix-Assisted Laser Desorption/Ionization Mass Spectrometry, Rapid Communications in Mass Spectrometry, vol. 10, 1995; pp. 377-382.

Jia Li et al., Single Nucleotide Polymorphism Determination Using Primer Extension and Time-of-Flight Mass Spectrometry, Electrophoresis, 1999, 20; pp. 1258-1265.

D. Loakes et al., Nitroindoles as Universal Bases, Nucleosides and Nucleotides, 14(3-5), 1995; pp. 1001-1003.

D. C. Muddiman et al., Sequencing and Characterization of Larger Oligonucleotides by Electrospray Ionization Fourier Transform Ion Cyclotron Resonance Mass Spectrometry, Reviews in Analytical Chemistry, 1998, vol. XVII, No. 1; pp. 1-68.

D. C. Muddiman et al., Characterization of Pcr Products from Bacilli Using Electrospray Ionization Fticr Mass Spectrometry, Analytical Chemistry, Vol. 68, No. 21, Nov. 1996; pp. 3705-3712.

D. C. Muddiman et al., Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry, Rapid Communications in Mass Spectrometry, 13, 1999; pp. 1201-1204.

D. C. Muddiman et al., Length and Base Composition of PCR-Amplified Nucleic Acids Using Mass Measurements from Electrospray Ionization Mass Spectrometry, Analytical Chemistry, vol. 69, No. 8, Apr. 1997; pp. 1543-1549.

A. R. Mushegian et al., A Minimal Gene Set For Cellular Life Derived by Comparison of Complete Bacterial Genomes, Proc. Natl. Acad. Sci. USA, vol. 93, Sep. 1996; pp. 10268-10273.

P. L. Ross et al., Analysis of DNA Fragments From Conventional and Microfabricated PCR Devices Using Delayed Extraction MALDI-TOF Mass Spectrometry, Analytical Chemistry, vol. 70, No. 10, May 1998; pp. 2067-2073.

M. Sala et al., Ambiguous Base Pairing of the Purine Analogue 1-(2deoxy-β-D-ribofuranosyl)-Imidazole-4-Carboxamide During PCR, Nucleic Acids Research, 1996, vol. 24, No. 17; pp. 3302-3306.

A. Van Aerschot et al., In Search of Acyclic Analogues as Universal Nucleosides in Degenerate Probes, Nucleosides & Nucleotides, 14(3-5), 1995; pp. 1053-1056.

D. S. Wunschel et al., Heterogeneity in *Bacillus cereus* PCR Products Detected by ESI-FTICR Mass Spectrometry, Analytical Chemistry, vol. 70, No. 6, 1998; pp. 1203-1207.

Alves-Silva, J. et al., "The Ancestry of Brazilian mtDNA Lineages," *Am. J. Hum. Genet.* (2000) 67:444-461.

Anderson et al., "Sequence and organization of the human mitochondrial genome," *Nature* (1981) 290:457-465.

Andreasson et al., "Mitochondrial Sequence Analysis for Forensic Identification Using Pyrosequencing Technology" *BioTechniques* (2002) 32:124-133.

Bahrmand et al., "Polymerase chain reaction of bacterial genomes with single universal primer: application to distinguishing mycobacteria species" *Molecular and Cellular Probes* (1996) 10:117-122.

Bahrmand et al., "Use of restriction enzyme analysis of amplified DNA coding for the hsp65 gene and polymerase chain reaction with universal primer for rapid differentiation of mycobacterium species in the clinical laboratory" *Scandinavian Journal of Infe* Scand J infect dis. 30:477-480; 1998.

Baker et al., "Review and re-analysis of domain-specific 16S primers" *J. Microbiol. Methods* (2003) 55:541-555.

Bastia et al., "Organelle DNA analysis of Solanum and Brassica somatic hybrids by PCR with 'universal primers'." *Theoretical and Applied Genetics* (2001) 102:1265-1272.

Baumer et al., "Age-related Human mtDNA Deletions: A Heterogeneous Set of Deletions Arising at a Single Pair of Directly Repeated Sequences" *Am. J. Hum. Genet.* (1994) 54:618-630.

Benson et al., "Advantages of *Thermococcus kodakaraensis* (KOD) DNA polymerase for PCR-mass spectrometry based analyses" *J. Am. Soc. Mass Spectrom.* (2003) 14:601-604.

Black et al., "Detection of trace levels of tricothecene mycotoxins in human urine by gas chromatography-mass spectrometry" *J. Chromatog* (1986) 367:103-115.

BLAST Search results (Mar. 2006).

Boivin-Jahns et al., "Bacterial Diversity in a Deep-Subsurface Clay Environment" *Applied and Environmental Microbiology* (1996) 62:3405-3412.

Campbell et al., "Detection of California serogroup Bunyaviruses in tissue culture and mosquito pools by PCR" *J. Virol. Methods* (1996) 57:175-179.

Carracedo et al., "DNA commission of the international society for forensic genetics: guidelines for mitochondrial DNA typing" *Forensic Science International* (2000) 110:79-85.

Case et al., "Maternal inheritance of mitochondrial DNA polymorphisms in cultured human fibroblasts," *Somatic Cell Genetics* (1981) 7:103-108.

Cespedes et al., "Polymerase chain reaction restriction fragment length polymorphism analysis of a short fragment of the cytochrome b gene for identification of flatfish species" *J. Food Protection* (1998) 61:1684-1685.

Chang, P.-K. et al., "aflT, a MFS transporter-encoding gene located in the aflatoxin gene cluster, does not have a significant role in aflatoxin secretion," Fungal Genet.Biol. (2004) 41:911-920.

Chen et al., "A universal PCR primer to detect members of the Potyviridae and its use to examine the taxonomic status of several members of the family" *Archives of Virology* (2001) 146:757-766.

Chen et al., "Universal primers for amplification of mitochondrial small subunit ribosomal RNA-encoding gene in scleractinian corals" *Marine Biotechnology* (2000) 2:146-153.

Chen, N. et al., "The genomic sequence of ectromelia virus, the causative agent of mousepox," *Virology* (2003) 317:165-186.

Cho et al., "Application of the ribonuclease P (RNase P) RNA gene sequence for phylogenetic analysis of the gene *Saccharomonospora*" *International Journal of Systematic Bacteriology* (1998) 48:1223-1230.

Conrads et al., "16S-23S rDNA internal transcribed spacer sequences for analysis of the phylogenetic relationships among species of the genus *Fusobacterium*" *International Journal of Systematic and Evolutionary Microbiology* (2002) 52:493-499.

Cornel et al., "Polymerase chain reaction species diagnostic assay for *Anopheles quadrimaculatus* cryptic species (*Diptera: Culicidae*) based on ribosomal DNA ITS2 sequences" *Journal of Medical Entomology* (1996) 33:109-116.

Crain et al., "Applications of mass spectrometry of the characterization of oligonucleotides and nucleic acids" *Curr. Opin. Biotechnol.* (1998) 9:25-34.

Crespillo et al., "Mitochondrial DNA sequences for 118 individuals from northeastern Spain" *Int. J. Legal Med.* (2000) 114:130-132.

Dasen et al., "Classification and identification of Propionibacteria based on 16S ribosomal RNA genes and PCR" *Systematic and Applied Microbiology* (1998) 21:251-259.

DeForce et al., "Analysis of oligonucleotides by ESI-MS" *Advances in Chromatography* (2000) 40:539-566.

DeForce et al., "Characterization of DNA Oligonucleotides by Coupling of Capillary Zone Electrophoresis to Electrospray Ionization Q-TOF Mass Spectrometry" *Analytical Chemistry* (1998) 70:3060-3068.

DeMesure et al., "A set of universal primers for amplification of polymorphic non-coding regions of mitochondrial and chloroplast DNA in plants" *Molecular Ecology* (1995) 4:129-131.

Dias Neto et al., "Shotgun sequencing of the human transcriptome with ORF expressed sequence tags" *PNAS* (2000) 97:3491-3496.

Dinauer et al., "Sequence-based typing of HLA class II DQB1" *Tissue Anigens* (2000) 55:364-368.

Dubernet et al., "A PCR-based method for identification of *Lactobacilli* at the genus level" *FEMS Microbiology Letters* (2002) 214:271-275.

Elnifro et al., "PCR and Restriction Endonuclease Analysis for Rapid Identification of Adenovirus Subgenera" *Journal of Clinical Microbiology* (2000) 38:2055-2061.

EMBL Accession No. S90302, Human, Muscle, Mitochondrial Mutant, 22 nt, segment 2 of 2 (XP002436791) Nov. 26, 1993.

Esmans et al., "Liquid Chromatography-Mass Spectrometry in Nucleoside, nucleotide and modified nucleotide characterization" *J. of Chromatography A* (1998) 794:109-127.

European Search Report for 02709785.6 dated Oct. 10, 2005.

Flora, et al., "Dual-micro-ESI source for precise mass determination on a quadrupole time-of-flight mass spectrometer for genomic and proteomic applications" *Anal. Bioanal. Chem.* (2002) 373:538-546.

Fox et al., "Identification and Detection of Bacteria: Electrospray MS-MS Versus Derivatization/GC-MS" *Proceedings of the ERDEC Scientific Conference on Chemical and Biological Defense Research* (1994) 39-44.

Fox et al., "Identification of Brucella by Ribosomal-spacer-region PCR and differentiation of, *Brucella canis* from other Brucella spp. pathogenic for humans by carbohdrate profiles" *Journal of Clinical Microbiology* (1998) 36:3217-3222.

Fox et al., "Report of the 'Bioterrorism Workshop' Duke University Thomas Center on Apr. 24, 2002 organized by US Army Research Office" *Journal of Microbiological Methods* (2002) 51:247-254.

Fuerstenau et al., "Molecular Weight Determination of Megadalton DNA Electrospray Ions Using Charge Detection Time-of-flight Mass Spectrometry" *Rapid Comm. Mass Spec.* (1995) 90:4961-4972.

Fujioka et al., "Analysis of enterovirus genotypes using single-strand conformation polymorphisms of polymerase chain reaction products" *J. Virol. Meth.* (1995) 51:253-258.

Gabriel et al., "Improved mtDNA sequence analysis of forensic remains using a "mini-primer set" amplification strategy" *Journal of Forensic Sciences* (2001) 46:247-253.

Gattermann et al., "Heteroplasmic Point Mutations of Mitochondrial DNA Affecting Subunit I of Cytochrome c Oxidase in Two Patients with Acquired Idiopathic Sideroblastic Anemia" *Blood* (1997) 90:4961-4972.

Giles et al., "Maternal inheritance of human mitochondrial DNA," *PNAS* (1980) 77:6715-6719.

Goto et al., "Applications of the partial 16S rDNA sequence as an index for rapid identification of species in the genus *Bacillus*" *J. Gen. Appl. Microbiol.* (2000) 46:1-8.

Greenberg et al., "Intraspecific nucleotide sequence variability surrounding the origin of replication in human mitochondrial DNA," *Gene* (1983) 21:33-49.

Griffey et al., "Detection of base pair mismatches in duplex DNA and RNA oligonucleotides using electrospray mass spectrometry" *Proceedings of SPIE—The International Society for Optical Engineering* (1997) 2985:82-86.

Griffin et al., "Direct genetic analysis by matrix-assisted laser desorption/ionization mass spectrometry" *PNAS* (1999) 96:6301-6306.

Griffin et al., "Single-nucleotide polymorphism analysis by MALDI-TOF mass spectrometry" *Trends in Biotechnology* (2000) 18:77-84.

Hahner et al., "Analysis of short tandem repeat polymorphisms by electrospray ion trap mass spectrometry" *Nucleic Acids Research* (2000) 28:E82.

Hannis et al., "Accurate characterization of the tyrosine hydroxylase forensic allele 9.3 through development of electrospray ionization Fourier transform ion cyclotron resonance mass spectrometry" *Rapid Communications in Mass Spectrometry* (1999) 13:954-9.

Hannis et al., "Detection of double-stranded PCR amplicons at the attomole level electrosprayed from low nanomolar solutions using FT-ICR mass spectrometry" *Fresenius Journal of Analytical Chemistry* (2001) 369: 246-251.

Hannis et al., "Genotyping complex short tandem repeats using electrospray ionization Fourier transform ion cyclotron resonance multistage mass spectrometry" *Proceedings of SPIE—The International Society for Optical Engineering* (2000) 3926:36-47.

Hannis et al., "Genotyping short tandem repeats using flow injection and electrospray ionization Fourier transform ion cyclotron resonance mass spectrometry" *Rapid Communications in Mass Spectrometry* (2001) 15:348-350.

Haugland et al., "Identification of putative sequence specific PCR primers for detection of the toxigenic fungal species *Stachybotrys chartarum*" *Mol. Cell. Probes* (1998) 12:387-396.

Hayashi et al., "Phylogenetic analysis of the human gut microbiota using 16S rDNA clone libraries and strictly anaerobic culture-based methods" *Microbiology and Immunology* (2002) 46:535-548.

Henchal et al., "Sensitivity and specificity of a universal primer set for the rapid diagnosis of dengue virus infections by polymerase chain reaction and nucleic acid hybridization" *American Journal of Tropical Medicine and Hygiene* (1991) 45:418-428.

Herrmann et al., "Differentiation of *Chlamydia* spp. By Sequence Determination and Restriction Endonuclease Cleavage of RNase P RNA Genes" *J. Clin. Microbiol.* (1996) 34:1897-1902.

Hoffman et al., "Universal primer set for the full-length amplification of all influenza A viruses" *Archives of Virology* (2001) 146:2275-2289.

Holland et al., "Mitochondrial DNA Sequence Analysis of Human Skeletal Remains: Identification of Remains from the Vietnam War," *Journal of Forensic Sciences* (1993) 38:542-553.

Holm et al., "Removing near-neighbour redundancy from large protein sequence collections" *Bioinformatics* (1998) 14:423-429.

Honda et al., "Universal method of hypersensitive nested PCR toward forensic DNA typing" *International Congress Series* (1998) 7:28-30.

Howell et al., "Persistent Heteroplasmy of a Mutation in the Human mtDNA Control Region: Hypermutation as an Apparent Consequence of Simple-Repeat Expansion/Contraction" *Am. J. Hum. Genet.* (2000) 66:1589-1598.

Hurst et al., "MALDI-TOF Analysis of Polymerase Chain Reaction Products from Methanotrophic Bacteria" *Anal. Chem.* (1998) 70:2693-2698.

Hutchison et al., "Maternal inheritance of mammalian mitochondrial DNA," *Nature* (1974) 251:536-538.

Ingman et al., "Mitochondrial genome variation and the origin of modern humans" *Nature* (2000) 408:708-713.

International Prelim. Exam. Report for PCT/US02/20336 dated May 12, 2004.

International Search Report for PCT/US02/20336 dated Feb. 3, 2003.

International Search Report for PCT/US03/38505 dated Apr. 12, 2005.

International Search Report for PCT/US03/38757 dated Jun. 24, 2004.

International Search Report for PCT/US03/38761 dated Dec. 30, 2005.

International Search Report for PCT/US03/38795 dated Apr. 19, 2004.

International Search Report for PCT/US03/38830 dated Aug. 25, 2004.

International Search Report for PCT/US2004/011877 dated Apr. 20, 2006.

International Search Report for PCT/US2005/000386 dated May 9, 2006.

International Search Report for PCT/US2005/018031 dated Jun. 28, 2006.

Isola et al., "MALDI-TOF mass spectrometric method for detection of hybridized DNA oligomers" *Analytical Chemistry* (2001) 73:2126-2131.

Jankowski et al., "Mass spectrometry of DNA. Part 2. Quantitative estimation of base composition" *European Journal of Mass Spectrometry in Biochemistry, Medicine, and Environmental Research* (1980) 1:45-52.

Jensen et al., "Rapid Identification of Bacteria on the Basis of Polymerase Chain Reaction-Amplified Ribosomal DNA Spacer Polymorphisms" *Appl. Environ. Microbiol.* (1993) 59:945-952.

Jiang et al., "A highly efficient and automated method of purifying and desalting PCR products for analysis by electrospray ionization mass spectrometry." *Anal. Biochem.* (2003) 316:50-57.

Jiang et al., "Multiple Trait Analysis of Genetic Mapping for Quantitative Trait Loci Genetics" *Genetics* (1995) 140:1111-1127.

Johnson et al., "Precise molecular weight determination of CPR products of the rRNA intergenic spacer region using electrospray quadrupole mass spectroemtry for differentiation of *B. subtilis* and *B. atrophaeus*, closely related species of *bacilli*" *Journal* J. Micr. Meth.; 40:241-254 2000.

Jurinke et al., "Detection of hepatitis B virus DNA in serum samples via nested PCR and MALDI-TOF mass spectrometry" *Genetic Analysis: Biomolecular Engineering* (1996) 13:67-71.

Kageyama et al., "Rapid detection of human fecal Eubacterium species and related genera by nested PCR method" *Microbiology and Immunology* (2001) 45:315-318.

Ke et al., "Development of a PCR Assay for Rapid Detection of Enterococci" *Journal of Clinical Microbiology* (1999) 37:3497-3503.

Keller et al., "Empirical Statistical Model To Estimate the Accuracy of Peptide Identifications Made by MS/MS and Database Search" *Anal. Chem* (2002) 74:5383-5392.

Kilpatrick et al., "Group-Specific Identification of Polioviruses by PCR Using Primer Containing Mixed-Base or Deoxyinosine Residues at Positions of Codon Degeneracy" *J. Clin. Microbiol.* (1996) 34:2990-2996.

Krahmer et al., "Electrospray quadrupole mass spectrometry analysis of model oligonucleotides and polymerase chain reaction products: determination of base substitutions, nucleotide additions/deletions, and chemical modifications" *Anal. Chem.* (1999) 71:28.

Krahmer et al., "MS for identification of single nucleotide polymorphisms and MS/MS for discrimination of isomeric PCR products" *Anal. Chem.* (2000) 72:4033-4040.

Kupke et al., "Molecular Characterization of Lantibiotic-synthesizing Enzyme EpiD Reveals a Function for Bacterial DFP Proteins i Coenzyme A Biosynthesis" *Journal of Biological Chemistry* (2000) 275:31838-31846.

Lacroix et al., "PCR-Based Technique for the Detection of Bacteria in Semen and Urine" *J. Microbiol. Meth.* (1996) 26:61-71.

Leif et al., "Isolation and characterization of the proton-translocating NADH: ubiquinone oxidoreductase from *Escherichia coli*" *Eur. J. Biochem.* (1995) 230:538-548.

Little et al., "Maldi on a Chip: Analysis of Arrays of Low-Femtomole to Subfemtomole Quantities of Synthetic Oligonucleotides and DNA Diagnostic Products Dispensed by a Piezoelectric Pipet" *Analytical Chemistry* (1997) 69:4540-4546.

Little, et al., "Rapid Sequencing of Oligonucleotides by High-Resolution Mass Spectrometry" *J. Am. Chem. Soc.* (1994) 116:4893-4897.

Liu et al., "An unusual gene arrangement for the putative chromosome replication origin and circadian expression of dnaN in *Synechococcus* sp. Strain PCC 7942" *Gene* (1996) 172:105-109.

Liu et al., "Improving the microdialysis procedure for electrospray ionization mass spectrometry of biological samples" *Journal of Mass Spectrometry* (1997) 32:425-431.

Love et al., "Cloning and sequence of the groESL heat-shock operon of *Pasteurella multocida*" *Gene* (1995) 166:179-180.

Maiwald et al., "Characterization of contaminating DNA in Taq polymerase which occurs during amplification with a primer set for *Legionella* 5S ribosomal RNA" *Molecular and Cellular Probes* (1994) 8:11-14.

Mangrum et al., "Solution composition and thermal denaturation for the production of single-stranded PCR amplicons: piperdine-induced destabilization of the DNA duplex?" *Journal of the American Society for Mass Spectrometry* (2002) 13:232-240.

Martemy Anov et al., "Extremely Thermostable Elongation Factor G from *Aquifex aeolicus*: Cloning, Expression, Purification, and Characterization in a Heterologous Translation System" *Protein Expr. Purif.* (2000) 18:257-261.

Matray et al., "Synthesis and properties of RNA analogs—oligoribonucleotide N3'->P5' phosphoramidates" *Nucleic Acids Res* (1999) 3976-3985.

McCabe et al., "Bacterial Species Identification after DNA Amplification with a Universal Primer Pair" *Molecular Genetics and Metabolism* (1999) 66:205-211.

Meiyu et al., "Detection of flaviviruses by reverse transcriptase-polymerase chain reaction with the universal primer set" *Microbiology and Immunology* (1997) 41:209-213.

Messmer et al., "Discrimination of *Streptococcus pneumoniae* from other upper respiratory tract streptococci by arbitrarily primed PCR" *Clinical Biochemistry* (1995) 28:567-572.

Miller et al., "A compendium of human mitochondrial DNA control region: development of an international standard forensic database," *Croat Med. J.* (2001) 42:315-327.

Moricca et al., "Detection of *Fusarium oxysporum f.sp. Vasinfectum* in cotton tissue by polymerase chain reaction" *Plant Pathology* (1998) 47:486-494.

Morse et al., "Nucleotide Sequence of Part of the ropC Gene Encoding the B Subunit of DNA-Dependent RNA Polymerase from some Gram-Positive Bacteria and Comparative Amino Acid Sequence Analysis" *System Appl. Microbiol.* (1996) 19:150-157.

Muddiman et al., "Application of secondary ion and matrix-assisted laser desorption-ionization time-of-flight mass spectrometry for the quantitative analysis of biological molecules" *Mass Spectrometry Reviews* (1995) 14:383-429.

Muddiman et al., "Important aspects concerning the quantification of biomolecules by time-of-flight secondary-ion mass spectrometry" *Applied Spectroscopy* (1996) 50:161-166.

Muhammad et al., "Electrospray ionization quadrupole time-of-flight mass spectrometry and quadrupole mass spectrometry for genotyping single nucleotide substitutions in intact polymerase chain reaction products in K-ras and p53" *Rapid Commun. Mass Spectro*Rap.Com.Mass.Spect. 16:2278-2285 2002.

Nagpal et al., "Utility of 16S-23S RNA spacer region methodology: how similar are interspace regions within a genome and between strains for closely related organisms?" *Journal of Microbiological Methods* (1998) 33:211-219.

Nakao et al., "Development of a Direct PCR Assay for Detection of the Diphtheria Toxin Gene" *J. Clin. Microbiol.* (1997) 35:1651-1655.

Naumov et al., "Discrimination of the Soil Yest Species *Williopsis saturnus* and *Williopsis suaveolens* by the Polymerase Chain Reaction with the Universal Primer N21" *Microbiology (Moscow)(Translation of Mikrobiologiya)* (2000) 69:229-233.

Nilsson et al., "Evaluation of mitochondrial DNA coding region assays for increased discrimination in forensic analysis" *Forensic Science International: Genetics* (2008) 2:1-8.

Nishikawa et al., "Reconstitution of active recombinant Shiga toxin (Stx)1 from recombinant Stxl-A and Stxl-B subunits independently produced by *E. coli* clones" *FEMS* (1999) 178:13-18.

Norder et al., "Typing of Hepatitis B Virus Genomes by a Simplified Polymerase Chain Reaction" *J. Med. Virol.* (1990) 31:215-221.

Null et al., "Determination of a correction to improve mass measurement accuracy of isotopically unresolved polymerase chain reaction amplicons by electrospray ionization Fourier transform ion cyclotron resonance mass spectrometry" *Rapid Comm. Mass Spectr* Rap.com. Mass.Spec. 17:1714-1722 2003.

Null et al., "Evaluation of sample preparation techniques for mass measurements of PCR products using ESI-FT-ICR mass spectrometry" *Journal of the American Society for Mass Spectrometry* (2002) 13:338-344.

Null et al., "Genotyping of Simple and Compound Short Tandem Repeat Loci Using Electrospray Ionization Fourier Transform Ion Cyclotron Resonance Mass Spectrometry" Analytical Chemistry (2001) 73:4514-4521.

Null et al., "Implications of hydrophobicity and free energy of solvation for characterization of nucleic acids by electrospray ionization mass spectrometry" *Anal. Chem.* (2003) 75:1331-1339.

Null et al., "Perspectives on the use of electrospray ionization Fourier transform ion cyclotron resonance mass spectrometry for short tandem repeat genotyping in the post-genome ere" *Journal of Mass Spectrometry* (2001) 36:589-606.

Null et al., "Preparation of single-stranded PCR products for electrospray ionization mass spectrometry using the DNA repair enzyme lambda exonuclease" *Analyst* (2000) 125:619-626.

Parson et al., "Population data for 101 Austrian Caucasian mitochondrial DNA d-loop sequences: Application of mtDNA sequence analysis to a forensic case" *Int. J. Legal Med.* (1998) 111:124-132.

Paterson et al., "Fine Mapping of Quantitative Trait Loci Using Selected Overlapping Recombinant Chromosomes, in an Interspecies Cross of Tomato" *Genetics* (1990) 124:735-742.

Peng et al., "Rapid detection of *Shigella* species in environmental sewage by an immunocapture PCR with universal primers" *Applied and Environmental Microbiology* (2002) 68:2580-2583.

Pomerantz et al., "Determination of oligonucleotide composition from mass spectrometrically measured molecular weight" *Journal of the American Society for Mass Spectrometry* (1993) 4:204-209.

Raaum, R. L. et al., "Catarrhine primate divergence dates estimated from complete mitochondrial genomes: concordance with fossil and nuclear DNA evidence," *J. Hum. Evol.* (2005) 48:237-257.

Reid et al., "Primary diagnosis of foot-and-mouth disease by reverse transcription polymerase chain reaction" *Journal of Virological Methods* (2000) 89:167-176.

Reilly et al., "Design and use of 16S ribosomal DNA-directed primers in competitive PCRs to enumerate proteolytic bacteria in the rumen" *Microb. Ecol.* (2002) 43:259-270.

Ross et al., "Discrimination of Single-Nucleotide Polymorphisms in Human DNA Using Peptide Nucleic Acid Probes Detected by MALDI-TOF Mass Spectrometry" *Anal. Chem.* (1997) 69:4197-4202.

Sauer et al., "A novel procedure for efficient genotyping of single nucleotide polymorphisms" *Nucleic Acids Research* (2000) 28:E13.

Scaramozzino et al., "Comparison of Flavivirus universal primer pairs and development of a rapid, highly sensitive heminested reverse transcription-PCR assay for detection of flaviviruses targeted to a conserved region of the NS5 gene sequences" *J. Clin. J. Clin.Micr* 39(5): 1922-1927.

Schram et al., "Mass Spectrometry of Nucleic Acid Components" *Biomedical Applications of Mass Spectrometry* (1990) 34:203-280.

Schultz et al., "Polymerase chain reaction products analyzed by charge detection mass spectrometry" *Rapid Communications in Mass Spectrometry* (1999) 13:15-20.

Senko et al., "Determination of Monoisotopic Masses and Ion Populations for Large Biomolecules from Resolved Isotopic Distributions," *J. Am. Soc. Mass Spectrom.* (1995) 6:229.

Seshardi et al., "Differential Expression of Translational Elements by Life Cycle Variants of *Coxiella burnetii*" *Infect. Immun.* (1999) 67:6026-6033.

Shaver et al., "Restriction fragment length polymorphism of rRNA operons for discrimination and intergenic spacer sequences for cataloging *Bacillus subtilis* sub-groups" *J. Microbiol Methods* (2002) 50:215-223.

Shaver et al., "Variation in 16S-23S rRNA intergenic spacer regions among *Bacillus subtilis* 168 isolates" *Molecular Microbiology* (2001) 42:101-109.

Srinivasan et al., "Matrix-assisted laser desorption/ionization time-of-flight mass spectrometry as a rapid screening method to detect mutations causing Tay-Sachs disease" *Rapid Communications in Mass Spectrometry* (1997) 11:1144-1150.

Steffens et al., "Sequence analysis of mitochondrial DNA hybervariable regions using infrared fluorescence detection" *BioTechniques* (1998) 24:1044-1046.

Stoneking et al., "Population variation of human mDNA control region sequences detected by enzymatic amplification and sequence-specific oligonucleotide probes," American Journal of Human Genetics (1991) 48:370-382.

Takahashi et al., "Characterization of gryA, gryB, grlA and grlB mutations in fluoroquinolone-resistant clinical isolates of *Staphylococcus aureus*" *J. Antimicrob. Chemother* (1998) 41:49-57.

Takeuchi et al., "Serotyping of Adenoviruses on Conjunctival Scrapings by PCR and Sequence Analysis" *Journal of Clinical Microbiology* (1999) 37:1839-1845.

Tatuch et al., "Heteroplasmic mtDNA mutation (T-G) at 8993 can cause Leigh disease when the percentage of abnormal mtDNA is high" *Am. J. Hum. Genet.* (1992) 50:852-858.

Tong et al., "Ligation reaction specificities of an NAD+-dependent DNA ligase from the hyperthermophile *Aquifex aeolicus*" *Nucleic Acids Res* (2000) 28:1447-1454.

Torroni et al., "Classification of European mtDNAs from an Analysis of Three European Populations" *Genetics* (1996) 144:1835-1850.

Van Baar et al., "Characterization of Bacteria by Matrix Assisted Laser Desorption/Ionization and Electrospray Mass Spectrometry" *FEMS Microbiol. Review* (2000) 24:195-219.

Van Camp et al., "Amplification and sequencing of variable regions in bacteria 23S ribosomal RNA genes with conserved primer sequences" *Current Microbiology* (1993) 27:147-151.

Van Der Vossen et al., "DNA based typing, identification and detection systems for food spoilage microorganisms: development and implementation" *Int. J. Food Microbiol.* (1996) 33:35-49.

Van Ert et al., "Mass spectrometry provides accurate characterization of two genetic marker types in *Bacillus anthracis*" *Biotechniques* (2004) 37:642-651.

Vanderhallen et al., "Identification of Encephalomyocarditis Virus in Clinical Samples by Reverse Transcription-PCR Followed by Genetic Typing Using Sequence Analysis" *J. Clin. Microbiol.* (1998) 36:3463-3467.

Walters et al., "Genotyping single nucleotide polymorphisms using intact polymerase chain reaction products by electrospray quadrupole mass spectrometry" *Rapid Communications in Mass Spectrometry* (2001) 15:1752-1759.

Welham et al., "The Characterization of Micro-organisms by Matrix-assisted Laser Desorption/Ionization Time-of-flight Mass Spectrometry" *Rapid Communications in Mass Spectrometry* (1998) 12:176-180.

Widjojoatmodjo et al., "Rapid Identification of Bacteria by PCR-Single-Strand Conformation Polymorphism" *Journal of Clinical Microbiology* (1994) 3002-3007.

Wolter et al., "Negative Ion FAB Mass Spectrometric Analysis of Non-Charged Key Intermediates in Oligonucleotide Synthesis: Rapid Identification of Partially Protected Dinucleoside Monophosphates" *Biomed. Environ. Mass Spectrom.* (1987) 14:111-116.

Woo et al., "Identification of *Leptospira inadai* by continuous monitoring of fluorescence during rapid cycle PCR" *Systematic and Applied Microbiology* (1998) 21:89-96.

Wunschel et al., "Analysis of double-stranded polymerase chain reaction products from the *Bacillus cereus* group by electrospray ionization Fourier transform ion cyclotron resonance mass spectrometry" Rapid Communications in Mass Spectrometry (1996) 10:29-.

Wunschel et al., "Discrimination Among the *B. cereus* Group, in Comparison to *B. subtilis*, by Structural Carbohydrate Profiles and Ribosomal RNA Spacer Region PCR" *System. Appl. Microbiol.* (1994) 17:625-635.

Wunschel et al., "Mass spectrometric characterization of DNA for molecular biological applications: Advances using MALDI and ESI" Advances in Mass Spectrometry (1998) 14:Chapter 15/377-Chapter 15/406.

Yao et al., "Mass Spectrometry Based Proteolytic Mapping for Rapid Virus Detection" *Anal. Chem.* (2002) 74:2529-2534.

Yasui et al., "A specific oligonucleotide primer for the rapid detection of *Lactobacillus lindneri* by polymerase chain reaction" *Can. J. Microbiol.* (1997) 43:157-163.

Zeng et al., "Precision Mapping of Quantitative Trait Loci" *Genetics* (1994) 136:1457-1468.

Deyde V.M., et al., "Genomic Signature-Based Identification of Influenza A Viruses Using RT-PCR/Electro-Spray Ionization Mass Spectrometry (ESI-MS) Technology," PLoS One, 2010, vol. 5 (10), pp. e13293.

Extended European Search Opinion for Application No. EP10175659.1, mailed on Feb. 21, 2011, 5 pages.

Extended European Search Report for Application No. EP10179789.2, mailed on Mar. 22, 2011, 9 pages.

Extended European Search Report for Application No. EP10179791.8, mailed on Mar. 17, 2011, 7 pages.

Extended European Search Report for Application No. EP10179795.9, mailed on Mar. 22, 2011, 9 pages.

Final Office Action mailed Apr. 14, 2011 for U.S. Appl. No. 12/049,949, filed Mar. 17, 2008.

Notice of Allowance mailed May 25, 2011 for U.S. Appl. No. 11/929,707, filed Oct. 30, 2007.

Ross P., et al., "High Level Multiplex Genotyping by MALDI TOF Mass Spectrometry," Nature Biotechnology, 1998, vol. 16 (13), pp. 1347-1351.

Aaserud D.J., et al., "DNA Sequencing with Blackbody Infrared Radioactive Dissociation of Electrosprayed Ions," International Journal of Mass Spectrometry and Icon Processes, 1997, vol. 167-168, pp. 705-712.

Adam E., et al., "Characterization of Intertype Specific Epitopes on Adenovirus Hexons," Archives of Virology, 1998, vol. 143 (9), pp. 1669-1682.

Adam E., et al "Intertype Specific Epitope Structure of Adenovirus Hexon," Acta Microbiologica at Immunologica Hungarica, 1998, vol. 45 (3-4), pp. 311-316.

Adam E., et al., "Molecular Structure of the Two-Dimensional Hexon Crystalline Array and of Adenovirus Capsid," Acta Microbiologica et Immunologica Hungarica, 1998, vol. 45 (3- 4), pp. 305-310.

Adrian T., et al., "DNA Restriction Analysis of Adenovirus Prototypes 1 to 41," Archives of Virology, 1986, vol. 91 (3-4), pp. 277-290.

Agostini H.T., et al., "Complete Genome of a JC Virus Genotype Type 6 from the Brain of an African American with Progressive Multifocal Leukoencephalopathy," Journal of Human Virology, 1998, vol. 1 (4), pp. 267-272. .

Aires De Sousa M., et al., "Bridges from Hospitals to the Laboratory: Genetic Portraits of Methicillin-Resistant *Staphylococcus aureus* Clones," FEMS Immunology and Medical Microbiology, 2004, vol. 40 (2), pp. 101-111.

Akalu A., et al., "Rapid Identification of Subgenera of Human Adenovirus by Serological and PCR Assays," Journal of Virological Methods, 1998, vol. 71 (2), pp. 187-196.

Alba M.M., et al., "VIDA: A Virus Database System for the Organization of Animal Virus Genome Open Reading Frames," Nucleic Acids Research, vol. 29 (1), pp. 133-136.

Allaouchiche B., et al., "Clinical Impact of Rapid Oxacillin Susceptibility Testing Using a PCR Assay in *Staphylococcus aureus bactaeremia*," The Journal of Infection, 1999, vol. 39 (3), pp. 198-204.

Allawl H.T., et al., "Thermodynamics and NMR of Internal G.T. Mismatches in DNA," Biochemistry, 1997, vol. 36 (34), pp. 10581-10594.

Altschuel S.F., et al., "Basic Local Alignment Search Tool," Journal of Molecular Biology, 1990, vol. 215 (3), pp. 403-410.

Altschuel S.F., et al., "Gapped BLAST and PSI-BLAST: A New Generation of Protein Database Search Programs," Nucleic Acids Research, 1997, vol. 25 (17), pp. 3389-3402.

Amano Y., et al., "Detection of Influenza Virus: Traditional Approaches and Development of Biosensors," Analytical and Bioanalytical Chemistry, 2005, vol. 381 (1), pp. 156-164.

Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.

Anderson M.L.M., "Quantitative Filter Hybridization" in: Nucleic Acid Hybridization, Hames B.D. ed., IRL Press, 1985, pp. 73-111.

Anthony R.M., et al., "Use of the Polymerase Chain Reaction for Rapid Detection of High- Level Mupirocin Resistance in *Staphylococci*," European Journal of Clinical Microbiology & Infectious Diseases, 1999, vol. 18 (1), pp. 30-34.

Arbique J., et al., "Comparison of the Velogene Rapid MRSA Identification Assay, Denka MRSAScreen Assay, and BBL Crystal MRSA ID System for Rapid Identification of Methicillin-Resistant *Staphylococcus aureus*," Diagnositic Microbiology and Infectious Diseases, 2001, vol. 40 (1-2), pp. 5-10.

Archer G.L., et al., "Detection of Methicillin Resistance in Staphylococci by Using a DNA Probe," Antimicrobial Agents and Chemotherapy, 1990, vol. 34 (9), pp. 1720-1724.

Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.

Arnal C., et al., "Quantification of Hepatitis A virus in shellfish by competitive reverse transcription PCRwith coextraction of standard RNA," Applied and Environmental Microbiology, 1999, vol. 65 (1), pp. 322-326.

Ausubel F.M., et al., eds., Current Protocols in Molecular Biology, vol. 1, John Wiley & Sons Inc., 2004, Table of Contents.

Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.

Ausubel F.M., et al., "Unit 2.11 "Synthesis and Purification of Oligonucleotides," in: Current Protocols in Molecular Biology," 1998, John Wiley & Sons, Inc., pp. 2.11 - 2.11.21.

Avellon A., et al., "Rapid and Sensitive Diagnosis of Human Adenovirus Infections by a Generic Polymerase Chain Reaction," Journal of Virological Methods, 2001, vol. 92 (2), pp. 113-120.

Azevedo A.M., et al., "Detection of Influenza, Parainfluenza, Adenovirus and Respiratory Syncytial Virus during Asthma Attacks in Children Older than 2 Years Old," Allergologia Immunopathologia, 2003, vol. 31 (6), pp. 311-317.

Baba T., et al., "Genome and Virulence Determinants of High Virulence Community-Acquired MRSA," Lancet, 2002, vol. 359 (9320), pp. 1819-1827.

Bai J., et al., "Matrix-Assisted Laser Desorption/Ionization Mass Spectrometry of Restriction Enzyme-Digested Plasmid DNA Using an Active Nation Substrate," Rapid Communications in Mass Spectrometry, 1994, vol. 8 (9), pp. 687-691.

Banik U., et al., "Multiplex PCR Assay for Rapid Identification of Oculopathogenic Adenoviruses by Amplification of the Fiber and Hexon Genes," Journal of Clincal Microbiology, 2005, vol. 43 (3), pp. 1064-1068.

Barbour A.G., at al., "Identification of an Uncultivatable Borrelia Species in the hard tick *Amblyomma americanum*: Possible Agent of a Lyme disease-like illness," The Journal of Infectious Diseases, 1996, vol. 173 (2), pp. 403-409.

Barns S.M., et al., "Detection of Diverse New Francisella-like Bacteria in Environmental Samples," Applied and Environmental Microbiology, 2005, vol. 71 (9), pp. 5494-5500.

Baron E.J., "Genetic Aspects of Methicillin Resistance in *Staphylococcus aureus* and MethodsUsed for its Detection in Clinical Laboratories in the United States," Journal of Chemotherapy, 1995, vol. 7 (Supl.3), pp. 87-92.

Barr I.G., et al., "An Influenza A(H3) Reassortant Was Epidemic in Australia and New Zealand in 2003," Journal of Medical Virology, 2005, vol. 76 (3), pp. 391-397.

Barski P., et al., "Rapid Assay for Detection of Methicillin-Resistant *Staphylococcus aureus* Using Multiplex PCR," Molecular and Cellular Probes, 1996, vol. 10 (6), pp. 471- 475.

Beall B., et al., "Sequencing emm-Specific PCR Products for Routine andAccurate Typing of Group A Streptococci," Journal of Clincal Microbiology, 1996, vol. 34 (4), pp. 953-958.

Beall B., et al., "Survey of emm Gene Sequences and T-Antigen Types fromSystemic *Streptococcus pyogenes* Infection Isolates Collected in San Francisco, California; Atlanta, Georgia; and Connecticut in 1994 and 1995," Journal of Clincal Microbiology, 1997, vol. 35 (5), pp. 1231-1235.

Benko, M. et al., "Family Adenoviridae, Virus taxonomy. VIIIth report of the International Committee on Taxonomy of Viruses," 2004, Academic Press, New York, pp. 213-228.

Benson D.A., et al., "GenBank," Nucleic Acids Research, 1999, vol. 27 (1), pp. 12-17.

Berencsi G., et al., "Molecular Biological Characterization of Adenovirus DNA," Acta Microbiologica et Immunologica Hungarica, 1998, vol. 45 (3-4), pp. 297-304.

Bisno A.L., "*Streptococcus pyogenes* in Infectious Diseases and Their Etiologic Agents Principles and Practice of Infectious Diseases," 1995, vol. 2, pp. 1786-1799.

Blaiotta G., et al., "PCR Detection of Staphylococcal Enterotoxin Genes in *Staphylococcus* Spp. Strains Isolated from Meat and Dairy Products. Evidence for New Variants of seG and Sel in *S. aureus* AB-8802," Journal of Applied Microbiology, 2004, vol. 97 (4), pp. 719-730.

Bowers K.M., et al., "Screening for Methicillin Resistance in *Staphylococars aureus* and Coagulasenegative Staphylococci: Evaluation of Three Selective and Mastalex-MRSA latex Agglutination," British Journal of Biomedical Science, 2003, vol. 60 (2), pp. 71-74.

Bonk T., et al., "Matrix-Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.

Borrow R., et al., "SiaD PCR Elisa for Confirmation and Identification of Serogroup Y and W135 Meningococcal Infections," FEMS Microbiology Letters, 1998, vol. 159 (2), pp. 209-214.

Boubaker K., et al., "*Panton-Valentine leukocidin* and Staphyloccocal Skin Infections in Schoolchildren," Emerging Infectious Diseases, 2004, vol. 10 (1), pp. 121-124.

Bowers K.M., et al., "Screening for Methicillin Resistance in Staphylococars Aureus and Coagulasenegative Staphylococci: Evaluation of Three Selective and Mastalex-Mrsa latex Agglutination," British Journal of Biomedical Science, 2003, Vol. 60 (2), pp. 71-74..

Brakstad O.G., et al., "Direct Identification of *Staphylococcus aureus* in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.

Brakstad O.G., et al., "Multiplex Polymerase Chain Reaction for Detection of Genes for *Staphylococcus aureus* Themonuclease and Methicillin Resistance and Correlation with Oxacillin Resistance," Acta Pathologica, Microbiologica et Immunologica Scandinavica, 1993, vol. 101 (9), pp. 681-688.

Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.

Brayshaw D.P., "Methicillin-Resistant *Staphylococcus aureus*: Evaluation of Detection Techniques on Laboratory-Passaged Organisms," British Journal of Biomedical Science, 1999, vol. 56 (3), pp. 170-176.

Brightwell G., et al., "Development of Internal Controls for PCR Detection of *Bacillus anthracis*," Molecular and Cellular Probes, 1998, vol. 12 (6), pp. 367-377.

Brightwell G., et al., "Genetic Targets for the Detection and Identifiaction of Venezuelan Equine Encephalitis Viruses," Archives of Virology, 1998, vol. 143 (4), pp. 731-742.

Bronzoni R.V.M., et al., "Duplex Reverse Transcription-PCR Followed by Nested PCR Assays for Detection and Identification of Brazilian Alphaviruses and Flaviviruses," Journal of Clincal Microbiology, 2005, vol. 43 (2), pp. 696-702.

Bronzoni R.V.M., et al., "Multiplex Nested PCR for Brazilian Alphavirus Diagnosis," Transactions of the Royal Society of Tropical Medicine and Hygiene, 2004, vol. 98 (8), pp. 456-461.

Brown I.H', "Advances in Molecular Diagnostics for Avian Influenza," Developments in Biologicals, 2006, vol. 124, pp. 93-97.

Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010.

Brunaud V., et al., "T-DNA Integration into the *Arabidopsis* Genome Depends on Sequence of Pre-Insertion Sites," EMBO Reports, 2002, vol. 3 (12), pp. 1152-1157.

Buck G.A., et al., "Design Strategies and Performance of Custom DNA Sequencing Primers," BioTechniques, 1999, vol. 27 (3), pp. 528-536.

Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.

Butel J.S., et al., "Cell and Molecular Biology of Simian Virus 40: Implications for Human Infections and Disease," Journal of the National Cancer Institute, 1999, vol. 91 (2), pp. 119-134.

Butler J., "DNA Profiling and Quantitation of Human DNA," CCQM Bio Analysis Working Group, 2005.

Butler J.M., et al., High Throughput Genotyping of Forensic STRs and SNPs using Time-of-Flight Mass Spectrometry [online], Feb. 2002, [retrieved on Feb. 9, 2011]. Retrieved from the Internet<URL: http://www.promega.com/geneticidproc/ussymp9proc/content/10.pdf>.

Carroll K.C., et al., "Rapid Detection of the *Staphylococcal mecA* Gene from BACTEC BloodCulture Bottles by the Polymerase Chain Reaction," American Journal of Clincal Pathology, 1996, vol. 106 (5), pp. 600-605.

Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.

Cavassini M., et al., "Evaluation of MRSA-Screen, a Simple Anti-PBP 2a Slide Latex AgglutinationKit, for Rapid Detection of Methicillin Resistance in *Staphylococcus aureus*," Journal of Clincal Microbiology, 1999, vol. 37 (5), pp. 1591-1594.

Certificate of Correction mailed Jan. 6, 2009 for U.S. Appl. No. 10/660,996, filed Sep. 12, 2003.

Certificate of Correction mailed Aug. 7, 2007 for U.S. Appl. No. 10/660,997, filed Sep. 12, 2003.

Certificate of Correction mailed Dec. 12, 2006 for U.S. Appl. No. 10/156,608, filed May 24, 2002.

Certificate of Correction mailed Jul. 17, 2007 for U.S. Appl. No. 09/891,793, filed Jun. 26, 2001.

Certificate of Correction mailed Mar. 31, 2008 for U.S. Appl. No. 09/891,793, filed Jun. 26, 2001.

Certificate of Correction mailed Mar. 31, 2008 for U.S. Appl. No. 10/156,608 filed May 2002.

Certificate of Correction mailed Mar. 31, 2008 for U.S. Appl. No. 10/660,997, filed Sep. 12, 2003.

Chamberlin M., et al., "New RNA Polymerase from *Escerichia coli* Infected with Bacteriophage T7," Nature, 1970, vol. 228 (5268), pp. 227-231.

Chandra S., et al., "Virus Reduction in the Preparation and Intravenous Globulin: In Vitro Experiments," Transfusion, 1999, vol. 39 (3), pp. 249-257.

Chaves F., et al., "Molecular Characterization of Resistance to Mupirocin in Methicillin-Susceptible and-Resistant Isolates of *Staphylococcus aureus* from Nasal Samples," Journal of Clincal Microbiology, 2004, vol. 42 (2), pp. 822-824.

Chelly J., et al., "Transcription of the Dystrophin Gene in Human Muscle and Non-Muscle Tissue," Nature, 1988, vol. 333 (6176), pp. 858-860.

Chen C.H., et al., Laser Desorption Mass Spectrometry for FastDNA Sequencing [online], Nov. 1994, Retrieved from the Internet URL:http://www.ornl.gove/sci/techresources/Human_Genome/publicat/94SANTA/sequencing/seqtoc.shtml>.

Chen R., et al., "Trapping, Detection, and Charge and Mass Measurement of Large Individual Ions (up to $1.1 \times 10^8$ Daltons) by Electrospray Ionization FTICR MS," 42nd ASMS Conference on Mass Spectrometry, 1994.

Chen Y.Z., et al., "A BAC-Based STS-Content Map Spanning a 35-Mb Region of Human Chromosome 1p35-36," Genomics, 2001, vol. 74 (1), pp. 55-70.

Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.

Chiu N. H., et al., "Mass Spectrometry of Single-Stranded Restriction Fragments Captured by an Undigested Complementary Sequence," Nucleic Acids Research, 2000, vol. 28 (8), pp. E31.

Chmielewicz B., et al., "Development of a PCR-Based Assay for Detection, Quantification, and Genotyping of Human Adenoviruses," Clinical Chemistry, 2005, vol. 51 (8), pp. 1365-1373.

Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.

Choi Y.K., et al., "Detection and Subtying of Swine Influenza H1 N1, H1 N2 and H3N2 Viruses in Clinical Samples Using Two Multiplex RT-PCR Assays," Journal of Virological Methods, 2002, vol. 102 (1-2), pp. 53-59.

Christel L.A., et al., "Rapid, Automated Nucleic Acid Probe Assays Using Silicon Microstructures forNucleic Acid Concentration," Journal of Biomechanical Engineering, 1999, vol. 121 (1), pp. 22-27.

Claas E.C., et al., "Internally Controlled Real-Time PCT Monitoring of Adenovirus DNA Load inSerum or Plasma of Transplant Recipients," Journal of Clincal Microbiology, 2005, vol. 43 (4), pp. 1738-1744.

Cloney L., et al., "Rapid Detection of mecA in Methicillin Resistant *Staphylococcus aureus* Using Cycling Probe Technology," Molecular and Cellular Probes, 1999, vol. 13 (13), pp. 191-197.

Collins D.W., et al., "Numerical Classification of Coding Sequences," Nucleic Acids Research, 1992, vol. 20 (6), pp. 1405-1410.

Contreras-Salazar B., et al., "Up Regulation of the Epstein-Barr Virus (EBV)-Encoded Membrane Protein LMP in the Burkitt's Lymphoma Line Daudi after Exposure to N-Butyrate and after EBV Superinfection," Journal of Virology, 1990, vol. 64 (11), pp. 5441-5447.

Co-pending U.S. Appl. No. 10/318,463, 2002.
Co-pending U.S. Appl. No. 10/318,681, 2002.
Co-pending U.S. Appl. No. 10/323,186, 2002.
Co-pending U.S. Appl. No. 10/323,187, 2002.
Co-pending U.S. Appl. No. 10/324,721, 2002.
Co-pending U.S. Appl. No. 10/521,662, 2005.
Co-pending U.S. Appl. No. 10/807,019, 2004.
Co-pending U.S. Appl. No. 10/845,052, 2004.
Co-pending U.S. Appl. No. 10/964,571, 2004.
Co-pending U.S. Appl. No. 11/209,439, 2005.
Co-pending U.S. Appl. No. 11/674,538, 2007.
Co-pending U.S. Appl. No. 11/682,259, 2007.
Co-pending U.S. Appl. No. 11/929,910, 2007.
Co-pending U.S. Appl. No. 11/930,108, 2007.
Co-pending U.S. Appl. No. 11/930,741, 2007.
Co-pending U.S. Appl. No. 90/010,209, 2008.
Co-pending U.S. Appl. No. 90/010,210, 2008.
Co-pending U.S. Appl. No. 90/010,447, 2009.
Co-pending U.S. Appl. No. 90/010,448, 2009.
Co-pending U.S. Appl. No. 60/639,068, filed on Dec. 22, 2004.
Co-pending U.S. Appl. No. 60/648,188, filed on Jan. 28, 2005.

Couto I., et al., "Development of Methicillin Resistance in Clinical Isolates of *Staphylococcus sciuri* by Transcriptional Activation of the mecA Homologue Native to the Species," Journal of Bacteriology, 2003, vol. 185 (2), pp. 645-653.

Crawford-Miksza L., et al., "Analysis of 15 Adenovirus Hexon Proteins Reveals the Location and Structure of Seven Hypervariable Regions Containing Serotype-Specific Residues," Journal of Virology, 1996, vol. 70 (3), pp. 1836-1844.

Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.

Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.

Cui L., et al., "Contribution of a Thickened Cell Wall and Its Glutamine Nonamidated Component to the Vancomycin Resistance Expressed by *Staphylococcus aureus* Mu50," Antimicrobial Agents and Chemotherapy, 2000, vol. 44 (9), pp. 2276-2285.

De Jong J.C., et al., "Adenoviruses from Human Immunodeficiency Virus-Infected Individuals,Including Two Strains That Represent New Candidate Serotypes Ad50 and Ad51 of Species B1 and D, Respectively," Journal of Clincal Microbiology, 1999, vol. 37 (12), pp. 3940-3945.

De La Puente-Redondo V.A., et al., "Comparison of Different PCR Approaches for Typing of *Francisella tularensis* Strains," Journal of Clinical Microbiology, 2000, vol. 38 (3), pp. 1016-1022.

Del Blanco Garcia N., et al., "Genotyping of *Francisella tularensis* Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.

Del Vecchio V.G., et al., "Molecular Genotyping of Methicillin-Resistant *Staphylococcus aureus* via Fluorophore-Enhanced Repetitive-Sequence PCR," Journal of Clincal Microbiology, 1995, vol. 33 (8), pp. 2141-2144.

Denis M., et al., "Development of a Semiquantitative PCR Assay Using Internal Standard and Colorimetricdetection on Microwell Plate for Pseudorabies Virus," Molecular and Cellular Probes, 1997, vol. 11 (6), pp. 439-448.

Deurenberg R.H., et al., "Rapid Detection of Panton-Valentine Leukocidin from Clinical Isolates of *Staphylococcus aureus* Strains by Real-Time PCR," FEMS Microbiology Letters, 2004, vol. 240 (2), pp. 225-228.

Deurenberg R.H., et al., "The Prevalence of the *Staphylococcus aureus tst* Gene among Community- and Hospital-Acquired Strains and Isolates from Wegener's Granulomatosis Patients," FEMS Microbiology Letters, 2005, vol. 245 (1), pp. 185-189.

Di Guilmi A.M., et al., "Human Adenovirus Serotype 3 (Ad3) and the Ad3 fiber Protein Bind to a 130-kDa Membrane Protein on HLa Cells," Virus Research, 1995, vol. 38 (1), pp. 71-81.

Diep B.A., et al., "Complete Genome Sequence of USA300, an Epidemic Clone of Community Acquired Meticillin-Resistant *Staphylococcus aureus*," Lancet, 2006, vol. 367 (9512), pp. 731-739.

Ding C., et al., "A High-Throughput Gene Expression Analysis Technique using Compettiive PCR and Matrixassisted Laser Desorption Ionization time-of-Flight MS," Proceedings of the National Academy of Sciences, 2003, vol. 100 (6), pp. 3059-3064.

Donehower L.A., et al., "The Use of Primers from Highly Conserved Pol Regions to Identify Uncharacterized Retroviruses by the Polymerase Chain Reaction," Journal of Virological Methods, 1990, vol. 28 (1), pp. 33-46.

Donofrio J.C., et al., "Detection of Influenza A and B in Respiratory Secretions with the Polymerase Chain Reaction," PCR Methods and Applications, 1992, vol. 1 (4), pp. 263- 268.

Doty P., et al., "Strand Separation and Specific Recombination in Deoxyribonucleic Acids: Physical Chemical Studies," Proceedings of the National Academy of Sciences of USA, 1960, vol. 46 (4), pp. 461-476.

Drosten C., et al., "Identification of a Novel Coronavirus in Patients with Severe Acute Respiratory Syndrome," New England Journal of Medicine, 2003, vol. 348 (20), pp. 1967-1976.

Ebner K., et al., "Molecular Detection and Quantitative Analysis of the Entire Spectrum of Human Adenoviruses by a Two-Reaction Real-Time PCR Assay," Journal of Clinical Microbiology, 2005, vol. 43 (7), pp. 3049-3053.

Ebner K., et al., "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.

Echavarria M., et al., "Detection of Adenoviruses (AdV) in Culture-Negative EnvironmentalSamples by PCR During an AdV-Associated Respiratory Disease Outbreak," Journal of Clinical Microbiology, 2000, vol. 38 (8), pp. 2982-2984.

Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.

Echavarria M., et al., "Prediction of Severe Disseminated Adenovirus Infection by Serum PCR," Lancet, 2001, vol. 358 (9279), pp. 384-385.

Echavarria M., et al., "Rapid Detection of Adenovirus in Throat Swab Specimens by PCR DuringRespiratory Disease Outbreaks among Military Recruits," Journal of Clinical Microbiology, 2003, vol. 41 (2), pp. 810-812. .

Echavarria M., et al., "Use of PCR to Demonstrate Presence of Adenovirus Species B, C, or F as Well as Coinfection with Two Adenovirus Species in Children with Flu-Like Symptoms," Journal of Clinical Microbiology, 2006, vol. 44 (2), pp. 625-627.

Ecker D. J., et al., "Rapid Identification and Strain-Typing of Respiratory Pathogens for Epidemic Surveillance," Proceedings of the National Academy of Sciences, 2005, vol. 102 (22), pp. 8012-8017.

Ecker D. J., et al., "The Ibis T5000 Universal Biosensor. An Automated Platform for Pathogen Identification and Strain Typing," Journal of the Association for Laboratory Automation, 2006, vol. 11 (6), pp. 341-351.

Ecker D.J., et al., "Ibis T5000: a universal biosensor approach for microbiology," Nature Reviews Microbiology, 2008, vol. 6 (7), pp. 553-558.

Edwards K.M., et al., "Adenovirus Infections in Young Children," Pediatrics, 1985, vol. 76 (3), pp. 420-424.

Ellis J. S., et al., "Molecular Diagnosis of Influenza," Reviews in Medical Virology, 2002, vol. 12 (6), pp. 375-389.

Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.

Elsayed S., et al., "Development and Validation of a Molecular Beacon Probe-Based Real-Time Polymerase Chain Reaction Assay for Rapid Detection of Methicillin Resistance in *Staphylococcus aureus*," Archives of pathology and laboratory medicine, 2003, vol. 127 (7), pp. 845-849.

EMBL "*Arabidopsis thaliana* T-DNA flanking sequence, left border, clone 346C06," Accession No. AJ552897, Mar. 29, 2003.

EMBL "Dog (Clone: CXX.147) primer for STS 147, 3' end, sequence tagged site," Accession No. L15697, Mar. 4, 2000.

EMBL, "Sequence 10 from patent US 6563025," Accession No. AR321656, Aug. 18, 2003.

EMBL "Synthetic Construct DNA, Reverse Primer for Human STS sts-AA031654 at 1 p36" Accession No. AB068711, May 21, 2003.

Enright M.C., et al., "A multilocus sequence typing scheme for *Streptococcus pneumoniae*: identification of clones associated with serious invasive disease," Microbiology, 1998, vol. 144 (Pt 11), pp. 3049-3060.

Enright M.C., et al., "Multilocus Sequence Typing for Characterization of Methicillin-Resistant and Methicillin-Susceptible Clones of *Staphylococcus aureus*," Journal of Clinical Microbiology, 2000, vol. 38(3), pp. 1008-1015.

Enright M.C., et al., "Multilocus Sequence Typing of *Streptococcus pyogenes* and theRelationships between Emm Type and Clone," Infection and Immunity, 2001, vol. 69 (4), pp. 2416-2427.

Enright M.C., et al., "The Evolutionary History of Methicillin-Resistant *Staphylococcus aureus*(MRSA)," Proceedings of the National Academy of Sciences of USA, 2002, vol. 99 (11), pp. 7687-7692.

Enright M.C., "The Evolution of a Resistant Pathogen—the Case of MRSA," Current Opinion inPharmacology, 2003, vol. 3 (5), pp. 474-479.

Eremeeva M.E., et al., "Evaluation of a PCR Assay for Quantitation of *Rickettsia rickettsii* and Closely Related Spotted Fever Group Rickettsiae," Journal of Clinical Microbiology, 2003, vol. 41 (12), pp. 5466-5472.

Erlich H.A., ed., PCR Technology: Principles and Applications for DNA Amplification, W.H. Freeman and Company, 1989.

Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.

European Search Report for Application No. EP10175659.1, mailed on Feb. 9, 2011, 4 pages.

Evans P., et al., "Practical Algorithms for Universal DNA Primer Design: An Exercise in Algorithm Engineering," Currents in Computational Molecular Biology, 2001, Les Publications CRM, pp. 25-26.

Ex Parte Re-Examination Certificate for U.S. Appl. No. 90/010,209 mailed Jul. 7, 2009.

Ex Parte Re-Examination Certificate for U.S. Appl. No. 90/010,210, mailed Dec. 28, 2010.

Ex Parte Re-Examination Certificate for U.S. Appl. No. 90/010,447 mailed Feb. 15, 2011.

Examiner Interview Summary mailed Oct. 3, 2005 for U.S. Appl. No. 10/3260,46 filed Dec. 18, 2002.

Examiner Interview Summary mailed Nov. 6, 2008 for U.S. Appl. No. 10/728,486, filed Dec. 5, 2003.

Examiner Interview Summary mailed Oct. 24, 2008 for U.S. Appl. No. 11/582,859, filed Oct. 17, 2006.

Examiner Interview Summary mailed Feb. 27, 2006 for U.S. Appl. No. 10/326,644, filed Dec. 18, 2002.

Examiner Interview Summary mailed Jan. 27, 2006 for U.S. Appl. No. 10/323,211, filed Dec. 18, 2002.

Examiner Interview Summary mailed May 28, 2008 for U.S. Appl. No. 10/660,998, filed Sep. 12, 2003.

Examiner Interview Summary mailed Oct. 28, 2008 for U.S. Appl. No. 11/331,987, filed Jan. 13, 2006.

Examiner Interview Summary mailed Oct. 29, 2008 for U.S. Appl. No. 11/331,978, filed Jan. 13, 2006.

Examiner Interview Summary mailed Jul. 31, 2006 for U.S. Appl. No. 10/326,643 filed Dec. 18, 2002.

Examiner Interview Summary Record mailed Oct. 29, 2009 for U.S. Appl. No. 10/660,122, filed Sep. 11, 2003.

Examiner Interview Summary Report mailed May 19, 2003 for U.S. Appl. No. 09/891,793 filed Jun. 26, 2001.

Facklam R., et al., "Emm Typing and Validation of Provisional M Types for Group A *Streptococci*," Emerging Infectious Diseases, 1999, vol. 5 (2), pp. 247-253.

Fang H., et al., "Rapid Screening and Identification of Methicillin-Resistant *Staphylococcus aureus* from Clinical Samples by Selective-Broth and Real-Time PCR Assay," Journal of Clinical Microbiology, 2003, vol. 41 (7), pp. 2894-2899.

Farlow J., et al., "*Francisella tularensis* Strain Typing Using Multiple-Locus, Variable-Number Tandem Repeat Analysis," Journal of Critical Microbiology, 2001, vol. 39 (9), pp. 3186-3192.

Farrell D. J., "The Reliability of Microscan Conventional and Rapid Panels to Identify *Staphylococcus aureus* and Detect Methicillin Resistance: An Evaluation Using the Tube Coagulase Test and mecA PCR," Pathology, 1997, vol. 29 (4), pp. 406-410.

Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.

Fedele C.G., et al., "Quantitation of Polyomavirus DNA by a Competitive Nested Polymerase Chain Reaction," Journal of Virological Methods, 2000, vol. 88 (1), pp. 51-61.

Feng P., "Impact of Molecular Biology on the Detection of Food Pathogens," Molecular Biotechnology, 1997, vol. 7 (3), pp. 267-278.

Figueiredo L.M., et al., "Identification of Brazilian Flavivirus by a simplified reverse transcription-polymerase chain reaction method using Flavivirus universal primers," American Journal of Tropical Medicine and Hygiene, 1998, vol. 59 (3), pp. 357-362.

Final Office Action mailed Aug. 6, 2010 for U.S. Appl. No. 11/929,910, filed Oct. 30, 2007.

Final Office Action mailed Jul. 8, 2010 for U.S. Appl. No. 12/326,800, filed Dec. 2, 2008.

Final Office Action mailed May 12, 2010 for U.S. Appl. No. 11/674,538, filed Feb. 13, 2007.

Final Office Action mailed Nov. 17,2009 for U.S. Appl. No. 11/582,875, filed Oct. 17, 2006.

Final Office Action mailed Nov. 20, 2009 for U.S. Appl. No. 11/331,987, filed Jan. 2006.

Final Office Action mailed Jun. 23, 2010 for U.S. Appl. No. 11/930,017, filed Oct. 30, 2007.

Final Office Action mailed Feb. 26, 2009 for U.S. Appl. No. 11/582,863, filed Oct. 17, 2006.

Final Office Action mailed Jan. 30, 2009 for U.S. Appl. No. 10/844,938 filed May 12, 2004.

Final Rejection mailed Oct. 14, 2009 for U.S. Appl. No. 10/943,344, filed Sep. 17, 2004.

Fong W.K., et al., "Rapid Solid-Phase Immunoassay for Detection of Methicillin-Resistant*Staphylococcus aureus* Using Cycling Probe Technology," Journal of Clinical Microbiology, 2000, vol. 38 (7), pp. 2525-2529.

Fox J.P., et al., "The Virus Watch Program: A Continuing Surveillance of Viral Infections in Metropolitan New York Families," American Journal of Epidemiology, 1969, vol. 89 (1), pp. 25-50.

Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.

Gaydos C.A., et al., "Adenovirus Vaccines in the U.S. Military," Military Medicine, 1995, vol. 160 (6), pp. 300-304.

Geha D.J., et al., "Multiplex PCR for Identification of Methicillin-Resistant Staphylococci in the Clinical Laboratory," Journal of Clinical Microbiology, 1994, vol. 32 (7), pp. 1768- 1772.

Genbank, "{Deletion 6} [Human, Muscle, Mitochondrial Mutant, 22 nt, Segment 2 of 2]," Accession No. S90302.1, Jun. 10, 1992.

Genbank "Acinetobacter genomosp. 10 strain CIP 70.12 RNA polymerase subunit B (rpoB) gene, complete cds," Accession No. 78099429, Mar. 11, 2006.

Genbank, "Bovine parainfluenza virus 3 strain Shipping Fever, complete genome," Accesion No. AF178655, Sep. 19, 2000.

Genbank, "*Clostridium tetani* E88, complete genome," Accession No. AE015927.1, Feb. 4, 2003.

Genbank "*E. coli* operon rpoBC coding for the beta- and beta'-subunits of RNA polymerase (genes rpoC and rpoB), and genes rplL, rlpJ, rplA, and rplK coding for 50S ribosomal subunit proteins L7/L12, L10, L1, and L11, respectively. (Map position 89-90 min.)," Accession No. 42813, Feb. 28, 1992.
Genbank, "*E.coli* 16S ribosomal RNA," Accession No. 174375, Aug. 11, 1995.
Gen Bank, "*E.coli* Open Reading Frame Upstream of Leu Operon," Accession No. M21150, Sep. 15, 1990.
Genbank "*E.coli* rRNA operon (rrnB) coding for Glu-tRNA-2, 5S, 16S and 23S rRNA," Accession No. 147581, Sep. 14, 1992.
Genbank, "*Enterococcus malodoratus* strain ATCC43197 elongation factor Tu (tufA) gene, partial cds," Accession No. AF274728, Dec. 11, 2000.
Genbank "*Escherichia coli* str. K-12 substr. MG1655, Complete Genome," Accession No. NC000913, Oct. 15, 2001.
Genbank, "Homo Sapiens Haplotype V Mitochondrion, Complete Genome", Accession No. AF381990.1, Dec. 28, 2001.
Genbank, "Human Adenovirus Type 4 Hexon Gene," for Accession No. X84646, Jun. 30, 1995.
Genbank, "Human coronavirus 229E, complete genome," Accession No. AF304460, Jul. 11, 2001.
Genbank, "Human Isolate L34 Mitochondrion D-loop Region", Accession No. U08081.1, Aug. 16, 1994.
GenBank, "il11b08.y1 Human insulinoma Homo sapiens cDNA clone Image:6029534 5-similar to SW:COX3_HUMAN P00414 Cytochrome C Oxidase Polypeptide III ;, mRNA sequence", Accession No. BQ581956.1, Jun. 20, 2002.
Genbank, "Influenza B Virus B/Panama/45/90 Polymerase (PB2) mRNA, Complete Cds", Accession No. AF005737, pp. 1-3, Oct. 4, 1997.
Genbank, "Mastadenovirus h7 hexon gene," Accession No. Z48571, Apr. 18, 2005.
GenBank, "or72a01.s1 NCI_CGAP_Lu5 Homo sapiens cDNA Clone Image:1601352 3-similar to SW:COX1_Human P00395 Cytochrome C Oxidase Polypeptide I ;, mRNA sequence", Accession No. A1002209.1, Jun. 10, 1998.
Genbank "*Staphylococcus aureus* RN4220 ErmC gene, partial cds," Accession No. 18542231, Sep. 16, 2003.
Genbank "*Staphylococcus aureus* Strain MSSA476, Complete Genome," Accession No. BX571857.1, Jun. 24, 2004.
Genbank, "*Staphylococcus aureus* subsp. *aureus Mu50*, complete genome," Accession No. 15922990, Oct. 4, 2001.
Genbank "*Staphylococcus aureus* Subsp. *Aureus MW2*, Complete Genome," Accession No. G121281729, May 31, 2002.
Genbank, "*Staphylococcus epidermidis* ATCC 12228, complete genome," Accession No. AE015929.1, Jan. 2, 2003.
Genbank "*Streptococcus agalactiae 2603V/R*, complete genome," Accession No. AE009948.1, Aug. 28, 2002.
Genbank, "*Streptococcus anginosus* Elongation Factor Tu (tuf) Gene, Partial cds," Accession No. AF276257.1, Jul. 1, 2001.
Genbank "*Streptococcus pneumoniae* isolate 95.1 In00S DNA gyrase subunit B (gyrB) gene, complete cds," Accession No. 73916349, Sep. 30, 2005.
Genbank, "*Streptococcus pyogenes* strain MGAS8232, complete genome," Accession No. AE009949.1, Apr. 3, 2002.
Genbank, "Venezuelan equine encephalitis virus nonstructural polyprotein and structural polyprotein genes, complete cds," Accession No. AF375051.1, Jun. 26, 2001.
Gu Z., et al., "Multiplexed, Real-Time PCR for Quantitative Detection of Human Adenovirus," Journal of Clinical Microbiology, 2003, vol. 41 (10), pp. 4636-4641.
Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2 (2), pp. 217-226.
Haff L.A., et al., "Multiplex Genotyping of PCR Products with Mass Tag-Labeled Primers," Nucleic Acids Research, 1997, vol. 25 (18), pp. 3749-3750.
Haines J.D., et al., "Medical Response to Bioterrorism: Are we Prepared," Journal of Oklahoma State Medical Association, 2000, vol. 93, pp. 187-196.
Hall T.A., et al., "Base Composition Analysis of Human Mitochondrial DNA Using Electrospray Ionization Mass Spectrometry: A Novel Tool for the Identification and Differentiation of Humans," Analytical Biochemistry, 2005, vol. 344 (1), pp. 53-69.

Hamdad F., et al., "Detection of Methicillin/Oxacillin Resistance and Typing in Aminoglycoside-Susceptible Methicillin-Resistant and Kanamycin-Tobramycin-Resistant Methicillin-Susceptible," Microbial Drug Resistance, 2006, vol. 12 (3), pp. 177-185.
Hamel S., et al., "Consensus PCR and Microarray for Diagnosis of the Genus *Staphylococcus*, Species, and Methicillin Resistance," Biotechniques, 2001, vol. 31 (6), pp. 1364-1372.
Hammerle T., et al., "A Sensitive PCR Assay System for the Quantitation of Viral Genome Equivalents:Hepatitis C Virus (HCV)," Archives of Virology, 1996, vol. 141 (11), pp. 2103-2114.
Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.
Hanssen A.M., et al., "*Sccmecin staphylococci*: Genes on the Move," FEMS Immuol Medical Microbiol, 2006, vol. 46, pp. 8-20.
Hasebe F. et al., "Combined Detection and Genotyping of Chikungunya Virus by a Specific Reverse Transcription-Polymerase Chain Reaction," Journal of Medical Virology, 2002, vol. 67 (3), pp. 370-374.
Hassan A.A., et al., "Inter- and Intraspecies Variations of the 16S-23S rDNA Intergenic Spacer Region of Various Streptococcal Species," Systematic and Applied Microbiology, 2003, vol. 26 (1), pp. 97-103.
He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.
Heim A., et al., "Rapid and Quantitative Detection of Human Adenovirus DNA by Real-Time PCR," Journal of Medical Virology, 2003, vol. 70, pp. 228-239.
Higgins G.S., et al., "Competitive Oligonucleotide Single-base Extension Combined with Mass Spectrometric Detection for Mutation Screening," Biotechniques, 1997, vol. 23 (4), pp. 710-714.
Higgins J.A., et al., "Sensitive and Rapid Identification of Biological Threat Agents," Annals of the New York Academy of Sciences, 1999, vol. 894, pp. 130-148.
Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.
Hiramatsu K., et al., "The Emergence and Evolution of Methicillin-Resistant *Staphylococcusaureus*," Trends Microbiology, 2001, vol. 9 (10), pp. 486-493.
Hodgson J.E., et al., "Molecular Characterization of the Gene Encoding High-Level Mupirocin Resistancein *Staphylococcus aureus* J2870," Antimicrobial Agents and Chemotherapy, 1994, vol. 38 (5), pp. 1205-1208.
Hoffman E., et al., "Rescue of Influenza B Virus from Eight Plasmids," Proceedings of the National Academy of Sciences, 2002, vol. 99 (17), pp. 11411-11416.
Hofstadler S.A., et al., "TIGER: The Universal Biosensor," International Journal of Mass Spectrometry, 2005, vol. 242, pp. 23-41.
Holden M.T., et al., "Complete Genomes of Two Clinical *Staphylocuccus aureus* Strain: Evidence for the Rapid Evolution of Virulence and Drug Resistance," Proceedings of the National Academy of Sciences, 2004, vol. 101 (26), pp. 9786-9791.
Holland M.M., et al., "Mitochondrial DNA Sequence Analsysis— Validation and Use for Forensic Casework," Forensic Science Review, 1999, vol. 11 (1), pp. 22-50.
Holmes E.G., et al., "Whole-Genome Analysis of Human Influenza A Virus Reveals Multiple Persistent Lineages and Reassortment among Recent H3N2 Viruses," Public Library of Science Biology, 2005, vol. 3 (9), pp. 1579-1589.
Hongoh Y., et al., "Evaluation of Primers and PCR Conditions for the Analysis of 16s rRNA Genes from a Naturalenvironment," FEMS Microbiology Letters, 2003, vol. 221 (2), pp. 299-304.
Hood E., et al., "Chemical and Biological Weapons: New Questions, New Answers," Environmental Health Perspectives, 1999, vol. 107 (12), pp. 931-932.

Houng H.S., et al., "Rapid Type-Specific Diagnosis of Adenovirus Type 4 Infection Using a Hexon- Based Quantitative Fluorogenic Pcr," Diagnostic Microbiology and Infectious Disease, 2002, vol. 42 (4), pp. 227-236.

Huber C.G., et al., "On-Line Cation Exchange for Suppression of Adduct Formation in Negative-Ion Electrospray Mass Spectrometry of Nucleic Acids," Analytical Chemistry, 1998, vol. 70 (24), pp. 5288-5295.

Huletsky A., et al., "New Real-Time Pcr Assay for Rapid Detection of Methicillin-Resistant *Staphylococcus aureus* Directly from Specimens Containing a Mixture of Staphylococci," Journal of Clinical Microbiology, 2004, Vol. 42 (5), pp. 1875-1884.

Huang C., et al., "Detection of Arboviral RNA Directly from Mosquito Homogenates by Reverse Transcription-Polymerase Chain Reaction," Journal of Virological Methods, 2001, vol. 94 (1-2), pp. 121-128.

Hung E.C., et al., "Detection of SARS coronavirus RNA in the cerebrospinal fluid of a patient with severe acute respiratory syndrome," Clinical Chemistry, 2003, vol. 49 (12), pp. 2108-2109.

Hurdle J.G., et al., "Analysis of Mupirocin Resistance and Fitness in *Staphylococcus aureus* by Molecular Genetic and Structural Modeling Techniques," Antimicrobial Agents and Chemotherapy, 2004, vol. 48 (11), pp. 4366-4376.

Hyde-Deruyscher R., et al., "Polyomavirus Early-Late Switch is not Regulated at the Level of Transcription Initiation and is associated with changes in RNA Processing," Proceedings of the National Academy of Sciences, 1988, vol. 85, pp. 8993-8997.

Ieven M., et al., "Rapid Detection of Methicillin Resistance in Coagulase-Negative Staphylococci by Commercially Available Fluorescence Test," Journal of Clinical Microbiology, 1995, vol. 33 (8), pp. 2183-2185.

Ihle O., et al., "Efficient Purification of DNA Fragments using a Protein Binding Membrane," Nucleic Acids Research, 2000, vol. 28 (16), pp. e76.

Inglis T.J., et al., "Rapid Genotypic Confirmation of Methicillin Resistance," Pathology, 1996, vol. 28 (3), pp. 259-261.

International Preliminary Examination Report for Application No. PCT/US2002/06763, mailed on Jun. 11, 2003, 6 pages.

International Preliminary Examination Report for Application No. PCT/US2003/09802, mailed on Apr. 8, 2005, 7 pages.

International Preliminary Examination Report for Application No. PCT/US2003/22835, mailed on Mar. 5, 2005, 4 pages.

International Preliminary Examination Report for Application No. PCT/US2003/38505, mailed on Mar. 3, 2006, 5 pages.

International Preliminary Examination Report for Application No. PCT/US2003/38757, mailed on Feb. 2, 2007, 5 pages.

International Preliminary Examination Report for Application No. PCT/US2003/38761, mailed on Jun. 27, 2006, 6 pages.

International Preliminary Report on Patentability and Written Opinion for Application No. PCT/US2005/00386, mailed on Jul. 10, 2006, 6 pages.

International Preliminary Report on Patentability and Written Opinion for Application No. PCT/US2005/030058, mailed on Aug. 20, 2007, 6 pages.

International Preliminary Report on Patentability and Written Opinion for Application No. PCT/US2005/033707, mailed on Mar. 20, 2007, 6 pages.

International Preliminary Report on Patentability for Application No. PCT/US2004/033742, mailed on Jun. 20, 2006, 1 page.

International Preliminary Report on Patentability for Application No. PCT/US2006/028397, mailed on Jan. 22, 2008, 1 page.

International Preliminary Report on Patentability for Application No. PCT/US2008/054926, mailed on Aug. 26, 2009, 1 page.

International Preliminary Report on Patentability, Written Opinion and International Search Report for Application No. PCT/US2004/015123, mailed on Oct. 3, 2005, 8 pages.

International Search Report and the Written Opinion for Application No. PCT/US2008/064891, mailed on Jun. 29, 2009, 15 pages.

International Search Report and Written Opinion for Application No. PCT/US2006/007747, mailed on Sep. 5, 2006, 13 pages.

International Search Report and Written Opinion for Application No. PCT/US2006/028397, mailed on Mar. 5, 2007, 14 pages.

International Search Report and Written Opinion for Application No. PCT/US2006/040747, mailed on Mar. 17, 2009, 19 pages.

International Search Report and Written Opinion for Application No. PCT/US2006/061307, mailed on Jan. 9, 2008, 21 pages.

International Search Report and Written Opinion for Application No. PCT/US2007/20045 mailed on Jan. 8, 2009, 18 pages.

International Search Report and Written Opinion for Application No. PCT/US2008/054926, mailed on Jan. 26, 2009, 15 pages.

International Search Report and Written Opinion for Application No. PCT/US2008/057901, mailed on Aug. 28, 2008, 14 pages.

International Search Report for Application No. PCT/US04/007236, mailed on Feb. 24, 2006, 2 pages.

International Search Report for Application No. PCT/US2002/06763, mailed on Oct. 23, 2002, 4 pages.

International Search Report for Application No. PCT/US2003/009802, mailed on Aug. 3, 2004, 2 pages.

International Search Report for Application No. PCT/US2003/22835, mailed on Dec. 12, 2003, 1 page.

International Search Report for Application No. PCT/US2004/012671, mailed on Sep. 28, 2007, 2 pages.

International Search Report for Application No. PCT/US2004/015123, mailed on Oct. 3, 2005, 2 pages.

International Search Report for Application No. PCT/US2004/015196, mailed on Jul. 1, 2005, 3 pages.

International Search Report for Application No. PCT/US2004/028869, mailed on Jul. 17, 2006, 4 pages.

International Search Report for Application No. PCT/US2004/033742, mailed on May 15, 2006, 2 pages.

International Search Report for Application No. PCT/US2005/005356, mailed on Aug. 7, 2007, 4 pages.

International Search Report for Application No. PCT/US2005/006133, mailed on Jul. 26, 2007, 4 pages.

International Search Report for Application No. PCT/US2005/009557, mailed on Sep. 19, 2005, 1 page.

International Search Report for Application No. PCT/US2005/018337, mailed on Oct. 10, 2006, 2 pages.

International Search Report for Application No. PCT/US2005/024799, mailed on Dec. 28, 2006, 4 pages.

International Search Report for Application No. PCT/US2005/030058, mailed on Aug. 20, 2007, 1 page.

International Search Report for Application No. PCT/US2005/033707, mailed on Feb. 6, 2006, 3 pages.

International Search Report for Application No. PCT/US2007/066194, mailed on Jan. 15, 2008, 4 pages.

International Search Report for Application No. PCT/US2008/057901, mailed on Jun. 29, 2009, 15 pages.

International Search Report for Application No. PCT/US2008/065332, mailed on Nov. 28, 2008, 5 pages.

International Search Report for Application No. PCT/US2009/045635, mailed on Oct. 7, 2009, 9 pages.

Inyaku K., et al., "Rapid Detection and Identification of Mycobacteria in Sputum Samples by NestedPolymerase Chain Reaction and Restriction Fragment Length Polymorphisms of dnaJ Heat ShockProtein Gene," Journal of Medical Sciences, 1993, vol. 42 (1), pp. 21-31.

Iqbal S.S., et al., "A Review of Molecular Recognition Technologies for Detection of Biological Threat Agents," Biosensors & Bioelectronics, 2000, vol. 15 (11-12), pp. 549-578.

Iteman I., et al., "Comparison of Conserved Structural and Regulatory Domains within Divergent 16S rRNA-23S rRNA Spacer Sequences of Cyanobacteria," Microbiology, 2000, vol. 146 (Pt 6), pp. 1275-1286.

Ito T., et al., "Insights on Antibiotic Resistance of *Staphylococcus aureus* from its Whole Genome: Genomic Island Scc," Drug Resistance Updates, 2003, vol. 6 (1), pp. 41-52.

Ito T., et al., "Structural Comparison of Three Types of Staphylococcal Cassette Chromosome mecIntegrated in the Chromosome in Methicillin-Resistant *Staphylococcus aureus*," Antimicrobial Agents and Chemotherapy, 2001, vol. 45 (5), pp. 1323-1336.

James A.M., et al., "*Borelia lonestari* Infection after a Bite by an Amblyomma Americanum Tick," The Journal of Infectious Diseases, 2001, vol. 183 (12), pp. 1810-1814.

Jansen R.C., et al., "Genotype-by-environment Interaction in Genetic Mapping of Multiple Quantitative Trait Loci," Theoretical and Applied Genetics, 1995, vol. 91, pp. 33-37.

Jaulhac B., et al., "Specific Detection of the Toxic Shock Syndrome Toxin-1 Gene Using the Polymerase Chain Reaction," Molecular and Cellular Probes, 1991, vol. 5, pp. 281-284.

Jaulhac B., et al., "Synthetic DNA Probes for Detection of Genes for Enterotoxins A, B, C, D, E and for Tsst-1 in Staphylococcal Strains," Journal of Applied Bacterial, 1992, vol. 72 (5), pp. 386-392.

Jeong J., et al., "Early Screening of Oxacillin-Resistant *Staphylococcus aureus* and *Staphylococcus epidermidis* From Blood Culture," Journal of Korean Medical Science, 2002, vol. 17, pp. 168-172.

Johansson A., et al., "Evaluation of PCR-based Methods for Discrimination of *Francisella* species and Subspecies and Development of a Specific PCR that Distinguishes the two Major Subspecies of *Francisella tularensis*," Journal of Clinical Microbiology, 2000, vol. 38 (11), pp. 4180-4185.

Johnson W.M., et al., "Detection of Genes for Enterotoxins, Exfoliative Toxins, and Toxic Shock Syndrome Toxin 1 in *Staphylococcus aureus* by the Polymerase Chain Reaction," Journal of Clinical Microbiology, 1991, vol. 29 (3), pp. 426-430.

Jonas D., et al., "Rapid PCR-Based Identification of Methicillin-Resistant *Staphylococcus aureus* from Screening Swabs," Journal of Clinical Microbiology, 2002, vol. 40 (5), pp. 1821-1823.

Jurinke C., et al., "Application of Nested PCR and Mass Spectrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.

Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.

Kajon A.E., et al., "Genome Type Analysis of Brazilian Adenovirus Strains of Serotypes 1, 2, 3, 5,and 7 Collected Between 1976 and 1995," Journal of Medical, 1999, vol. 58 (4), pp. 408-412.

Kasai H., at al., "Construction of the gyrB Database for the Identification and Classification of Bacteria," Genome Informatics. Workshop on Genome Informatics, 1998, pp. 13-21.

Katano H., et al., "Identification of Adeno-Associated Virus Contamination In Cell and Virus Stocks by PCR," Biotechniques, 2004, vol. 36 (4), pp. 676-680.

Katayama Y., et al., "Genetic Organization of the Chromosome Region Surrounding mecA inClinical Staphylococcal Strains: Role of IS431-Mediated mecI Deletion in Expression of Resistance inmed-Canying, Low-Level Methicillin-Resistant *Staphylococcus haemolyticus*," Antimicrobial Agents and Chemotherapy, 2001, vol. 45 (7), pp. 1955-1963.

Kearns A.M., et al., "Rapid Detection of Methicillin-Resistant Staphylococci by Multiplex PCR," The Journal of Hospital Inspection, 1999, vol. 43 (1), pp. 33-37.

Khan A.S., et al., "An Outbreak of Crimean-Congo Haemorrhagic Fever in the United Arab Emirates, 1994-1995," The American Journal of Tropical Medicine and Hygiene, 1997, vol. 57 (5), pp. 519-525.

Khan S.A., et al., "Simultaneous Detection of Erythromycin-Resistant Methylase Genes ermA and ermC from *Staphylococcus* Spp. By Multiplex-PCR," Molecular and Cellular Probes, 1999, vol. 13 (5), pp. 381-387.

Kidd A.H., et al., "Rapid Subgenus Identification of Human Adenovirus Isolates by a General PCR," Journal of Clinical Microbiology, 1996, vol. 34 (3), pp. 622-627.

Kidd-Ljunggren K., et al., "The hepatitis B virus X gene: analysis of functional domain variation and gene phylogeny using multiple sequences," Journal of General Virology, 1995, vol. 76 (pt 9), pp. 2119-2130.

Kikuchi K., et al., "Restriction Fragment Length Polymorphism Analysis of Clinical Isolates of Mycobacterium Haemophilum," Journal of Clinical Microbiology, 1994, vol. 32 (7), pp. 1763-1767.

Kilbourne E.D., "Influenza Pandemics of the 20th Century," Emerging Infectious Diseases Journal, 2006, vol. 12 (1), pp. 9-14.

Kilbourne E.D., "Influenza Pandemics: Can We Prepare for the Unpredictable," Viral Immunology, 2004, vol. 17 (3), pp. 350-357.

Kim B.J., et al., "Identification of Mycobacterial Species by Comparative Sequence Analysis of the RNA Polymerase Gene (rpoB)," Journal of Clinical Microbiology, 1999, vol. 37 (6), pp. 1714-1720.

Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.

Kirpekar F., et al., "Matrix Assisted Laser Desorption/lonization Mass Spectrometry of Enzymatically Synthesized RNA up to 150 kDa," Nucleic Acids Research, 1994, vol. 22 (19), pp. 3866-3870.

Kitagawa Y., at al., "Rapid Diagnosis of Methicillin-Resistant *Staphylococcus aureus* Bacteremia by Nested Polymerase Chain Reaction," Annals of Surgery, 1996, vol. 224 (5), pp. 665-671.

Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.

Kolbert C.P., et al., "Branched-DNA Assay for Detection of the mecA Gene in Oxacillin-Resistant and Oxacillin-Sensitive Staphylococci," Journal of Clinical Microbiology, 1998, vol. 36 (9), pp. 2640-2644.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Krafft A.E., et al., "Evaluation of PCR Testing of Ethanol-Fixed Nasal Swab Specimens as anAugmented Surveillance Strategy for Influenza Virus and Adenovirus Identification," Journal of Clincal Microbiology, 2005, vol. 43 (4), pp. 1768-1775.

Kramer L.D., et al., "Dection of Encephalitis Viruses in Mosquitoes (Diptera: *Culicidea*) and Avian Tissues," Journal of Medical Entomology, 2002, vol. 39 (2), pp. 312-323.

Kramer L.D., et al., "Dection of St. Louis *Encephalitis* and Western Equine *Encephalomyelitis* RNAin Mosquitoes Tested Without Maintainance of a Cold Chain," Journal of the American Mosquito Control Association, 2001, vol. 17 (4), pp. 213-215.

Kresken M., et al., "Prevalence of Mupirocin Resistance in Clinical Isolates of *Staphylococccus aureus* and *Staphylococcus epidermidis*: Results of the Antimicrobial Resistance Surveillance Study of the Paul-Ehrlich-Society for Chemotherapy, 2001," International Journal of Antimicrobial Agents, 2004, vol. 23 (6), pp. 577-581.

Krishnan P.U., et al., "Detection of Methicillin and Mupirocin Resistance in *Staphylococcus aureus*isolates Using Conventional and Molecular Methods: A Descriptive Study from a Burns Unit with Highprevalence of MRSA," Journal of Clinical Pathology, 2002, vol. 55 (10), pp. 745-748.

Kroes I., et al., "Bacterial Diversity Within the Human Subgingival Crevice," Proceeding of the National Academy of Sciences, 1999, vol. 96 (25), pp. 14547-14552.

Krossoy B., et al., "The Putative Polymerase Sequence of Infectious Salmon Anemia Virus Suggests a New Genus within the Orthomyxoviridae," Journal of Virology, 1999, vol. 73 (3), pp. 2136-2142.

Ksiazek T.G., et al., "A Novel Coronavirus Associated with Severe Acute Respiratory Syndrome," The New England Journal of Medicine, 2003, vol. 348 (20), pp. 1953-1966.

Kuroda M., et al., "Whole Genome Sequencing of Meticillin-Resistant *Staphylococcus aureus*," The Lancet, 2001, vol. 357 (9264), pp. 1225-1240.

Kwok S., et al., "Avoiding False Positives with PCR," Nature, 1989, vol. 339 (6221), pp. 237-238.

Labandeira-Rey, M. at al., "*Staphylococcus aureus Panton Valentine Leukocidin* CausesNecrotizing Pneumonia," Sciencexpress, 2007, 8 pages.

Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.

Laken S.J., et al., "Genotyping by Mass Spectrometric Analysis of Short DNA Fragments," Nature Biotechnology, 1998, vol. 16 (13), pp. 1352-1356.

Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.

Lambert A.J., et al., "Detection of North American Eastern and Western Equine EncephalitisViruses by Nucleic Acid Amplification Assays," Journal of Clinical Microbiology, 2003, vol. 41 (1), pp. 379-385.

Lau L. T., et al, "A Real-Time PCR for SARS-Coronavirus Incorporating Target Gene Pre-Amplification," Biochemical and Biophysical Research Communications, 2003, vol. 312 (4), pp. 1290-1296.

Lau L.T., et al., "Nucleic Acid Sequence-Based Amplification Methods to Detect Avian Influenza Virus," Biochemical and Biophysical Research Communications, 2004, vol. 313 (2), pp. 336-342.

Le Cann P., et al., "Quantification of Human Astroviruses in Sewage Using Real-Time RT-PCR," Research in Microbiology, 2004, vol. 155 (1), pp. 11-15.

Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.

Lednicky J.A., et al., "Polyomaviruses and Human Tumors: A Brief Review of Current Concenpts and Interpretations," Frontiers Bioscience, 1999, vol. 4, pp. D153-D164.

Lee J.A., et al., "Rapid Identification of Human Adenovirus Types 3 and 7 from Respiratory Specimens via Multiplex Type-Specific PCR," Journal of Clinical Microbiology, 2005, vol. 43 (11), pp. 5509-5514.

Lee J.H., et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.

Lengyel A., et al., "Characterization of the Main Protein Components of Adenovirus Virion and itsPossible Use in Laboratory Diagnostics," Acta Microbiologica lmmunologica Hungarica, 1998, vol. 43 (3-4), pp. 281-283.

Leroy E.M., et al., "Diagnosis of *Ebola haemorrhagic* Fever by RT-PCR in an Epidemic Setting," Journal of Medicinal Virology, 2000, vol. 60 (4), pp. 463-467.

Levi K., et al., "Evaluation of an Isothermal Signal Amplification Method for Rapid Detection of Methicillin-Resistant *Staphylococcus aureus* from Patient-Screening Swabs," Journal of Clinical Microbiology, 2003, vol. 41 (7), pp. 3187-3191.

Levine S.M., et al., "PCR-Based Detection of *Bacillus anthracis* in Formalin-Fixed Tissue from a Patient Receiving Ciprofloxacin," Journal of Clinical Microbiology, 2002, vol. 40 (11), pp. 4360-4362.

Levison P.R., et al., "Recent Developments of Magnetic Beads for Use in Nucleic Acid Purification," Journal of Chromatography, 1998, vol. A816, pp. 107-111.

Lewers K.S., et al., "Detection of Linked QTL for Soybean Brown Stem Rot Resistance in "BSR 101"as Expressed in a Growth Chamber Environment," Molecular Breeding, 1999, vol. 5, pp. 33-42.

Li C., et al., "Evolution of H9N2 Influenza Viruses from Domestic Poultry in Mainland China," Virology, 2005, vol. 340 (1), pp. 70-83.

Li Q., et al., "Genetic Variability of Hexon Loops 1 and 2 between Seven Genome Types of Adenovirus Serotype 7," Archives of Virology, 1999, vol. 144 (9), pp. 1739-1749.

Li Q., et al., "Screening of the High Yield Influenza B Virus on MDCK c14d Cloning of its Whole Genome," International Congress Series, 2004, pp. 610-614.

Li Q.G., et al., "Analysis of 15 Different Genome Types of Adenovirus Type 7 Isolated on FiveContinents," Journal of Virology, 1986, vol. 60 (1), pp. 331-335.

Li Q.G., et al., "Comparison of 17 Genome Types of Adenovirus Type 3 Identified among Strains Recovered from Six Continents," Journal of Clinical Microbiology, 1988, vol. 26 (5), pp. 1009-1015.

Liebermann H., et al., "Mapping of Epitopes on the Fiber Knobs of Human Adenovirus Serotypes 8 and 15," Intervirology, 2002, vol. 45 (1), pp. 59-66.

Liebermann H., et al., "Mapping of Linear Epitopes on Fibre Knob of Human Adenovirus Serotype 5," Virus Research, 2001, vol. 73 (2), pp. 145-151.

Lim L.P., et al., "The MicroRNAs of *Caenorhabditis elegans*," Genes and Development, 2003, vol. 17 (8), pp. 991-1008.

Limbach P.A., et al., "Enzymatic Sequencing of Oligonucleotides with Electrospray Mass Spectrometry," 42nd ASMS Conference on Mass Spectrometry, 1994.

Limoncu M.H., et al., "Emergence of Phenotypic Resistance to Ciprofloxacin and Levofloxacin Inmethicillin-Resistant and Methicillin-Sensitive *Staphylococcus aureus*Strains," International Journal of Antimicrobial Agents, 2003, vol. 21 (5), pp. 420-424.

Lin B., et al., "Use of Oligonucleotide Microarrays for Rapid Detection and Serotyping of Acute Respiratory Disease-Associated Adenoviruses," Journal of Clinical Microbiology, 2004, vol. 42 (7), pp. 3232-3239.

Lin P.H., et al., "Oxidative Damage to Mitochondrial DNA in Atrial Muscle of Patients with Atrial Fibrillation," Free Radical Biology and Medicine, 2003, vol. 35 (10), pp. 1310-1318.

Lina G., et al., "Bacterial Competition for Human Nasal Cavity Colonization: Role of *Staphylococcalagr alleles*," Applied and Environmental Microbiology, 2003, vol. 69 (1), pp. 18-23.

Lina G., et al., "Involvement of *Panton-Valentine Leukocidin*-Producing *Staphylococcus aureus* in Primary Skin Infections and Pneumonia," Clinical Infectious Diseases, 1999, vol. 29 (5), pp. 1128-1132.

Linssen B., et al., "Development of Reverse Transcription-PCR Assays Specific for Detection of Equine Encephalitis Viruses," Journal of Clinical Microbiology, 2000, vol. 38 (4), pp. 1527-1535.

Liu J.H., et al., "Interregional Transmission of the Internal Protein Genes of H2 Influenza Virus in Migratory Ducks from North America to Eurasia," Virus Genes, 2004, vol. 29 (1), pp. 81-86.

Livermore D.M., "The Threat from the Pink Corner," Annals of Medicine, 2003, vol. 35 (4), pp. 226-234.

Loo J.A., et al., "Applying Charge Discrimination with Electrospray Ionization-Mass Spectrometry to Protein Analysis," Journal of American Society for Mass Spectrometry, 1995, vol. 6, pp. 1098-1104.

Loott T.J., et al., "Nucleotide Sequence Analysis of the 5-8s rDNA and Adjacent ITS2 Region of *Candidaalbicans* and Related Species," Yeast, 1993, vol. 9, pp. 1199-1206.

Louie L., et al., "Evaluation of Three Rapid Methods for Detection of Methicillin Resistance in *Staphylococcus aureus*," Journal of Clinical Microbiology, 2000, vol. 38 (6), pp. 2170-2173.

Lovseth A., et al., "Modified Multiplex PCR Method for Detection of Pyrogenic Exotoxin Genes in Staphylococcal Isolates," Journal of Clinical Microbiology, 2004, vol. 42 (8), pp. 3869-3872.

Lowe T., et al., "A Computer Program for Selection of Oligonucleotide Primers for Polymerase Chain Reactions," Nucleic Acids Research, 1990, vol. 18 (7), pp. 1757-1761.

Lu X., et al., "Molecular Typing of Human Adenoviruses by PCR and Sequencing of a Partial Region of the Hexon Gene," Archives of Virology, 2006, vol. 151 (8), pp. 1587-1602.

Lubman D.M., Application for Continuation Grant by David Mitchell Lubman dated Jun. 4, 1996 and Jun. 14, 1996.

Lubman D.M., Application for Continuation Grant by David Mitchell Lubman dated Jun. 10, 1994 and Jun. 24, 1994.

Lubman D.M., Application for Grant by David Mitchell Lubman dated Sep. 1, 1994 and Sep. 27, 1994.

Lubman D.M., Application for Grant by David Mitchell Lubman dated Oct. 25, 1992 and Oct. 29, 1992.

Ludwig S.L., et al., "Prevalence of Antibodies to Adenovirus Serotypes 4 and 7 among Unimmunized US Army Trainees: Results of a Retrospective Nationwide Seroprevalence Survey," The Journal of Infectious Diseases, 1998, vol. 178 (6), pp. 1776-1778.

Ludwig W., et al., "Bacterial Phylogeny Based on 16S and 23S rRNA Sequence Analysis," FEMS Microbiolofy Reviews, 1994, vol. 15 (2-3), pp. 155-173.

Lukashov V.V., et al., "Evolutionary Relationships among Parvoviruses: Virus-Host Coevolution among Autonomous Primate Parvoviruses and Links between Adeno-Associated and Avian Parvoviruses," Journal of Virology, 2001, vol. 75 (6), pp. 2729-2740.

Ma X.X., et al., "Novel Type of Staphylococcal Cassette Chromosome mec Identified in Community-Acquired Methicillin-Resistant *Staphylococcus aureus*Strains," Antimicrobial Agents and Chemotherapy, 2002, vol. 46 (4), pp. 1147-1152.

Mack D.H., et al., "A Sensitive Method for the Identification of Uncharacterized Viruses Related Toknown Virus Groups:

Hepadnavirus Model System," Proceedings of the National Academy of Sciences, 1988, vol. 85 (18), pp. 6977-6981.

Magnuson V.L., et al., "Substrate Nucleotide-Determined Non-Templated Addition of Adenine by TagDNA Polymerase: Implications for PCR-Based Genotyping and Cloning," BioTechniques, 1996, vol. 21 (4), pp. 700-709.

Malasig M.D., et al., "Simplified Microneutralization Test for Serotyping Adenovirus Isolates," Journal of Clinical Microbiology, 2001, vol. 39, (8), pp. 2984-2986.

Manian F.A., "Asymptomatic Nasal Carriage of Mupirocin-Resistant, Methicillin-Resistant *Staphylococcus aureus* (MRSA) in a Pet Dog Associated with MRSA Infection in Household Contacts," Clinical Infectious Diseases, 2003, vol. 36 (2), pp. e26-e28.

Marks F., et al., "Genotyping of *Plasmodium falciparum* Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.

Marmur J., et al., "Strand Separation and Specific Recombination in Deoxyribonucleic Acids: Biological Studies," Proceedings of the National Academy of Sciences, 1960, vol. 46 (4), pp. 453-461.

Martineau F., et al., "Development of a PCR Assay for Identification of *Staphylococci* at Genus andSpecies Levels," Journal of Clinical Microbiology, 2001, vol. 39 (7), pp. 2541-2547.

Martineau F., et al., "Species-Specific and Ubiquitous-DNA-Based Assays for Rapid Identification of *Staphylococcus aureus*," Journal of Clinical Microbiology, 1998, vol. 36 (3), pp. 618-623.

Martin-Lopez J.V., et al., "Simultaneous PCR Detection of ica Cluster and Methicillin and Mupirocinresistance Genes in Catheter-Isolated *Staphylococcus*," International Microbiology, 2004, vol. 7 (1), pp. 63-66.

Mason V.P., et al., "Diversity and linkage of Replication and Mobilisation Genes in *Bacillus* Rolling Irclereplicating Plasmids from Diverse Geographical Origins," FEMS Microbiology Ecology, 2002, vol. 42 (2), pp. 235-241.

Matsuoka M., et al., "Characteristic Expression of Three Genes, msr(A), mph(C) and erm(Y), Thatconfer Resistance to Macrolide Antibiotics on *Staphylococcus aureus*," FEMS Microbiology Letters, 2003, vol. 220 (2), pp. 287-293.

May A.G., "Percent Sequence Identity: The Need to be Explicit," Structure, 2004, vol. 12 (5), pp. 737-738.

McLafferty F.W., et al., "Comparison of Algorithms and Databases for Matching Unknown Mass Spectra," Journal of the American Society for Mass Spectrometry, 1998, vol. 9 (1), pp. 92-95.

McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.

Mehrotra M., et al., "Multiplex PCR for Detection of Genes for *Staphylococcus aureus* Enterotoxins, Exfoliative Toxins, Toxic Shock Syndrome Toxin 1, and Methicillin Resistance," Journal of Clinical Microbiology, 2000, vol. 38 (3), pp. 1032-1035.

Mellor J., et al., "Genotype Dependence of Hepatitis C Virus Load Measurement in Commercially Available Quantitative Assays," Journal of Clinical Microbiology, 1999, vol. 37 (8), pp. 2525-2532.

Merlino J., et al., "New Chromogenic Identification and Detection of *Staphylococcus aureus* andMethicillin-Resistant *S. aureus*," Journal of Clinical Microbiology, 2000, vol. 38 (6), pp. 2378-2380.

Merlino J., et al., "Rapid Detection of Non-Multidrug-Resistant and Multidrug-Resistant Methicillin- Resistant *Staphylococcus aureus* Using Cycling Probe Technology for the mecA Gene," European Journal of Clinical Microbiology & Infectious Diseases, 2003, vol. 22 (5), pp. 322-323.

Metzgar D., et al., "PCR Analysis of Egyptian Respiratory Adenovirus Isolates, Including Identification of Species, Serotypes and Coinfections," Journal of Clinical Microbiology, 2005, vol. 43 (11), pp. 5743-5752.

Miragaia M., et al., "Genetic Diversity among Methicillin-Resistant *Staphylococcus epidemidis*(MRSE," Microbial Drug Resistance, 2005, vol. 11 (2), pp. 83-93.

Miura-Ochiai R., at al., "Quantitative Detection and Rapid Identification of Human Adenoviruses," Journal of Clinical Microbiology, 2007, vol. 45 (3), pp. 958-967.

Mollet C., et al., "rpoB Sequence Analysis as a Novel Basis for Bacterial Identification," Molecular Microbiology, 1997, vol. 26 (5), pp. 1005-1011.

Monroy A.M., et al., "Exvaluation of Reverse Transcriptase Polymerase Chain Reaction for theDetection of Eastern Equine Encephalumyelitis Virus during Vector Surveillance," Journal of Medical Entomology, 1996, vol. 33 (3), pp. 449-457.

Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.

Morinaga N., et al., "Purification, Cloning and Charactarizarion of Variant LukE-LukD with Strong Leukocidal Activity of Staphylococcal Bi-Component Leukotoxin Family," Microbiology and Immunology, 2003, vol. 47 (1), pp. 81-90.

Murakami K., et al., "Identification of Methicillin-Resistant Strains of Staphylococci by PolymeraseChain Reaction," Journal of Clinical Microbiology, 1991, vol. 29 (10), pp. 2240-2244.

Na B.K., et al., "Detection and Typing of Respiratory Adenoviruses in a Single-Tube Multiplex Polymerase Chain Reaction," Journal of Medical Virology, 2002, vol. 66 (4), pp. 512-517.

Nagy M., et al., "Sequence Analysis of Porcine Adenovirus Serotype 5 Fibre Gene: Evidence for Recombination," Virus Genes, 2002, vol. 24 (2), pp. 181-185.

Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.

Nakagawa S., et al., "Gene sequences and specific detection for *Panton-Valentine leukocidin*," Biochemical and Biophysical Research Communications, 2005, vol. 328 (4), pp. 995-1002.

Narita S., et al., "Phage conversion of *Panton-Valentine leukocidin in Staphylococcus aureus*: molecular analysis of a PVL-converting phage, cpSLT," Gene, 2001, vol. 268 (1-2), pp. 195-206.

NEB Catalog. 1998/1999 pp. 1, 79, 121 and 284.

Neumann G., et al., "Host Range Restriction and Pathogenicity in the Context of Influenza Pandemic," Emerging Infectious Diseases, 2006, vol. 12 (6), pp. 881-886.

Newcombe J., et al., "PCR of Peripheral Blood for Diagnosis of Meningococcal Disease," Journal of Clinical Microbiology, 1996, vol. 34 (7), pp. 1637-1640.

Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.

Ng E.K., et al., "Serial Analysis of the Plasma Concentration of SARS Coronavirus RNA in Pediatric Patients with Severe Acute Respiratory Syndrome," Clinical Chemistry, 2003, vol. 49 (12), pp. 2085-2088.

Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.

Non-Final Office Action mailed Feb. 2, 2007 for U.S. Appl. No. 10/844,938, filed May 12, 2004.

Non-Final Office Action mailed Oct. 2, 2009 for U.S. Appl. No. 11/929,707, filed Oct. 30, 2007.

Non-Final Office Action mailed Aug. 4, 2010 for U.S. Appl. No. 12/049,949, filed Mar. 17, 2008.

Non-Final Office Action mailed Apr. 6, 2009 for U.S. Appl. No. 11/331,987, filed Jan. 13, 2006.

Non-Final Office Action mailed Apr. 7, 2006 for U.S. Appl. No. 10/964,571, filed Oct. 12, 2004.

Non-Final Office Action mailed Aug. 7, 2007 for U.S. Appl. No. 10/844,938, filed May 12, 2004.

Non-Final Office Action mailed Jun. 10, 2009 for U.S. Appl. No. 10/844,938, filed May 12, 2004.

Non-Final Office Action mailed Jan. 12, 2010 for U.S. Appl. No. 11/491,376, filed Jul. 21, 2006.

Non-Final Office Action mailed Sep. 16, 2009 for U.S. Appl. No. 11/233,630, filed Sep. 21, 2005.

Non-Final Office Action mailed Apr. 17, 2009 for U.S. Appl. No. 12/211,641, filed Sep. 16, 2008.

Non-Final Office Action mailed Nov. 19, 2003 for U.S. Appl. No. 09/798,007, filed Mar. 2, 2001.
Non-Final Office Action mailed Aug. 20, 2007 for U.S. Appl. No. 11/582,863, filed Oct. 17, 2006.
Non-Final Office Action mailed May 20, 2008 for U.S. Appl. No. 10/844,938, filed May 12, 2004.
Non-Final Office Action mailed Oct. 20, 2004 for U.S. Appl. No. 09/891,793, filed Jun. 26, 2001.
Non-Final Office Action mailed Feb. 23, 2009 for U.S. Appl. No. 10/660,122, filed Sep. 11, 2003.
Non-Final Office Action mailed May 26, 2010 for U.S. Appl. No. 11/869,449, filed Oct. 9, 2007.
Non-Final Office Action mailed Jul. 27, 2006 for U.S. Appl. No. 11/209,439, filed Aug. 8, 2005.
Non-Final Office Action mailed Jun. 28, 2010 for U.S. Appl. No. 11/930,002, filed Oct. 30, 2007.
Non-Final Office Action mailed Sep. 28, 2009 for U.S. Appl. No. 11/930,017, filed Oct. 30, 2007.
Non-Final Office Action mailed Dec. 29, 2010 for U.S. Appl. No. 12/616,422, filed Nov. 11, 2009.
Non-Final Office Action mailed Apr. 30, 2010 for U.S. Appl. No. 11/930,108, filed Oct. 31, 2007.
Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.
Notice of Allowance mailed Apr. 1, 2011 for U.S. Appl. No. 11/233,630, filed Sep. 21, 2005.
Notice of Allowance mailed Jun. 3, 2009 for U.S. Appl. No. 11/331,978, filed Jan. 13, 2006.
Notice of Allowance mailed Aug. 5, 2010 for U.S. Appl. No. 11/233,630, filed Sep. 21, 2005.
Notice of Allowance mailed Aug. 6, 2009 for U.S. Appl. No. 10/728,486, filed Dec. 5, 2003.
Ikrsi Notice of Allowance mailed Dec. 10, 2010 for U.S. Appl. No. 11/233,630, filed Sep. 21, 2005.
Notice of Allowance mailed Dec. 10, 2010 for U.S. Appl. No. 11/491,376, filed Jul. 21, 2006.
Notice of Allowance mailed Nov. 12, 2009 for U.S. Appl. No. 10/728,486, filed Dec. 5, 2003.
Notice of Allowance mailed Dec. 15, 2008 for U.S. Appl. No. 11/331,978, filed Jan. 13, 2006.
Notice of Allowance mailed Sep. 18, 2009 for U.S. Appl. No. 10/660,998, filed Sep. 12, 2003.
Notice of Allowance mailed Nov. 24, 2009 for U.S. Appl. No. 11/331,978, filed Jan. 13, 2006.
Notice of Allowance mailed Oct. 29, 2009 for U.S. Appl. No. 10/660,122, filed Sep. 11, 2003.
Nubel U., et al., "PCR primers to amplify 16S rRNA genes from Cyanobacteria," Applied andEnvironmental Microbiology, 1997, vol. 63 (8), pp. 3327-3332.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Nunes E.L., et al., "Detection of ileS-2 Gene Encoding Mupirocin Resistance in Methicillin-ResistantStaphylococcus aureus by Multiplex PCR," Diagnostic Microbiology and Infectious Disease, 1999, vol. 34 (2), pp. 77-81.
Nygren M., et al., "Quantification of HIV-1 Using Multiple Quantitative Polymerase Chain ReactionStandards and Bioluminometric Detection," Analytical Biochemistry, 2001, vol. 288 (1), pp. 28-38.
Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.
Oberacher H., et al., "Increased foresnic efficiency of DNA fingerprints through simultaneous resolution of length and nucleotide variability by high-performance mass spectrometry," Human Mutation, 2008, vol. 29 (3), pp. 427-432.
Oberste M.S., et al., "Improved molecular identification of enteroviruses by RT-PCR and amplicon sequencing," Journal of Medical Virology, 2003, vol. 26 (3), pp. 375-377.
Oberste M.S., et al., "Molecular epidemiology and type-specific detection of echovirus 11 isolates fromthe Americas, Europe, Africa, Australia, southern Asia and the Middle East," Virus Research, 2003, vol. 91 (2), pp. 241-248.
Oberste M.S., et al., "Molecular phylogeny and proposed classification of the Simian picornaviruses," Journal of Virology, 2002, vol. 76 (3), pp. 1244-1251.
Office Action mailed Apr. 1, 2004 for U.S. Appl. No. 10/156,608, filed May 24, 2002.
Office Action mailed May 1, 2006 for U.S. Appl. No. 10/660,998, filed Sep. 12, 2003.
Office Action mailed Feb. 2, 2011 for U.S. Appl. No. 11/869,449, filed Oct. 9, 2007.
Office Action mailed Jan. 2, 2009 for U.S. Appl. No. 11/060,135, filed Feb. 17, 2005.
Office Action mailed Jun. 2, 2006 for U.S. Appl. No. 10/933,928, filed Sep. 3, 2004.
Office Action mailed Jun. 2, 2008 for U.S. Appl. No. 11/331,978, filed Jan. 13, 2006.
Office Action mailed Oct. 2, 2008 for U.S. Appl. No. 11/233,630, filed Sep. 21, 2005.
Office Action mailed Aug. 3, 2006 for U.S. Appl. No. 10/660,998, filed Sep. 12, 2003.
Office Action mailed Aug. 3, 2009 for U.S. Appl. No. 11/754,174, filed May 25, 2007.
Office Action mailed Dec. 3, 2003 for U.S. Appl. No. 10/325,527, filed Dec. 18, 2002.
Office Action mailed Feb. 3, 2011 for U.S. Appl. No. 12/326,800, filed Dec. 2, 2008.
Office Action mailed Nov. 3, 2008 for U.S. Appl. No. 10/728,486, filed Dec. 5, 2003.
Office Action mailed Apr. 4, 2008 for U.S. Appl. No. 10/829,826, filed Apr. 22, 2004.
Office Action mailed Dec. 4, 2006 for Indian Application No. 1136KOLNP2003 filed Mar. 4, 2002.
Office Action mailed Feb. 4, 2009 for U.S. Appl. No. 11/404,561, filed Apr. 12, 2006.
Office Action mailed May 4, 2010 for U.S. Appl. No. 90/010,447, filed Apr. 9, 2009.
Office Action mailed May 4, 2010 for U.S. Appl. No. 90/010,448, filed Apr. 9, 2009.
Office Action mailed Nov. 4, 2009 for European Application No. 02709785.6 filed Mar. 4, 2002.
Office Action mailed Sep. 4, 2008 for Australian Application No. 2003297687 filed Dec. 5, 2003.
Office Action mailed Aug. 5, 2010 for European Application No. 02709785.6 filed Mar. 4, 2002.
Office Action mailed Sep. 5, 2006 for U.S. Appl. No. 10/660,996, filed Sep. 12, 2003.
Office Action mailed Jan. 6, 2011 for Israel Application No. 157661 filed Mar. 4, 2002.
Office Action mailed Jul. 6, 2006 for U.S. Appl. No. 10/660,122, filed Sep. 11, 2003.
Office Action mailed Jul. 6, 2007 for U.S. Appl. No. 10/829,826, filed Apr. 22, 2004.
Office Action mailed Mar. 6, 2009 for U.S. Appl. No. 11/233,630, filed Sep. 21, 2005.
Office Action mailed Nov. 6, 2002 for U.S. Appl. No. 09/798,007, filed Mar. 2, 2001.
Office Action mailed Apr. 7, 2009 for Canadian Application No. 2525498 filed May 13, 2004.
Office Action mailed Apr. 7, 2009 for European Application No. 07760292.8 filed Apr. 6, 2007.
Office Action mailed Apr. 7, 2009 for U.S. Appl. No. 10/660,998, filed Sep. 12, 2003.
Office Action mailed Aug. 7, 2007 for U.S. Appl. No. 10/660,998, filed Sep. 12, 2003.
Office Action mailed Feb. 7, 2008 for European Application No. 03796752.8 filed Dec. 5, 2003.
Office Action mailed Jun. 7, 2010 for European Application No. 06800205.4 filed Jul. 27, 2006.
Office Action mailed Jan. 8, 2003 for U.S. Appl. No. 09/798,007, filed Mar. 2, 2001.

Office Action mailed Jan. 8, 2007 for U.S. Appl. No. 09/891,793, filed Jun. 26, 2001.
Office Action mailed Mar. 8, 2005 for U.S. Appl. No. 09/891,793, filed Jun. 26, 2001.
Office Action mailed Mar. 8, 2007 for U.S. Appl. No. 11/060,135, filed Feb. 17, 2005.
Office Action mailed Sep. 8, 2006 for Chinese Application No. 02809122.1 filed Mar. 4, 2002.
Office Action mailed Dec. 9, 2004 for U.S. Appl. No. 10/156,608, filed May 24, 2002.
Office Action mailed Dec. 9, 2009 for U.S. Appl. No. 90/010,210, filed Jun. 27, 2008.
Office Action mailed Dec. 9, 2009 for U.S. Appl. No. 90/010,447, filed Apr. 9, 2009.
Office Action mailed Dec. 9, 2009 for U.S. Appl. No. 90/010,448, filed Apr. 9, 2009.
Office Action mailed Feb. 9, 2007 for Chinese Application No. 02809122.1 filed Mar. 4, 2002.
Office Action mailed Jan. 9, 2008 for Japanese Application No. 2002570692 filed Mar. 4, 2002.
Office Action mailed Jul. 9, 2008 for U.S. Appl. No. 10/660,122, filed Sep. 11, 2003.
Office Action mailed Jul. 9, 2008 for U.S. Appl. No. 11/331,987, filed Jan. 13, 2006.
Office Action mailed Mar. 9, 2004 for U.S. Appl. No. 09/891,793, filed Jun. 26, 2001.
Office Action mailed Nov. 9, 2010 for U.S. Appl. No. 11/331,987, filed Jan. 13, 2006.
Office Action mailed Aug. 10, 2004 for U.S. Appl. No. 09/891,793, filed Jun. 26, 2001.
Office Action mailed Aug. 10, 2004 for U.S. Appl. No. 09/798,007, filed Mar. 2, 2001.
Office Action mailed Aug. 10, 2004 for U.S. Appl. No. 10/156,608, filed May 24, 2002.
Office Action mailed Aug. 10, 2004 for U.S. Appl. No. 10/326,642, filed Dec. 18, 2002.
Office Action mailed Dec. 10, 2008 for U.S. Appl. No. 10/829,826, filed Apr. 22, 2004.
Office Action mailed Dec. 10, 2009 for U.S. Appl. No. 11/929,910, filed Oct. 30, 2007.
Office Action mailed Feb. 10, 2005 for U.S. Appl. No. 09/79,8007, filed Mar. 2, 2001.
Office Action mailed Feb. 10, 2006 for Australian Application No. 2002244250 filed Mar. 4, 2002.
Office Action mailed Jun. 10, 2009 for U.S. Appl. No. 90/010,210, filed Jun. 27, 2008.
Office Action mailed Jun. 10, 2010 for U.S. Appl. No. 90/010,447, filed Apr. 9, 2009.
Office Action mailed Jun. 10, 2010 for U.S. Appl. No. 90/010,448, filed Apr. 9, 2009.
Office Action mailed Sep. 10, 2008 for Australian Application No. 2003302236 filed Dec. 5, 2003.
Office Action mailed Aug. 11, 2005 for U.S. Appl. No. 09/891,793, filed Jun. 26, 2001.
Office Action mailed Aug. 11, 2010 for U.S. Appl. No. 90/010,447, filed Apr. 9, 2009.
Office Action mailed Aug. 11, 2010 for U.S. Appl. No. 90/010,448, filed Apr. 9, 2009.
Office Action mailed Dec. 11, 2007 for U.S. Appl. No. 10/660,998, filed Sep. 12, 2003.
Office Action mailed Jul. 11, 2003 for U.S. Appl. No. 09/798,007, filed Mar. 2, 2001.
Office Action mailed Jun. 11, 2010 for U.S. Appl. No. 90/010,210, filed Jun. 27, 2008.
Office Action mailed Mar. 11, 2005 for U.S. Appl. No. 10/325,527, filed Dec. 18, 2002.
Office Action mailed May 11, 2007 for U.S. Appl. No. 10/728,486, filed Dec. 5, 2003.
Office Action mailed Feb. 12, 2009 for U.S. Appl. No. 11/136,134, filed May 24, 2005.
Office Action mailed Jul. 12, 2006 for U.S. Appl. No. 09/891,793, filed Jun. 26, 2001.
Office Action mailed Jul. 12, 2006 for U.S. Appl. No. 10/660,996, filed Sep. 12, 2003.
Office Action mailed Jun. 12, 2009 for Chinese Application No. 200480016187.9 filed May 13, 2004.
Office Action mailed Mar. 12, 2008 for European Application No. 06849755.1 filed Apr. 12, 2006.
Office Action mailed May 12, 2002 for U.S. Appl. No. 09/798,007, filed Mar. 2, 2001.
Office Action mailed Aug. 13, 2009 for U.S. Appl. No. 11/674,538, filed Feb. 13, 2007.
Office Action mailed Jul. 13, 2004 for U.S Appl. No. 09/891,793, filed Jun. 26, 2001.
Office Action mailed Jul. 13, 2007 for U.S. Appl. No. 11/233,630, filed Sep. 21, 2005.
Office Action mailed Jul. 13, 2010 for U.S. Appl. No. 11/929,930, filed Oct. 30, 2007.
Office Action mailed Nov. 13, 2003 for U.S. Appl. No. 09/891,793, filed Jun. 26, 2001.
Office Action mailed Sep. 13, 2006 for U.S. Appl. No. 09/891,793, filed Jun. 26, 2001.
Office Action mailed Jul. 14, 2004 for U.S. Appl. No. 10/326,642, filed Dec. 18, 2002.
Office Action mailed Jun. 14, 2004 for U.S. Appl. No. 09/891,793, filed Jun. 26, 2001.
Office Action mailed Mar. 14, 2011 for U.S. Appl. No. 11/930,002, filed Oct. 30, 2007.
Office Action mailed Aug. 15, 2008 for U.S. Appl. No. 11/331,978, filed Jan. 13, 2006.
Office Action mailed Dec. 15, 2008 for Israel Application No. 157661 filed Mar. 4, 2002.
Office action mailed Dec. 15, 2010 for Canadian Application No. 2508726 filed Dec. 5, 2003.
Office Action mailed Jan. 15, 2008 for Israel Application No. 157661 filed Mar. 4, 2002.
Office Action mailed Jul. 15, 2009 for U.S. Appl. No. 11/060,135, filed Feb. 17, 2005.
Office Action mailed Mar. 15, 2010 for European Application No. 08730682.5 filed Feb. 25, 2008.
Office Action mailed Nov. 15, 2007 for U.S. Appl. No. 11/331,978, filed Jan. 13, 2006.
Office Action mailed Sep. 15, 2005 for U.S. Appl. No. 10/156,608, filed May 24, 2002.
Office Action mailed Apr. 16, 2002 for U.S. Appl. No. 09/798,007, filed Mar. 2, 2001.
Office Action mailed Apr. 16, 2008 for U.S. Appl. No. 11/233,630, filed Sep. 21, 2005.
Office Action mailed Apr. 16, 2009 for U.S. Appl. No. 90/010,210, filed Jun. 27, 2008.
Office Action mailed Aug. 16, 2004 for U.S. Appl. No. 10/325,527, filed Dec. 18, 2002.
Office Action mailed Aug. 16, 2010 for U.S. Appl. No. 11/929,707, filed Oct. 30, 2007.
Office Action mailed Feb. 16, 2011 for U.S. Appl. No. 11/929,910, filed Oct. 30, 2007.
Office Action mailed Jul. 16, 2007 for U.S. Appl. No. 11/331,987, filed Jan. 13, 2006.
Office Action mailed Mar. 16, 2006 for U.S. Appl. No. 09/891,793, filed Jun. 26, 2001.
Office Action mailed Mar. 16, 2010 for Canadian Application No. 2616281 filed Jul. 21, 2006.
Office Action mailed May 16, 2008 for U.S. Appl. No. 11/404,561, filed Apr. 12, 2006.
Office Action mailed Nov. 16, 2009 for Japanese Application No. 2005508488 filed Dec. 5, 2003.
Office Action mailed Nov. 16, 2009 for Japanese Application No. 2005508560 filed Dec. 5, 2003.
Office Action mailed Jun. 17, 2008 for U.S. Appl. No. 11/582,863, filed Oct. 17, 2006.
Office Action mailed Mar. 17, 2006 for U.S. Appl. No. 10/660,122, filed Sep. 11, 2003.
Office Action mailed Oct. 17, 2007 for U.S. Appl. No. 10/728,486, filed Dec. 5, 2003.

Office Action mailed Oct. 17, 2008 for U.S. Appl. No. 11/331,978, filed Jan. 13, 2006.
Office Action mailed Sep. 17, 2008 for European Application No. 03796752.8 filed Dec. 5, 2003.
Office Action mailed Sep. 17, 2008 for U.S. Appl. No. 10/660,122, filed Sep. 11, 2003.
Office Action mailed Feb. 18, 2010 for European Application No. 03814656.9 filed Dec. 5, 2003.
Office Action mailed Jan. 18, 2011 for U.S. Appl. No. 11/930,108, filed Oct. 31, 2007.
Office Action mailed May 18, 2005 for New Zealand Application No. 527857 filed Mar. 4, 2002.
Office Action mailed Sep. 18, 2006 for U.S. Appl. No. 10/660,997, filed Sep. 12, 2003.
Office Action mailed Sep. 18, 2008 for Australian Application No. 2003298030 filed Dec. 5, 2003.
Office Action mailed Sep. 2008 for U.S. Appl. No. 10/660,998, filed Sep. 12, 2003.
Office Action mailed Jan. 19, 2007 for U.S. Appl. No. 11/059,776, filed Feb. 17, 2005.
Office Action mailed May 19, 2005 for U.S. Appl. No. 09/891,793, filed Jun. 26, 2001.
Office Action mailed Nov. 19, 2004 for U.S. Appl. No. 10/156,608, filed May 24, 2002.
Office Action mailed Oct. 19, 2007 for U.S. Appl. No. 11/210,516, filed Aug. 24, 2005.
Office Action mailed Sep. 19, 2006 for U.S. Appl. No. 10/660,122, filed Sep. 11, 2003.
Office Action mailed Sep. 19, 2007 for U.S. Appl. No. 10/660,122, filed Sep. 11, 2003.
Office Action mailed Apr. 20, 2007 for U.S. Appl. No. 10/660,122, filed Sep. 11, 2003.
Office Action mailed Apr. 20, 2009 for U.S. Appl. No. 10/891,337, filed Jul. 14, 2004.
Office Action mailed Dec. 20, 2006 for U.S. Appl. No. 10/728,486, filed Dec. 5, 2003.
Office Action mailed Jul. 20, 2005 for U.S. Appl. No. 10/156,608, filed May 24, 2002.
Office Action mailed Jun. 20, 2002 for U.S. Appl. No. 09/798,007, filed Mar. 2, 2001.
Office Action mailed Jun. 20, 2007 for U.S. Appl. No. 11/136,134, filed May 24, 2005.
Office Action mailed Nov. 20, 2003 for U.S. Appl. No. 10/323,438, filed Dec. 18, 2002.
Office Action mailed Nov. 20, 2006 for U.S. Appl. No. 09/891,793, filed Jun. 26, 2001.
Office Action mailed Nov. 20, 2006 for European Application No. 02709785.6 filed Mar. 4, 2002.
Office Action mailed Sep. 20, 2010 for U.S. Appl. No. 90/010,447, filed Apr. 9, 2009.
Office Action mailed Sep. 20, 2010 for U.S. Appl. No. 90/010,448, filed Apr. 9, 2009.
Office Action mailed Apr. 21, 2009 for U.S. Appl. No. 90/010,209, filed Jun. 27, 2008.
Office Action mailed Mar. 21, 2008 for U.S. Appl. No. 10/660,122, filed Sep. 11, 2003.
Office Action mailed May 21, 2008 for U.S. Appl. No. 10/943,344, filed Sep. 17, 2004.
Office Action mailed May 21, 2009 for U.S. Appl. No. 11/136,134, filed May 24, 2005.
Office Action mailed Nov. 21, 2003 for U.S. Appl. No. 10/326,642 filed Dec. 18, 2002.
Office Action mailed Nov. 21, 2006 for U.S. Appl. No. 10/660,997, filed Sep. 12, 2003.
Office Action mailed Oct. 21, 2005 for U.S. Appl. No. 10/326,641, filed Dec. 18, 2002.
Office Action mailed Oct. 21, 2009 for U.S. Appl. No. 12/326,800, filed Dec. 2, 2008.
Office Action mailed Apr. 22, 2009 for U.S. Appl. No. 11/491,376, filed Jul. 21, 2006.
Office Action mailed Jul. 22, 2008 for U.S. Appl. No. 90/010,209, filed Jun. 27, 2008.
Office Action mailed Jul. 22, 2008 for U.S. Appl. No. 90/010,210, filed Jun. 27, 2008.
Office Action mailed Nov. 22, 2006 for U.S. Appl. No. 10/660,996, filed Sep. 12, 2003.
Office Action mailed Oct. 22, 2007 for U.S. Appl. No. 11/331,987, filed Jan. 31, 2006.
Office Action mailed Sep. 22, 2003 for U.S. Appl. No. 09/798,007, filed Mar. 2, 2001.
Office Action mailed Sep. 22, 2010 for Canadian Application No. 2510007 filed Dec. 5, 2003.
Office Action mailed Apr. 23, 2010 for U.S. Appl. No. 90/010,210, filed Jun. 27, 2008.
Office Action mailed Feb. 23, 2009 for U.S. Appl. No. 10/943,344, filed Sep. 17, 2004.
Office Action mailed Jan. 23, 2008 for U.S. Appl. No. 10/728,486, filed Dec. 5, 2003.
Office Action mailed Jan. 23, 2008 for U.S. Appl. No. 11/059,776, filed Feb. 17, 2005.
Office Action mailed May 23, 2003 for U.S. Appl. No. 09/891,793, filed Jun. 26, 2001.
Office Action mailed May 23, 2005 for U.S. Appl. No. 10/156,608, filed May 24, 2002.
Office Action mailed Oct. 23, 2003 for New Zealand Application No. 527857 filed Mar. 4, 2002.
Office Action mailed Apr. 24, 2009 for U.S. Appl. No. 90/010,447, filed Apr. 9, 2009.
Office Action mailed Apr. 24, 2009 for U.S. Appl. No. 90/010,448, filed Apr. 9, 2009.
Office Action mailed Aug. 24, 2010 for U.S. Appl. No. 90/010,210, filed Jun. 27, 2008.
Office Action mailed Dec. 24, 2004 for New Zealand Application No. 527857 filed Mar. 4, 2002.
Office Action mailed Feb. 24, 2004 for U.S. Appl. No. 10/326,642, filed Dec. 18, 2002.
Office Action mailed Jan. 24, 2005 for U.S. Appl. No. 10/326,642, filed Dec. 18, 2002.
Office Action mailed Jan. 24, 2007 for U.S. Appl. No. 10/660,998, filed Sep. 12, 2003.
Office Action mailed Jul. 24, 2007 for Mexican Application No. PAA2003007927 filed Sep. 2, 2003.
Office Action mailed Jul. 24, 2007 for U.S. Appl. No. 11/060,135, filed Feb. 17, 2005.
Office Action mailed Jul. 24, 2009 for U.S. Appl. No. 11/754,182, filed May 25, 2007.
Office Action mailed Jun. 24, 2008 for European Application No. 06800205.4 filed Jul. 27, 2006.
Office Action mailed Mar. 24, 2011 for U.S. Appl. No. 11/929,930, filed Oct. 30, 2007.
Office Action mailed Nov. 24, 2009 for U.S. Appl. No. 90/010,210, filed Jun. 27, 2008.
Office Action mailed Sep. 24, 2009 for U.S. Appl. No. 90/010,210, filed Jun. 27, 2008.
Office Action mailed Aug. 25, 2009 for U.S. Appl. No. 11/754,169, filed May 25, 2007.
Office Action mailed Jun. 25, 2009 for U.S. Appl. No. 11/869,449, filed Oct. 9, 2007.
Office Action mailed Jun. 25, 2009 for U.S. Appl. No. 90/010,210, filed Jun. 27, 2008.
Office Action mailed Mar. 25, 2008 for U.S. Appl. No. 11/060,135, filed Feb. 17, 2005.
Office Action mailed Aug. 26, 2003 for U.S. Appl. No. 09/891,793, filed Jun. 26, 2001.
Office Action mailed Aug. 26, 2010 for Canadian Application No. 2508584 filed Dec. 5, 2003.
Office Action mailed Jul. 26, 2004 for U.S. Appl. No. 10/323,438, filed Dec. 18, 2002.
Office Action mailed Mar. 26, 2008 for U.S. Appl. No. 11/136,134, filed May 24, 2005.
Office Action mailed May 26, 2005 for U.S. Appl. No. 10/156,608, filed May 24, 2002.
Office Action mailed May 26, 2006 for U.S. Appl. No. 10/660,997, filed Sep. 12, 2003.

Office Action mailed Feb. 27, 2003 for U.S. Appl. No. 09/798,007, filed Mar. 2, 2001.
Office Action mailed Feb. 27, 2007 for U.S. Appl. No. 10/943,344, filed Sep. 17, 2004.
Office Action mailed Jul. 27, 2006 for U.S. Appl. No. 10/728,486, filed Dec. 5, 2003.
Office Action mailed Jul. 27, 2009 for Canadian Application No. 2439655 filed Mar. 4, 2002.
Office Action mailed Feb. 28, 2006 for U.S. Appl. No. 10/660,996, filed Sep. 12, 2003.
Office Action mailed Jul. 28, 2009 for U.S. Appl. No. 11/754,163, filed May 25, 2007.
Office Action mailed Jul. 28, 2010 for U.S. Appl. No. 90/010,210, filed Jun. 27, 2008.
Office Action mailed May 23, 2003 for U.S. Appl. No. 09/798,007, filed Mar. 2, 2001.
Office Action mailed Mar. 29, 2010 for Australian Application No. 2006272776 filed Jul. 21, 2006.
Office Action mailed May 29, 2007 for U.S. Appl. No. 11/059,776, filed Feb. 17, 2005.
Office Action mailed Oct. 29, 2009 for U.S. Appl. No. 90/010,447, filed Apr. 9, 2009.
Office Action mailed Oct. 29, 2009 for U.S. Appl. No. 90/010,448 filed Apr. 9, 2009.
Office Action mailed Jul. 30, 2008 for Australian Application No. 2004248107 filed Apr. 23, 2004.
Office Action mailed Jul. 30, 2009 for Japanese Application No. 2002570692 filed Mar. 4, 2002.
Office Action mailed Jun. 30, 2004 for U.S. Appl. No. 09/798,007, filed Mar. 2, 2001.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Office Action mailed May 30, 2006 for U.S. Appl. No. 10/660,996, filed Sep. 12, 2003.
Office Action mailed Nov. 30, 2009 for U.S. Appl. No. 10/660,122, filed Sep. 11, 2003.
Office Action mailed Sep. 30, 2005 for Chinese Application No. 02809122.1 filed Mar. 4, 2002.
Office Action mailed Jan. 31, 2003 for U.S. Appl. No. 09/798,007, filed Mar. 2, 2001.
Office Action mailed Jan. 31, 2007 for Philippines Application No. PH12003500824 filed Mar. 4, 2002.
Office Action mailed Oct. 31, 2008 for U.S. Appl. No. 11/136,134, filed May 24, 2005.
O'Guinn M.L., et al., "Field Detection of Eastern Equine Encephalitis Virus in the Amazon BasinRegion of Peru Using Reverse Transcription-Polymerase Chain Reaction Adapted for FieldIdentification of Arthropod-Borne Pathogens," American Journal of Tropical Medicine and Hygiene, 2004, vol. 70 (2), pp. 164-171.
Oizumi N., et al., "Relationship between mutations in the DNA gyrase and topoisomerase IV genes and nadifloxacin resistance in clinically isolated quinolone-resistant *Staphylococcus aureus*," Journal of Infection and Chemotherapy, 2001, vol. 7 (3), pp. 191-194.
Okada M., et al., "Detection and sequence-based typing of human adenoviruses using sensitiveuniversal primer sets for the hexon gene," Archives of Virology, 2007, vol. 152 (1), pp. 1-9.
Okuma K., et al., "Dissemination of New Methicillin-Resistant *Staphylococcus aureus* Clones in the Community," Journal of Clinical Microbiology, 2002, vol. 40 (11), pp. 4289-4294.
Oliveira D.C., et al., "Genetic Organization of the Downstream Region of the mecA Element inMethicillin-Resistant *Staphylococcus aureus* Isolates Carrying Different Polymorphisms of This Region," Antimicrobial Agents and Chemotherapy, 2000, vol. 44 (7), pp. 1906-1910.
Oliveira D.C., et al., "Multiplex PCR Strategy for Rapid Identification of Structural Types and Variants of the mec Element in Methicillin-Resistant *Staphylococcus aureus*," Antimicrobial Agents and Chemotherapy, 2002, vol. 46 (7), pp. 2155-2161.

Olsen B., et al., "Transhemispheric Exchange of Lyme Disease Spyrochetes by Seabirds," Journal of Clinical Microbiology, 1995, vol. 33 (12), pp. 3270-3274.
Osiowy C., et al., "Direct Detection of Respiratory Syncytial Virus, Parainfluenza Virus, and Adenovirus in Clinical Respiratory Specimens by a Multiplex Reverse Transcription- PCR Assay," Journal of Clinical Microbiology, 1998, vol. 36 (11), pp. 3149-3154.
Ostrander E.A., et al., "Identification and Characterization of Dinucleotide Repeat (CA)n Markers for Genetic Mapping in Dog," Genomics, 1993, vol. 16 (1), pp. 207-213.
Ounissi H., et al., "Gene Homogeneity for Aminoglycoside-Modifying Enzymes in Gram-PositiveCocci," Antimicrobial Agents and Chemotherapy, 1990, vol. 34 (11), pp. 2164-2168.
Palys T., et al., "Discovery and Classification of Ecological Diversity in the Bacterial World: the Role of DNA Sequence Data," International Journal of Systematic Bacteriology, 1997, vol. 47 (4), pp. 1145-1156.
Pan Zq., et al., "Oligonucleotide-targeted degradation of U1 and U2 snRNAs reveals differential interactions of simian virus 40 pre-mRNAs with snRNPs," Nucleic Acids Research, 1989, vol. 17 (16), pp. 6553-6568.
Pannetier C., et al., "Quantitative Titration of Nucleic Acids by Enzymatic Amplification Reactions run to Saturation," Nucleic Acids Research, 1993, vol. 21 (3), pp. 577-583.
Partial European Search Report for Application No. EP01106974, mailed on Dec. 16, 2002, 2 pages.
Pastorino B., at al., "Development of a TaqMan PCR assay without RNA extraction step for the detection and quantification of African Chikungunya viruses," Journal of Virological Methods, 2005, vol. 124 (1-2), pp. 65-71.
Pawa A., et al., "Co-transfer of plasmids in association with conjugative transfer of mupirocin or mupirocin and penicillin resistance in methicillin-resistant *Staphylococcus aureus*," Journal of Clinical Microbiology, 2000, vol. 49 (12), pp. 1103-1107.
Payne D., et al., "Antimicrobials: The Challenge of Antibiotic Resistant Bacterial Pathogens: The Medical Need, The Market and Prospects for New Antimicrobial Agents," Current Opinion in Microbiology, 2004, vol. 7, pp. 435-438.
Perez-Roth E., et al., "Multiplex PCR for Simultaneous Identification of *Staphylococcus aureus* andDetection of Methicillin and Mupirocin Resistance," Journal of Clinical Microbiology, 2001, vol. 39 (11), pp. 4037-4041.
Peters S.E., et al., "Quantification of the detection of *Pneumocystis carinii* by DNA amplification," Molecular and Cellur Probes, 1992 vol. 6, (2), pp. 115-117.
Pfeffer M., et al., "Genus-Specific Detection of Alphaviruses by a Semi-Nested ReverseTranscription-Polymerase Chain Reaction," American Journal of Tropical Medicine and Hygiene, 1997, vol. 57 (6), pp. 709-718.
Pfeffer M., et al., "Specific Detection of Chikungunya Virus Using a RT-PCR/Nested PCR Combination," Journal of Veterinary Medicine B, 2002, vol. 49 (1), pp. 49-54.
Pieles U., et al., "Matrix-Assisted Laser Desorption Ionization Time-of-Flight Spectrometry: APowerful Tool for the Mass and Sequence Analysis of Natural and Modified Oligonucleotides, 787 reexamination," Nucleic Acids Research, 1993, vol. 21 (14), pp. 3191-3196.
Pillai S.D., et al., "Rapid molecular detection of microbial pathogens: breakthroughs and challenges," Archives of Virology, 1997, vol. 13, pp. 67-82.
Piper J., et al., "Commercially Available Technique for Rapid Laboratory Detection of MethicillinResistance Among *Staphylococcus aureus*," Diagnostic Microbiology and Infectious Disease, 1988, vol. 11 (3), pp. 177-180.
Poddar S.K., et al., "Detection of adenovirus using PCR and molecular beacon," Journal of Virological Methods, 1999, vol. 82 (1), pp. 19-26.
Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.
Pring-Akerblom P., et al., "PCR-based detection and typing of human adenoviruses in clinical samples," Research in Virology, 1997, vol. 148 (3), pp. 225-231.

Promega. T4 Polynucleotide Kinase, Technical Bulletin No. 519, 2002.

Puthavathana P., et al., "Molecular characterization of the complete genome of human influenza H5N1 virus Isolates from Thailand," Journal of General Virology, 2005, vol. 86 (2), pp. 423-433.

Qadri S.M., et al., "Rapid Detection of Methicillin-Resistant *Staphylococcus aureus* by CrystalMRSA ID System," Journal of Clinical Microbiology, 1994, vol. 32 (7), pp. 1830-1832.

Ramisse V., et al., "Identification and characterization of *Bacillus anthracis* by multiplex PCR analysis of sequences on plasmids pX01 and pX02 and chromosomal DNA," Ferns Microbiology Letters, 1996, vol. 145 (1), pp. 9-16.

Reischl U., "Application of Molecular Biology-Based Methods to theDiagnosis of Infectious Diseases 1, e72-e77.," Frontiers in Bioscience, 1996, vol. 1 (1), pp. e72-e77.

Reischl U., et al., "Rapid Identification of Methicillin-Resistant *Staphylococcus aureus* and Simultaneous Species Confirmation Using Real-Time Fluorescence PCR," Journal of Clinical Microbiology, 2000, vol. 38 (6), pp. 2429-2433.

Roberts M.M., et al., "Three-Dimensional Structure of the Adenovirus Major Coat Protein Hexon," Science, 1986, vol. 232 (4754), pp. 1148-1151.

Roberts M.S., et al., "Recombination and Migration Rates in Natural Populations of *Bacillus subtilis* and *Bacillus mojavensis*," Evolution, 1995, vol. 49 (6), pp. 1081-1094.

Robinson D.A., et al., "Multilocus sequence typing and the evolution of methicillin-resistant*Staphylococcus aureus*," Clinical Microbiology and Infection, 2004, vol. 10, pp. 92-97.

Rong S., et al., "Design and Application of 60mer Oligonucleotide Microarray in SARS Coronavirus Detection," Chinese Science Bulletin, 2003, vol. 48 (12), pp. 1165-1169.

Rota P.A., et al., "Sequencing of a cDNA clone of the nucleoprotein gene of influenza B/Ann Arbor/1/86," Nucleic Acids Research, 1989, vol. 17 (9), pp. 3595.

Ruan Y., et al., "Comparative full-length genome sequence analysis of 14 SARS coronavirus isolates and common mutations associated with the putative origins of infection," The Lancet, 2003, vol. 361, pp. 1779-1785, 1832.

Rupf S., et al., "Quantitative determination of *Streptococcus mutans* by using competitive polymerasechain reaction," European Journal of Oral Sciences, 1999, vol. 107 (2), pp. 75-81.

Russell K.L., et al., "Transmission Dynamics and Prospective Environmental Sampling of Adenovirus in a Military Recruit Setting," Journal of Infectious Diseases, 2006, vol. 194 (7), pp. 877-885.

Sabat A., et al., "Comparison of PCR-Based Methods for Typing *Staphylococcus aureus* Isolates" Journal of Clinical Microbiology, 2006, vol. 44 (10), pp. 3804-3807.

Sackesen C., et al., "Use of polymerase chain reaction for detection of adenovirus in children withor without wheezing," Turkish Journal of Pediatrics, 2005, vol. 47 (3), pp. 227-231.

Sakai H., et al., "Simultaneous Detection of *Staphylococcus aureus* and Coagulase-Negative Staphylococci in Positive Blood Cultures by Real-Time PCR with Two Fluorescence Resonance Energy Transfer Probe Sets," Journal of Clinical Microbiology, 2004, vol. 42 (12), pp. 5739-5744.

Sambrook J., et al., "Molecular Cloning-A Laboratory Manual," 1989, Cold Spring Harbor Laboratory Press, Table of Contents.

Sampath R., et al., "Global Surveillance of Emerging Influenza Virus Genotypes by Mass Spectrometry," Plos ONE, 2007, vol. 2 (5), pp. e489.

Sampath R., et al., "Rapid Identification of Emerging Infectious Agents using PCR and Electrospray Ionization Mass Spectrometry," Annals of the New York Academy of Science, 2007, vol. 1102, pp. 109-120.

Sampath R., et al., "Rapid Identification of Emerging Pathogens: Coronavirus," Emerging Infectious Diseases, 2005, vol. 11 (3), pp. 373-379.

Sanchez A., et al., "Detection and molecularcharacterization of *Ebola* viruses causing disease in human and nonhuman primates," Journal of Infectious Diseases, 1999, vol. 179 (1), pp. S164-S169.

Sanchez J.L., et al., "Epidemic of Adenovirus-Induced Respiratory Illness Among US Military Recruits: Epidemiologic and Immunologic Risk Factors in Healthy, Young adults," Journal of Medical Virology, 2001, vol. 65 (4), pp. 710-718.

Sanchez-Seco M.P., et al., "A Generic Nested-RT-PCR followed by Sequencing for Detection and Identification of Members of the Alphavirus Genus," Journal of Virological Methods, 2001, vol. 95 (1-2), pp. 153-161.

Santos S.R., et al., "Identification and phylogenetic sorting of bacterial lineages with universally conserved genes and proteins," Environmental Microbiology, 2004, vol. 6 (7), pp. 754-759.

Sarantis H., et al., "Comprehensive Detection and Serotyping of Human Adenoviruses by PCR and Sequencing," Journal of Clinical Microbiology, 2004, Vol. 42 (9), pp. 3963- 3969.

Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.

Scheffner M., et al., "The E6 Oncoprotein Encoded by Human Papillomavirus Types 16 and 18 Promotes the Degradation of p53," Cell, 1990, vol. 63 (6), pp. 1129-1136.

Scheuermann R.H., et al., "Polymerase chain-reaction-based mRNA quantification Using an internal standard: analysis of oncogene expression," Methods in Enzymology, 1993, vol. 218, pp. 446-473.

Schlecht N. F., et al., "Viral Load as a Predictor of the Risk of Cervical Intraepithelial Neoplasia," British Journal of Cancer, 2003, vol. 103 (4), pp. 519-524.

Schmidt T.M., et al., "Analysis of a marine pikoplankton community by 16s rRNA gene cloning and sequencing," Journal of Bacteriology, 1991, vol. 173 (14), pp. 4371-4378.

Schmitz F.J., et al., "Development of a Multiplex-PCR for Direct Detection of the Genes for Enterotoxin B and C, and Toxic Shock Syndrome Toxin-1 in *Staphylococcus aureus* Isolates," Journal of Medical Microbiology, 1998, vol. 47 (4), pp. 335-340.

Schmitz F.J., et al., "Development of Resistance to Ciprofloxacin, Rifampin, and Mupirocin inMethicillin-Susceptible and-Resistant *Staphylococcus aureus* Isolates," Antimicrobial Agents and Chemotherapy, 2000, vol. 44 (11), pp. 3229-3231.

Schmitz F.J., et al., "Specific information concerning taxonomy, pathogenicity and methicillin esistance of staphylococci obtained by a multiplex PCR," Journal of Medical Microbiology, 1997, vol. 46 (9), pp. 773-778.

Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP Analysis," Clinical Genetics, 1989, vol. 36 (6), pp. 419-426.

Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.

Sciacchitano C.J., "Analysis of Polymerase Chain Reaction-Amplified DNA Fragments of *Clostridium botulinum* Type E Neurotoxin Gene by High Performance Capillary Electrophoresis," Journal of Liquid Chromatography & Related Technologies, 1996, vol. 19 (13), pp. 2165-2178.

Scott-Taylor T.H., et al., "Conserved Sequences of the Adenovirus Genome for Detection of all Human Adenovirus Types by Hybridization," Journal of Clinical Microbiology, 1992, vol. 30 (7), pp. 1703-1710.

Seifarth W., et al., "Rapid identification of all known retroviral reverse transcriptase sequences with a novel versatile detection assay," AIDS Research and Human Retroviruses, 2000, vol. 16 (8), pp. 721-729.

Sellner L., et al., "A Single-Tube Nested RT-PCR for the Detection of Ross River Virus," Methods in Molecular Biology, 1998, vol. 92, pp. 145-152.

Sellner L.N., et al., "Sensitive detection of Ross River virus—a one-tube nested RT-PCR," Journal of Virological Methods, 1994, vol. 49 (1), pp. 47-58.

Shadan F.F., et al., "n-Butyrate, a Cell Cycle Blocker, Inhibits the Replication of Polyomaviruses and Papillomaviruses but Not That of Adenoviruses and Herpesviruses," Journal of Virology, 1994, vol. 68 (8), pp. 4785-4796.

Shimaoka M., et al., "Detection of the gene for toxic shock syndrome toxin 1 in *Staphylococcusaureus* by enzyme-labelled oligonucleotideprobes," Journal of Medical Microbiology, 1996, vol. 44 (3), pp. 215-218.

Shimaoka M., et al., "Development of Enzyme-Labeled Oligonucleotide Probe for Detection of mecA gene in Methicillin-Resistant *Staphylococcus aureus*," Journal of Clinical Microbiology, 1994, vol. 32 (8), pp. 1866-1869.

Shrestha N. K., et al., "Rapid Identification of *Staphylococcus aureus* and the mecA Gene fromBacT/ALERT Blood Culture Bottles by Using the Lightcycler System," Journal of Clinical Microbiology, 2002, vol. 40 (7), pp. 2659-2661.

Simonsen L., et al., "The Impact of Influenza Epidemics on Hospitalizations," Journal of Infectious Diseases, 2000, vol. 181 (3), pp. 831-837.

Skov R.L., et al., "Evaluation of a new 3-h hybridization method for detecting the mecA gene in *Staphylococcus aureus* and comparison with existing genotypic and phenotypic susceptibility testing methods," Journal of Antimicrobial Chemotherapy, 1999, vol. 43 (4), pp. 467-475.

Smirnov I.P., et al., "Application of DNA-binding polymers for preparation of DNA for analysis by matrix-assisted laser desorption/ionization mass spectrometry," Rapid Communications in Mass Spectrometry, 2001, vol. 15 (16), pp. 1427-1432.

Smith T.F., "Comparison of Biosequences," Advances in Applied Mathematics, 1981, vol. 2, pp. 482-489.

Song F., et al., "Identification of cry11-type Genes from *Bacilus thuringiensis* Strains and Characterization of a Novel Cry11-Type Gene," Applied and Environmental Microbiology, 2003, vol. 69, pp. 5207-5211.

Spackman E., et al., "Development of a real-time reverse transcriptase PCR assay for type A influenzavirus and the avian H5 and H7 hemagglutinin subtypes," Journal of Clinical Microbiology, 2002, vol. 40 (9), pp. 3256-3260.

Spiess L., et al., "Trehalose is a potent PCR enhancer: Lowering of DNA melting temperature and thermal stabilization of Taq polymerase by the disaccharide trehalose," Clinical Chemistry, 2004, vol. 50 (7), pp. 1256-1259.

Stephensen C.B., et al., "Phylogenetic analysis of a highly conserved region of the poymerase gene from 11 coronaviruses and development of a consensus poymerase chain reaction assay," Virus Research, 1999, vol. 60 (2), pp. 181-189.

Stone B., et al., "Rapid detection and simultaneous subtype differentiation of influenza a viruses by real time PCR," Journal of Virological Methods, 2004, vol. 117 (2), pp. 103-112.

Stratagene Catalog. 1988, p. 39.

Strommenger B., et al., "Multiplex PCR Assay for Simultaneous Detection of Nine Clinically Relevant Antibiotic Resistance Genes in *Staphylococcus aureus*," Journal of Clinical Microbiology, 2003, vol. 41 (9), pp. 4089-4094.

Studdert M.J., et al., "Polymerase Chain Reaction Tests for the Identification of Ross River, Kunjin and Murray Valley Encephalitis Virus Infections in Horses," Australian Veterinary Journal, 2003, vol. 81 (1-2), pp. 76-80.

Stuhlmeier R., et al., "Fast, Simultaneous, and Sensitive Detection of Staphylococci," Journal of Clinical Pathology, 2003, vol. 56 (10), pp. 782-785.

Sumner J.W., et al., "PCR Amplification and Comparison of Nucleotide Sequences from the groESL Heat Shock Operon of *Ehrlichia* Species," Journal of Critical Microbiology, 1997, vol. 35 (8), pp. 2087-2092.

Sundsfjord A., at al., "Genetic Methods for Detection of Antimicrobial Resistance," APMIS : Acta Pathologica, Microbiologica, et Immunologica Scandinavica, 2004, vol. 112 (11-12), pp. 815-837.

Supplementary European Search Report for Application No. 04775904.8, mailed on Jul. 7, 2008, 8 pages.

Supplementary European Search Report for Application No. EP03796752.8, mailed on Aug. 7, 2007, 3 pages.

Supplementary European Search Report for Application No. EP03810055.8, mailed on Jun. 8, 2007, 4 pages.

Supplementary European Search Report for Application No. EP03814656, mailed on Oct. 16, 2007, 2 pages.

Supplementary European Search Report for Application No. EP04752257.8, mailed on Feb. 15, 2006, 2 pages.

Supplementary European Search Report for Application No. EP05753037, mailed on Aug. 21, 2009, 2 pages.

Supplementary Partial European Search Report for Application No. EP05751872.2, mailed on Jan. 28, 2008, 8 pages.

Supplementary Partial European Search Report for Application No. EP05856582.1, mailed on Oct. 27, 2008, 10 pages.

Swaminathan B., et al., "PulseNet: The Molecular Subtyping Network for Foodborne Bacterial Disease Surveillance, United States," Emerging Infectious Diseases, 2001, vol. 7 (3), pp. 382-389.

Swanborg R.H., et al., "Human Herpesvirus 6 and *Chlamydia pneumoniae* as Etiologic Agents in Multiplesclerosis—a Critical Review," Microbes and Infection / Institut Pasteur, 2002, vol. 4 (13), pp. 1327-1333.

Swenson J.M., et al., "Performance of Eight Methods, Including Two New Rapid Methods, for Detection of Oxacillin Resistance in a Challenge Set of *Staphylococcus aureus* Organisms," Journal of Clinical Microbiology, 2001, vol. 39 (10), pp. 3785-3788.

Takagaki Y., et al., "Four Factors are Required for 3'-End Cleavage of Pre-mRNAs," Genes and Development, 1989, vol. 3 (11), pp. 1711-1724.

Takahata M., et al., "Mutations in the GyrA and Gr1A Genes of Quinolone-Resistant Clinical Isolates of Methicillin-Resistant *Staphylococcus aureus*," The Journal of Antimicrobial Chemotherapy, 1996, vol. 38 (3), pp. 543-546.

Takayama R., et al., "Quantification of Adenovirus Species B and C Viremia by Real-Time PCR in Adults and Children Undergoing Stem Cell Transplantation," Journal of Medical Virology, 2007, vol. 79 (3), pp. 278-284.

Talaat A.M., et al., "Genome-Directed Primers for Selective Labeling of Bacterial Transcripts for DNA Microarray Analysis," Nature Biotechnology, 2000, vol. 17, pp. 679-682.

Tan T.Y., "Use of Molecular Techniques for the Detection of Antibiotic Resistance in Bacteria," Expert review of Molecular diagnostics, 2003, vol. 3 (1), pp. 93-103.

Tanabe F., et al., "The Properties and Mec A Gene of the Methicillin-Resistant *Staphylococcus aureus* Isolated in Fukushima Medical College Hospital," Fukushima Journal of Medical Science, 1993, vol. 39 (1), pp. 35-42.

Tang K., et al., "Detection of 500-Nucleotide DNA by Laser Desorption Mass Spectrometry," Rapid Communications in Mass Spectrometry, 1994, vol. 8 (9), pp. 727-730.

Tang K., et al., Double-Stranded DNA Analysis by Matrix Assisted Laser Desorption/Ionization, 42nd ASMS Conference on Mass Spectrometry, 1994.

Tang K., et al., "Matrix-Assisted Laser Desorption/Ionization of Restriction Enzyme-Digested DNA," Rapid Communications in Mass Spectrometry, 1994, vol. 8 (2), pp. 183-186.

Tang K., et al., "Matrix-Assisted Laser Desorption/Ionization Mass Spectrometry of Oligonucleotides," Dissertation submitted to the Faculty of Vanderbilt University, 1994.

Tarassishin L., et al., "Adenovirus Core Protein VII Displays a Linear Epitope Conserved in a Range of Human Adenoviruses," Journal of General Virology, 1999, vol. 80 (Pt 1), pp. 47-50.

Tarassishin L., et al., "An Epitope on the Adenovirus Fibre Tail is Common to all Human Subgroups," Archives of Virology, 2000, vol. 145 (4), pp. 805-811.

Taubenberger J.K., et al., "Characterization of the 1918 Influenza Virus Polymerase Genes," Nature, 2005, vol. 437 (7060), pp. 889-893.

Thiel V., et al., "Infectious RNA Transcribed in Vitro from a cDNA Copy of the Human Coronavirus Genome Cloned in Vaccinia Virus," The Journal of General Virology, 2001, vol. 82 (Pt 6), pp. 1273-1281.

Tenover F.C., et al., "Characterization of a Strain of Community-Associated Methicillin-Resistant*Slaphylococcus aureus* Widely Disseminated in the United States," Journal of Clinical Microbiology, 2006, vol. 44 (1), pp. 108-118.

Teramura T., et al., "Quantitative Detection of Serum Adenovirus in a Transplant Recipient," Lancet, 2002, vol. 359 (9321), pp. 1945.

Thiel V., et al., "Infectious RNA Transcribed in Vitro from a cDNA Copy of the Human Coronavirus Genome Cloned in Vaccinia Virus," The Journal of General Virology, 2001, vol. 82 (Pt 6), pp. 1273-1281.

Thompson J.D., et al., "Clustal W: Improving the Sensitivity of Progressive Multiple Sequence Alignmen Through Sequence Weighting, Position-Specific Gap Penalties and Weight Matrix Choice," Nucleic Acids Research, 1994, vol. 22 (22), pp. 4673-4680.

Thompson W.W., et al., "Influenza-Associated Hospitalizations in the United States," The Journal of the American Medical Association, 2004, vol. 292 (11), pp. 1333-1340.

Tokue Y., et al., "Comparison of a Polymerase Chain Reaction Assay and a Conventional Microbiologic Method for Detection of Methicillin-Resistant Staphylococcus aureus," Antimicrobial Agents and Chemotherapy, 1992, vol. 36 (1), pp. 6-9.

Top FH Jr., "Control of Adenovirus Acute Respiratory Disease in U.S. Army Trainees," The Yale Journal of Biology and Medicine, 1975, vol. 48 (3), pp. 185-195.

Towner K.J., et al., "Development and Evaluation of a PCR-Based Immunoassay for the Rapid Detection of Methicillin-Resistant Staphylococcus aureus," Journal of Medical Microbiology, 1998, vol. 47 (7), pp. 607-613.

Tsuneyoshi, et al., "Mass Spectrometric Gene Diagnosis of One-Base Substitution from Polymerase Chain Reaction Amplified Human DNA," Rapid Communications in Mass Spectomerty, 1997, vol. 11 (7), pp. 719-722.

Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.

Udo E.E., et al., "A Chromosomal Location of the MupA Gene in Staphylococcus aureus Expressing High-Level Mupirocin Resistance," The Journal of Antimicrobial Chemotherapy, 2003, vol. 51 (5), pp. 1283-1286.

Udo E.E., et al., "Genetic Analysis of Methicillin-Resistant Staphylococcus aureus Expressing High-and Low-Level Mupirocin Resistance," Journal of Medical Microbiology, 2001, vol. 50 (10), pp. 909-915.

Udo E.E., et al., "Rapid Detection of Methicillin Resistance in Staphylococci Using a Slide Latex Agglutination Kit," International Journal of Antimicrobial Agents, 2000, vol. 15 (1), pp. 19-24.

Unal S., et al., "Detection of Methicillin-Resistant Staphylococci by Using the Polymerase Chain Reaction," Journal of Clinical Microbiology, 1992, vol. 30 (7), pp. 1685-1691.

Upton A., et al., "Mupirocin and Staphylococcus aureus: A Recent Paradigm of Emerging Antibiotic Resistance," The Journal of Antimicrobial Chemotherapy, 2003, vol. 51 (3), pp. 613-617.

U.S. Appl. No. 60/36,9405, 2002.
U.S. Appl. No. 60/397,365, 2002.
U.S. Appl. No. 60/431,319, 2002.
U.S. Appl. No. 60/443,443, 2003.
U.S. Appl. No. 60/443,788, 2003.
U.S. Appl. No. 60/447,529, 2003.
U.S. Appl. No. 60/453,607, 2003.
U.S. Appl. No. 60/461,494, 2003.
U.S. Appl. No. 60/470,175, 2003.
U.S. Appl. No. 60/501,926, 2003.
U.S. Appl. No. 60/509,911, 2003.
U.S. Appl. No. 60/604,329, 2004.
U.S. Appl. No. 60/615,387, 2004.
U.S. Appl. No. 60/701,404, 2005.
U.S. Appl. No. 60/705,631, 2005.
U.S. Appl. No. 60/720,843, 2005.
U.S. Appl. No. 60/747,607, 2006.
U.S. Appl. No. 60/771,101, 2006.
U.S. Appl. No. 60/773,124, 2006.
U.S. Appl. No. 60/891,479, 2007.
U.S. Appl. No. 60/941,641, 2007.

Vabret A., et al., "Development of a PCR-and Hybridization-Based Assay (PCR Adenovirus Consensus) for the Detection and the Species Identification of Adenoviruses in Respiratory Specimens," Journal of Clinical Virology, 2004, vol. 31 (2), pp. 116-122.

Van Der Zee H., et al., "Rapid and Alternative Screening Methods for Microbiological Analysis," Journal of AOAC International, 1997, vol. 80 (4), pp. 934-940.

Van Dinten L.C., et al., "Proteolytic Processing of the Open Reading Frame lb-Encoded Part of Arterivirus Replicase Is Mediated by nsp4 Serine Protease and is Essential for Virus Replication," Journal of Virology, 1999, vol. 73 (3), pp. 2027-2037.

Van Elden L.J., et al., "Clinical Diagnosis of Influenza Virus Infection: Evaluation of Diagnostic Tools in General Practice," The British Journal of General Practice, 2001, vol. 51 (469), pp. 630-634.

Van Elden L.J., et al., "Simultaneous Detection of Influenza Viruses A and B Using Real-Time Quantitative PCR," Journal of Clinical Microbiology, 2001, vol. 39 (1), pp. 196-200.

Van Leeuwen W.B., et al., "Multilocus Sequence Typing of Staphylococcus aureus with DNA Array Technology," Journal of Clinical Microbiology, 2003, vol. 41 (7), pp. 3323-3326.

Van Leeuwen W.B., et al., "Rapid Detection of Methicillin-Resistance in Staphylococcus aureus Isolates by the MRSA-Screen Latex Agglutination Test," Journal of Clinical Microbiology, 1999, vol. 37 (9), pp. 3029-3030.

Vanchiere J.A et al "Detection of BK Virus and Simian Virus 40 in the Urine of Healthy Children," Journal of Medical Virology, 2005, vol. 75 (3), pp. 447-454.

Vannuffel P., et al., "Rapid and Specific Molecular Identification of Methicillin-Resistant Staphylococcus aureus in Endotracheal Aspirates from Mechanically Ventilated Patients," Journal of Clinical Microbiology, 1998, vol. 36 (8), pp. 2366-2368.

Vannuffel P., et al., "Specific Detection of Methicillin-Resistant Staphylococcus Species by Multiplex PCR," Journal of Clinical Microbiology, 1995, vol. 33 (11), pp. 2864-2867.

Verma S., et al., "Modified Oligonucleotides: Synthesis and Strategy for Users," Annual Review of Biochemistry, 1998, pp. 99-134.

Videla C., et al., "Genomic Analysis of Adenovirus Isolated from Argentinian Children with Acute Lower Respiratory Infections," Journal of Clinical Virology, 1999, vol. 14 (1), pp. 67-71.

Vilchez R.A. et al., "Detection of Polyomavirus Simian Virus 40 Tumor Antigen DNA in Aids-Related Systemic Non-Hodgkin Lymphoma," Journal of Acquired Immune Deficiencysyndromes, 2002, vol. 29 (2), pp. 109-116.

Voelter C., et al., "Screening Human Tumor Samples with a Broad-Spectrum Polymerase Chain Reaction Method for the Detection of Polyomaviruses," Virology, 1997, vol. 237 (2), pp. 389-396.

Volokhov D., et al., "Microarray Analysis of Erythromycin Resistance Determinants," Journal of Applied Microbiology, 2003, vol. 95 (4), pp. 787-798.

Von Eiff C., et al., "Pathogenesis of Infections Due to Coagulase-Negative Staphylococci," The Lancet Infectious Diseases, 2002, vol. 2 (11), pp. 677-685.

Von Wintzingerode F., et al., "Base-Specific Fragmentation of Amplified 16S rRNA Genes Analyzed by Mass Spectrometry: A Tool for Rapid Bacterial Identification," Proceedings of the National Academy of Sciences, 2002, vol. 99 (10), pp. 7039-7044.

Walker E.S., et al., "A Decline in Mupirocin Resistance in Methicillin-Resistant Staphylococcus aureus Accompanied Administrative Control of Prescriptions," Journal of Clinical Microbiology, 2004, vol. 42 (6), pp. 2792-2795.

Wallace S.S., et al., "The Enigma of Endonuclease VIII," DNA Repair, 2003, vol. 2 (5), pp. 441-453.

Wallet F., et al., "Choice of a Routine Method for Detecting Methicillin-Resistance in Staphylococci," The Journal of Antimicrobial Chemotherapy, 1996, vol. 37 (5), pp. 901-909.

Wang G., et al., "Targeted Mutagenesis in Mammalian Cells Mediated by Intracellular Triple Helix Formation," Molecular and Cellular Biology, 1995, vol. 15 (3), pp. 1759-1768.

Ward C.L., et al., "Design and Performance Testing of Quantitative Real Time PCR Assays for Influenza A and B Viral Load Measurement," Journal of Clinical Virology, 2004, vol. 29 (3), pp. 179-188.

Watanabe K., et al., "ICB Database: the gyrB Database for Identification and Classification of Bacteria," Nucleic Acids Research, 2001, vol. 29 (1), pp. 344-345.

Weissenbacher M., et al., "Etiologic and Clinical Evaluation of Acute Lower Respiratory TractInfections in Young Argentinean Children: An Overview," Reviews of Infectious Diseases, 1990, vol. 12 (Suppl 8), pp. S889-S898.

Wertheim H.F., et al., "Effect of Mupirocin Treatment on Nasal, Pharyngeal, and Perineal Carriage of Staphylococcus aureus in Healthy Adults," Antimicrobial Agents and Chemotherapy, 2005, vol. 49 (4), pp. 1465-1467.

Westermann P., et al., "Inhibition of Expression of SV40 Virus Large T-Antigen by Antisense Oligodeoxyribonucleotides," Biomedica Biochimica Acta, 1989, vol. 1, pp. 85-93.

Whiley D.M., et al., "Simultaneous Detection and Differentiation of Human Polyomaviruses JC and BK by a Rapid and Sensitive PCR-ELAHA Assay and a Survey of the JCV Subtypes within an Australian Population," Journal of Medical Virology, 2004, vol. 72 (3), pp. 467-472.

Wichelhaus T.A., et al., "Rapid Detection of Epidemic Strains of MethicillinResistant*Staphylococcus aureus*," Journal of Clinical Microbiology, 1999, vol. 37 (3), pp. 690-693.

Wickham T.J., "Targeting Adenovirus," Gene Therapy, 2000, vol. 7 (2), pp. 110-114.

Widjojoatmodjo M.N., et al., "The Magnetic Immuno Polymerase Chain Reaction Assay for Direct Detection of *Salmonellae* in Fecal Samples," Journal of Clinical Microbiology, 1992, vol. 30 (12), pp. 3195-3199.

Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4 (7), pp. 566-577.

Wood S.R., et al., "Rapid Detection and Serotyping of Adenovirus by Direct Immunofluorescence," Journal of Medical Virology, 1997, vol. 51 (3), pp. 198-201.

Wright K.E., et al., "Typing and Subtyping of Influenza Viruses in Clinical Samples by PCR," Journal of Clinical Microbiology, 1995, vol. 33 (5), pp. 1180-1184.

Written Opinion for Application No. PCT/US2004/33742, mailed on May 15, 2006, 5 pages.

Wu S., et al., "Genetic Organization of the mecA Region in Methicillin-Susceptible and Methicillin-Resistant Strains of *Staphylococcus sciuri*," The Journal of Bacteriology, 1998, vol. 180 (2), pp. 236-242.

Wu X. et al., "Establishment of a Fluorescent Polymerase Chain Reaction Method for the Detection of SARS-Associated Coronavhus and its Clinical Application," Chinese Medical Journal, 2003, vol. 116 (7), pp. 988-990.

Xu L., et al., "Electrophore Mass Tag Dideoxy DNA Sequencing," Analytical Chemistry, 1997, vol. 69 (17), pp. 3595-3602.

Xu W., et al., "Species-Specific Identification of Human Adenoviruses by a Multiplex PCR Assay," Journal of Clinical Microbiology, 2000, vol. 38 (11), pp. 4114-4120.

Xu W., et al., "Type-Specific Identification of Human Adenovirus, 3, 7, and 21 by a Multiplex PCR Assay," Journal of Medical Virology, 2001, vol. 64 (4), pp. 537-542.

Xu X., 7 et al., "Intercontinental Circulation of Human Influenza A(H1N2) Reassortant Viruses During the 2001-2002 Influenza Season," The Journal of Infectious Diseases, 2002, vol. 186 (10), pp. 1490-1493.

Ye K., et al., "Three Distinct Promoters Direct Transcription of Different 5' Untranslated Regions of the Human Interleukin 1 Type 1 Receptor. A Possible Mechanism for Control of Translation," Cytokine, 1996, vol. 8 (6), pp. 421-429.

Yun H.J., et al., "Increased Antibacterial Activity of OW286, A Novel Fluoronaphthyridone Antibiotic, Against *Staphylococcus aureus* Strains with Defined Mutations in DNA Gyrase and Toposiomerase IV," International Journal of Antimicrobial Agents, 2005, vol. 25 (4), pp. 334-337.

Zhang J., et al., "PowerBLAST: A New Network BLAST Application for Interactive or Automated Sequence Analysis and Annotation," Genome Research, 1997, vol. 7 (6), pp. 649-656.

Zhang K., et al., "New Quadriplex PCR Assay for Detection of Methicillin and Mupirocin Resistance and Simultaneous Discrimination of *Staphylococcus aureus* from Coagulase-Negative Staphylococci," Journal of Clinical Microbiology, 2004, vol. 42 (11), pp. 4947-4955.

Zhang W.D., et al., "Detection and Identification of Human Influenza Viruses by the Polymerase Chain Reaction," Journal of Virological Methods, 1991, vol. 33 (1-2), pp. 165-189.

Zhang Y.Q., et al., "Genome-Based Analysis of Virulence Genes in a Non-Biofilm-Forming *Staphylococcus epidemidis* Strain (ATCC 12228)," Molecular Microbiology, 2003, vol. 49 (6), pp. 1577-1593.

\* cited by examiner 16S rRNA Domain III

Fig. 4

*tag  
mass (T*-T)=x $\overset{*}{\text{T}}\text{ACG}\overset{*}{\text{T}}\text{ACG}\overset{*}{\text{T}}$  
$\overset{*}{\text{A}}\text{TGCA}\overset{*}{\text{T}}\text{GCA}$ → $\overset{*}{\text{T}}\text{ACG}\overset{*}{\text{T}}\text{ACG}\overset{*}{\text{T}}$ (Watson)

↘ $\text{A}\overset{*}{\text{T}}\text{GCA}\overset{*}{\text{T}}\text{GCA}$ (Crick)

*tag  
mass (C*-C)=y $\text{TA}\overset{*}{\text{C}}\text{GTA}\overset{*}{\text{C}}\text{GT}$  
$\text{ATGCATGCA}$  
  $\overset{*}{\phantom{A}}\phantom{TG}\overset{*}{\phantom{A}}$ → $\text{TA}\overset{*}{\text{C}}\text{GTA}\overset{*}{\text{C}}\text{GT}$ (Watson)

↘ $\text{ATG}\overset{*}{\text{C}}\text{ATG}\overset{*}{\text{C}}\text{A}$ (Crick)

Fig. 5

B. anthracis ($A_{14}G_9C_{14}T_9$) $MW_{meas}$ = 14072.2)

B. anthracis* ($A_1A^*{}_{13}G_9C_{14}T_9$) $MW_{meas}$ = 14280.9)

13500    14000    14500
MW

ESI-FTICR-MS of Synthetic Bacillus Anthracis 16S_1337 46 bp Duplex $\Delta m/z = 0.077 = 1/13$ (R-13H+)$^{13-}$ (F-13H+)$^{13-}$ Na+

SEQUENCE LISTING

<160> NUMBER OF SEQ ID NOS: 23

<210> SEQ ID NO 1
<211> LENGTH: 13
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 1
cgtggtgacc ctt                                                            13

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgtcgtcacc gcta                                                           14

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgtggtaccc ctt                                                            13

<210> SEQ ID NO 4
<211> LENGTH: 90
<212> TYPE: RNA
<213> ORGANISM: Bacillus anthracis
<220> FEATURE:
<221> NAME/KEY: modified_base
<222> LOCATION: (20)..(20)
<223> OTHER INFORMATION: n is a, c, g, or u

<400> SEQUENCE: 4
gcgaagaacc uuaccaggun uugacauccu cugacaaccc uagagauagg gcuucuccuu         60
cgggagcaga gugacaggug gugcaugguu                                          90

<210> SEQ ID NO 5
<211> LENGTH: 90
<212> TYPE: RNA
<213> ORGANISM: Bacillus cereus

<400> SEQUENCE: 5
gcgaagaacc uuaccagguc uugacauccu cugaaaaccc uagagauagg gcuucuccuu         60
cgggagcaga gugacaggug gugcaugguu                                          90

<210> SEQ ID NO 6
<211> LENGTH: 1912
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(7)
<223> OTHER INFORMATION: n is a, c, g, or u
<220> FEATURE:
<221> NAME/KEY: modified_base
<222> LOCATION: (19)..(19)
<223> OTHER INFORMATION: n is a, c, g, or u
<220> FEATURE:
<221> NAME/KEY: modified_base
```

```
<222> LOCATION: (28)..(30)
<223> OTHER INFORMATION: n is a, c, g, or u
<220> FEATURE:
<221> NAME/KEY: modified_base
<222> LOCATION: (43)..(45)
<223> OTHER INFORMATION: n is a, c, g, or u
<220> FEATURE:
<221> NAME/KEY: modified_base
<222> LOCATION: (48)..(48)
<223> OTHER INFORMATION: n is a, c, g, or u
<220> FEATURE:
<221> NAME/KEY: modified_base
<222> LOCATION: (50)..(50)
<223> OTHER INFORMATION: n is a, c, g, or u
<220> FEATURE:
<221> NAME/KEY: modified_base
<222> LOCATION: (52)..(52)
<223> OTHER INFORMATION: n is a, c, g, or u
<220> FEATURE:
<221> NAME/KEY: modified_base
<222> LOCATION: (66)..(66)
<223> OTHER INFORMATION: n is a, c, g, or u
<220> FEATURE:
<221> NAME/KEY: modified_base
<222> LOCATION: (69)..(225)
<223> OTHER INFORMATION: This region may encompass 0-157 variable bases,
      a, c, g, or u
<220> FEATURE:
<221> NAME/KEY: modified_base
<222> LOCATION: (228)..(228)
<223> OTHER INFORMATION: n is a, c, g, or u
<220> FEATURE:
<221> NAME/KEY: modified_base
<222> LOCATION: (232)..(233)
<223> OTHER INFORMATION: n is a, c, g, or u
<220> FEATURE:
<221> NAME/KEY: modified_base
<222> LOCATION: (246)..(247)
<223> OTHER INFORMATION: n is a, c, g, or u
<220> FEATURE:
<221> NAME/KEY: modified_base
<222> LOCATION: (249)..(249)
<223> OTHER INFORMATION: n is a, c, g, or u
<220> FEATURE:
<221> NAME/KEY: modified_base
<222> LOCATION: (251)..(254)
<223> OTHER INFORMATION: n is a, c, g, or u
<220> FEATURE:
<221> NAME/KEY: modified_base
<222> LOCATION: (256)..(257)
<223> OTHER INFORMATION: n is a, c, g, or u
<220> FEATURE:
<221> NAME/KEY: modified_base
<222> LOCATION: (259)..(259)
<223> OTHER INFORMATION: n is a, c, g, or u
<220> FEATURE:
<221> NAME/KEY: modified_base
<222> LOCATION: (262)..(270)
<223> OTHER INFORMATION: n is a, c, g, or u
<220> FEATURE:
<221> NAME/KEY: modified_base
<222> LOCATION: (273)..(273)
<223> OTHER INFORMATION: n is a, c, g, or u
<220> FEATURE:
<221> NAME/KEY: modified_base
<222> LOCATION: (275)..(275)
<223> OTHER INFORMATION: n is a, c, g, or u
<220> FEATURE:
<221> NAME/KEY: modified_base
<222> LOCATION: (277)..(283)
<223> OTHER INFORMATION: n is a, c, g, or u
<220> FEATURE:
<221> NAME/KEY: modified_base
<222> LOCATION: (288)..(294)
<223> OTHER INFORMATION: n is a, c, g, or u
<220> FEATURE:
<221> NAME/KEY: modified_base
<222> LOCATION: (302)..(303)
<223> OTHER INFORMATION: n is a, c, g, or u
<220> FEATURE:
```

-continued

```
<221> NAME/KEY: modified_base
<222> LOCATION: (306)..(319)
<223> OTHER INFORMATION: n is a, c, g, or u
<220> FEATURE:
<221> NAME/KEY: modified_base
<222> LOCATION: (324)..(374)
<223> OTHER INFORMATION: This region may encompass 0-51 variable bases,
      a, c, g, or u
<220> FEATURE:
<221> NAME/KEY: modified_base
<222> LOCATION: (375)..(382)
<223> OTHER INFORMATION: n is a, c, g, or u
<220> FEATURE:
<221> NAME/KEY: modified_base
<222> LOCATION: (385)..(393)
<223> OTHER INFORMATION: n is a, c, g, or u
<220> FEATURE:
<221> NAME/KEY: modified_base
<222> LOCATION: (395)..(398)
<223> OTHER INFORMATION: n is a, c, g, or u
<220> FEATURE:
<221> NAME/KEY: modified_base
<222> LOCATION: (401)..(401)
<223> OTHER INFORMATION: n is a, c, g, or u
<220> FEATURE:
<221> NAME/KEY: modified_base
<222> LOCATION: (404)..(404)
<223> OTHER INFORMATION: n is a, c, g, or u
<220> FEATURE:
<221> NAME/KEY: modified_base
<222> LOCATION: (406)..(406)
<223> OTHER INFORMATION: n is a, c, g, or u
<220> FEATURE:
<221> NAME/KEY: modified_base
<222> LOCATION: (413)..(414)
<223> OTHER INFORMATION: n is a, c, g, or u
<220> FEATURE:
<221> NAME/KEY: modified_base
<222> LOCATION: (420)..(420)
<223> OTHER INFORMATION: n is a, c, g, or u
<220> FEATURE:
<221> NAME/KEY: modified_base
<222> LOCATION: (424)..(425)
<223> OTHER INFORMATION: n is a, c, g, or u
<220> FEATURE:
<221> NAME/KEY: modified_base
<222> LOCATION: (432)..(432)
<223> OTHER INFORMATION: n is a, c, g, or u
<220> FEATURE:
<221> NAME/KEY: modified_base
<222> LOCATION: (434)..(436)
<223> OTHER INFORMATION: n is a, c, g, or u
<220> FEATURE:
<221> NAME/KEY: modified_base
<222> LOCATION: (439)..(442)
<223> OTHER INFORMATION: n is a, c, g, or u
<220> FEATURE:
<221> NAME/KEY: modified_base
<222> LOCATION: (447)..(447)
<223> OTHER INFORMATION: n is a, c, g, or u
<220> FEATURE:
<221> NAME/KEY: modified_base
<222> LOCATION: (449)..(450)
<223> OTHER INFORMATION: n is a, c, g, or u
<220> FEATURE:
<221> NAME/KEY: modified_base
<222> LOCATION: (459)..(460)
<223> OTHER INFORMATION: n is a, c, g, or u
<220> FEATURE:
<221> NAME/KEY: modified_base
<222> LOCATION: (462)..(463)
<223> OTHER INFORMATION: n is a, c, g, or u
<220> FEATURE:
<221> NAME/KEY: modified_base
<222> LOCATION: (465)..(465)
<223> OTHER INFORMATION: n is a, c, g, or u
<220> FEATURE:
<221> NAME/KEY: modified_base
<222> LOCATION: (472)..(472)
<223> OTHER INFORMATION: n is a, c, g, or u
```

```
<220> FEATURE:
<221> NAME/KEY: modified_base
<222> LOCATION: (476)..(476)
<223> OTHER INFORMATION: n is a, c, g, or u
<220> FEATURE:
<221> NAME/KEY: modified_base
<222> LOCATION: (484)..(484)
<223> OTHER INFORMATION: n is a, c, g, or u
<220> FEATURE:
<221> NAME/KEY: modified_base
<222> LOCATION: (489)..(489)
<223> OTHER INFORMATION: n is a, c, g, or u
<220> FEATURE:
<221> NAME/KEY: modified_base
<222> LOCATION: (493)..(493)
<223> OTHER INFORMATION: n is a, c, g, or u
<220> FEATURE:
<221> NAME/KEY: modified_base
<222> LOCATION: (515)..(516)
<223> OTHER INFORMATION: n is a, c, g, or u
<220> FEATURE:
<221> NAME/KEY: modified_base
<222> LOCATION: (522)..(522)
<223> OTHER INFORMATION: n is a, c, g, or u
<220> FEATURE:
<221> NAME/KEY: modified_base
<222> LOCATION: (525)..(527)
<223> OTHER INFORMATION: n is a, c, g, or u
<220> FEATURE:
<221> NAME/KEY: modified_base
<222> LOCATION: (534)..(535)
<223> OTHER INFORMATION: n is a, c, g, or u
<220> FEATURE:
<221> NAME/KEY: modified_base
<222> LOCATION: (537)..(537)
<223> OTHER INFORMATION: n is a, c, g, or u
<220> FEATURE:
<221> NAME/KEY: modified_base
<222> LOCATION: (540)..(541)
<223> OTHER INFORMATION: n is a, c, g, or u
<220> FEATURE:
<221> NAME/KEY: modified_base
<222> LOCATION: (546)..(548)
<223> OTHER INFORMATION: n is a, c, g, or u
<220> FEATURE:
<221> NAME/KEY: modified_base
<222> LOCATION: (552)..(552)
<223> OTHER INFORMATION: n is a, c, g, or u
<220> FEATURE:
<221> NAME/KEY: modified_base
<222> LOCATION: (554)..(555)
<223> OTHER INFORMATION: n is a, c, g, or u
<220> FEATURE:
<221> NAME/KEY: modified_base
<222> LOCATION: (563)..(565)
<223> OTHER INFORMATION: n is a, c, g, or u
<220> FEATURE:
<221> NAME/KEY: modified_base
<222> LOCATION: (568)..(568)
<223> OTHER INFORMATION: n is a, c, g, or u
<220> FEATURE:
<221> NAME/KEY: modified_base
<222> LOCATION: (571)..(571)
<223> OTHER INFORMATION: n is a, c, g, or u
<220> FEATURE:
<221> NAME/KEY: modified_base
<222> LOCATION: (574)..(575)
<223> OTHER INFORMATION: n is a, c, g, or u
<220> FEATURE:
<221> NAME/KEY: modified_base
<222> LOCATION: (577)..(578)
<223> OTHER INFORMATION: n is a, c, g, or u
<220> FEATURE:
<221> NAME/KEY: modified_base
<222> LOCATION: (579)..(580)
<223> OTHER INFORMATION: This region may encompass 0-2 variable bases,
      a, c, g, or u
<220> FEATURE:
<221> NAME/KEY: modified_base
<222> LOCATION: (582)..(582)
```

-continued

```
<223> OTHER INFORMATION: n is a, c, g, or u
<220> FEATURE:
<221> NAME/KEY: modified_base
<222> LOCATION: (584)..(584)
<223> OTHER INFORMATION: n is a, c, g, or u
<220> FEATURE:
<221> NAME/KEY: modified_base
<222> LOCATION: (590)..(592)
<223> OTHER INFORMATION: n is a, c, g, or u
<220> FEATURE:
<221> NAME/KEY: modified_base
<222> LOCATION: (595)..(595)
<223> OTHER INFORMATION: n is a, c, g, or u
<220> FEATURE:
<221> NAME/KEY: modified_base
<222> LOCATION: (597)..(603)
<223> OTHER INFORMATION: n is a, c, g, or u
<220> FEATURE:
<221> NAME/KEY: modified_base
<222> LOCATION: (606)..(606)
<223> OTHER INFORMATION: n is a, c, g, or u
<220> FEATURE:
<221> NAME/KEY: modified_base
<222> LOCATION: (609)..(640)
<223> OTHER INFORMATION: This region may encompass 0-32 variable bases,
      a, c, g, or u
<220> FEATURE:
<221> NAME/KEY: modified_base
<222> LOCATION: (645)..(646)
<223> OTHER INFORMATION: n is a, c, g, or u
<220> FEATURE:
<221> NAME/KEY: modified_base
<222> LOCATION: (649)..(655)
<223> OTHER INFORMATION: n is a, c, g, or u
<220> FEATURE:
<221> NAME/KEY: modified_base
<222> LOCATION: (657)..(658)
<223> OTHER INFORMATION: n is a, c, g, or u
<220> FEATURE:
<221> NAME/KEY: modified_base
<222> LOCATION: (662)..(664)
<223> OTHER INFORMATION: n is a, c, g, or u
<220> FEATURE:
<221> NAME/KEY: modified_base
<222> LOCATION: (669)..(669)
<223> OTHER INFORMATION: n is a, c, g, or u
<220> FEATURE:
<221> NAME/KEY: modified_base
<222> LOCATION: (674)..(674)
<223> OTHER INFORMATION: n is a, c, g, or u
<220> FEATURE:
<221> NAME/KEY: modified_base
<222> LOCATION: (699)..(699)
<223> OTHER INFORMATION: n is a, c, g, or u
<220> FEATURE:
<221> NAME/KEY: modified_base
<222> LOCATION: (703)..(704)
<223> OTHER INFORMATION: n is a, c, g, or u
<220> FEATURE:
<221> NAME/KEY: modified_base
<222> LOCATION: (707)..(707)
<223> OTHER INFORMATION: n is a, c, g, or u
<220> FEATURE:
<221> NAME/KEY: modified_base
<222> LOCATION: (714)..(716)
<223> OTHER INFORMATION: n is a, c, g, or u
<220> FEATURE:
<221> NAME/KEY: modified_base
<222> LOCATION: (721)..(721)
<223> OTHER INFORMATION: n is a, c, g, or u
<220> FEATURE:
<221> NAME/KEY: modified_base
<222> LOCATION: (723)..(723)
<223> OTHER INFORMATION: n is a, c, g, or u
<220> FEATURE:
<221> NAME/KEY: modified_base
<222> LOCATION: (725)..(725)
<223> OTHER INFORMATION: n is a, c, g, or u
<220> FEATURE:
<221> NAME/KEY: modified_base
```

```
<222> LOCATION: (737)..(737)
<223> OTHER INFORMATION: n is a, c, g, or u
<220> FEATURE:
<221> NAME/KEY: modified_base
<222> LOCATION: (739)..(741)
<223> OTHER INFORMATION: n is a, c, g, or u
<220> FEATURE:
<221> NAME/KEY: modified_base
<222> LOCATION: (743)..(743)
<223> OTHER INFORMATION: n is a, c, g, or u
<220> FEATURE:
<221> NAME/KEY: modified_base
<222> LOCATION: (747)..(747)
<223> OTHER INFORMATION: n is a, c, g, or u
<220> FEATURE:
<221> NAME/KEY: modified_base
<222> LOCATION: (750)..(757)
<223> OTHER INFORMATION: n is a, c, g, or u
<220> FEATURE:
<221> NAME/KEY: modified_base
<222> LOCATION: (760)..(764)
<223> OTHER INFORMATION: n is a, c, g, or u
<220> FEATURE:
<221> NAME/KEY: modified_base
<222> LOCATION: (767)..(767)
<223> OTHER INFORMATION: n is a, c, g, or u
<220> FEATURE:
<221> NAME/KEY: modified_base
<222> LOCATION: (771)..(777)
<223> OTHER INFORMATION: n is a, c, g, or u
<220> FEATURE:
<221> NAME/KEY: modified_base
<222> LOCATION: (781)..(781)
<223> OTHER INFORMATION: n is a, c, g, or u
<220> FEATURE:
<221> NAME/KEY: modified_base
<222> LOCATION: (785)..(791)
<223> OTHER INFORMATION: n is a, c, g, or u
<220> FEATURE:
<221> NAME/KEY: modified_base
<222> LOCATION: (792)..(792)
<223> OTHER INFORMATION: a, c, g, u, or not present
<220> FEATURE:
<221> NAME/KEY: modified_base
<222> LOCATION: (793)..(794)
<223> OTHER INFORMATION: n is a, c, g, or u
<220> FEATURE:
<221> NAME/KEY: modified_base
<222> LOCATION: (796)..(802)
<223> OTHER INFORMATION: n is a, c, g, or u
<220> FEATURE:
<221> NAME/KEY: modified_base
<222> LOCATION: (805)..(811)
<223> OTHER INFORMATION: n is a, c, g, or u
<220> FEATURE:
<221> NAME/KEY: modified_base
<222> LOCATION: (814)..(814)
<223> OTHER INFORMATION: n is a, c, g, or u
<220> FEATURE:
<221> NAME/KEY: modified_base
<222> LOCATION: (818)..(823)
<223> OTHER INFORMATION: n is a, c, g, or u
<220> FEATURE:
<221> NAME/KEY: modified_base
<222> LOCATION: (826)..(826)
<223> OTHER INFORMATION: n is a, c, g, or u
<220> FEATURE:
<221> NAME/KEY: modified_base
<222> LOCATION: (829)..(834)
<223> OTHER INFORMATION: n is a, c, g, or u
<220> FEATURE:
<221> NAME/KEY: modified_base
<222> LOCATION: (840)..(843)
<223> OTHER INFORMATION: n is a, c, g, or u
<220> FEATURE:
<221> NAME/KEY: modified_base
<222> LOCATION: (850)..(850)
<223> OTHER INFORMATION: n is a, c, g, or u
<220> FEATURE:
<221> NAME/KEY: modified_base
```

```
<222> LOCATION: (855)..(855)
<223> OTHER INFORMATION: n is a, c, g, or u
<220> FEATURE:
<221> NAME/KEY: modified_base
<222> LOCATION: (859)..(859)
<223> OTHER INFORMATION: n is a, c, g, or u
<220> FEATURE:
<221> NAME/KEY: modified_base
<222> LOCATION: (862)..(862)
<223> OTHER INFORMATION: n is a, c, g, or u
<220> FEATURE:
<221> NAME/KEY: modified_base
<222> LOCATION: (866)..(866)
<223> OTHER INFORMATION: n is a, c, g, or u
<220> FEATURE:
<221> NAME/KEY: modified_base
<222> LOCATION: (869)..(870)
<223> OTHER INFORMATION: n is a, c, g, or u
<220> FEATURE:
<221> NAME/KEY: modified_base
<222> LOCATION: (872)..(872)
<223> OTHER INFORMATION: n is a, c, g, or u
<220> FEATURE:
<221> NAME/KEY: modified_base
<222> LOCATION: (874)..(874)
<223> OTHER INFORMATION: n is a, c, g, or u
<220> FEATURE:
<221> NAME/KEY: modified_base
<222> LOCATION: (878)..(878)
<223> OTHER INFORMATION: n is a, c, g, or u
<220> FEATURE:
<221> NAME/KEY: modified_base
<222> LOCATION: (882)..(883)
<223> OTHER INFORMATION: n is a, c, g, or u
<220> FEATURE:
<221> NAME/KEY: modified_base
<222> LOCATION: (885)..(885)
<223> OTHER INFORMATION: n is a, c, g, or u
<220> FEATURE:
<221> NAME/KEY: modified_base
<222> LOCATION: (894)..(899)
<223> OTHER INFORMATION: n is a, c, g, or u
<220> FEATURE:
<221> NAME/KEY: modified_base
<222> LOCATION: (904)..(909)
<223> OTHER INFORMATION: n is a, c, g, or u
<220> FEATURE:
<221> NAME/KEY: modified_base
<222> LOCATION: (916)..(916)
<223> OTHER INFORMATION: n is a, c, g, or u
<220> FEATURE:
<221> NAME/KEY: modified_base
<222> LOCATION: (919)..(919)
<223> OTHER INFORMATION: n is a, c, g, or u
<220> FEATURE:
<221> NAME/KEY: modified_base
<222> LOCATION: (921)..(924)
<223> OTHER INFORMATION: n is a, c, g, or u
<220> FEATURE:
<221> NAME/KEY: modified_base
<222> LOCATION: (932)..(932)
<223> OTHER INFORMATION: n is a, c, g, or u
<220> FEATURE:
<221> NAME/KEY: modified_base
<222> LOCATION: (937)..(937)
<223> OTHER INFORMATION: n is a, c, g, or u
<220> FEATURE:
<221> NAME/KEY: modified_base
<222> LOCATION: (941)..(941)
<223> OTHER INFORMATION: n is a, c, g, or u
<220> FEATURE:
<221> NAME/KEY: modified_base
<222> LOCATION: (969)..(969)
<223> OTHER INFORMATION: n is a, c, g, or u
<220> FEATURE:
<221> NAME/KEY: modified_base
<222> LOCATION: (972)..(973)
<223> OTHER INFORMATION: n is a, c, g, or u
<220> FEATURE:
<221> NAME/KEY: modified_base
```

-continued

```
<222> LOCATION: (980)..(980)
<223> OTHER INFORMATION: n is a, c, g, or u
<220> FEATURE:
<221> NAME/KEY: modified_base
<222> LOCATION: (983)..(987)
<223> OTHER INFORMATION: n is a, c, g, or u
<220> FEATURE:
<221> NAME/KEY: modified_base
<222> LOCATION: (989)..(992)
<223> OTHER INFORMATION: n is a, c, g, or u
<220> FEATURE:
<221> NAME/KEY: modified_base
<222> LOCATION: (994)..(996)
<223> OTHER INFORMATION: n is a, c, g, or u
<220> FEATURE:
<221> NAME/KEY: modified_base
<222> LOCATION: (998)..(999)
<223> OTHER INFORMATION: n is a, c, g, or u
<220> FEATURE:
<221> NAME/KEY: modified_base
<222> LOCATION: (1000)..(1036)
<223> OTHER INFORMATION: This region may encompass 0-37 variable bases,
      a, c, g, or u
<220> FEATURE:
<221> NAME/KEY: modified_base
<222> LOCATION: (1037)..(1048)
<223> OTHER INFORMATION: n is a, c, g, or u
<220> FEATURE:
<221> NAME/KEY: modified_base
<222> LOCATION: (1050)..(1052)
<223> OTHER INFORMATION: n is a, c, g, or u
<220> FEATURE:
<221> NAME/KEY: modified_base
<222> LOCATION: (1057)..(1059)
<223> OTHER INFORMATION: n is a, c, g, or u
<220> FEATURE:
<221> NAME/KEY: modified_base
<222> LOCATION: (1063)..(1067)
<223> OTHER INFORMATION: n is a, c, g, or u
<220> FEATURE:
<221> NAME/KEY: modified_base
<222> LOCATION: (1084)..(1085)
<223> OTHER INFORMATION: n is a, c, g, or u
<220> FEATURE:
<221> NAME/KEY: modified_base
<222> LOCATION: (1092)..(1093)
<223> OTHER INFORMATION: n is a, c, g, or u
<220> FEATURE:
<221> NAME/KEY: modified_base
<222> LOCATION: (1095)..(1095)
<223> OTHER INFORMATION: n is a, c, g, or u
<220> FEATURE:
<221> NAME/KEY: modified_base
<222> LOCATION: (1105)..(1105)
<223> OTHER INFORMATION: n is a, c, g, or u
<220> FEATURE:
<221> NAME/KEY: modified_base
<222> LOCATION: (1118)..(1118)
<223> OTHER INFORMATION: n is a, c, g, or u
<220> FEATURE:
<221> NAME/KEY: modified_base
<222> LOCATION: (1121)..(1122)
<223> OTHER INFORMATION: This region may encompass 0-2 variable bases,
      a, c, g, or u
<220> FEATURE:
<221> NAME/KEY: modified_base
<222> LOCATION: (1131)..(1131)
<223> OTHER INFORMATION: n is a, c, g, or u
<220> FEATURE:
<221> NAME/KEY: modified_base
<222> LOCATION: (1133)..(1133)
<223> OTHER INFORMATION: n is a, c, g, or u
<220> FEATURE:
<221> NAME/KEY: modified_base
<222> LOCATION: (1138)..(1138)
<223> OTHER INFORMATION: n is a, c, g, or u
<220> FEATURE:
<221> NAME/KEY: modified_base
<222> LOCATION: (1145)..(1145)
<223> OTHER INFORMATION: n is a, c, g, or u
```

-continued

```
<220> FEATURE:
<221> NAME/KEY: modified_base
<222> LOCATION: (1155)..(1155)
<223> OTHER INFORMATION: n is a, c, g, or u
<220> FEATURE:
<221> NAME/KEY: modified_base
<222> LOCATION: (1157)..(1158)
<223> OTHER INFORMATION: n is a, c, g, or u
<220> FEATURE:
<221> NAME/KEY: modified_base
<222> LOCATION: (1164)..(1164)
<223> OTHER INFORMATION: n is a, c, g, or u
<220> FEATURE:
<221> NAME/KEY: modified_base
<222> LOCATION: (1166)..(1166)
<223> OTHER INFORMATION: n is a, c, g, or u
<220> FEATURE:
<221> NAME/KEY: modified_base
<222> LOCATION: (1176)..(1180)
<223> OTHER INFORMATION: n is a, c, g, or u
<220> FEATURE:
<221> NAME/KEY: modified_base
<222> LOCATION: (1188)..(1202)
<223> OTHER INFORMATION: n is a, c, g, or u
<220> FEATURE:
<221> NAME/KEY: modified_base
<222> LOCATION: (1205)..(1205)
<223> OTHER INFORMATION: n is a, c, g, or u
<220> FEATURE:
<221> NAME/KEY: modified_base
<222> LOCATION: (1207)..(1213)
<223> OTHER INFORMATION: n is a, c, g, or u
<220> FEATURE:
<221> NAME/KEY: modified_base
<222> LOCATION: (1214)..(1313)
<223> OTHER INFORMATION: This region may encompass 0-100 variable bases,
     a, c, g, or u
<220> FEATURE:
<221> NAME/KEY: modified_base
<222> LOCATION: (1314)..(1320)
<223> OTHER INFORMATION: n is a, c, g, or u
<220> FEATURE:
<221> NAME/KEY: modified_base
<222> LOCATION: (1328)..(1328)
<223> OTHER INFORMATION: n is a, c, g, or u
<220> FEATURE:
<221> NAME/KEY: modified_base
<222> LOCATION: (1336)..(1336)
<223> OTHER INFORMATION: n is a, c, g, or u
<220> FEATURE:
<221> NAME/KEY: modified_base
<222> LOCATION: (1352)..(1353)
<223> OTHER INFORMATION: n is a, c, g, or u
<220> FEATURE:
<221> NAME/KEY: modified_base
<222> LOCATION: (1359)..(1359)
<223> OTHER INFORMATION: n is a, c, g, or u
<220> FEATURE:
<221> NAME/KEY: modified_base
<222> LOCATION: (1377)..(1377)
<223> OTHER INFORMATION: n is a, c, g, or u
<220> FEATURE:
<221> NAME/KEY: modified_base
<222> LOCATION: (1392)..(1400)
<223> OTHER INFORMATION: n is a, c, g, or u
<220> FEATURE:
<221> NAME/KEY: modified_base
<222> LOCATION: (1404)..(1404)
<223> OTHER INFORMATION: n is a, c, g, or u
<220> FEATURE:
<221> NAME/KEY: modified_base
<222> LOCATION: (1406)..(1406)
<223> OTHER INFORMATION: n is a, c, g, or u
<220> FEATURE:
<221> NAME/KEY: modified_base
<222> LOCATION: (1408)..(1408)
<223> OTHER INFORMATION: n is a, c, g, or u
<220> FEATURE:
<221> NAME/KEY: modified_base
<222> LOCATION: (1410)..(1410)
```

-continued

```
<223> OTHER INFORMATION: n is a, c, g, or u
<220> FEATURE:
<221> NAME/KEY: modified_base
<222> LOCATION: (1411)..(1445)
<223> OTHER INFORMATION: This region may encompass 3-35 variable bases,
      a, c, g, or u
<220> FEATURE:
<221> NAME/KEY: modified_base
<222> LOCATION: (1446)..(1446)
<223> OTHER INFORMATION: n is a, c, g, or u
<220> FEATURE:
<221> NAME/KEY: modified_base
<222> LOCATION: (1448)..(1448)
<223> OTHER INFORMATION: n is a, c, g, or u
<220> FEATURE:
<221> NAME/KEY: modified_base
<222> LOCATION: (1450)..(1450)
<223> OTHER INFORMATION: n is a, c, g, or u
<220> FEATURE:
<221> NAME/KEY: modified_base
<222> LOCATION: (1455)..(1461)
<223> OTHER INFORMATION: n is a, c, g, or u
<220> FEATURE:
<221> NAME/KEY: modified_base
<222> LOCATION: (1468)..(1470)
<223> OTHER INFORMATION: n is a, c, g, or u
<220> FEATURE:
<221> NAME/KEY: modified_base
<222> LOCATION: (1472)..(1473)
<223> OTHER INFORMATION: This region may encompass 0-2 variable bases,
      a, c, g, or u
<220> FEATURE:
<221> NAME/KEY: modified_base
<222> LOCATION: (1474)..(1474)
<223> OTHER INFORMATION: n is a, c, g, or u
<220> FEATURE:
<221> NAME/KEY: modified_base
<222> LOCATION: (1477)..(1479)
<223> OTHER INFORMATION: n is a, c, g, or u
<220> FEATURE:
<221> NAME/KEY: modified_base
<222> LOCATION: (1489)..(1489)
<223> OTHER INFORMATION: n is a, c, g, or u
<220> FEATURE:
<221> NAME/KEY: modified_base
<222> LOCATION: (1495)..(1495)
<223> OTHER INFORMATION: n is a, c, g, or u
<220> FEATURE:
<221> NAME/KEY: modified_base
<222> LOCATION: (1504)..(1504)
<223> OTHER INFORMATION: n is a, c, g, or u
<220> FEATURE:
<221> NAME/KEY: modified_base
<222> LOCATION: (1507)..(1507)
<223> OTHER INFORMATION: n is a, c, g, or u
<220> FEATURE:
<221> NAME/KEY: modified_base
<222> LOCATION: (1513)..(1513)
<223> OTHER INFORMATION: n is a, c, g, or u
<220> FEATURE:
<221> NAME/KEY: modified_base
<222> LOCATION: (1520)..(1520)
<223> OTHER INFORMATION: n is a, c, g, or u
<220> FEATURE:
<221> NAME/KEY: modified_base
<222> LOCATION: (1522)..(1525)
<223> OTHER INFORMATION: n is a, c, g, or u
<220> FEATURE:
<221> NAME/KEY: modified_base
<222> LOCATION: (1531)..(1531)
<223> OTHER INFORMATION: n is a, c, g, or u
<220> FEATURE:
<221> NAME/KEY: modified_base
<222> LOCATION: (1537)..(1537)
<223> OTHER INFORMATION: n is a, c, g, or u
<220> FEATURE:
<221> NAME/KEY: modified_base
<222> LOCATION: (1539)..(1539)
<223> OTHER INFORMATION: n is a, c, g, or u
<220> FEATURE:
```

```
<221> NAME/KEY: modified_base
<222> LOCATION: (1549)..(1553)
<223> OTHER INFORMATION: n is a, c, g, or u
<220> FEATURE:
<221> NAME/KEY: modified_base
<222> LOCATION: (1557)..(1558)
<223> OTHER INFORMATION: n is a, c, g, or u
<220> FEATURE:
<221> NAME/KEY: modified_base
<222> LOCATION: (1560)..(1560)
<223> OTHER INFORMATION: n is a, c, g, or u
<220> FEATURE:
<221> NAME/KEY: modified_base
<222> LOCATION: (1562)..(1563)
<223> OTHER INFORMATION: n is a, c, g, or u
<220> FEATURE:
<221> NAME/KEY: modified_base
<222> LOCATION: (1566)..(1566)
<223> OTHER INFORMATION: n is a, c, g, or u
<220> FEATURE:
<221> NAME/KEY: modified_base
<222> LOCATION: (1568)..(1571)
<223> OTHER INFORMATION: n is a, c, g, or u
<220> FEATURE:
<221> NAME/KEY: modified_base
<222> LOCATION: (1573)..(1574)
<223> OTHER INFORMATION: n is a, c, g, or u
<220> FEATURE:
<221> NAME/KEY: modified_base
<222> LOCATION: (1576)..(1580)
<223> OTHER INFORMATION: n is a, c, g, or u
<220> FEATURE:
<221> NAME/KEY: modified_base
<222> LOCATION: (1584)..(1584)
<223> OTHER INFORMATION: n is a, c, g, or u
<220> FEATURE:
<221> NAME/KEY: modified_base
<222> LOCATION: (1587)..(1587)
<223> OTHER INFORMATION: n is a, c, g, or u
<220> FEATURE:
<221> NAME/KEY: modified_base
<222> LOCATION: (1589)..(1591)
<223> OTHER INFORMATION: n is a, c, g, or u
<220> FEATURE:
<221> NAME/KEY: modified_base
<222> LOCATION: (1592)..(1592)
<223> OTHER INFORMATION: n is a, c, g, u, or not present
<220> FEATURE:
<221> NAME/KEY: modified_base
<222> LOCATION: (1596)..(1600)
<223> OTHER INFORMATION: n is a, c, g, or u
<220> FEATURE:
<221> NAME/KEY: modified_base
<222> LOCATION: (1603)..(1604)
<223> OTHER INFORMATION: n is a, c, g, or u
<220> FEATURE:
<221> NAME/KEY: modified_base
<222> LOCATION: (1608)..(1608)
<223> OTHER INFORMATION: n is a, c, g, or u
<220> FEATURE:
<221> NAME/KEY: modified_base
<222> LOCATION: (1614)..(1614)
<223> OTHER INFORMATION: n is a, c, g, or u
<220> FEATURE:
<221> NAME/KEY: modified_base
<222> LOCATION: (1616)..(1619)
<223> OTHER INFORMATION: n is a, c, g, or u
<220> FEATURE:
<221> NAME/KEY: modified_base
<222> LOCATION: (1630)..(1633)
<223> OTHER INFORMATION: n is a, c, g, or u
<220> FEATURE:
<221> NAME/KEY: modified_base
<222> LOCATION: (1635)..(1635)
<223> OTHER INFORMATION: n is a, c, g, or u
<220> FEATURE:
<221> NAME/KEY: modified_base
<222> LOCATION: (1641)..(1642)
<223> OTHER INFORMATION: n is a, c, g, or u
<220> FEATURE:
```

```
<221> NAME/KEY: modified_base
<222> LOCATION: (1646)..(1646)
<223> OTHER INFORMATION: n is a, c, g, or u
<220> FEATURE:
<221> NAME/KEY: modified_base
<222> LOCATION: (1660)..(1662)
<223> OTHER INFORMATION: n is a, c, g, or u
<220> FEATURE:
<221> NAME/KEY: modified_base
<222> LOCATION: (1668)..(1668)
<223> OTHER INFORMATION: n is a, c, g, or u
<220> FEATURE:
<221> NAME/KEY: modified_base
<222> LOCATION: (1670)..(1670)
<223> OTHER INFORMATION: n is a, c, g, or u
<220> FEATURE:
<221> NAME/KEY: modified_base
<222> LOCATION: (1672)..(1674)
<223> OTHER INFORMATION: n is a, c, g, or u
<220> FEATURE:
<221> NAME/KEY: modified_base
<222> LOCATION: (1689)..(1689)
<223> OTHER INFORMATION: n is a, c, g, or u
<220> FEATURE:
<221> NAME/KEY: modified_base
<222> LOCATION: (1694)..(1694)
<223> OTHER INFORMATION: n is a, c, g, or u
<220> FEATURE:
<221> NAME/KEY: modified_base
<222> LOCATION: (1715)..(1717)
<223> OTHER INFORMATION: n is a, c, g, or u
<220> FEATURE:
<221> NAME/KEY: modified_base
<222> LOCATION: (1720)..(1720)
<223> OTHER INFORMATION: n is a, c, g, or u
<220> FEATURE:
<221> NAME/KEY: modified_base
<222> LOCATION: (1722)..(1723)
<223> OTHER INFORMATION: n is a, c, g, or u
<220> FEATURE:
<221> NAME/KEY: modified_base
<222> LOCATION: (1726)..(1734)
<223> OTHER INFORMATION: n is a, c, g, or u
<220> FEATURE:
<221> NAME/KEY: modified_base
<222> LOCATION: (1737)..(1738)
<223> OTHER INFORMATION: n is a, c, g, or u
<220> FEATURE:
<221> NAME/KEY: modified_base
<222> LOCATION: (1742)..(1746)
<223> OTHER INFORMATION: n is a, c, g, or u
<220> FEATURE:
<221> NAME/KEY: modified_base
<222> LOCATION: (1747)..(1830)
<223> OTHER INFORMATION: This region may encompass 4-84 variable bases,
      a, c, g, or u
<220> FEATURE:
<221> NAME/KEY: modified_base
<222> LOCATION: (1831)..(1835)
<223> OTHER INFORMATION: n is a, c, g, or u
<220> FEATURE:
<221> NAME/KEY: modified_base
<222> LOCATION: (1837)..(1837)
<223> OTHER INFORMATION: n is a, c, g, or u
<220> FEATURE:
<221> NAME/KEY: modified_base
<222> LOCATION: (1839)..(1839)
<223> OTHER INFORMATION: n is a, c, g, or u
<220> FEATURE:
<221> NAME/KEY: modified_base
<222> LOCATION: (1842)..(1851)
<223> OTHER INFORMATION: n is a, c, g, or u
<220> FEATURE:
<221> NAME/KEY: modified_base
<222> LOCATION: (1854)..(1854)
<223> OTHER INFORMATION: n is a, c, g, or u
<220> FEATURE:
<221> NAME/KEY: modified_base
<222> LOCATION: (1859)..(1861)
<223> OTHER INFORMATION: n is a, c, g, or u
```

```
<220> FEATURE:
<221> NAME/KEY: modified_base
<222> LOCATION: (1878)..(1878)
<223> OTHER INFORMATION: n is a, c, g, or u
<220> FEATURE:
<221> NAME/KEY: modified_base
<222> LOCATION: (1881)..(1881)
<223> OTHER INFORMATION: n is a, c, g, or u
<220> FEATURE:
<221> NAME/KEY: modified_base
<222> LOCATION: (1884)..(1886)
<223> OTHER INFORMATION: n is a, c, g, or u
<220> FEATURE:
<221> NAME/KEY: modified_base
<222> LOCATION: (1890)..(1891)
<223> OTHER INFORMATION: n is a, c, g, or u
<220> FEATURE:
<221> NAME/KEY: modified_base
<222> LOCATION: (1894)..(1894)
<223> OTHER INFORMATION: n is a, c, g, or u
<220> FEATURE:
<221> NAME/KEY: modified_base
<222> LOCATION: (1897)..(1897)
<223> OTHER INFORMATION: n is a, c, g, or u
<220> FEATURE:
<221> NAME/KEY: modified_base
<222> LOCATION: (1912)..(1912)
<223> OTHER INFORMATION: n is a, c, g, or u

<400> SEQUENCE: 6
nnnnnnnaga guugaucnu ggcucagnnn gaacgcuggc ggnnngcnun anacaugcaa      60
gucgancgnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnagngg cnnacggguy     240
aguaanncnu nnnnannunc cnnnnnnnnn ggnananunn nnngaaannn nnnnuaauac     300
cnnaunnnnn nnnnnnnnna aagnnnnnnn nnnnnnnnnn nnnnnnnnnn nnnnnnnnnn     360
nnnnnnnnnn nnnnnnnnnn nngannnnnn nnngnnnnau nagnunguug gunngguaan     420
ggcnnaccaa gncnnngann nnuagcngnn cugagaggnn gnncgccac anuggnacug       480
aganacggnc canacuccua cgggaggcag cagunnggaa unuunnncaa uggnngnaan     540
ncugannnag cnannccgcg ugnnnganga nggnnunnnn gnunguaaan nncununnnn     600
nnngangann nnnnnnnnnn nnnnnnnnnn nnnnnnnnnn ugacnnuann nnnnnannaa     660
gnnncggcna acuncgugcc agcagccgcg guaauacgna ggnngcagc guunnncgga       720
nunanugggc guaaagngnn ngaggnggn nnnnnnngun nnnngunaaa nnnnnnngcu      780
naacnnnnnn nnnncnnnnn nnacnnnnnn ncungagnnn nnnagnggnn nnnngaauun     840
nnnguguagn ggugnaaunc gnaganaunn gnangaanac cnnungcgaa ggcnnnnnnc     900
uggnnnnnna cugacncuna nnnncgaaag cnugggnagc naacaggauu agauacccug     960
guaguccang cnnuaaacgn ugnnnnnunn nngnnngnnn nnnnnnnnnn nnnnnnnnnn    1020
nnnnnnnnnn nnnnnnnnnn nnnnnnnan nnaacgnnnu aannnnnccg ccugggagu      1080
acgnncgcaa gnnunaaacu caaangaauu dacgggncc nngcacaagc ngnggagnau    1140
guggnuuaau ucgangnnac gcgnanaacc uuaccnnnnn uugacaunnn nnnnnnnnnn    1200
nngananann nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
acaggugnug cauggnuguc gucagcucgu gnngugagnu guuggguuaa gucccgnaac    1380
gagcgcaacc cnnnnnnnnn guuchancn nnnnnnnnnn nnnnnnnnnn nnnnnnnnnn     1440
nnnnnngngn acucnnnnnn nacugccnnn gnnnaannng gaggaaggng gggangacgu    1500
```

```
caanucnuca ugncccuuan gnnnngggcu ncacacnunc uacaauggnn nnnacanngn    1560
gnngcnannn ngnnannnnn agcnaancnn nnaaannnnn ucnnaguncg gaungnnnnc    1620
ugcaacucgn nnncnugaag nngganucgc uaguaaucgn nnaucagnan gnnncgguga    1680
auacguucnc gggncuugua cacaccgccc gucannncan gnnagnnnnn nnnnccnnaa    1740
gnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnncnang gnnnnnnnnn nganugggnn    1860
naagucguaa caagguancc nuannngaan nugnggnugg aucaccuccu un           1912
```

```
<210> SEQ ID NO 7
<211> LENGTH: 3702
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(35)
<223> OTHER INFORMATION: This region may encompass 0-35 variable bases,
      a, c, g, or u
<220> FEATURE:
<221> NAME/KEY: modified_base
<222> LOCATION: (36)..(38)
<223> OTHER INFORMATION: n is a, c, g, or u
<220> FEATURE:
<221> NAME/KEY: modified_base
<222> LOCATION: (42)..(46)
<223> OTHER INFORMATION: n is a, c, g, or u
<220> FEATURE:
<221> NAME/KEY: modified_base
<222> LOCATION: (50)..(50)
<223> OTHER INFORMATION: n is a, c, g, or u
<220> FEATURE:
<221> NAME/KEY: modified_base
<222> LOCATION: (52)..(56)
<223> OTHER INFORMATION: n is a, c, g, or u
<220> FEATURE:
<221> NAME/KEY: modified_base
<222> LOCATION: (68)..(68)
<223> OTHER INFORMATION: n is a, c, g, or u
<220> FEATURE:
<221> NAME/KEY: modified_base
<222> LOCATION: (72)..(77)
<223> OTHER INFORMATION: n is a, c, g, or u
<220> FEATURE:
<221> NAME/KEY: modified_base
<222> LOCATION: (80)..(80)
<223> OTHER INFORMATION: n is a, c, g, or u
<220> FEATURE:
<221> NAME/KEY: modified_base
<222> LOCATION: (84)..(84)
<223> OTHER INFORMATION: n is a, c, g, or u
<220> FEATURE:
<221> NAME/KEY: modified_base
<222> LOCATION: (91)..(91)
<223> OTHER INFORMATION: n is a, c, g, or u
<220> FEATURE:
<221> NAME/KEY: modified_base
<222> LOCATION: (93)..(99)
<223> OTHER INFORMATION: n is a, c, g, or u
<220> FEATURE:
<221> NAME/KEY: modified_base
<222> LOCATION: (101)..(102)
<223> OTHER INFORMATION: n is a, c, g, or u
<220> FEATURE:
<221> NAME/KEY: modified_base
<222> LOCATION: (104)..(106)
<223> OTHER INFORMATION: n is a, c, g, or u
<220> FEATURE:
<221> NAME/KEY: modified_base
<222> LOCATION: (108)..(109)
<223> OTHER INFORMATION: n is a, c, g, or u
```

```
<220> FEATURE:
<221> NAME/KEY: modified_base
<222> LOCATION: (111)..(113)
<223> OTHER INFORMATION: n is a, c, g, or u
<220> FEATURE:
<221> NAME/KEY: modified_base
<222> LOCATION: (116)..(117)
<223> OTHER INFORMATION: n is a, c, g, or u
<220> FEATURE:
<221> NAME/KEY: modified_base
<222> LOCATION: (120)..(121)
<223> OTHER INFORMATION: n is a, c, g, or u
<220> FEATURE:
<221> NAME/KEY: modified_base
<222> LOCATION: (123)..(130)
<223> OTHER INFORMATION: n is a, c, g, or u
<220> FEATURE:
<221> NAME/KEY: modified_base
<222> LOCATION: (132)..(135)
<223> OTHER INFORMATION: n is a, c, g, or u
<220> FEATURE:
<221> NAME/KEY: modified_base
<222> LOCATION: (136)..(136)
<223> OTHER INFORMATION: n is a, c, g, u, or not present
<220> FEATURE:
<221> NAME/KEY: modified_base
<222> LOCATION: (138)..(138)
<223> OTHER INFORMATION: n is a, c, g, or u
<220> FEATURE:
<221> NAME/KEY: modified_base
<222> LOCATION: (141)..(143)
<223> OTHER INFORMATION: n is a, c, g, or u
<220> FEATURE:
<221> NAME/KEY: modified_base
<222> LOCATION: (145)..(145)
<223> OTHER INFORMATION: n is a, c, g, or u
<220> FEATURE:
<221> NAME/KEY: modified_base
<222> LOCATION: (147)..(147)
<223> OTHER INFORMATION: n is a, c, g, or u
<220> FEATURE:
<221> NAME/KEY: modified_base
<222> LOCATION: (159)..(159)
<223> OTHER INFORMATION: n is a, c, g, or u
<220> FEATURE:
<221> NAME/KEY: modified_base
<222> LOCATION: (165)..(169)
<223> OTHER INFORMATION: n is a, c, g, or u
<220> FEATURE:
<221> NAME/KEY: modified_base
<222> LOCATION: (170)..(371)
<223> OTHER INFORMATION: This region may encompass 0-202 variable bases,
      a, c, g, or u
<220> FEATURE:
<221> NAME/KEY: modified_base
<222> LOCATION: (372)..(376)
<223> OTHER INFORMATION: n is a, c, g, or u
<220> FEATURE:
<221> NAME/KEY: modified_base
<222> LOCATION: (378)..(380)
<223> OTHER INFORMATION: n is a, c, g, or u
<220> FEATURE:
<221> NAME/KEY: modified_base
<222> LOCATION: (381)..(403)
<223> OTHER INFORMATION: This region may encompass 4-23 variable bases,
      a, c, g, or u
<220> FEATURE:
<221> NAME/KEY: modified_base
<222> LOCATION: (404)..(407)
<223> OTHER INFORMATION: n is a, c, g, or u
<220> FEATURE:
<221> NAME/KEY: modified_base
<222> LOCATION: (409)..(411)
<223> OTHER INFORMATION: n is a, c, g, or u
<220> FEATURE:
<221> NAME/KEY: modified_base
<222> LOCATION: (414)..(418)
<223> OTHER INFORMATION: n is a, c, g, or u
<220> FEATURE:
<221> NAME/KEY: modified_base
```

```
<222> LOCATION: (422)..(422)
<223> OTHER INFORMATION: n is a, c, g, or u
<220> FEATURE:
<221> NAME/KEY: modified_base
<222> LOCATION: (433)..(433)
<223> OTHER INFORMATION: n is a, c, g, or u
<220> FEATURE:
<221> NAME/KEY: modified_base
<222> LOCATION: (438)..(442)
<223> OTHER INFORMATION: n is a, c, g, or u
<220> FEATURE:
<221> NAME/KEY: modified_base
<222> LOCATION: (448)..(448)
<223> OTHER INFORMATION: n is a, c, g, or u
<220> FEATURE:
<221> NAME/KEY: modified_base
<222> LOCATION: (454)..(455)
<223> OTHER INFORMATION: n is a, c, g, or u
<220> FEATURE:
<221> NAME/KEY: modified_base
<222> LOCATION: (458)..(458)
<223> OTHER INFORMATION: n is a, c, g, or u
<220> FEATURE:
<221> NAME/KEY: modified_base
<222> LOCATION: (459)..(461)
<223> OTHER INFORMATION: This region may encompass 0-3 variable bases,
      a, c, g, or u
<220> FEATURE:
<221> NAME/KEY: modified_base
<222> LOCATION: (462)..(463)
<223> OTHER INFORMATION: n is a, c, g, or u
<220> FEATURE:
<221> NAME/KEY: modified_base
<222> LOCATION: (468)..(468)
<223> OTHER INFORMATION: n is a, c, g, or u
<220> FEATURE:
<221> NAME/KEY: modified_base
<222> LOCATION: (470)..(473)
<223> OTHER INFORMATION: n is a, c, g, or u
<220> FEATURE:
<221> NAME/KEY: modified_base
<222> LOCATION: (478)..(478)
<223> OTHER INFORMATION: n is a, c, g, or u
<220> FEATURE:
<221> NAME/KEY: modified_base
<222> LOCATION: (489)..(489)
<223> OTHER INFORMATION: n is a, c, g, u, or not present
<220> FEATURE:
<221> NAME/KEY: modified_base
<222> LOCATION: (490)..(491)
<223> OTHER INFORMATION: n is a, c, g, or u
<220> FEATURE:
<221> NAME/KEY: modified_base
<222> LOCATION: (493)..(493)
<223> OTHER INFORMATION: n is a, c, g, or u
<220> FEATURE:
<221> NAME/KEY: modified_base
<222> LOCATION: (495)..(496)
<223> OTHER INFORMATION: n is a, c, g, or u
<220> FEATURE:
<221> NAME/KEY: modified_base
<222> LOCATION: (499)..(499)
<223> OTHER INFORMATION: n is a, c, g, or u
<220> FEATURE:
<221> NAME/KEY: modified_base
<222> LOCATION: (501)..(501)
<223> OTHER INFORMATION: n is a, c, g, or u
<220> FEATURE:
<221> NAME/KEY: modified_base
<222> LOCATION: (502)..(592)
<223> OTHER INFORMATION: This region may encompass 0-91 variable bases,
      a, c, g, or u
<220> FEATURE:
<221> NAME/KEY: modified_base
<222> LOCATION: (593)..(601)
<223> OTHER INFORMATION: n is a, c, g, or u
<220> FEATURE:
<221> NAME/KEY: modified_base
<222> LOCATION: (602)..(602)
<223> OTHER INFORMATION: n is a, c, g, u, or not present
```

```
<220> FEATURE:
<221> NAME/KEY: modified_base
<222> LOCATION: (603)..(606)
<223> OTHER INFORMATION: n is a, c, g, or u
<220> FEATURE:
<221> NAME/KEY: modified_base
<222> LOCATION: (608)..(610)
<223> OTHER INFORMATION: n is a, c, g, or u
<220> FEATURE:
<221> NAME/KEY: modified_base
<222> LOCATION: (614)..(618)
<223> OTHER INFORMATION: n is a, c, g, or u
<220> FEATURE:
<221> NAME/KEY: modified_base
<222> LOCATION: (622)..(622)
<223> OTHER INFORMATION: n is a, c, g, or u
<220> FEATURE:
<221> NAME/KEY: modified_base
<222> LOCATION: (626)..(634)
<223> OTHER INFORMATION: n is a, c, g, or u
<220> FEATURE:
<221> NAME/KEY: modified_base
<222> LOCATION: (636)..(638)
<223> OTHER INFORMATION: n is a, c, g, or u
<220> FEATURE:
<221> NAME/KEY: modified_base
<222> LOCATION: (642)..(642)
<223> OTHER INFORMATION: n is a, c, g, or u
<220> FEATURE:
<221> NAME/KEY: modified_base
<222> LOCATION: (644)..(644)
<223> OTHER INFORMATION: n is a, c, g, or u
<220> FEATURE:
<221> NAME/KEY: modified_base
<222> LOCATION: (646)..(647)
<223> OTHER INFORMATION: n is a, c, g, or u
<220> FEATURE:
<221> NAME/KEY: modified_base
<222> LOCATION: (650)..(650)
<223> OTHER INFORMATION: n is a, c, g, or u
<220> FEATURE:
<221> NAME/KEY: modified_base
<222> LOCATION: (654)..(657)
<223> OTHER INFORMATION: n is a, c, g, or u
<220> FEATURE:
<221> NAME/KEY: modified_base
<222> LOCATION: (661)..(666)
<223> OTHER INFORMATION: n is a, c, g, or u
<220> FEATURE:
<221> NAME/KEY: modified_base
<222> LOCATION: (667)..(668)
<223> OTHER INFORMATION: This region may encompass 1-2 variable bases,
      a, c, g, or u
<220> FEATURE:
<221> NAME/KEY: modified_base
<222> LOCATION: (669)..(670)
<223> OTHER INFORMATION: n is a, c, g, or u
<220> FEATURE:
<221> NAME/KEY: modified_base
<222> LOCATION: (671)..(671)
<223> OTHER INFORMATION: n is a, c, g, u, or not present
<220> FEATURE:
<221> NAME/KEY: modified_base
<222> LOCATION: (672)..(673)
<223> OTHER INFORMATION: n is a, c, g, or u
<220> FEATURE:
<221> NAME/KEY: modified_base
<222> LOCATION: (674)..(690)
<223> OTHER INFORMATION: This region may encompass 3-17 variable bases,
      a, c, g, or u
<220> FEATURE:
<221> NAME/KEY: modified_base
<222> LOCATION: (691)..(691)
<223> OTHER INFORMATION: n is a, c, g, or u
<220> FEATURE:
<221> NAME/KEY: modified_base
<222> LOCATION: (696)..(698)
<223> OTHER INFORMATION: n is a, c, g, or u
<220> FEATURE:
<221> NAME/KEY: modified_base
```

-continued

```
<222> LOCATION: (700)..(703)
<223> OTHER INFORMATION: n is a, c, g, or u
<220> FEATURE:
<221> NAME/KEY: modified_base
<222> LOCATION: (705)..(705)
<223> OTHER INFORMATION: n is a, c, g, or u
<220> FEATURE:
<221> NAME/KEY: modified_base
<222> LOCATION: (708)..(708)
<223> OTHER INFORMATION: n is a, c, g, or u
<220> FEATURE:
<221> NAME/KEY: modified_base
<222> LOCATION: (710)..(711)
<223> OTHER INFORMATION: n is a, c, g, or u
<220> FEATURE:
<221> NAME/KEY: modified_base
<222> LOCATION: (713)..(716)
<223> OTHER INFORMATION: n is a, c, g, or u
<220> FEATURE:
<221> NAME/KEY: modified_base
<222> LOCATION: (719)..(720)
<223> OTHER INFORMATION: n is a, c, g, or u
<220> FEATURE:
<221> NAME/KEY: modified_base
<222> LOCATION: (724)..(726)
<223> OTHER INFORMATION: n is a, c, g, or u
<220> FEATURE:
<221> NAME/KEY: modified_base
<222> LOCATION: (728)..(731)
<223> OTHER INFORMATION: n is a, c, g, or u
<220> FEATURE:
<221> NAME/KEY: modified_base
<222> LOCATION: (737)..(742)
<223> OTHER INFORMATION: n is a, c, g, or u
<220> FEATURE:
<221> NAME/KEY: modified_base
<222> LOCATION: (746)..(746)
<223> OTHER INFORMATION: n is a, c, g, or u
<220> FEATURE:
<221> NAME/KEY: modified_base
<222> LOCATION: (756)..(762)
<223> OTHER INFORMATION: n is a, c, g, or u
<220> FEATURE:
<221> NAME/KEY: modified_base
<222> LOCATION: (767)..(767)
<223> OTHER INFORMATION: n is a, c, g, or u
<220> FEATURE:
<221> NAME/KEY: modified_base
<222> LOCATION: (772)..(772)
<223> OTHER INFORMATION: n is a, c, g, or u
<220> FEATURE:
<221> NAME/KEY: modified_base
<222> LOCATION: (774)..(774)
<223> OTHER INFORMATION: n is a, c, g, or u
<220> FEATURE:
<221> NAME/KEY: modified_base
<222> LOCATION: (776)..(777)
<223> OTHER INFORMATION: This region may encompass 0-2 variable bases,
      a, c, g, or u
<220> FEATURE:
<221> NAME/KEY: modified_base
<222> LOCATION: (778)..(778)
<223> OTHER INFORMATION: n is a, c, g, or u
<220> FEATURE:
<221> NAME/KEY: modified_base
<222> LOCATION: (784)..(784)
<223> OTHER INFORMATION: n is a, c, g, or u
<220> FEATURE:
<221> NAME/KEY: modified_base
<222> LOCATION: (789)..(789)
<223> OTHER INFORMATION: n is a, c, g, or u
<220> FEATURE:
<221> NAME/KEY: modified_base
<222> LOCATION: (797)..(797)
<223> OTHER INFORMATION: n is a, c, g, or u
<220> FEATURE:
<221> NAME/KEY: modified_base
<222> LOCATION: (804)..(804)
<223> OTHER INFORMATION: n is a, c, g, or u
<220> FEATURE:
```

```
<221> NAME/KEY: modified_base
<222> LOCATION: (809)..(811)
<223> OTHER INFORMATION: n is a, c, g, or u
<220> FEATURE:
<221> NAME/KEY: modified_base
<222> LOCATION: (812)..(812)
<223> OTHER INFORMATION: n is a, c, g, u, or not present
<220> FEATURE:
<221> NAME/KEY: modified_base
<222> LOCATION: (813)..(813)
<223> OTHER INFORMATION: n is a, c, g, or u
<220> FEATURE:
<221> NAME/KEY: modified_base
<222> LOCATION: (815)..(815)
<223> OTHER INFORMATION: n is a, c, g, or u
<220> FEATURE:
<221> NAME/KEY: modified_base
<222> LOCATION: (826)..(826)
<223> OTHER INFORMATION: n is a, c, g, or u
<220> FEATURE:
<221> NAME/KEY: modified_base
<222> LOCATION: (829)..(830)
<223> OTHER INFORMATION: n is a, c, g, or u
<220> FEATURE:
<221> NAME/KEY: modified_base
<222> LOCATION: (840)..(844)
<223> OTHER INFORMATION: n is a, c, g, or u
<220> FEATURE:
<221> NAME/KEY: modified_base
<222> LOCATION: (846)..(846)
<223> OTHER INFORMATION: n is a, c, g, or u
<220> FEATURE:
<221> NAME/KEY: modified_base
<222> LOCATION: (849)..(849)
<223> OTHER INFORMATION: n is a, c, g, or u
<220> FEATURE:
<221> NAME/KEY: modified_base
<222> LOCATION: (852)..(854)
<223> OTHER INFORMATION: n is a, c, g, or u
<220> FEATURE:
<221> NAME/KEY: modified_base
<222> LOCATION: (857)..(859)
<223> OTHER INFORMATION: n is a, c, g, or u
<220> FEATURE:
<221> NAME/KEY: modified_base
<222> LOCATION: (862)..(864)
<223> OTHER INFORMATION: n is a, c, g, or u
<220> FEATURE:
<221> NAME/KEY: modified_base
<222> LOCATION: (865)..(897)
<223> OTHER INFORMATION: This region may encompass 4-33 variable bases,
      a, c, g, or u
<220> FEATURE:
<221> NAME/KEY: modified_base
<222> LOCATION: (898)..(900)
<223> OTHER INFORMATION: n is a, c, g, or u
<220> FEATURE:
<221> NAME/KEY: modified_base
<222> LOCATION: (904)..(905)
<223> OTHER INFORMATION: n is a, c, g, or u
<220> FEATURE:
<221> NAME/KEY: modified_base
<222> LOCATION: (910)..(910)
<223> OTHER INFORMATION: n is a, c, g, or u
<220> FEATURE:
<221> NAME/KEY: modified_base
<222> LOCATION: (918)..(918)
<223> OTHER INFORMATION: n is a, c, g, or u
<220> FEATURE:
<221> NAME/KEY: modified_base
<222> LOCATION: (920)..(921)
<223> OTHER INFORMATION: n is a, c, g, or u
<220> FEATURE:
<221> NAME/KEY: modified_base
<222> LOCATION: (925)..(927)
<223> OTHER INFORMATION: n is a, c, g, or u
<220> FEATURE:
<221> NAME/KEY: modified_base
<222> LOCATION: (929)..(929)
<223> OTHER INFORMATION: n is a, c, g, or u
```

-continued

```
<220> FEATURE:
<221> NAME/KEY: modified_base
<222> LOCATION: (931)..(931)
<223> OTHER INFORMATION: n is a, c, g, or u
<220> FEATURE:
<221> NAME/KEY: modified_base
<222> LOCATION: (934)..(934)
<223> OTHER INFORMATION: n is a, c, g, or u
<220> FEATURE:
<221> NAME/KEY: modified_base
<222> LOCATION: (937)..(940)
<223> OTHER INFORMATION: n is a, c, g, or u
<220> FEATURE:
<221> NAME/KEY: modified_base
<222> LOCATION: (942)..(946)
<223> OTHER INFORMATION: n is a, c, g, or u
<220> FEATURE:
<221> NAME/KEY: modified_base
<222> LOCATION: (949)..(949)
<223> OTHER INFORMATION: n is a, c, g, or u
<220> FEATURE:
<221> NAME/KEY: modified_base
<222> LOCATION: (952)..(952)
<223> OTHER INFORMATION: n is a, c, g, or u
<220> FEATURE:
<221> NAME/KEY: modified_base
<222> LOCATION: (957)..(958)
<223> OTHER INFORMATION: n is a, c, g, or u
<220> FEATURE:
<221> NAME/KEY: modified_base
<222> LOCATION: (959)..(963)
<223> OTHER INFORMATION: This region may encompass 1-5 variable bases,
      a, c, g, or u
<220> FEATURE:
<221> NAME/KEY: modified_base
<222> LOCATION: (964)..(968)
<223> OTHER INFORMATION: n is a, c, g, or u
<220> FEATURE:
<221> NAME/KEY: modified_base
<222> LOCATION: (970)..(970)
<223> OTHER INFORMATION: n is a, c, g, or u
<220> FEATURE:
<221> NAME/KEY: modified_base
<222> LOCATION: (973)..(973)
<223> OTHER INFORMATION: n is a, c, g, or u
<220> FEATURE:
<221> NAME/KEY: modified_base
<222> LOCATION: (976)..(976)
<223> OTHER INFORMATION: n is a, c, g, or u
<220> FEATURE:
<221> NAME/KEY: modified_base
<222> LOCATION: (979)..(979)
<223> OTHER INFORMATION: n is a, c, g, or u
<220> FEATURE:
<221> NAME/KEY: modified_base
<222> LOCATION: (984)..(984)
<223> OTHER INFORMATION: n is a, c, g, or u
<220> FEATURE:
<221> NAME/KEY: modified_base
<222> LOCATION: (990)..(992)
<223> OTHER INFORMATION: n is a, c, g, or u
<220> FEATURE:
<221> NAME/KEY: modified_base
<222> LOCATION: (995)..(996)
<223> OTHER INFORMATION: n is a, c, g, or u
<220> FEATURE:
<221> NAME/KEY: modified_base
<222> LOCATION: (998)..(998)
<223> OTHER INFORMATION: n is a, c, g, or u
<220> FEATURE:
<221> NAME/KEY: modified_base
<222> LOCATION: (1002)..(1004)
<223> OTHER INFORMATION: n is a, c, g, or u
<220> FEATURE:
<221> NAME/KEY: modified_base
<222> LOCATION: (1008)..(1012)
<223> OTHER INFORMATION: n is a, c, g, or u
<220> FEATURE:
<221> NAME/KEY: modified_base
<222> LOCATION: (1014)..(1017)
```

-continued

```
<223> OTHER INFORMATION: n is a, c, g, or u
<220> FEATURE:
<221> NAME/KEY: modified_base
<222> LOCATION: (1022)..(1022)
<223> OTHER INFORMATION: n is a, c, g, or u
<220> FEATURE:
<221> NAME/KEY: modified_base
<222> LOCATION: (1027)..(1027)
<223> OTHER INFORMATION: n is a, c, g, or u
<220> FEATURE:
<221> NAME/KEY: modified_base
<222> LOCATION: (1029)..(1031)
<223> OTHER INFORMATION: n is a, c, g, or u
<220> FEATURE:
<221> NAME/KEY: modified_base
<222> LOCATION: (1036)..(1036)
<223> OTHER INFORMATION: n is a, c, g, or u
<220> FEATURE:
<221> NAME/KEY: modified_base
<222> LOCATION: (1040)..(1042)
<223> OTHER INFORMATION: n is a, c, g, or u
<220> FEATURE:
<221> NAME/KEY: modified_base
<222> LOCATION: (1046)..(1047)
<223> OTHER INFORMATION: n is a, c, g, or u
<220> FEATURE:
<221> NAME/KEY: modified_base
<222> LOCATION: (1052)..(1052)
<223> OTHER INFORMATION: n is a, c, g, or u
<220> FEATURE:
<221> NAME/KEY: modified_base
<222> LOCATION: (1058)..(1062)
<223> OTHER INFORMATION: n is a, c, g, or u
<220> FEATURE:
<221> NAME/KEY: modified_base
<222> LOCATION: (1067)..(1067)
<223> OTHER INFORMATION: n is a, c, g, or u
<220> FEATURE:
<221> NAME/KEY: modified_base
<222> LOCATION: (1069)..(1073)
<223> OTHER INFORMATION: n is a, c, g, or u
<220> FEATURE:
<221> NAME/KEY: modified_base
<222> LOCATION: (1080)..(1080)
<223> OTHER INFORMATION: n is a, c, g, or u
<220> FEATURE:
<221> NAME/KEY: modified_base
<222> LOCATION: (1087)..(1094)
<223> OTHER INFORMATION: n is a, c, g, or u
<220> FEATURE:
<221> NAME/KEY: modified_base
<222> LOCATION: (1103)..(1108)
<223> OTHER INFORMATION: n is a, c, g, or u
<220> FEATURE:
<221> NAME/KEY: modified_base
<222> LOCATION: (1115)..(1116)
<223> OTHER INFORMATION: n is a, c, g, or u
<220> FEATURE:
<221> NAME/KEY: modified_base
<222> LOCATION: (1121)..(1122)
<223> OTHER INFORMATION: n is a, c, g, or u
<220> FEATURE:
<221> NAME/KEY: modified_base
<222> LOCATION: (1124)..(1124)
<223> OTHER INFORMATION: n is a, c, g, or u
<220> FEATURE:
<221> NAME/KEY: modified_base
<222> LOCATION: (1126)..(1126)
<223> OTHER INFORMATION: n is a, c, g, or u
<220> FEATURE:
<221> NAME/KEY: modified_base
<222> LOCATION: (1129)..(1129)
<223> OTHER INFORMATION: n is a, c, g, or u
<220> FEATURE:
<221> NAME/KEY: modified_base
<222> LOCATION: (1134)..(1135)
<223> OTHER INFORMATION: n is a, c, g, or u
<220> FEATURE:
<221> NAME/KEY: modified_base
<222> LOCATION: (1137)..(1137)
```

```
<223> OTHER INFORMATION: n is a, c, g, or u
<220> FEATURE:
<221> NAME/KEY: modified_base
<222> LOCATION: (1140)..(1140)
<223> OTHER INFORMATION: n is a, c, g, or u
<220> FEATURE:
<221> NAME/KEY: modified_base
<222> LOCATION: (1142)..(1142)
<223> OTHER INFORMATION: n is a, c, g, or u
<220> FEATURE:
<221> NAME/KEY: modified_base
<222> LOCATION: (1146)..(1148)
<223> OTHER INFORMATION: n is a, c, g, or u
<220> FEATURE:
<221> NAME/KEY: modified_base
<222> LOCATION: (1150)..(1151)
<223> OTHER INFORMATION: n is a, c, g, or u
<220> FEATURE:
<221> NAME/KEY: modified_base
<222> LOCATION: (1165)..(1166)
<223> OTHER INFORMATION: n is a, c, g, or u
<220> FEATURE:
<221> NAME/KEY: modified_base
<222> LOCATION: (1172)..(1175)
<223> OTHER INFORMATION: n is a, c, g, or u
<220> FEATURE:
<221> NAME/KEY: modified_base
<222> LOCATION: (1182)..(1185)
<223> OTHER INFORMATION: n is a, c, g, or u
<220> FEATURE:
<221> NAME/KEY: modified_base
<222> LOCATION: (1188)..(1188)
<223> OTHER INFORMATION: n is a, c, g, or u
<220> FEATURE:
<221> NAME/KEY: modified_base
<222> LOCATION: (1190)..(1195)
<223> OTHER INFORMATION: n is a, c, g, or u
<220> FEATURE:
<221> NAME/KEY: modified_base
<222> LOCATION: (1196)..(1198)
<223> OTHER INFORMATION: This region may encompass 0-3 variable bases,
      a, c, g, or u
<220> FEATURE:
<221> NAME/KEY: modified_base
<222> LOCATION: (1199)..(1206)
<223> OTHER INFORMATION: n is a, c, g, or u
<220> FEATURE:
<221> NAME/KEY: modified_base
<222> LOCATION: (1209)..(1209)
<223> OTHER INFORMATION: n is a, c, g, or u
<220> FEATURE:
<221> NAME/KEY: modified_base
<222> LOCATION: (1222)..(1231)
<223> OTHER INFORMATION: n is a, c, g, or u
<220> FEATURE:
<221> NAME/KEY: modified_base
<222> LOCATION: (1234)..(1241)
<223> OTHER INFORMATION: n is a, c, g, or u
<220> FEATURE:
<221> NAME/KEY: modified_base
<222> LOCATION: (1242)..(1242)
<223> OTHER INFORMATION: n is a, c, g, u, or not present
<220> FEATURE:
<221> NAME/KEY: modified_base
<222> LOCATION: (1243)..(1246)
<223> OTHER INFORMATION: n is a, c, g, or u
<220> FEATURE:
<221> NAME/KEY: modified_base
<222> LOCATION: (1250)..(1251)
<223> OTHER INFORMATION: n is a, c, g, or u
<220> FEATURE:
<221> NAME/KEY: modified_base
<222> LOCATION: (1253)..(1260)
<223> OTHER INFORMATION: n is a, c, g, or u
<220> FEATURE:
<221> NAME/KEY: modified_base
<222> LOCATION: (1266)..(1266)
<223> OTHER INFORMATION: n is a, c, g, or u
<220> FEATURE:
<221> NAME/KEY: modified_base
```

-continued

```
<222> LOCATION: (1272)..(1272)
<223> OTHER INFORMATION: n is a, c, g, or u
<220> FEATURE:
<221> NAME/KEY: modified_base
<222> LOCATION: (1275)..(1278)
<223> OTHER INFORMATION: n is a, c, g, or u
<220> FEATURE:
<221> NAME/KEY: modified_base
<222> LOCATION: (1279)..(1281)
<223> OTHER INFORMATION: This region may encompass 0-3 variable bases,
      a, c, g, or u
<220> FEATURE:
<221> NAME/KEY: modified_base
<222> LOCATION: (1282)..(1284)
<223> OTHER INFORMATION: n is a, c, g, or u
<220> FEATURE:
<221> NAME/KEY: modified_base
<222> LOCATION: (1285)..(1289)
<223> OTHER INFORMATION: This region may encompass 0-5 variable bases,
      a, c, g, or u
<220> FEATURE:
<221> NAME/KEY: modified_base
<222> LOCATION: (1290)..(1295)
<223> OTHER INFORMATION: n is a, c, g, or u
<220> FEATURE:
<221> NAME/KEY: modified_base
<222> LOCATION: (1297)..(1297)
<223> OTHER INFORMATION: n is a, c, g, or u
<220> FEATURE:
<221> NAME/KEY: modified_base
<222> LOCATION: (1300)..(1301)
<223> OTHER INFORMATION: n is a, c, g, or u
<220> FEATURE:
<221> NAME/KEY: modified_base
<222> LOCATION: (1303)..(1304)
<223> OTHER INFORMATION: n is a, c, g, or u
<220> FEATURE:
<221> NAME/KEY: modified_base
<222> LOCATION: (1306)..(1308)
<223> OTHER INFORMATION: n is a, c, g, or u
<220> FEATURE:
<221> NAME/KEY: modified_base
<222> LOCATION: (1310)..(1310)
<223> OTHER INFORMATION: n is a, c, g, or u
<220> FEATURE:
<221> NAME/KEY: modified_base
<222> LOCATION: (1312)..(1312)
<223> OTHER INFORMATION: n is a, c, g, or u
<220> FEATURE:
<221> NAME/KEY: modified_base
<222> LOCATION: (1314)..(1314)
<223> OTHER INFORMATION: n is a, c, g, or u
<220> FEATURE:
<221> NAME/KEY: modified_base
<222> LOCATION: (1318)..(1319)
<223> OTHER INFORMATION: n is a, c, g, or u
<220> FEATURE:
<221> NAME/KEY: modified_base
<222> LOCATION: (1321)..(1321)
<223> OTHER INFORMATION: n is a, c, g, or u
<220> FEATURE:
<221> NAME/KEY: modified_base
<222> LOCATION: (1323)..(1325)
<223> OTHER INFORMATION: n is a, c, g, or u
<220> FEATURE:
<221> NAME/KEY: modified_base
<222> LOCATION: (1328)..(1329)
<223> OTHER INFORMATION: n is a, c, g, or u
<220> FEATURE:
<221> NAME/KEY: modified_base
<222> LOCATION: (1331)..(1331)
<223> OTHER INFORMATION: n is a, c, g, or u
<220> FEATURE:
<221> NAME/KEY: modified_base
<222> LOCATION: (1336)..(1336)
<223> OTHER INFORMATION: n is a, c, g, or u
<220> FEATURE:
<221> NAME/KEY: modified_base
<222> LOCATION: (1341)..(1341)
<223> OTHER INFORMATION: n is a, c, g, or u
```

-continued

```
<220> FEATURE:
<221> NAME/KEY: modified_base
<222> LOCATION: (1348)..(1348)
<223> OTHER INFORMATION: n is a, c, g, or u
<220> FEATURE:
<221> NAME/KEY: modified_base
<222> LOCATION: (1350)..(1351)
<223> OTHER INFORMATION: n is a, c, g, or u
<220> FEATURE:
<221> NAME/KEY: modified_base
<222> LOCATION: (1353)..(1355)
<223> OTHER INFORMATION: n is a, c, g, or u
<220> FEATURE:
<221> NAME/KEY: modified_base
<222> LOCATION: (1361)..(1361)
<223> OTHER INFORMATION: n is a, c, g, or u
<220> FEATURE:
<221> NAME/KEY: modified_base
<222> LOCATION: (1365)..(1365)
<223> OTHER INFORMATION: n is a, c, g, or u
<220> FEATURE:
<221> NAME/KEY: modified_base
<222> LOCATION: (1368)..(1368)
<223> OTHER INFORMATION: n is a, c, g, or u
<220> FEATURE:
<221> NAME/KEY: modified_base
<222> LOCATION: (1369)..(1369)
<223> OTHER INFORMATION: n is a, c, g, u, or not present
<220> FEATURE:
<221> NAME/KEY: modified_base
<222> LOCATION: (1370)..(1375)
<223> OTHER INFORMATION: n is a, c, g, or u
<220> FEATURE:
<221> NAME/KEY: modified_base
<222> LOCATION: (1383)..(1383)
<223> OTHER INFORMATION: n is a, c, g, or u
<220> FEATURE:
<221> NAME/KEY: modified_base
<222> LOCATION: (1387)..(1387)
<223> OTHER INFORMATION: n is a, c, g, or u
<220> FEATURE:
<221> NAME/KEY: modified_base
<222> LOCATION: (1390)..(1390)
<223> OTHER INFORMATION: n is a, c, g, or u
<220> FEATURE:
<221> NAME/KEY: modified_base
<222> LOCATION: (1394)..(1399)
<223> OTHER INFORMATION: n is a, c, g, or u
<220> FEATURE:
<221> NAME/KEY: modified_base
<222> LOCATION: (1401)..(1402)
<223> OTHER INFORMATION: n is a, c, g, or u
<220> FEATURE:
<221> NAME/KEY: modified_base
<222> LOCATION: (1404)..(1404)
<223> OTHER INFORMATION: n is a, c, g, or u
<220> FEATURE:
<221> NAME/KEY: modified_base
<222> LOCATION: (1408)..(1410)
<223> OTHER INFORMATION: n is a, c, g, or u
<220> FEATURE:
<221> NAME/KEY: modified_base
<222> LOCATION: (1415)..(1415)
<223> OTHER INFORMATION: n is a, c, g, or u
<220> FEATURE:
<221> NAME/KEY: modified_base
<222> LOCATION: (1435)..(1435)
<223> OTHER INFORMATION: n is a, c, g, or u
<220> FEATURE:
<221> NAME/KEY: modified_base
<222> LOCATION: (1437)..(1437)
<223> OTHER INFORMATION: n is a, c, g, or u
<220> FEATURE:
<221> NAME/KEY: modified_base
<222> LOCATION: (1440)..(1440)
<223> OTHER INFORMATION: n is a, c, g, or u
<220> FEATURE:
<221> NAME/KEY: modified_base
<222> LOCATION: (1446)..(1447)
<223> OTHER INFORMATION: n is a, c, g, or u
```

```
<220> FEATURE:
<221> NAME/KEY: modified_base
<222> LOCATION: (1454)..(1454)
<223> OTHER INFORMATION: n is a, c, g, or u
<220> FEATURE:
<221> NAME/KEY: modified_base
<222> LOCATION: (1463)..(1464)
<223> OTHER INFORMATION: n is a, c, g, or u
<220> FEATURE:
<221> NAME/KEY: modified_base
<222> LOCATION: (1467)..(1467)
<223> OTHER INFORMATION: n is a, c, g, or u
<220> FEATURE:
<221> NAME/KEY: modified_base
<222> LOCATION: (1470)..(1476)
<223> OTHER INFORMATION: n is a, c, g, or u
<220> FEATURE:
<221> NAME/KEY: modified_base
<222> LOCATION: (1481)..(1481)
<223> OTHER INFORMATION: n is a, c, g, or u
<220> FEATURE:
<221> NAME/KEY: modified_base
<222> LOCATION: (1484)..(1485)
<223> OTHER INFORMATION: n is a, c, g, or u
<220> FEATURE:
<221> NAME/KEY: modified_base
<222> LOCATION: (1488)..(1488)
<223> OTHER INFORMATION: n is a, c, g, or u
<220> FEATURE:
<221> NAME/KEY: modified_base
<222> LOCATION: (1491)..(1491)
<223> OTHER INFORMATION: n is a, c, g, or u
<220> FEATURE:
<221> NAME/KEY: modified_base
<222> LOCATION: (1496)..(1496)
<223> OTHER INFORMATION: n is a, c, g, or u
<220> FEATURE:
<221> NAME/KEY: modified_base
<222> LOCATION: (1501)..(1508)
<223> OTHER INFORMATION: n is a, c, g, or u
<220> FEATURE:
<221> NAME/KEY: modified_base
<222> LOCATION: (1514)..(1519)
<223> OTHER INFORMATION: n is a, c, g, or u
<220> FEATURE:
<221> NAME/KEY: modified_base
<222> LOCATION: (1521)..(1525)
<223> OTHER INFORMATION: n is a, c, g, or u
<220> FEATURE:
<221> NAME/KEY: modified_base
<222> LOCATION: (1526)..(1712)
<223> OTHER INFORMATION: This region may encompass 0-187 variable bases,
      a, c, g, or u
<220> FEATURE:
<221> NAME/KEY: modified_base
<222> LOCATION: (1713)..(1717)
<223> OTHER INFORMATION: n is a, c, g, or u
<220> FEATURE:
<221> NAME/KEY: modified_base
<222> LOCATION: (1723)..(1724)
<223> OTHER INFORMATION: n is a, c, g, or u
<220> FEATURE:
<221> NAME/KEY: modified_base
<222> LOCATION: (1731)..(1736)
<223> OTHER INFORMATION: n is a, c, g, or u
<220> FEATURE:
<221> NAME/KEY: modified_base
<222> LOCATION: (1737)..(1839)
<223> OTHER INFORMATION: This region may encompass 0-103 variable bases,
      a, c, g, or u
<220> FEATURE:
<221> NAME/KEY: modified_base
<222> LOCATION: (1840)..(1845)
<223> OTHER INFORMATION: n is a, c, g, or u
<220> FEATURE:
<221> NAME/KEY: modified_base
<222> LOCATION: (1850)..(1856)
<223> OTHER INFORMATION: n is a, c, g, or u
<220> FEATURE:
<221> NAME/KEY: modified_base
```

```
<222> LOCATION: (1858)..(1859)
<223> OTHER INFORMATION: n is a, c, g, or u
<220> FEATURE:
<221> NAME/KEY: modified_base
<222> LOCATION: (1861)..(1867)
<223> OTHER INFORMATION: n is a, c, g, or u
<220> FEATURE:
<221> NAME/KEY: modified_base
<222> LOCATION: (1872)..(1880)
<223> OTHER INFORMATION: n is a, c, g, or u
<220> FEATURE:
<221> NAME/KEY: modified_base
<222> LOCATION: (1885)..(1885)
<223> OTHER INFORMATION: n is a, c, g, or u
<220> FEATURE:
<221> NAME/KEY: modified_base
<222> LOCATION: (1887)..(1887)
<223> OTHER INFORMATION: n is a, c, g, or u
<220> FEATURE:
<221> NAME/KEY: modified_base
<222> LOCATION: (1891)..(1892)
<223> OTHER INFORMATION: n is a, c, g, or u
<220> FEATURE:
<221> NAME/KEY: modified_base
<222> LOCATION: (1894)..(1895)
<223> OTHER INFORMATION: n is a, c, g, or u
<220> FEATURE:
<221> NAME/KEY: modified_base
<222> LOCATION: (1898)..(1898)
<223> OTHER INFORMATION: n is a, c, g, or u
<220> FEATURE:
<221> NAME/KEY: modified_base
<222> LOCATION: (1903)..(1903)
<223> OTHER INFORMATION: n is a, c, g, or u
<220> FEATURE:
<221> NAME/KEY: modified_base
<222> LOCATION: (1907)..(1909)
<223> OTHER INFORMATION: This region may encompass 1-3 variable bases,
      a, c, g, or u
<220> FEATURE:
<221> NAME/KEY: modified_base
<222> LOCATION: (1910)..(1914)
<223> OTHER INFORMATION: n is a, c, g, or u
<220> FEATURE:
<221> NAME/KEY: modified_base
<222> LOCATION: (1919)..(1919)
<223> OTHER INFORMATION: n is a, c, g, or u
<220> FEATURE:
<221> NAME/KEY: modified_base
<222> LOCATION: (1921)..(1922)
<223> OTHER INFORMATION: n is a, c, g, or u
<220> FEATURE:
<221> NAME/KEY: modified_base
<222> LOCATION: (1924)..(1928)
<223> OTHER INFORMATION: n is a, c, g, or u
<220> FEATURE:
<221> NAME/KEY: modified_base
<222> LOCATION: (1930)..(1930)
<223> OTHER INFORMATION: n is a, c, g, or u
<220> FEATURE:
<221> NAME/KEY: modified_base
<222> LOCATION: (1934)..(1934)
<223> OTHER INFORMATION: n is a, c, g, or u
<220> FEATURE:
<221> NAME/KEY: modified_base
<222> LOCATION: (1936)..(1938)
<223> OTHER INFORMATION: n is a, c, g, or u
<220> FEATURE:
<221> NAME/KEY: modified_base
<222> LOCATION: (1940)..(1940)
<223> OTHER INFORMATION: n is a, c, g, or u
<220> FEATURE:
<221> NAME/KEY: modified_base
<222> LOCATION: (1945)..(1945)
<223> OTHER INFORMATION: n is a, c, g, or u
<220> FEATURE:
<221> NAME/KEY: modified_base
<222> LOCATION: (1950)..(1955)
<223> OTHER INFORMATION: n is a, c, g, or u
<220> FEATURE:
```

```
<221> NAME/KEY: modified_base
<222> LOCATION: (1957)..(1957)
<223> OTHER INFORMATION: n is a, c, g, or u
<220> FEATURE:
<221> NAME/KEY: modified_base
<222> LOCATION: (1959)..(1959)
<223> OTHER INFORMATION: n is a, c, g, or u
<220> FEATURE:
<221> NAME/KEY: modified_base
<222> LOCATION: (1961)..(1962)
<223> OTHER INFORMATION: n is a, c, g, or u
<220> FEATURE:
<221> NAME/KEY: modified_base
<222> LOCATION: (1965)..(1970)
<223> OTHER INFORMATION: n is a, c, g, or u
<220> FEATURE:
<221> NAME/KEY: modified_base
<222> LOCATION: (1975)..(1975)
<223> OTHER INFORMATION: n is a, c, g, or u
<220> FEATURE:
<221> NAME/KEY: modified_base
<222> LOCATION: (1981)..(1983)
<223> OTHER INFORMATION: n is a, c, g, or u
<220> FEATURE:
<221> NAME/KEY: modified_base
<222> LOCATION: (1990)..(1991)
<223> OTHER INFORMATION: n is a, c, g, or u
<220> FEATURE:
<221> NAME/KEY: modified_base
<222> LOCATION: (1995)..(1995)
<223> OTHER INFORMATION: n is a, c, g, or u
<220> FEATURE:
<221> NAME/KEY: modified_base
<222> LOCATION: (1997)..(1997)
<223> OTHER INFORMATION: n is a, c, g, or u
<220> FEATURE:
<221> NAME/KEY: modified_base
<222> LOCATION: (2000)..(2000)
<223> OTHER INFORMATION: n is a, c, g, or u
<220> FEATURE:
<221> NAME/KEY: modified_base
<222> LOCATION: (2002)..(2002)
<223> OTHER INFORMATION: n is a, c, g, or u
<220> FEATURE:
<221> NAME/KEY: modified_base
<222> LOCATION: (2004)..(2004)
<223> OTHER INFORMATION: n is a, c, g, or u
<220> FEATURE:
<221> NAME/KEY: modified_base
<222> LOCATION: (2005)..(2005)
<223> OTHER INFORMATION: n is a, c, g, u, or not present
<220> FEATURE:
<221> NAME/KEY: modified_base
<222> LOCATION: (2009)..(2010)
<223> OTHER INFORMATION: n is a, c, g, or u
<220> FEATURE:
<221> NAME/KEY: modified_base
<222> LOCATION: (2016)..(2017)
<223> OTHER INFORMATION: n is a, c, g, or u
<220> FEATURE:
<221> NAME/KEY: modified_base
<222> LOCATION: (2019)..(2021)
<223> OTHER INFORMATION: n is a, c, g, or u
<220> FEATURE:
<221> NAME/KEY: modified_base
<222> LOCATION: (2025)..(2026)
<223> OTHER INFORMATION: n is a, c, g, or u
<220> FEATURE:
<221> NAME/KEY: modified_base
<222> LOCATION: (2034)..(2036)
<223> OTHER INFORMATION: n is a, c, g, or u
<220> FEATURE:
<221> NAME/KEY: modified_base
<222> LOCATION: (2039)..(2044)
<223> OTHER INFORMATION: n is a, c, g, or u
<220> FEATURE:
<221> NAME/KEY: modified_base
<222> LOCATION: (2045)..(2045)
<223> OTHER INFORMATION: n is a, c, g, u, or not present
<220> FEATURE:
```

```
<221> NAME/KEY: modified_base
<222> LOCATION: (2046)..(2046)
<223> OTHER INFORMATION: n is a, c, g, or u
<220> FEATURE:
<221> NAME/KEY: modified_base
<222> LOCATION: (2047)..(2165)
<223> OTHER INFORMATION: This region may encompass 0-119 variable bases,
      a, c, g, or u
<220> FEATURE:
<221> NAME/KEY: modified_base
<222> LOCATION: (2166)..(2168)
<223> OTHER INFORMATION: n is a, c, g, or u
<220> FEATURE:
<221> NAME/KEY: modified_base
<222> LOCATION: (2173)..(2175)
<223> OTHER INFORMATION: n is a, c, g, or u
<220> FEATURE:
<221> NAME/KEY: modified_base
<222> LOCATION: (2176)..(2177)
<223> OTHER INFORMATION: This region may encompass 0-2 variable bases,
      a, c, g, or u
<220> FEATURE:
<221> NAME/KEY: modified_base
<222> LOCATION: (2178)..(2178)
<223> OTHER INFORMATION: n is a, c, g, or u
<220> FEATURE:
<221> NAME/KEY: modified_base
<222> LOCATION: (2180)..(2187)
<223> OTHER INFORMATION: n is a, c, g, or u
<220> FEATURE:
<221> NAME/KEY: modified_base
<222> LOCATION: (2188)..(2189)
<223> OTHER INFORMATION: This region may encompass 0-2 variable bases,
      a, c, g, or u
<220> FEATURE:
<221> NAME/KEY: modified_base
<222> LOCATION: (2190)..(2196)
<223> OTHER INFORMATION: n is a, c, g, or u
<220> FEATURE:
<221> NAME/KEY: modified_base
<222> LOCATION: (2197)..(2199)
<223> OTHER INFORMATION: This region may encompass 0-3 variable bases,
      a, c, g, or u
<220> FEATURE:
<221> NAME/KEY: modified_base
<222> LOCATION: (2200)..(2200)
<223> OTHER INFORMATION: n is a, c, g, or u
<220> FEATURE:
<221> NAME/KEY: modified_base
<222> LOCATION: (2203)..(2203)
<223> OTHER INFORMATION: n is a, c, g, or u
<220> FEATURE:
<221> NAME/KEY: modified_base
<222> LOCATION: (2204)..(2207)
<223> OTHER INFORMATION: This region may encompass 0-4 variable bases,
      a, c, g, or u
<220> FEATURE:
<221> NAME/KEY: modified_base
<222> LOCATION: (2208)..(2213)
<223> OTHER INFORMATION: n is a, c, g, or u
<220> FEATURE:
<221> NAME/KEY: modified_base
<222> LOCATION: (2214)..(2320)
<223> OTHER INFORMATION: This region may encompass 0-107 variable bases,
      a, c, g, or u
<220> FEATURE:
<221> NAME/KEY: modified_base
<222> LOCATION: (2321)..(2324)
<223> OTHER INFORMATION: n is a, c, g, or u
<220> FEATURE:
<221> NAME/KEY: modified_base
<222> LOCATION: (2325)..(2326)
<223> OTHER INFORMATION: This region may encompass 0-2 variable bases,
      a, c, g, or u
<220> FEATURE:
<221> NAME/KEY: modified_base
<222> LOCATION: (2327)..(2331)
<223> OTHER INFORMATION: n is a, c, g, or u
<220> FEATURE:
<221> NAME/KEY: modified_base
```

-continued

```
<222> LOCATION: (2332)..(2335)
<223> OTHER INFORMATION: This region may encompass 0-4 variable bases,
      a, c, g, or u
<220> FEATURE:
<221> NAME/KEY: modified_base
<222> LOCATION: (2336)..(2339)
<223> OTHER INFORMATION: n is a, c, g, or u
<220> FEATURE:
<221> NAME/KEY: modified_base
<222> LOCATION: (2341)..(2342)
<223> OTHER INFORMATION: n is a, c, g, or u
<220> FEATURE:
<221> NAME/KEY: modified_base
<222> LOCATION: (2348)..(2348)
<223> OTHER INFORMATION: n is a, c, g, or u
<220> FEATURE:
<221> NAME/KEY: modified_base
<222> LOCATION: (2349)..(2365)
<223> OTHER INFORMATION: This region may encompass 0-17 variable bases,
      a, c, g, or u
<220> FEATURE:
<221> NAME/KEY: modified_base
<222> LOCATION: (2366)..(2377)
<223> OTHER INFORMATION: n is a, c, g, or u
<220> FEATURE:
<221> NAME/KEY: modified_base
<222> LOCATION: (2384)..(2385)
<223> OTHER INFORMATION: n is a, c, g, or u
<220> FEATURE:
<221> NAME/KEY: modified_base
<222> LOCATION: (2400)..(2400)
<223> OTHER INFORMATION: n is a, c, g, or u
<220> FEATURE:
<221> NAME/KEY: modified_base
<222> LOCATION: (2402)..(2405)
<223> OTHER INFORMATION: n is a, c, g, or u
<220> FEATURE:
<221> NAME/KEY: modified_base
<222> LOCATION: (2407)..(2408)
<223> OTHER INFORMATION: n is a, c, g, or u
<220> FEATURE:
<221> NAME/KEY: modified_base
<222> LOCATION: (2412)..(2412)
<223> OTHER INFORMATION: n is a, c, g, or u
<220> FEATURE:
<221> NAME/KEY: modified_base
<222> LOCATION: (2414)..(2415)
<223> OTHER INFORMATION: n is a, c, g, or u
<220> FEATURE:
<221> NAME/KEY: modified_base
<222> LOCATION: (2417)..(2418)
<223> OTHER INFORMATION: n is a, c, g, or u
<220> FEATURE:
<221> NAME/KEY: modified_base
<222> LOCATION: (2422)..(2422)
<223> OTHER INFORMATION: n is a, c, g, or u
<220> FEATURE:
<221> NAME/KEY: modified_base
<222> LOCATION: (2424)..(2426)
<223> OTHER INFORMATION: n is a, c, g, or u
<220> FEATURE:
<221> NAME/KEY: modified_base
<222> LOCATION: (2428)..(2431)
<223> OTHER INFORMATION: n is a, c, g, or u
<220> FEATURE:
<221> NAME/KEY: modified_base
<222> LOCATION: (2434)..(2441)
<223> OTHER INFORMATION: n is a, c, g, or u
<220> FEATURE:
<221> NAME/KEY: modified_base
<222> LOCATION: (2450)..(2451)
<223> OTHER INFORMATION: n is a, c, g, or u
<220> FEATURE:
<221> NAME/KEY: modified_base
<222> LOCATION: (2457)..(2457)
<223> OTHER INFORMATION: n is a, c, g, or u
<220> FEATURE:
<221> NAME/KEY: modified_base
<222> LOCATION: (2459)..(2462)
<223> OTHER INFORMATION: n is a, c, g, or u
```

```
<220> FEATURE:
<221> NAME/KEY: modified_base
<222> LOCATION: (2468)..(2468)
<223> OTHER INFORMATION: n is a, c, g, or u
<220> FEATURE:
<221> NAME/KEY: modified_base
<222> LOCATION: (2475)..(2475)
<223> OTHER INFORMATION: n is a, c, g, or u
<220> FEATURE:
<221> NAME/KEY: modified_base
<222> LOCATION: (2477)..(2477)
<223> OTHER INFORMATION: n is a, c, g, or u
<220> FEATURE:
<221> NAME/KEY: modified_base
<222> LOCATION: (2482)..(2485)
<223> OTHER INFORMATION: n is a, c, g, or u
<220> FEATURE:
<221> NAME/KEY: modified_base
<222> LOCATION: (2487)..(2488)
<223> OTHER INFORMATION: n is a, c, g, or u
<220> FEATURE:
<221> NAME/KEY: modified_base
<222> LOCATION: (2489)..(2541)
<223> OTHER INFORMATION: This region may encompass 6-53 variable bases,
      a, c, g, or u
<220> FEATURE:
<221> NAME/KEY: modified_base
<222> LOCATION: (2542)..(2543)
<223> OTHER INFORMATION: n is a, c, g, or u
<220> FEATURE:
<221> NAME/KEY: modified_base
<222> LOCATION: (2545)..(2548)
<223> OTHER INFORMATION: n is a, c, g, or u
<220> FEATURE:
<221> NAME/KEY: modified_base
<222> LOCATION: (2550)..(2552)
<223> OTHER INFORMATION: n is a, c, g, or u
<220> FEATURE:
<221> NAME/KEY: modified_base
<222> LOCATION: (2554)..(2556)
<223> OTHER INFORMATION: n is a, c, g, or u
<220> FEATURE:
<221> NAME/KEY: modified_base
<222> LOCATION: (2558)..(2564)
<223> OTHER INFORMATION: n is a, c, g, or u
<220> FEATURE:
<221> NAME/KEY: modified_base
<222> LOCATION: (2566)..(2566)
<223> OTHER INFORMATION: n is a, c, g, or u
<220> FEATURE:
<221> NAME/KEY: modified_base
<222> LOCATION: (2575)..(2576)
<223> OTHER INFORMATION: n is a, c, g, or u
<220> FEATURE:
<221> NAME/KEY: modified_base
<222> LOCATION: (2587)..(2588)
<223> OTHER INFORMATION: n is a, c, g, or u
<220> FEATURE:
<221> NAME/KEY: modified_base
<222> LOCATION: (2590)..(2591)
<223> OTHER INFORMATION: n is a, c, g, or u
<220> FEATURE:
<221> NAME/KEY: modified_base
<222> LOCATION: (2595)..(2595)
<223> OTHER INFORMATION: n is a, c, g, or u
<220> FEATURE:
<221> NAME/KEY: modified_base
<222> LOCATION: (2598)..(2599)
<223> OTHER INFORMATION: n is a, c, g, or u
<220> FEATURE:
<221> NAME/KEY: modified_base
<222> LOCATION: (2602)..(2602)
<223> OTHER INFORMATION: n is a, c, g, or u
<220> FEATURE:
<221> NAME/KEY: modified_base
<222> LOCATION: (2606)..(2607)
<223> OTHER INFORMATION: n is a, c, g, or u
<220> FEATURE:
<221> NAME/KEY: modified_base
<222> LOCATION: (2610)..(2610)
```

-continued

```
<223> OTHER INFORMATION: n is a, c, g, or u
<220> FEATURE:
<221> NAME/KEY: modified_base
<222> LOCATION: (2616)..(2616)
<223> OTHER INFORMATION: n is a, c, g, or u
<220> FEATURE:
<221> NAME/KEY: modified_base
<222> LOCATION: (2619)..(2620)
<223> OTHER INFORMATION: n is a, c, g, or u
<220> FEATURE:
<221> NAME/KEY: modified_base
<222> LOCATION: (2625)..(2625)
<223> OTHER INFORMATION: n is a, c, g, or u
<220> FEATURE:
<221> NAME/KEY: modified_base
<222> LOCATION: (2633)..(2633)
<223> OTHER INFORMATION: n is a, c, g, or u
<220> FEATURE:
<221> NAME/KEY: modified_base
<222> LOCATION: (2638)..(2639)
<223> OTHER INFORMATION: n is a, c, g, or u
<220> FEATURE:
<221> NAME/KEY: modified_base
<222> LOCATION: (2649)..(2650)
<223> OTHER INFORMATION: n is a, c, g, or u
<220> FEATURE:
<221> NAME/KEY: modified_base
<222> LOCATION: (2652)..(2656)
<223> OTHER INFORMATION: n is a, c, g, or u
<220> FEATURE:
<221> NAME/KEY: modified_base
<222> LOCATION: (2657)..(2660)
<223> OTHER INFORMATION: This region may encompass 0-4 variable bases,
      a, c, g, or u
<220> FEATURE:
<221> NAME/KEY: modified_base
<222> LOCATION: (2662)..(2666)
<223> OTHER INFORMATION: n is a, c, g, or u
<220> FEATURE:
<221> NAME/KEY: modified_base
<222> LOCATION: (2668)..(2668)
<223> OTHER INFORMATION: n is a, c, g, or u
<220> FEATURE:
<221> NAME/KEY: modified_base
<222> LOCATION: (2669)..(2674)
<223> OTHER INFORMATION: This region may encompass 0-6 variable bases,
      a, c, g, or u
<220> FEATURE:
<221> NAME/KEY: modified_base
<222> LOCATION: (2675)..(2679)
<223> OTHER INFORMATION: n is a, c, g, or u
<220> FEATURE:
<221> NAME/KEY: modified_base
<222> LOCATION: (2681)..(2683)
<223> OTHER INFORMATION: n is a, c, g, or u
<220> FEATURE:
<221> NAME/KEY: modified_base
<222> LOCATION: (2690)..(2691)
<223> OTHER INFORMATION: n is a, c, g, or u
<220> FEATURE:
<221> NAME/KEY: modified_base
<222> LOCATION: (2694)..(2694)
<223> OTHER INFORMATION: n is a, c, g, or u
<220> FEATURE:
<221> NAME/KEY: modified_base
<222> LOCATION: (2703)..(2704)
<223> OTHER INFORMATION: n is a, c, g, or u
<220> FEATURE:
<221> NAME/KEY: modified_base
<222> LOCATION: (2716)..(2717)
<223> OTHER INFORMATION: n is a, c, g, or u
<220> FEATURE:
<221> NAME/KEY: modified_base
<222> LOCATION: (2758)..(2758)
<223> OTHER INFORMATION: n is a, c, g, or u
<220> FEATURE:
<221> NAME/KEY: modified_base
<222> LOCATION: (2766)..(2766)
<223> OTHER INFORMATION: n is a, c, g, or u
<220> FEATURE:
```

```
<221> NAME/KEY: modified_base
<222> LOCATION: (2769)..(2769)
<223> OTHER INFORMATION: n is a, c, g, or u
<220> FEATURE:
<221> NAME/KEY: modified_base
<222> LOCATION: (2771)..(2771)
<223> OTHER INFORMATION: n is a, c, g, or u
<220> FEATURE:
<221> NAME/KEY: modified_base
<222> LOCATION: (2774)..(2774)
<223> OTHER INFORMATION: n is a, c, g, or u
<220> FEATURE:
<221> NAME/KEY: modified_base
<222> LOCATION: (2777)..(2784)
<223> OTHER INFORMATION: n is a, c, g, or u
<220> FEATURE:
<221> NAME/KEY: modified_base
<222> LOCATION: (2792)..(2800)
<223> OTHER INFORMATION: n is a, c, g, or u
<220> FEATURE:
<221> NAME/KEY: modified_base
<222> LOCATION: (2802)..(2802)
<223> OTHER INFORMATION: n is a, c, g, or u
<220> FEATURE:
<221> NAME/KEY: modified_base
<222> LOCATION: (2804)..(2804)
<223> OTHER INFORMATION: n is a, c, g, or u
<220> FEATURE:
<221> NAME/KEY: modified_base
<222> LOCATION: (2806)..(2806)
<223> OTHER INFORMATION: n is a, c, g, or u
<220> FEATURE:
<221> NAME/KEY: modified_base
<222> LOCATION: (2810)..(2810)
<223> OTHER INFORMATION: n is a, c, g, or u
<220> FEATURE:
<221> NAME/KEY: modified_base
<222> LOCATION: (2813)..(2814)
<223> OTHER INFORMATION: n is a, c, g, or u
<220> FEATURE:
<221> NAME/KEY: modified_base
<222> LOCATION: (2816)..(2816)
<223> OTHER INFORMATION: n is a, c, g, or u
<220> FEATURE:
<221> NAME/KEY: modified_base
<222> LOCATION: (2818)..(2821)
<223> OTHER INFORMATION: n is a, c, g, or u
<220> FEATURE:
<221> NAME/KEY: modified_base
<222> LOCATION: (2824)..(2824)
<223> OTHER INFORMATION: n is a, c, g, or u
<220> FEATURE:
<221> NAME/KEY: modified_base
<222> LOCATION: (2832)..(2835)
<223> OTHER INFORMATION: n is a, c, g, or u
<220> FEATURE:
<221> NAME/KEY: modified_base
<222> LOCATION: (2837)..(2837)
<223> OTHER INFORMATION: n is a, c, g, or u
<220> FEATURE:
<221> NAME/KEY: modified_base
<222> LOCATION: (2839)..(2839)
<223> OTHER INFORMATION: n is a, c, g, or u
<220> FEATURE:
<221> NAME/KEY: modified_base
<222> LOCATION: (2843)..(2847)
<223> OTHER INFORMATION: n is a, c, g, or u
<220> FEATURE:
<221> NAME/KEY: modified_base
<222> LOCATION: (2862)..(2862)
<223> OTHER INFORMATION: n is a, c, g, or u
<220> FEATURE:
<221> NAME/KEY: modified_base
<222> LOCATION: (2863)..(2863)
<223> OTHER INFORMATION: n is a, c, g, u, or not present
<220> FEATURE:
<221> NAME/KEY: modified_base
<222> LOCATION: (2865)..(2865)
<223> OTHER INFORMATION: n is a, c, g, or u
<220> FEATURE:
```

```
<221> NAME/KEY: modified_base
<222> LOCATION: (2867)..(2867)
<223> OTHER INFORMATION: n is a, c, g, or u
<220> FEATURE:
<221> NAME/KEY: modified_base
<222> LOCATION: (2875)..(2876)
<223> OTHER INFORMATION: n is a, c, g, or u
<220> FEATURE:
<221> NAME/KEY: modified_base
<222> LOCATION: (2878)..(2880)
<223> OTHER INFORMATION: n is a, c, g, or u
<220> FEATURE:
<221> NAME/KEY: modified_base
<222> LOCATION: (2882)..(2884)
<223> OTHER INFORMATION: n is a, c, g, or u
<220> FEATURE:
<221> NAME/KEY: modified_base
<222> LOCATION: (2886)..(2886)
<223> OTHER INFORMATION: n is a, c, g, or u
<220> FEATURE:
<221> NAME/KEY: modified_base
<222> LOCATION: (2889)..(2903)
<223> OTHER INFORMATION: n is a, c, g, or u
<220> FEATURE:
<221> NAME/KEY: modified_base
<222> LOCATION: (2907)..(2908)
<223> OTHER INFORMATION: n is a, c, g, or u
<220> FEATURE:
<221> NAME/KEY: modified_base
<222> LOCATION: (2911)..(2911)
<223> OTHER INFORMATION: n is a, c, g, or u
<220> FEATURE:
<221> NAME/KEY: modified_base
<222> LOCATION: (2918)..(2918)
<223> OTHER INFORMATION: n is a, c, g, or u
<220> FEATURE:
<221> NAME/KEY: modified_base
<222> LOCATION: (2923)..(2923)
<223> OTHER INFORMATION: n is a, c, g, or u
<220> FEATURE:
<221> NAME/KEY: modified_base
<222> LOCATION: (2925)..(2927)
<223> OTHER INFORMATION: n is a, c, g, or u
<220> FEATURE:
<221> NAME/KEY: modified_base
<222> LOCATION: (2930)..(2937)
<223> OTHER INFORMATION: n is a, c, g, or u
<220> FEATURE:
<221> NAME/KEY: modified_base
<222> LOCATION: (2940)..(2941)
<223> OTHER INFORMATION: n is a, c, g, or u
<220> FEATURE:
<221> NAME/KEY: modified_base
<222> LOCATION: (2944)..(2950)
<223> OTHER INFORMATION: n is a, c, g, or u
<220> FEATURE:
<221> NAME/KEY: modified_base
<222> LOCATION: (2955)..(2955)
<223> OTHER INFORMATION: n is a, c, g, or u
<220> FEATURE:
<221> NAME/KEY: modified_base
<222> LOCATION: (2957)..(2961)
<223> OTHER INFORMATION: n is a, c, g, or u
<220> FEATURE:
<221> NAME/KEY: modified_base
<222> LOCATION: (2964)..(2965)
<223> OTHER INFORMATION: n is a, c, g, or u
<220> FEATURE:
<221> NAME/KEY: modified_base
<222> LOCATION: (2970)..(2970)
<223> OTHER INFORMATION: n is a, c, g, or u
<220> FEATURE:
<221> NAME/KEY: modified_base
<222> LOCATION: (2973)..(2973)
<223> OTHER INFORMATION: n is a, c, g, or u
<220> FEATURE:
<221> NAME/KEY: modified_base
<222> LOCATION: (2976)..(2989)
<223> OTHER INFORMATION: n is a, c, g, or u
<220> FEATURE:
```

```
<221> NAME/KEY: modified_base
<222> LOCATION: (2996)..(2997)
<223> OTHER INFORMATION: n is a, c, g, or u
<220> FEATURE:
<221> NAME/KEY: modified_base
<222> LOCATION: (2998)..(2998)
<223> OTHER INFORMATION: n is a, c, g, u, or not present
<220> FEATURE:
<221> NAME/KEY: modified_base
<222> LOCATION: (2999)..(3006)
<223> OTHER INFORMATION: n is a, c, g, or u
<220> FEATURE:
<221> NAME/KEY: modified_base
<222> LOCATION: (3008)..(3008)
<223> OTHER INFORMATION: n is a, c, g, or u
<220> FEATURE:
<221> NAME/KEY: modified_base
<222> LOCATION: (3010)..(3011)
<223> OTHER INFORMATION: This region may encompass 0-2 variable bases,
      a, c, g, or u
<220> FEATURE:
<221> NAME/KEY: modified_base
<222> LOCATION: (3012)..(3019)
<223> OTHER INFORMATION: n is a, c, g, or u
<220> FEATURE:
<221> NAME/KEY: modified_base
<222> LOCATION: (3024)..(3024)
<223> OTHER INFORMATION: n is a, c, g, or u
<220> FEATURE:
<221> NAME/KEY: modified_base
<222> LOCATION: (3027)..(3029)
<223> OTHER INFORMATION: n is a, c, g, or u
<220> FEATURE:
<221> NAME/KEY: modified_base
<222> LOCATION: (3031)..(3032)
<223> OTHER INFORMATION: n is a, c, g, or u
<220> FEATURE:
<221> NAME/KEY: modified_base
<222> LOCATION: (3036)..(3036)
<223> OTHER INFORMATION: n is a, c, g, or u
<220> FEATURE:
<221> NAME/KEY: modified_base
<222> LOCATION: (3042)..(3042)
<223> OTHER INFORMATION: n is a, c, g, or u
<220> FEATURE:
<221> NAME/KEY: modified_base
<222> LOCATION: (3054)..(3055)
<223> OTHER INFORMATION: n is a, c, g, or u
<220> FEATURE:
<221> NAME/KEY: modified_base
<222> LOCATION: (3061)..(3061)
<223> OTHER INFORMATION: n is a, c, g, or u
<220> FEATURE:
<221> NAME/KEY: modified_base
<222> LOCATION: (3065)..(3066)
<223> OTHER INFORMATION: n is a, c, g, or u
<220> FEATURE:
<221> NAME/KEY: modified_base
<222> LOCATION: (3077)..(3077)
<223> OTHER INFORMATION: n is a, c, g, or u
<220> FEATURE:
<221> NAME/KEY: modified_base
<222> LOCATION: (3079)..(3080)
<223> OTHER INFORMATION: n is a, c, g, or u
<220> FEATURE:
<221> NAME/KEY: modified_base
<222> LOCATION: (3082)..(3082)
<223> OTHER INFORMATION: n is a, c, g, or u
<220> FEATURE:
<221> NAME/KEY: modified_base
<222> LOCATION: (3088)..(3090)
<223> OTHER INFORMATION: n is a, c, g, or u
<220> FEATURE:
<221> NAME/KEY: modified_base
<222> LOCATION: (3093)..(3093)
<223> OTHER INFORMATION: n is a, c, g, or u
<220> FEATURE:
<221> NAME/KEY: modified_base
<222> LOCATION: (3095)..(3098)
<223> OTHER INFORMATION: n is a, c, g, or u
```

-continued

```
<220> FEATURE:
<221> NAME/KEY: modified_base
<222> LOCATION: (3101)..(3102)
<223> OTHER INFORMATION: n is a, c, g, or u
<220> FEATURE:
<221> NAME/KEY: modified_base
<222> LOCATION: (3105)..(3106)
<223> OTHER INFORMATION: n is a, c, g, or u
<220> FEATURE:
<221> NAME/KEY: modified_base
<222> LOCATION: (3110)..(3117)
<223> OTHER INFORMATION: n is a, c, g, or u
<220> FEATURE:
<221> NAME/KEY: modified_base
<222> LOCATION: (3121)..(3122)
<223> OTHER INFORMATION: n is a, c, g, or u
<220> FEATURE:
<221> NAME/KEY: modified_base
<222> LOCATION: (3125)..(3126)
<223> OTHER INFORMATION: n is a, c, g, or u
<220> FEATURE:
<221> NAME/KEY: modified_base
<222> LOCATION: (3128)..(3128)
<223> OTHER INFORMATION: n is a, c, g, or u
<220> FEATURE:
<221> NAME/KEY: modified_base
<222> LOCATION: (3130)..(3130)
<223> OTHER INFORMATION: n is a, c, g, or u
<220> FEATURE:
<221> NAME/KEY: modified_base
<222> LOCATION: (3134)..(3136)
<223> OTHER INFORMATION: n is a, c, g, or u
<220> FEATURE:
<221> NAME/KEY: modified_base
<222> LOCATION: (3139)..(3139)
<223> OTHER INFORMATION: n is a, c, g, or u
<220> FEATURE:
<221> NAME/KEY: modified_base
<222> LOCATION: (3141)..(3141)
<223> OTHER INFORMATION: n is a, c, g, or u
<220> FEATURE:
<221> NAME/KEY: modified_base
<222> LOCATION: (3146)..(3147)
<223> OTHER INFORMATION: n is a, c, g, or u
<220> FEATURE:
<221> NAME/KEY: modified_base
<222> LOCATION: (3150)..(3153)
<223> OTHER INFORMATION: n is a, c, g, or u
<220> FEATURE:
<221> NAME/KEY: modified_base
<222> LOCATION: (3156)..(3159)
<223> OTHER INFORMATION: n is a, c, g, or u
<220> FEATURE:
<221> NAME/KEY: modified_base
<222> LOCATION: (3167)..(3169)
<223> OTHER INFORMATION: n is a, c, g, or u
<220> FEATURE:
<221> NAME/KEY: modified_base
<222> LOCATION: (3176)..(3177)
<223> OTHER INFORMATION: n is a, c, g, or u
<220> FEATURE:
<221> NAME/KEY: modified_base
<222> LOCATION: (3180)..(3182)
<223> OTHER INFORMATION: n is a, c, g, or u
<220> FEATURE:
<221> NAME/KEY: modified_base
<222> LOCATION: (3194)..(3194)
<223> OTHER INFORMATION: n is a, c, g, or u
<220> FEATURE:
<221> NAME/KEY: modified_base
<222> LOCATION: (3198)..(3203)
<223> OTHER INFORMATION: n is a, c, g, or u
<220> FEATURE:
<221> NAME/KEY: modified_base
<222> LOCATION: (3210)..(3210)
<223> OTHER INFORMATION: n is a, c, g, or u
<220> FEATURE:
<221> NAME/KEY: modified_base
<222> LOCATION: (3214)..(3214)
<223> OTHER INFORMATION: n is a, c, g, or u
```

```
<220> FEATURE:
<221> NAME/KEY: modified_base
<222> LOCATION: (3233)..(3233)
<223> OTHER INFORMATION: n is a, c, g, or u
<220> FEATURE:
<221> NAME/KEY: modified_base
<222> LOCATION: (3237)..(3237)
<223> OTHER INFORMATION: n is a, c, g, or u
<220> FEATURE:
<221> NAME/KEY: modified_base
<222> LOCATION: (3239)..(3239)
<223> OTHER INFORMATION: n is a, c, g, or u
<220> FEATURE:
<221> NAME/KEY: modified_base
<222> LOCATION: (3254)..(3254)
<223> OTHER INFORMATION: n is a, c, g, or u
<220> FEATURE:
<221> NAME/KEY: modified_base
<222> LOCATION: (3257)..(3260)
<223> OTHER INFORMATION: n is a, c, g, or u
<220> FEATURE:
<221> NAME/KEY: modified_base
<222> LOCATION: (3270)..(3270)
<223> OTHER INFORMATION: n is a, c, g, or u
<220> FEATURE:
<221> NAME/KEY: modified_base
<222> LOCATION: (3273)..(3273)
<223> OTHER INFORMATION: n is a, c, g, or u
<220> FEATURE:
<221> NAME/KEY: modified_base
<222> LOCATION: (3282)..(3285)
<223> OTHER INFORMATION: n is a, c, g, or u
<220> FEATURE:
<221> NAME/KEY: modified_base
<222> LOCATION: (3309)..(3309)
<223> OTHER INFORMATION: n is a, c, g, or u
<220> FEATURE:
<221> NAME/KEY: modified_base
<222> LOCATION: (3312)..(3312)
<223> OTHER INFORMATION: n is a, c, g, or u
<220> FEATURE:
<221> NAME/KEY: modified_base
<222> LOCATION: (3326)..(3326)
<223> OTHER INFORMATION: n is a, c, g, or u
<220> FEATURE:
<221> NAME/KEY: modified_base
<222> LOCATION: (3329)..(3330)
<223> OTHER INFORMATION: n is a, c, g, or u
<220> FEATURE:
<221> NAME/KEY: modified_base
<222> LOCATION: (3343)..(3344)
<223> OTHER INFORMATION: n is a, c, g, or u
<220> FEATURE:
<221> NAME/KEY: modified_base
<222> LOCATION: (3356)..(3357)
<223> OTHER INFORMATION: n is a, c, g, or u
<220> FEATURE:
<221> NAME/KEY: modified_base
<222> LOCATION: (3364)..(3364)
<223> OTHER INFORMATION: n is a, c, g, or u
<220> FEATURE:
<221> NAME/KEY: modified_base
<222> LOCATION: (3367)..(3367)
<223> OTHER INFORMATION: n is a, c, g, or u
<220> FEATURE:
<221> NAME/KEY: modified_base
<222> LOCATION: (3371)..(3371)
<223> OTHER INFORMATION: n is a, c, g, or u
<220> FEATURE:
<221> NAME/KEY: modified_base
<222> LOCATION: (3382)..(3382)
<223> OTHER INFORMATION: n is a, c, g, or u
<220> FEATURE:
<221> NAME/KEY: modified_base
<222> LOCATION: (3384)..(3384)
<223> OTHER INFORMATION: n is a, c, g, or u
<220> FEATURE:
<221> NAME/KEY: modified_base
<222> LOCATION: (3402)..(3402)
<223> OTHER INFORMATION: n is a, c, g, or u
```

-continued

```
<220> FEATURE:
<221> NAME/KEY: modified_base
<222> LOCATION: (3413)..(3413)
<223> OTHER INFORMATION: n is a, c, g, or u
<220> FEATURE:
<221> NAME/KEY: modified_base
<222> LOCATION: (3415)..(3416)
<223> OTHER INFORMATION: n is a, c, g, or u
<220> FEATURE:
<221> NAME/KEY: modified_base
<222> LOCATION: (3418)..(3418)
<223> OTHER INFORMATION: n is a, c, g, or u
<220> FEATURE:
<221> NAME/KEY: modified_base
<222> LOCATION: (3420)..(3420)
<223> OTHER INFORMATION: n is a, c, g, or u
<220> FEATURE:
<221> NAME/KEY: modified_base
<222> LOCATION: (3422)..(3422)
<223> OTHER INFORMATION: n is a, c, g, or u
<220> FEATURE:
<221> NAME/KEY: modified_base
<222> LOCATION: (3424)..(3426)
<223> OTHER INFORMATION: n is a, c, g, or u
<220> FEATURE:
<221> NAME/KEY: modified_base
<222> LOCATION: (3429)..(3431)
<223> OTHER INFORMATION: n is a, c, g, or u
<220> FEATURE:
<221> NAME/KEY: modified_base
<222> LOCATION: (3436)..(3438)
<223> OTHER INFORMATION: n is a, c, g, or u
<220> FEATURE:
<221> NAME/KEY: modified_base
<222> LOCATION: (3440)..(3442)
<223> OTHER INFORMATION: n is a, c, g, or u
<220> FEATURE:
<221> NAME/KEY: modified_base
<222> LOCATION: (3445)..(3446)
<223> OTHER INFORMATION: n is a, c, g, or u
<220> FEATURE:
<221> NAME/KEY: modified_base
<222> LOCATION: (3448)..(3448)
<223> OTHER INFORMATION: n is a, c, g, or u
<220> FEATURE:
<221> NAME/KEY: modified_base
<222> LOCATION: (3466)..(3468)
<223> OTHER INFORMATION: n is a, c, g, or u
<220> FEATURE:
<221> NAME/KEY: modified_base
<222> LOCATION: (3470)..(3470)
<223> OTHER INFORMATION: n is a, c, g, or u
<220> FEATURE:
<221> NAME/KEY: modified_base
<222> LOCATION: (3473)..(3474)
<223> OTHER INFORMATION: n is a, c, g, or u
<220> FEATURE:
<221> NAME/KEY: modified_base
<222> LOCATION: (3476)..(3476)
<223> OTHER INFORMATION: n is a, c, g, or u
<220> FEATURE:
<221> NAME/KEY: modified_base
<222> LOCATION: (3478)..(3478)
<223> OTHER INFORMATION: n is a, c, g, or u
<220> FEATURE:
<221> NAME/KEY: modified_base
<222> LOCATION: (3485)..(3487)
<223> OTHER INFORMATION: n is a, c, g, or u
<220> FEATURE:
<221> NAME/KEY: modified_base
<222> LOCATION: (3489)..(3489)
<223> OTHER INFORMATION: n is a, c, g, or u
<220> FEATURE:
<221> NAME/KEY: modified_base
<222> LOCATION: (3495)..(3497)
<223> OTHER INFORMATION: n is a, c, g, or u
<220> FEATURE:
<221> NAME/KEY: modified_base
<222> LOCATION: (3502)..(3504)
<223> OTHER INFORMATION: n is a, c, g, or u
```

```
<220> FEATURE:
<221> NAME/KEY: modified_base
<222> LOCATION: (3508)..(3509)
<223> OTHER INFORMATION: n is a, c, g, or u
<220> FEATURE:
<221> NAME/KEY: modified_base
<222> LOCATION: (3512)..(3512)
<223> OTHER INFORMATION: n is a, c, g, or u
<220> FEATURE:
<221> NAME/KEY: modified_base
<222> LOCATION: (3514)..(3515)
<223> OTHER INFORMATION: n is a, c, g, or u
<220> FEATURE:
<221> NAME/KEY: modified_base
<222> LOCATION: (3522)..(3523)
<223> OTHER INFORMATION: n is a, c, g, or u
<220> FEATURE:
<221> NAME/KEY: modified_base
<222> LOCATION: (3525)..(3526)
<223> OTHER INFORMATION: n is a, c, g, or u
<220> FEATURE:
<221> NAME/KEY: modified_base
<222> LOCATION: (3529)..(3532)
<223> OTHER INFORMATION: n is a, c, g, or u
<220> FEATURE:
<221> NAME/KEY: modified_base
<222> LOCATION: (3538)..(3539)
<223> OTHER INFORMATION: n is a, c, g, or u
<220> FEATURE:
<221> NAME/KEY: modified_base
<222> LOCATION: (3546)..(3546)
<223> OTHER INFORMATION: n is a, c, g, or u
<220> FEATURE:
<221> NAME/KEY: modified_base
<222> LOCATION: (3556)..(3558)
<223> OTHER INFORMATION: n is a, c, g, or u
<220> FEATURE:
<221> NAME/KEY: modified_base
<222> LOCATION: (3562)..(3562)
<223> OTHER INFORMATION: n is a, c, g, or u
<220> FEATURE:
<221> NAME/KEY: modified_base
<222> LOCATION: (3564)..(3566)
<223> OTHER INFORMATION: n is a, c, g, or u
<220> FEATURE:
<221> NAME/KEY: modified_base
<222> LOCATION: (3568)..(3571)
<223> OTHER INFORMATION: n is a, c, g, or u
<220> FEATURE:
<221> NAME/KEY: modified_base
<222> LOCATION: (3575)..(3576)
<223> OTHER INFORMATION: n is a, c, g, or u
<220> FEATURE:
<221> NAME/KEY: modified_base
<222> LOCATION: (3579)..(3581)
<223> OTHER INFORMATION: n is a, c, g, or u
<220> FEATURE:
<221> NAME/KEY: modified_base
<222> LOCATION: (3584)..(3584)
<223> OTHER INFORMATION: n is a, c, g, or u
<220> FEATURE:
<221> NAME/KEY: modified_base
<222> LOCATION: (3586)..(3604)
<223> OTHER INFORMATION: This region may encompass 0-19 variable bases,
      a, c, g, or u
<220> FEATURE:
<221> NAME/KEY: modified_base
<222> LOCATION: (3605)..(3605)
<223> OTHER INFORMATION: n is a, c, g, or u
<220> FEATURE:
<221> NAME/KEY: modified_base
<222> LOCATION: (3606)..(3607)
<223> OTHER INFORMATION: This region may encompass 0-2 variable bases,
      a, c, g, or u
<220> FEATURE:
<221> NAME/KEY: modified_base
<222> LOCATION: (3610)..(3612)
<223> OTHER INFORMATION: n is a, c, g, or u
<220> FEATURE:
<221> NAME/KEY: modified_base
```

```
<222> LOCATION: (3614)..(3618)
<223> OTHER INFORMATION: n is a, c, g, or u
<220> FEATURE:
<221> NAME/KEY: modified_base
<222> LOCATION: (3622)..(3623)
<223> OTHER INFORMATION: n is a, c, g, or u
<220> FEATURE:
<221> NAME/KEY: modified_base
<222> LOCATION: (3625)..(3628)
<223> OTHER INFORMATION: n is a, c, g, or u
<220> FEATURE:
<221> NAME/KEY: modified_base
<222> LOCATION: (3631)..(3631)
<223> OTHER INFORMATION: n is a, c, g, or u
<220> FEATURE:
<221> NAME/KEY: modified_base
<222> LOCATION: (3638)..(3640)
<223> OTHER INFORMATION: n is a, c, g, or u
<220> FEATURE:
<221> NAME/KEY: modified_base
<222> LOCATION: (3642)..(3644)
<223> OTHER INFORMATION: n is a, c, g, or u
<220> FEATURE:
<221> NAME/KEY: modified_base
<222> LOCATION: (3647)..(3647)
<223> OTHER INFORMATION: n is a, c, g, or u
<220> FEATURE:
<221> NAME/KEY: modified_base
<222> LOCATION: (3651)..(3654)
<223> OTHER INFORMATION: n is a, c, g, or u
<220> FEATURE:
<221> NAME/KEY: modified_base
<222> LOCATION: (3656)..(3657)
<223> OTHER INFORMATION: n is a, c, g, or u
<220> FEATURE:
<221> NAME/KEY: modified_base
<222> LOCATION: (3659)..(3662)
<223> OTHER INFORMATION: n is a, c, g, or u
<220> FEATURE:
<221> NAME/KEY: modified_base
<222> LOCATION: (3664)..(3665)
<223> OTHER INFORMATION: n is a, c, g, or u
<220> FEATURE:
<221> NAME/KEY: modified_base
<222> LOCATION: (3668)..(3670)
<223> OTHER INFORMATION: n is a, c, g, or u
<220> FEATURE:
<221> NAME/KEY: modified_base
<222> LOCATION: (3673)..(3675)
<223> OTHER INFORMATION: n is a, c, g, or u
<220> FEATURE:
<221> NAME/KEY: modified_base
<222> LOCATION: (3683)..(3686)
<223> OTHER INFORMATION: n is a, c, g, or u
<220> FEATURE:
<221> NAME/KEY: modified_base
<222> LOCATION: (3688)..(3689)
<223> OTHER INFORMATION: n is a, c, g, or u
<220> FEATURE:
<221> NAME/KEY: modified_base
<222> LOCATION: (3690)..(3690)
<223> OTHER INFORMATION: n is a, c, g, u, or not present
<220> FEATURE:
<221> NAME/KEY: modified_base
<222> LOCATION: (3691)..(3691)
<223> OTHER INFORMATION: n is a, c, g, or u
<220> FEATURE:
<221> NAME/KEY: modified_base
<222> LOCATION: (3693)..(3693)
<223> OTHER INFORMATION: n is a, c, g, or u
<220> FEATURE:
<221> NAME/KEY: modified_base
<222> LOCATION: (3697)..(3700)
<223> OTHER INFORMATION: n is a, c, g, or u
<220> FEATURE:
<221> NAME/KEY: modified_base
<222> LOCATION: (3701)..(3702)
<223> OTHER INFORMATION: This region may encompass 0-2 variable bases,
      a, c, g, or u
```

<400> SEQUENCE: 7

```
nnnnnnnnnn nnnnnnnnnn nnnnnnnnnn nnnnnnnnaa gnnnnnaagn gnnnnnggug    60
gaugccungg cnnnnnnagn cgangaagga ngnnnnnnnc nncnnnannc nnnggnnagn   120
ngnnnnnnnn cnnnnnancc nnngnunucc gaaugnnnna acccnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnannn nnnnnnnnnn nnnnnnnnnn nnnnnngnn nacnnnnnga   420
anugaaacau cunaguannn nnaggaanag aaannaannn nnngauuncn nnnguagngg   480
cgagcgaann ngnannagnc nnnnnnnnnn nnnnnnnnnn nnnnnnnnnn nnnnnnnnnn   540
nnnnnnnnnn nnnnnnnnnn nnnnnnnnnn nnnnnnnnnn nnnnnnnnnn nnnnnnnnnn   600
nnnnnnannn gaannnnnug gnaagnnnnn nnnannngg unanannccn guannnnaaa   660
nnnnnnnnnn nnnnnnnnnn nnnnnnnnnn naguannncn nnncncgngn nannnngunn   720
gaannngnnn ngaccannnn nnaagncuaa auacunnnnn nngaccnaua gngnannnag   780
uacngugang gaaaggngaa aagnaccccnn nnnangggag ugaaanagnn ccugaaaccn   840
nnnncnuana annngunnna gnnnnnnnnn nnnnnnnnnn nnnnnnnnnn nnnnnnnnnn   900
uganngcgun ccuuuugnan naugnnncg nganuunnnn unnnngcna gnuuannnn    960
nnnnnnnngn agncgnagng aaancgagun nnaanngnc gnnnagunnn nngnnnnaga  1020
cncgaancnn ngugancuan nnaugnncag gnugaagnnn nnguaanann nnnuggaggn  1080
ccgaacnnnn nnnnguugaa aannnnnngg augannugug nnungnggng aaanncnaan  1140
cnaacnnngn nauagcuggu ucucnncgaa annnnuuuag gnnnngcnun nnnnnnnnnn  1200
nnnnnnggng guagagcacu gnnnnnnnnn nggnnnnnnn nnnnnnuacn nannnnnnnn  1260
aaacuncgaa uncnnnnnnn nnnnnnnnnn nnnnngnagn nanncnnngn gngnuaannu  1320
ncnnngunna nagggnaaca ncccagancn ncnnnuaagg ncccnaannn nnnnnuaagu  1380
ggnaaangan gugnnnnnnc nnanacannn agganguugg cuuagaagca gccancnuun  1440
aaaganngcg uaanagcuca cunnucnagn nnnnnngcgc ngannaunua ncgggncuaa  1500
nnnnnnnncc gaannnnnng nnnnnnnnnn nnnnnnnnnn nnnnnnnnnn nnnnnnnnnn  1560
nnnnnnnnnn nnnnnnnnnn nnnnnnnnnn nnnnnnnnnn nnnnnnnnnn nnnnnnnnnn  1620
nnnnnnnnnn nnnnnnnnnn nnnnnnnnnn nnnnnnnnnn nnnnnnnnnn nnnnnnnnnn  1680
nnnnnnnnnn nnnnnnnnnn nnnnnnnnnn nnnnnnnnnn nnnnnnggu agnngagcgu nnnnnnnnnn  1740
nnnnnnnnnn nnnnnnnnnn nnnnnnnnnn nnnnnnnnnn nnnnnnnnnn nnnnnnnnnn  1800
nnnnnnnnnn nnnnnnnnnn nnnnnnnnnn nnnnnnnnnn nnnngaagn nnnnnngnna  1860
nnnnnnnugg annnnnnnnn agugngnaug ngnnaunag uancgannnn nnngugana  1920
nncnnnnncn ccgnannncn aaggnuuccn nnnnnangnu nnucnnnnnn gggunagucg  1980
nnnccuaagn ngagncngan angnnuagnn gauggnnann ngguunauau uccnnnacnn  2040
nnnnnnnnnn nnnnnnnnnn nnnnnnnnnn nnnnnnnnnn nnnnnnnnnn nnnnnnnnnn  2100
nnnnnnnnnn nnnnnnnnnn nnnnnnnnnn nnnnnnnnnn nnnnnnnnnn nnnnnnnnnn  2160
nnnnnnnga cgnnnnnngn nnnnnnnnnn nnnnnnnnnn ggnnnnnnnn nnnnnnnnnn  2220
nnnnnnnnnn nnnnnnnnnn nnnnnnnnnn nnnnnnnnnn nnnnnnnnnn nnnnnnnnnn  2280
nnnnnnnnnn nnnnnnnnnn nnnnnnnnnn nnnnnnnnnn nnnnnnnnnn nnnnnnnnnc  2340
```

-continued

| | |
|---|---|
| nngaaaannn nnnnnnnnnn nnnnnnnnnn nnnnnncgu accnnaaacc gacacaggun | 2400 |
| gnnnngnnga gnanncnnag gngnnngnnn naannnnnnn naaggaacun ngcaaanunn | 2460 |
| nnccguancu ucggnanaag gnnnncnnnn nnnnnnnnnn nnnnnnnnnn nnnnnnnnnn | 2520 |
| nnnnnnnnnn nnnnnnnnnn nnngnnnnan nnannngnnn nnnncnacug uuuannaaaa | 2580 |
| acacagnncn nugcnaannc gnaagnngan guauanggnn ugacnccugc ccngugcnng | 2640 |
| aagguuaann gnnnnnnnnn gnnnnngnnn nnnnnnnnna nnnaagcccn ngunaacggc | 2700 |
| ggnnguaacu auaacnnucc uaagguagcg aaauuccuug ucggguaagu uccgaccngc | 2760 |
| acgaanggng naangannnn nnnncugucu cnnnnnnnnn cncngngaan uunnanunnn | 2820 |
| ngunaagaug cnnnnuncnc gcnnnnngac ggaaagaccc cnngnancuu uacunnannn | 2880 |
| unnnanugnn nnnnnnnnnn nnnugnnnag nauaggungg agncnnngan nnnnnnncgn | 2940 |
| nagnnnnnnn ggagncnnnn nugnnauacn acncunnnnn nnnnnnnnnu cuaacnnnnn | 3000 |
| nnnnnnancn nnnnnnnnng acanugnnng nngggnaguu unacugggc ggunnccucc | 3060 |
| naaannguaa cggaggngnn cnaaggunnn cunannnngg nnggnnaucn nnnnnnnagu | 3120 |
| nnaanngnan aagnnngcnu nacugnnagn nnnacnnnnc gagcagnnnc gaaagnnggn | 3180 |
| nnuagugauc cggnggunnn nnnuggaagn gccnucgcuc aacggauaaa agnuacncng | 3240 |
| gggauaacag gcunaunnnn cccaagagun canaucgacg gnnnnguuug gcaccucgau | 3300 |
| gucggcucnu cncauccugg ggcugnagnn ggucccaagg gunnggcugu ucgccnnuua | 3360 |
| aagnggnacg ngagcugggu unanaacguc gugagacagu unggucccua ucngnngngn | 3420 |
| gngnnngann nuugannngn nnugnncnua guacgagagg accggnnngn acnnancncu | 3480 |
| ggugnnncng uugunnngcc annngcanng cngnnuagcu annunnggnn nngauaanng | 3540 |
| cugaangcau cuaagnnnga ancnnncnnn nagannagnn nucncnnnnn nnnnnnnnnn | 3600 |
| nnnnnnnagn nncnnnnnag annannnngu ngauaggnnn gnnnugnaag nnnngnnann | 3660 |
| nnunnagnnn acnnnuacua aunnnncnnn ngncuunnnn nn | 3702 |

```
<210> SEQ ID NO 8
<211> LENGTH: 377
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(59)
<223> OTHER INFORMATION: n is a, c, g, or u
<220> FEATURE:
<221> NAME/KEY: modified_base
<222> LOCATION: (73)..(73)
<223> OTHER INFORMATION: n is a, c, g, or u
<220> FEATURE:
<221> NAME/KEY: modified_base
<222> LOCATION: (77)..(79)
<223> OTHER INFORMATION: n is a, c, g, or u
<220> FEATURE:
<221> NAME/KEY: modified_base
<222> LOCATION: (81)..(82)
<223> OTHER INFORMATION: n is a, c, g, or u
<220> FEATURE:
<221> NAME/KEY: modified_base
<222> LOCATION: (85)..(87)
<223> OTHER INFORMATION: n is a, c, g, or u
<220> FEATURE:
<221> NAME/KEY: modified_base
<222> LOCATION: (90)..(92)
<223> OTHER INFORMATION: n is a, c, g, or u
<220> FEATURE:
<221> NAME/KEY: modified_base
```

```
<222> LOCATION: (94)..(94)
<223> OTHER INFORMATION: n is a, c, g, or u
<220> FEATURE:
<221> NAME/KEY: modified_base
<222> LOCATION: (98)..(100)
<223> OTHER INFORMATION: n is a, c, g, or u
<220> FEATURE:
<221> NAME/KEY: modified_base
<222> LOCATION: (102)..(108)
<223> OTHER INFORMATION: n is a, c, g, or u
<220> FEATURE:
<221> NAME/KEY: modified_base
<222> LOCATION: (110)..(111)
<223> OTHER INFORMATION: n is a, c, g, or u
<220> FEATURE:
<221> NAME/KEY: modified_base
<222> LOCATION: (113)..(117)
<223> OTHER INFORMATION: n is a, c, g, or u
<220> FEATURE:
<221> NAME/KEY: modified_base
<222> LOCATION: (121)..(121)
<223> OTHER INFORMATION: n is a, c, g, or u
<220> FEATURE:
<221> NAME/KEY: modified_base
<222> LOCATION: (125)..(125)
<223> OTHER INFORMATION: n is a, c, g, or u
<220> FEATURE:
<221> NAME/KEY: modified_base
<222> LOCATION: (127)..(127)
<223> OTHER INFORMATION: n is a, c, g, or u
<220> FEATURE:
<221> NAME/KEY: modified_base
<222> LOCATION: (134)..(134)
<223> OTHER INFORMATION: n is a, c, g, or u
<220> FEATURE:
<221> NAME/KEY: modified_base
<222> LOCATION: (136)..(139)
<223> OTHER INFORMATION: n is a, c, g, or u
<220> FEATURE:
<221> NAME/KEY: modified_base
<222> LOCATION: (145)..(168)
<223> OTHER INFORMATION: n is a, c, g, or u
<220> FEATURE:
<221> NAME/KEY: modified_base
<222> LOCATION: (171)..(171)
<223> OTHER INFORMATION: n is a, c, g, or u
<220> FEATURE:
<221> NAME/KEY: modified_base
<222> LOCATION: (179)..(179)
<223> OTHER INFORMATION: n is a, c, g, or u
<220> FEATURE:
<221> NAME/KEY: modified_base
<222> LOCATION: (182)..(182)
<223> OTHER INFORMATION: n is a, c, g, or u
<220> FEATURE:
<221> NAME/KEY: modified_base
<222> LOCATION: (185)..(189)
<223> OTHER INFORMATION: n is a, c, g, or u
<220> FEATURE:
<221> NAME/KEY: modified_base
<222> LOCATION: (196)..(197)
<223> OTHER INFORMATION: n is a, c, g, or u
<220> FEATURE:
<221> NAME/KEY: modified_base
<222> LOCATION: (203)..(210)
<223> OTHER INFORMATION: n is a, c, g, or u
<220> FEATURE:
<221> NAME/KEY: modified_base
<222> LOCATION: (212)..(213)
<223> OTHER INFORMATION: n is a, c, g, or u
<220> FEATURE:
<221> NAME/KEY: modified_base
<222> LOCATION: (215)..(227)
<223> OTHER INFORMATION: n is a, c, g, or u
<220> FEATURE:
<221> NAME/KEY: modified_base
<222> LOCATION: (230)..(230)
<223> OTHER INFORMATION: n is a, c, g, or u
<220> FEATURE:
<221> NAME/KEY: modified_base
```

```
<222> LOCATION: (238)..(241)
<223> OTHER INFORMATION: n is a, c, g, or u
<220> FEATURE:
<221> NAME/KEY: modified_base
<222> LOCATION: (243)..(243)
<223> OTHER INFORMATION: n is a, c, g, or u
<220> FEATURE:
<221> NAME/KEY: modified_base
<222> LOCATION: (250)..(259)
<223> OTHER INFORMATION: n is a, c, g, or u
<220> FEATURE:
<221> NAME/KEY: modified_base
<222> LOCATION: (261)..(275)
<223> OTHER INFORMATION: n is a, c, g, or u
<220> FEATURE:
<221> NAME/KEY: modified_base
<222> LOCATION: (277)..(278)
<223> OTHER INFORMATION: n is a, c, g, or u
<220> FEATURE:
<221> NAME/KEY: modified_base
<222> LOCATION: (280)..(294)
<223> OTHER INFORMATION: n is a, c, g, or u
<220> FEATURE:
<221> NAME/KEY: modified_base
<222> LOCATION: (296)..(299)
<223> OTHER INFORMATION: n is a, c, g, or u
<220> FEATURE:
<221> NAME/KEY: modified_base
<222> LOCATION: (303)..(303)
<223> OTHER INFORMATION: n is a, c, g, or u
<220> FEATURE:
<221> NAME/KEY: modified_base
<222> LOCATION: (307)..(313)
<223> OTHER INFORMATION: n is a, c, g, or u
<220> FEATURE:
<221> NAME/KEY: modified_base
<222> LOCATION: (315)..(316)
<223> OTHER INFORMATION: n is a, c, g, or u
<220> FEATURE:
<221> NAME/KEY: modified_base
<222> LOCATION: (318)..(324)
<223> OTHER INFORMATION: n is a, c, g, or u
<220> FEATURE:
<221> NAME/KEY: modified_base
<222> LOCATION: (327)..(327)
<223> OTHER INFORMATION: n is a, c, g, or u
<220> FEATURE:
<221> NAME/KEY: modified_base
<222> LOCATION: (331)..(331)
<223> OTHER INFORMATION: n is a, c, g, or u
<220> FEATURE:
<221> NAME/KEY: modified_base
<222> LOCATION: (335)..(342)
<223> OTHER INFORMATION: n is a, c, g, or u
<220> FEATURE:
<221> NAME/KEY: modified_base
<222> LOCATION: (344)..(346)
<223> OTHER INFORMATION: n is a, c, g, or u
<220> FEATURE:
<221> NAME/KEY: modified_base
<222> LOCATION: (353)..(353)
<223> OTHER INFORMATION: n is a, c, g, or u
<220> FEATURE:
<221> NAME/KEY: modified_base
<222> LOCATION: (359)..(359)
<223> OTHER INFORMATION: n is a, c, g, or u
<220> FEATURE:
<221> NAME/KEY: modified_base
<222> LOCATION: (362)..(377)
<223> OTHER INFORMATION: n is a, c, g, or u

<400> SEQUENCE: 8
nnnnnnnnnn nnnnnnnnnn nnnnnnnnnn nnnnnnnnnn nnnnnnnnnn nnnnnnnng      60 aggaaagucc ggncucnnna nncannnugn nngnuaannn cnnnnnnngn nannnnngac     120
naguncnaca gagngnnnnc cgccnnnnnn nnnnnnnnnn nnnnnnnngg naagggugna     180
anggnnnnnu aagagnncac cgnnnnnnnn gnnannnnnn nnnnnnnggn aaacuccnnn     240
```

```
ngnagcaagn nnnnnnnng nnnnnnnnnn nnnngnncn nnnnnnnnnn nnnnannnng    300
cungagnnnn nnngnnannn nnnnccnaga naugnnnnnn nncnnnacag aanccggcnu    360
annnnnnnnn nnnnnnn                                                   377

<210> SEQ ID NO 9
<211> LENGTH: 43
<212> TYPE: RNA
<213> ORGANISM: Escherichia coli

<400> SEQUENCE: 9
augucuggga aacugccuga uggaggggga uaacuacugg aaa                      43

<210> SEQ ID NO 10
<211> LENGTH: 58
<212> TYPE: RNA
<213> ORGANISM: Homo sapiens

<400> SEQUENCE: 10
aucaguuaug guuccuuugg ucgcucgcuc cucuccuacu uggauaacug ugguaauu      58

<210> SEQ ID NO 11
<211> LENGTH: 13
<212> TYPE: RNA
<213> ORGANISM: Homo sapiens

<400> SEQUENCE: 11
cacccucuaa auc                                                       13

<210> SEQ ID NO 12
<211> LENGTH: 43
<212> TYPE: RNA
<213> ORGANISM: Actinomyces israelii

<400> SEQUENCE: 12
cacgugagua accugccccu cacuucugga uaaccgcuug aaa                      43

<210> SEQ ID NO 13
<211> LENGTH: 43
<212> TYPE: RNA
<213> ORGANISM: Corynebacterium diphtheriae

<400> SEQUENCE: 13 cacguggug aucgccucg uacuucggga uaagccuggg aaa                        43

<210> SEQ ID NO 14
<211> LENGTH: 43
<212> TYPE: RNA
<213> ORGANISM: Mycobacterium avium

<400> SEQUENCE: 14
cacgugggca aucuacccug cacuucggga uaagccuggg aaa                      43

<210> SEQ ID NO 15
<211> LENGTH: 44
<212> TYPE: RNA
<213> ORGANISM: Mycobacterium leprae

<400> SEQUENCE: 15 cacguggua aucgcccug cacuucaggg auaagcuugg gaaa                       44

<210> SEQ ID NO 16
<211> LENGTH: 43
```

```
<212> TYPE: RNA
<213> ORGANISM: Mycobacterium tuberculosis

<400> SEQUENCE: 16
cacgugggug aucugcccug cacuucggga uaagccuggg aaa          43

<210> SEQ ID NO 17
<211> LENGTH: 43
<212> TYPE: RNA
<213> ORGANISM: Nocardia asteroides

<400> SEQUENCE: 17
cacgugggug aucugccucg uacuucggga uaagccuggg aaa          43

<210> SEQ ID NO 18
<211> LENGTH: 43
<212> TYPE: RNA
<213> ORGANISM: Streptomyces acidiscabies

<400> SEQUENCE: 18
cacgugggca aucugcccuu cacucuggga caagcccugg aaa          43

<210> SEQ ID NO 19
<211> LENGTH: 43
<212> TYPE: RNA
<213> ORGANISM: Streptomyces albidoflavus

<400> SEQUENCE: 19
cacgugggca aucugcccug cacucuggga caagcccugg aaa          43

<210> SEQ ID NO 20
<211> LENGTH: 43
<212> TYPE: RNA
<213> ORGANISM: Streptomyces albus

<400> SEQUENCE: 20
cacgugggca aucugcccug cacucuggga caagcccugg aaa          43

<210> SEQ ID NO 21
<211> LENGTH: 43
<212> TYPE: RNA
<213> ORGANISM: Streptomyces ambofaciens

<400> SEQUENCE: 21
cacgugggca aucugcccug cacucuggga caagcccugg aaa          43

<210> SEQ ID NO 22
<211> LENGTH: 59
<212> TYPE: RNA
<213> ORGANISM: Unknown Organism
<220> FEATURE:
<223> OTHER INFORMATION: Description of Unknown Organism: Illustrative
      oligonucleotide

<400> SEQUENCE: 22
uggucgcucg cuccucuccu acuuggauaa cugugguaau ucuagagcua auacaugcc    59

<210> SEQ ID NO 23
<211> LENGTH: 43
<212> TYPE: RNA
<213> ORGANISM: Unknown Organism
<220> FEATURE:
```

-continued

```
<223> OTHER INFORMATION: Description of Unknown Organism: Illustrative
      oligonucleotide
<400> SEQUENCE: 23
auggaggggg auaacuacug gaaacgguag cuaauaccgc aua                    43
```

SYSTEM FOR INDENTIFICATION OF PATHOGENS

CROSS-REFERENCE TO RELATED APPLICATIONS

This application is a continuation-in-part of U.S. application Ser. No. 09/891,793, filed on Jun. 26, 2001. This application is also a continuation-in-part of U.S. application Ser. No. 10/728,486 titled "Methods For Rapid Identification of Pathogens In Humans and Animals," filed on Dec. 5, 2003.

This application also claims the benefit of U.S. Provisional Application 60/509,911, titled "Database For Microbial Investigations," filed on Oct. 9, 2003.

In addition, this application is related to U.S. application Ser. No. 10/418,514, (U.S. Publication No. US2004-0209260), filed on Apr. 18, 2003.

Each of the above applications is incorporated by reference in its entirety into this application.

STATEMENT OF GOVERNMENT SUPPORT

This invention was made with United States Government support under DARPA contract MDA972-00-C-0053. The United States Government has certain rights in the invention.

FIELD OF THE INVENTION

The present invention relates generally to the field of investigational bioinformatics and more particularly to secondary structure defining databases. The present invention further relates to methods for interrogating a database as a source of molecular masses of known bioagents for comparing against the molecular mass of an unknown or selected bioagent to determine either the identity of the selected bioagent, and/or to determine the origin of the selected bioagent. The identification of the bioagent is important for determining a proper course of treatment and/or irradication of the bioagent in such cases as biological warfare. Furthermore, the determination of the geographic origin of a selected bioagent will facilitate the identification of potential criminal identity. The present invention also relates to methods for rapid detection and identification of bioagents from environmental, clinical or other samples. The methods provide for detection and characterization of a unique base composition signature (BCS) from any bioagent, including bacteria and viruses. The unique BCS is used to rapidly identify the bioagent.

BACKGROUND OF THE INVENTION

In the United States, hospitals report well over 5 million cases of recognized infectious disease-related illnesses annually. Significantly greater numbers remain undetected, both in the inpatient and community setting, resulting in substantial morbidity and mortality. Critical intervention for infectious disease relies on rapid, sensitive and specific detection of the offending pathogen, and is central to the mission of microbiology laboratories at medical centers. Unfortunately, despite the recognition that outcomes from infectious illnesses are directly associated with time to pathogen recognition, as well as accurate identification of the class and species of microbe, and ability to identify the presence of drug resistance isolates, conventional hospital laboratories often remain encumbered by traditional slow multi-step culture based assays. Other limitations of the conventional laboratory which have become increasingly apparent include: extremely prolonged wait-times for pathogens with long generation time (up to several weeks); requirements for additional testing and wait times for speciation and identification of antimicrobial resistance; diminished test sensitivity for patients who have received antibiotics; and absolute inability to culture certain pathogens in disease states associated with microbial infection.

For more than a decade, molecular testing has been heralded as the diagnostic tool for the new millennium, whose ultimate potential could include forced obsolescence of traditional hospital laboratories. However, despite the fact that significant advances in clinical application of PCR techniques have occurred, the practicing physician still relies principally on standard techniques. A brief discussion of several existing applications of PCR in the hospital-based setting follows.

Generally speaking molecular diagnostics have been championed for identifying organisms that cannot be grown in vitro, or in instances where existing culture techniques are insensitive and/or require prolonged incubation times. PCR-based diagnostics have been successfully developed for a wide variety of microbes. Application to the clinical arena has met with variable success, with only a few assays achieving acceptance and utility.

One of the earliest, and perhaps most widely recognized applications of PCR for clinical practice is in detection of *Mycobacterium tuberculosis*. Clinical characteristics favoring development of a nonculture-based test for tuberculosis include week to month long delays associated with standard testing, occurrence of drug-resistant isolates and public health imperatives associated with recognition, isolation and treatment. Although frequently used as a diagnostic adjunctive, practical and routine clinical application of PCR remains problematic due to significant inter-laboratory variation in sensitivity, and inadequate specificity for use in low prevalence populations, requiring further development at the technical level. Recent advances in the laboratory suggest that identification of drug resistant isolates by amplification of mutations associated with specific antibiotic resistance (e.g., rpoB gene in rifampin resistant strains) may be forthcoming for clinical use, although widespread application will require extensive clinical validation.

One diagnostic assay, which has gained widespread acceptance, is for *C. trachomatis*. Conventional detection systems are limiting due to inadequate sensitivity and specificity (direct immunofluorescence or enzyme immunoassay) or the requirement for specialized culture facilities, due to the fastidious characteristics of this microbe. Laboratory development, followed by widespread clinical validation testing in a variety of acute and nonacute care settings have demonstrated excellent sensitivity (90-100%) and specificity (97%) of the PCR assay leading to its commercial development. Proven efficacy of the PCR assay from both genital and urine sampling, have resulted in its application to a variety of clinical setting, most recently including routine screening of patients considered at risk.

While the full potential for PCR diagnostics to provide rapid and critical information to physicians faced with difficult clinical-decisions has yet to be realized, one recently developed assay provides an example of the promise of this evolving technology. Distinguishing life-threatening causes of fever from more benign causes in children is a fundamental clinical dilemma faced by clinicians, particularly when infections of the central nervous system are being considered. Bacterial causes of meningitis can be highly aggressive, but generally cannot be differentiated on a clinical basis from aseptic meningitis, which is a relatively benign condition that can be managed on an outpatient basis. Existing blood culture methods often take several days to turn positive, and are often confounded by poor sensitivity or false-negative findings in patients receiving empiric antimicrobials. Testing and application of a PCR assay for enteroviral meningitis has been found to be highly sensitive. With reporting of results within 1 day, preliminary clinical trials have shown significant reductions in hospital costs, due to decreased duration of hospital stays and reduction in antibiotic therapy. Other viral PCR assays, now routinely available include those for herpes simplex virus, cytomegalovirus, hepatitis and HIV. Each has a demonstrated cost savings role in clinical practice, including detection of otherwise difficult to diagnose infections and newly realized capacity to monitor progression of disease and response to therapy, vital in the management of chronic infectious diseases.

The concept of a universal detection system has been forwarded for identification of bacterial pathogens, and speaks most directly to the possible clinical implications of a broad-based screening tool for clinical use. Exploiting the existence of highly conserved regions of DNA common to all bacterial species in a PCR assay would empower physicians to rapidly identify the presence of bacteremia, which would profoundly impact patient care. Previous empiric decision making could be abandoned in favor of educated practice, allowing appropriate and expeditious decision-making regarding need for antibiotic therapy and hospitalization.

Experimental work using the conserved features of the 16S rRNA common to almost all bacterial species, is an area of active investigation. Hospital test sites have focused on "high yield" clinical settings where expeditious identification of the presence of systemic bacterial infection has immediate high morbidity and mortality consequences. Notable clinical infections have included evaluation of febrile infants at risk for sepsis, detection of bacteremia in febrile neutropenic cancer patients, and examination of critically ill patients in the intensive care unit. While several of these studies have reported promising results (with sensitivity and specificity well over 90%), significant technical difficulties (described below) remain, and have prevented general acceptance of this assay in clinics and hospitals (which remain dependent on standard blood culture methodologies). Even the revolutionary advances of real-time PCR technique, which offers a quantitative more reproducible and technically simpler system remains encumbered by inherent technical limitations of the PCR assay.

The principle shortcomings of applying PCR assays to the clinical setting include: inability to eliminate background DNA contamination; interference with the PCR amplification by substrates present in the reaction; and limited capacity to provide rapid reliable speciation, antibiotic resistance and subtype identification. Some laboratories have recently made progress in identifying and removing inhibitors; however background contamination remains problematic, and methods directed towards eliminating exogenous sources of DNA report significant diminution in assay sensitivity. Finally, while product identification and detailed characterization has been achieved using sequencing techniques, these approaches are laborious and time-intensive thus detracting from its clinical applicability.

Rapid and definitive microbial identification is desirable for a variety of industrial, medical, environmental, quality, and research reasons. Traditionally, the microbiology laboratory has functioned to identify the etiologic agents of infectious diseases through direct examination and culture of specimens. Since the mid-1980s, researchers have repeatedly demonstrated the practical utility of molecular biology techniques, many of which form the basis of clinical diagnostic assays. Some of these techniques include nucleic acid hybridization analysis, restriction enzyme analysis, genetic sequence analysis, and separation and purification of nucleic acids (See, e.g., J. Sambrook, E. F. Fritsch, and T. Maniatis, Molecular Cloning: A Laboratory Manual, 2nd Ed., Cold Spring Harbor Laboratory Press, Cold Spring Harbor, N.Y., 1989). These procedures, in general, are time-consuming and tedious. Another option is the polymerase chain reaction (PCR) or other amplification procedure which amplifies a specific target DNA sequence based on the flanking primers used. Finally, detection and data analysis convert the hybridization event into an analytical result.

Other not yet fully realized applications of PCR for clinical medicine is the identification of infectious causes of disease previously described as idiopathic (e.g. *Bartonella henselae* in bacillary angiomatosis, and *Tropheryma whippellii* as the uncultured *bacillus* associated with Whipple's disease). Further, recent epidemiological studies which suggest a strong association between *Chlamydia pneumonia* and coronary artery disease, serve as example of the possible widespread, yet undiscovered links between pathogen and host which may ultimately allow for new insights into pathogenesis and novel life sustaining or saving therapeutics.

For the practicing clinician, PCR technology offers a yet unrealized potential for diagnostic omnipotence in the arena of infectious disease. A universal reliable infectious disease detection system would certainly become a fundamental tool in the evolving diagnostic armamentarium of the $21^{st}$ century clinician. For front line emergency physicians, or physicians working in disaster settings, a quick universal detection system, would allow for molecular triage and early aggressive targeted therapy. Preliminary clinical studies using species specific probes suggest that implementing rapid testing in acute care setting is feasible. Resources could thus be appropriately applied, and patients with suspected infections could rapidly be risk stratified to the different treatment settings, depending on the pathogen and virulence. Furthermore, links with data management systems, locally regionally and nationally, would allow for effective epidemiological surveillance, with obvious benefits for antibiotic selection and control of disease outbreaks.

For the hospitalists, the ability to speciate and subtype would allow for more precise decision-making regarding antimicrobial agents. Patients who are colonized with highly contagious pathogens could be appropriately isolated on entry into the medical setting without delay. Targeted therapy will diminish development of antibiotic resistance. Furthermore, identification of the genetic basis of antibiotic resistant strains would permit precise pharmacologic intervention. Both physician and patient would benefit with less need for repetitive testing and elimination of wait times for test results.

It is certain that the individual patient will benefit directly from this approach. Patients with unrecognized or difficult to diagnose infections would be identified and treated promptly. There will be reduced need for prolonged inpatient stays, with resultant decreases in iatrogenic events.

Mass spectrometry provides detailed information about the molecules being analyzed, including high mass accuracy. It is also a process that can be easily automated. Low-resolution MS may be unreliable when used to detect some known agents, if their spectral lines are sufficiently weak or sufficiently close to those from other living organisms in the sample. DNA chips with specific probes can only determine the presence or absence of specifically anticipated organisms. Because there are hundreds of thousands of species of benign bacteria, some very similar in sequence to threat organisms, even arrays with 10,000 probes lack the breadth needed to detect a particular organism.

Antibodies face more severe diversity limitations than arrays. If antibodies are designed against highly conserved targets to increase diversity, the false alarm problem will dominate, again because threat organisms are very similar to benign ones. Antibodies are only capable of detecting known agents in relatively uncluttered environments.

Several groups have described detection of PCR products using high resolution electrospray ionization-Fourier transform-ion cyclotron resonance mass spectrometry (ESI-FT-ICR MS). Accurate measurement of exact mass combined with knowledge of the number of at least one nucleotide allowed calculation of the total base composition for PCR duplex products of approximately 100 base pairs. (Aaserud et al., *J. Am. Soc. Mass Spec.*, 1996, 7, 1266-1269; Muddiman et al., *Anal. Chem.*, 1997, 69, 1543-1549; Wunschel et al., *Anal. Chem.*, 1998, 70, 1203-1207; Muddiman et al., *Rev. Anal. Chem.*, 1998, 17, 1-68). Electrospray ionization-Fourier transform-ion cyclotron resistance (ESI-FT-ICR) MS may be used to determine the mass of double-stranded, 500 base-pair PCR products via the average molecular mass (Hurst et al., *Rapid Commun. Mass Spec.* 1996, 10, 377-382). The use of matrix-assisted laser desorption ionization-time of flight (MALDI-TOF) mass spectrometry for characterization of PCR products has been described. (Muddiman et al., *Rapid Commun. Mass Spec.*, 1999, 13, 1201-1204). However, the degradation of DNAs over about 75 nucleotides observed with MALDI limited the utility of this method.

U.S. Pat. No. 5,849,492 describes a method for retrieval of phylogenetically informative DNA sequences which comprise searching for a highly divergent segment of genomic DNA surrounded by two highly conserved segments, designing the universal primers for PCR amplification of the highly divergent region, amplifying the genomic DNA by PCR technique using universal primers, and then sequencing the gene to determine the identity of the organism.

U.S. Pat. No. 5,965,363 discloses methods for screening nucleic acids for polymorphisms by analyzing amplified target nucleic acids using mass spectrometric techniques and to procedures for improving mass resolution and mass accuracy of these methods.

WO 99/14375 describes methods, PCR primers and kits for use in analyzing preselected DNA tandem nucleotide repeat alleles by mass spectrometry.

WO 98/12355 discloses methods of determining the mass of a target nucleic acid by mass spectrometric analysis, by cleaving the target nucleic acid to reduce its length, making the target single-stranded and using MS to determine the mass of the single-stranded shortened target. Also disclosed are methods of preparing a double-stranded target nucleic acid for MS analysis comprising amplification of the target nucleic acid, binding one of the strands to a solid support, releasing the second strand and then releasing the first strand which is then analyzed by MS. Kits for target nucleic acid preparation are also provided.

PCT WO97/33000 discloses methods for detecting mutations in a target nucleic acid by nonrandomly fragmenting the target into a set of single-stranded nonrandom length fragments and determining their masses by MS.

U.S. Pat. No. 5,605,798 describes a fast and highly accurate mass spectrometer-based process for detecting the presence of a particular nucleic acid in a biological sample for diagnostic purposes.

WO 98/21066 describes processes for determining the sequence of a particular target nucleic acid by mass spectrometry. Processes for detecting a target nucleic acid present in a biological sample by PCR amplification and mass spectrometry detection are disclosed, as are methods for detecting a target nucleic acid in a sample by amplifying the target with primers that contain restriction sites and tags, extending and cleaving the amplified nucleic acid, and detecting the presence of extended product, wherein the presence of a DNA fragment of a mass different from wild-type is indicative of a mutation. Methods of sequencing a nucleic acid via mass spectrometry methods are also described.

WO 97/37041, WO 99/31278 and U.S. Pat. No. 5,547,835 describe methods of sequencing nucleic acids using mass spectrometry. U.S. Pat. Nos. 5,622,824, 5,872,003 and 5,691,141 describe methods, systems and kits for exonuclease-mediated mass spectrometric sequencing.

Thus, there is a need for a method for bioagent detection and identification which is both specific and rapid, and in which no nucleic acid sequencing is required. The present invention addresses this need.

SUMMARY OF THE INVENTION

The present invention is directed to method of identifying an unknown bioagent using a database, such as a database stored on, for example, a local computer or perhaps a database accessible over a network or on the internet. This database of molecular masses of known bioagents provides a standard of comparison for determining both identity and geographic origin of the unknown bioagent. The nucleic acid from said bioagent is first contacted with at least one pair of oligonucleotide primers which hybridize to sequences of said nucleic acid that flank a variable nucleic acid sequence of the bioagent. Using PCR technology an amplification product of this variable nucleic acid sequence is made. After standard isolation, the molecular mass of this amplification product is determined using known mass-spec techniques. This molecular mass is compared to the molecular mass of known bioagents within the database, for identifying the unknown bioagent.

This invention is also directed to databases having cell-data positional significance comprising at least a first table that includes a plurality of data-containing cells. The table is organized into at least a first row and a second row, each row having columns which are aligned relative to each other so that inter-row conserved regions are aligned. This alignment facilitates the analysis of regions, which are highly conserved between species. This alignment further provides insight into secondary polymer structure by this alignment. Although this invention is directed to a database where each row describes any polymer, in a preferred embodiment, the polymer is an RNA. Other alignments that operate in the same manner are also contemplated.

Another embodiment of this invention is a method for reconciling the content of two databases such that the content of each is a mirror of the other.

Another embodiment is directed to determining the geographic origin of a bioagent using a database of molecular masses of known bioagents comprising contacting a nucleic acid from the selected bioagent with at least one pair of oligonucleotide primers which hybridize to sequences of the nucleic acid, where the sequences flank a variable nucleic acid sequence of the bioagent. This hybridized region is isolated and amplified through standard PCR techniques known in the art. The molecular mass is determined of this amplified product through any technique known in the art such as, Mass-spectrometry for example. This molecular mass is compared to the molecular masses stored in the database of known bioagents thereby determining a group of probabilistically reasonable geographic origins for the selected bioagent.

Figures 1, 1A:
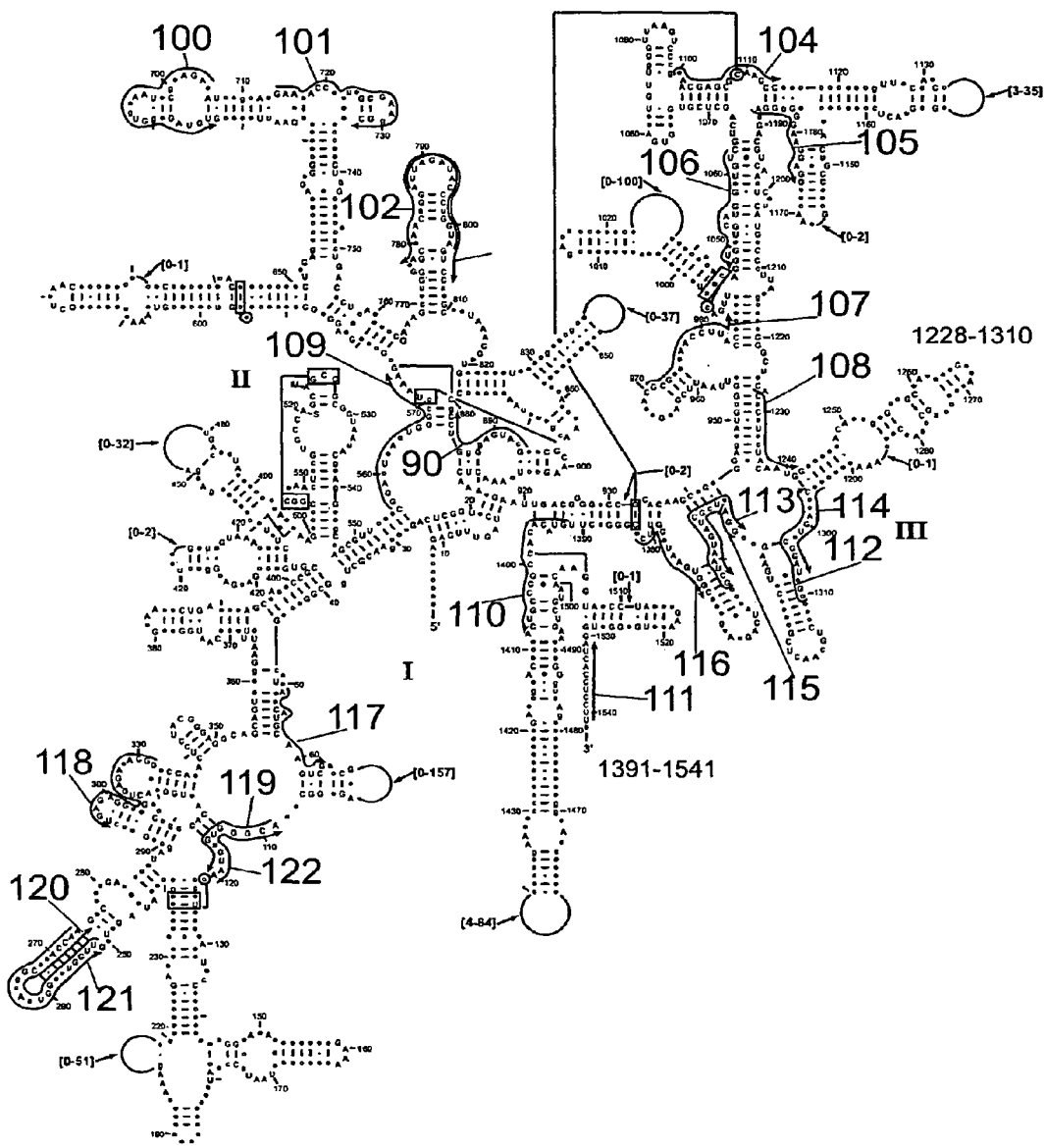
FIGS. 1A-1I are representative consensus diagrams that show examples of conserved regions from 16S rRNA (FIGS. 1A-1B), 23S rRNA (3'-half, FIGS. 1C-1D; 5'-half, FIGS. 1E-F), 23S rRNA Domain I (FIG. 1G), 23S rRNA Domain IV (FIG. 1H) and 16S rRNA Domain HE (FIG. 1I) which are suitable for use in the present invention. Lines with arrows are examples of regions to which intelligent primer pairs for PCR are designed. The label for each primer pair represents the starting and ending base number of the amplified region on the consensus diagram. Bases in capital letters are greater than 95% conserved; bases in lower case letters are 90-95% conserved, filled circles are 80-90% conserved; and open circles are less than 80% conserved. The label for each primer pair represents the starting and ending base number of the amplified region on the consensus diagram.

FIG. 2 shows a typical primer amplified region from the 16S rRNA Domain III shown in FIG. 1C.

FIG. 3 is a schematic diagram showing conserved regions in RNase P. Bases in capital letters are greater than 90% conserved; bases in lower case letters are 80-90% conserved; filled circles designate bases which are 70-80% conserved; and open circles designate bases that are less than 70% conserved.

FIG. 4 is a schematic diagram of base composition signature determination using nucleotide analog "tags" to determine base composition signatures.

FIG. 5 shows the deconvoluted mass spectra of a *Bacillus anthracis* region with and without the mass tag phosphorothioate A (A*). The two spectra differ in that the measured molecular weight of the mass tag-containing sequence is greater than the unmodified sequence.

FIG. 6 shows base composition signature (BCS) spectra from PCR products from *Staphylococcus aureus* (*S. aureus* 16S_1337F) and *Bacillus anthracus* (*B. anthr.* 16S_1337F), amplified using the same primers. The two strands differ by only two (AT→CG) substitutions and are clearly distinguished on the basis of their BCS.

FIG. 7 shows that a single difference between two sequences (A14 in *B. anthracis* vs. A15 in *B. cereus*) can be easily detected using ESI-TOF mass spectrometry.

FIG. 8 is an ESI-TOF of *Bacillus anthracis* spore coat protein sspE 56mer plus calibrant. The signals unambiguously identify *B. anthracis* versus other *Bacillus* species.

FIG. 9 is an ESI-TOF of a *B. anthracis* synthetic 16S_1228 duplex (reverse and forward strands). The technique easily distinguishes between the forward and reverse strands.

FIG. 10 is an ESI-FTICR-MS of a synthetic *B. anthracis* 16S_1337 46 base pair duplex.

FIG. 11 is an ESI-TOF-MS of a 56mer oligonucleotide (3 scans) from the *B. anthracis* saspB gene with an internal mass standard. The internal mass standards are designated by asterisks.

FIG. 12 is an ESI-TOF-MS of an internal standard with 5 mM TBA-TFA buffer showing that charge stripping with tributylammonium trifluoroacetate reduces the most abundant charge state from $[M-8H+]^{8-}$ to $[M-3H+]^{3-}$.

FIG. 13 is a portion of a secondary structure defining database according to one embodiment of the present invention, where two examples of selected sequences are displayed graphically thereunder.

FIG. 14 is a three dimensional graph demonstrating the grouping of sample molecular weight according to species.

FIG. 15 is a three dimensional graph demonstrating the grouping of sample molecular weights according to species of virus and mammal infected.

FIG. 16 is a three dimensional graph demonstrating the grouping of sample molecular weights according to species of virus, and animal-origin of infectious agent.

FIG. 17 is a figure depicting how the triangulation method of the present invention provides for the identification of an unknown bioagent without prior knowledge of the unknown agent. The use of different primer sets to distinguish and identify the unknown is also depicted as primer sets I, II and III within this figure. A three dimensional graph depicts all of bioagent space (170), including the unknown bioagent, which after use of primer set I (171) according to a method according to the present invention further differentiates and classifies bioagents according to major classifications (176) which, upon further analysis using primer set II (172) differentiates the unknown agent (177) from other, known agents (173) and finally, the use of a third primer set (175) further specifies subgroups within the family of the unknown (174).

FIGS. 18A, 18B, and 18C illustrate block diagrams of three embodiments of a bioagent identification system.

FIG. 19 illustrates a logic chart for a bioagent identification module configured to receive data including a mass of an amplification product or a base composition.

DESCRIPTION OF PREFERRED EMBODIMENTS

The present invention provides a combination of a non-PCR biomass detection mode, preferably high-resolution MS, with PCR-based BCS technology using "intelligent primers" which hybridize to conserved sequence regions of nucleic acids derived from a bioagent and which bracket variable sequence regions that uniquely identify the bioagent. The high-resolution MS technique is used to determine the molecular mass and base composition signature (BCS) of the amplified sequence region. This unique "base composition signature" (BCS) is then input to a maximum-likelihood detection algorithm for matching against a database of base composition signatures in the same amplified region. The present method combines PCR-based amplification technology (which provides specificity) and a molecular mass detection mode (which provides speed and does not require nucleic acid sequencing of the amplified target sequence) for bioagent detection and identification.

The present methods allow extremely rapid and accurate detection and identification of bioagents compared to existing methods. Furthermore, this rapid detection and identification is possible even when sample material is impure. Thus, the method is useful in a wide variety of fields, including, but not limited to, environmental testing (e.g., detection and discrimination of pathogenic vs. non-pathogenic bacteria in water or other samples), germ warfare (allowing immediate identification of the bioagent and appropriate treatment), pharmacogenetic analysis and medical diagnosis (including cancer diagnosis based on mutations and polymorphisms; drug resistance and susceptibility testing; screening for and/or diagnosis of genetic diseases and conditions; and diagnosis of infectious diseases and conditions). The methods leverage ongoing biomedical research in virulence, pathogenicity, drug resistance and genome sequencing into a method which provides greatly improved sensitivity, specificity and reliability compared to existing methods, with lower rates of false positives.

The present methods can be used, for example, to detect and classify any biological agent, including bacteria, viruses, fungi and toxins. As one example, where the agent is a biological threat, the information obtained is used to determine practical information needed for countermeasures, including toxin genes, pathogenicity islands and antibiotic resistance genes. In addition, the methods can be used to identify natural or deliberate engineering events including chromosome fragment swapping, molecular breeding (gene shuffling) and emerging infectious diseases.

Bacteria have a common set of absolutely required genes. About 250 genes are present in all bacterial species (*Proc. Natl. Acad. Sci. U.S.A.*, 1996, 93, 10268; *Science*, 1995, 270, 397), including tiny genomes like *Mycoplasma, Ureaplasma* and *Rickettsia*. These genes encode proteins involved in translation, replication, recombination and repair, transcription, nucleotide metabolism, amino acid metabolism, lipid metabolism, energy generation, uptake, secretion and the like. Examples of these proteins are DNA polymerase III beta, elongation factor TU, heat shock protein groEL, RNA polymerase beta, phosphoglycerate kinase, NADH dehydrogenase, DNA ligase, DNA topoisomerase and elongation factor G. Operons can also be targeted using the present method. One example of an operon is the bfp operon from enteropathogenic *E. coli*. Multiple core chromosomal genes can be used to classify bacteria at a genus or genus species level to determine if an organism has threat potential. The methods can also be used to detect pathogenicity markers (plasmid or chromosomal) and antibiotic resistance genes to confirm the threat potential of an organism and to direct countermeasures.

A theoretically ideal bioagent detector would identify, quantify, and report the complete nucleic acid sequence of every bioagent that reached the sensor. The complete sequence of the nucleic acid component of a pathogen would provide all relevant information about the threat, including its identity and the presence of drug-resistance or pathogenicity markers. This ideal has not yet been achieved. However, the present invention provides a straightforward strategy for obtaining information with the same practical value using base composition signatures (BCS). While the base composition of a gene fragment is not as information-rich as the sequence itself, there is no need to analyze the complete sequence of the gene if the short analyte sequence fragment is properly chosen. A database of reference sequences can be prepared in which each sequence is indexed to a unique base composition signature, so that the presence of the sequence can be inferred with accuracy from the presence of the signature. The advantage of base composition signatures is that they can be quantitatively measured in a massively parallel fashion using multiplex PCR (PCR in which two or more primer pairs amplify target sequences simultaneously) and mass spectrometry. These multiple primer amplified regions uniquely identify most threat and ubiquitous background bacteria and viruses. In addition, cluster-specific primer pairs distinguish important local clusters (e.g., anthracis group).

In the context of this invention, a "bioagent" is any organism, living or dead, or a nucleic acid derived from such an organism. Examples of bioagents include, but are not limited to, cells (including, but not limited to, human clinical samples, bacterial cells and other pathogens), viruses, toxin genes and bioregulating compounds. Samples may be alive or dead or in a vegetative state (for example, vegetative bacteria or spores) and may be encapsulated or bioengineered.

As used herein, a "base composition signature" (BCS) is the exact base composition from selected fragments of nucleic acid sequences that uniquely identifies the target gene and source organism. BCS can be thought of as unique indexes of specific genes.

Figures 1, 1A, 2:
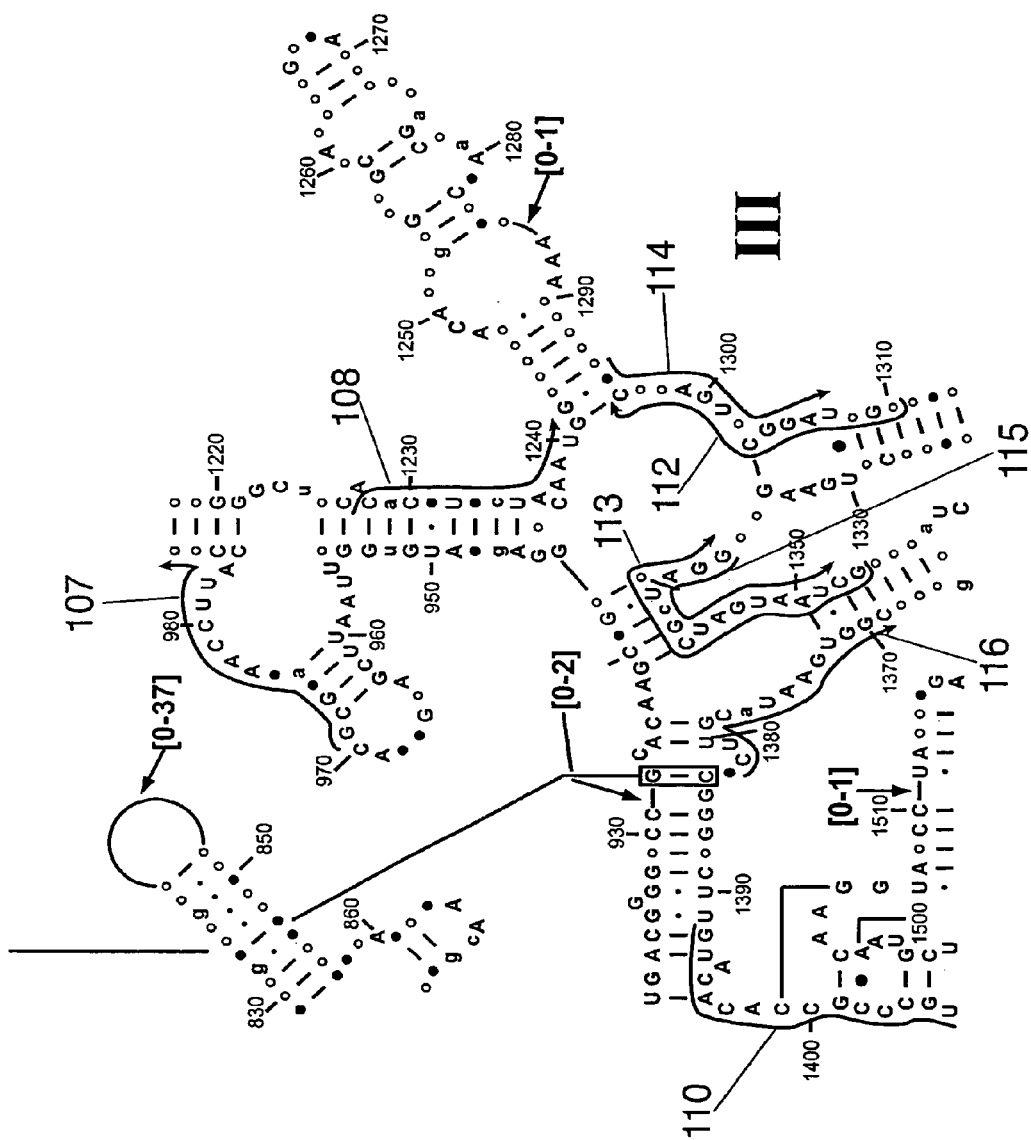
Figures 1, 1A, 2, 3:
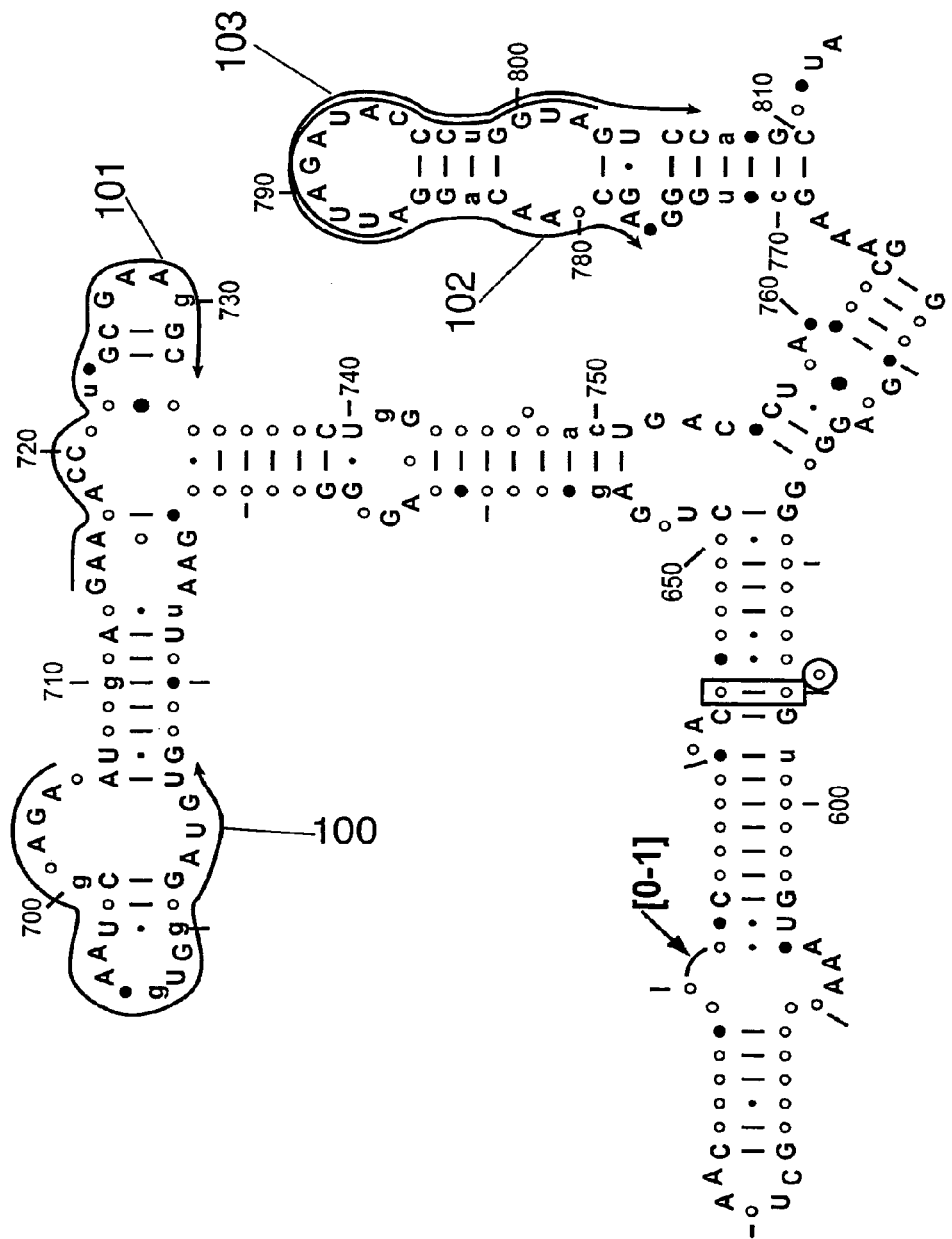
Figures 1, 1A, 2, 3, 4:
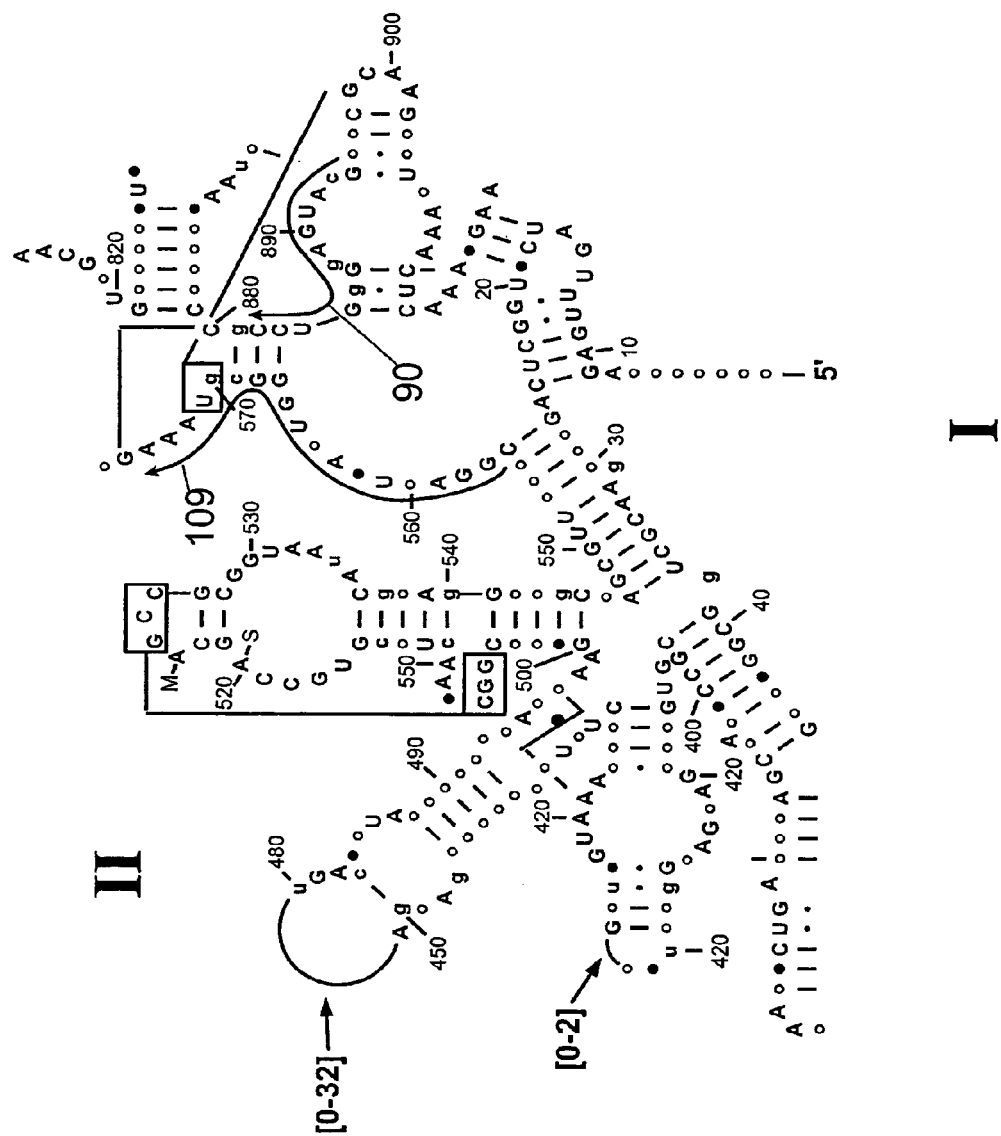

As used herein, "intelligent primers" are primers which bind to sequence regions which flank an intervening variable region. In a preferred embodiment, these sequence regions which flank the variable region are highly conserved among different species of bioagent. For example, the sequence regions may be highly conserved among all *Bacillus* species. By the term "highly conserved," it is meant that the sequence regions exhibit between about 80-100%, more preferably between about 90-100% and most preferably between about 95-100% identity. Examples of intelligent primers which amplify regions of the 16S and 23S rRNA are shown in FIGS. 1A-1I. A typical primer amplified region in 16S rRNA is shown in FIG. 2. The arrows represent primers which bind to highly conserved regions which flank a variable region in 16S rRNA domain III. The amplified region is the stem-loop structure under "1100-1188."

One main advantage of the detection methods of the present invention is that the primers need not be specific for a particular bacterial species, or even genus, such as *Bacillus* or *Streptomyces*. Instead, the primers recognize highly conserved regions across hundreds of bacterial species including, but not limited to, the species described herein. Thus, the same primer pair can be used to identify any desired bacterium because it will bind to the conserved regions which flank a variable region specific to a single species, or common to several bacterial species, allowing nucleic acid amplification of the intervening sequence and determination of its molecular weight and base composition. For example, the 16S_971-1062, 16S_1228-1310 and 16S_1100-1188 regions are 98-99% conserved in about 900 species of bacteria (16S=16S rRNA, numbers indicate nucleotide position). In one embodiment of the present invention, primers used in the present method bind to one or more of these regions or portions thereof.

As will be appreciated by those of skill in the art, each representative primer pair is preferably designed to yield amplification products, i.e. amplicons, having molecular masses which vary amongst different bioagents. Consequently, the amplification products have the capacity to yield identifying information to distinguish between a plurality of bioagents. In one embodiment, such amplification products have the capacity to yield identifying information sufficient to distinguish among three or more bioagents. In other embodiments, such amplification products have the capacity to yield identifying information sufficient to distinguish among as many as five, 10, 50, 100 or more bioagents. Such amplification products enable unbiased simultaneous parallel identification of bioagents in clinical or environmental samples in a manner not previously possible because existing bioagent detection methods such as probe-based methods and culture methods are biased toward detection of particular bioagents.

The present invention provides a combination of a non-PCR biomass detection mode, preferably high-resolution MS, with nucleic acid amplification-based BCS technology using "intelligent primers" which hybridize to conserved regions and which bracket variable regions that uniquely identify the bioagent(s). Although the use of PCR is preferred, other nucleic acid amplification techniques may also be used, including ligase chain reaction (LCR) and strand displacement amplification (SDA). The high-resolution MS technique allows separation of bioagent spectral lines from background spectral lines in highly cluttered environments. The resolved spectral lines are then translated to BCS which are input to a maximum-likelihood detection algorithm matched against spectra for one or more known BCS. Preferably, the bioagent BCS spectrum is matched against one or more databases of BCS from vast numbers of, bioagents. Preferably, the matching is done using a maximum-likelihood detection algorithm.

In one embodiment, base composition signatures are quantitatively measured in a massively parallel fashion using the polymerase chain reaction (PCR), preferably multiplex PCR, and mass spectrometric (MS) methods. Sufficient quantities of nucleic acids should be present for detection of bioagents by MS. A wide variety of techniques for preparing large amounts of purified nucleic acids or fragments thereof are well known to those of skill in the art. PCR requires one or more pairs of oligonucleotide primers which bind to regions which flank the target sequence(s) to be amplified. These primers prime synthesis of a different strand of DNA, with synthesis occurring in the direction of one primer towards the other primer. The primers, DNA to be amplified, a thermostable DNA polymerase (e.g. Taq polymerase), the four deoxynucleotide triphosphates, and a buffer are combined to initiate DNA synthesis. The solution is denatured by heating, then cooled to allow annealing of newly added primer, followed by another round of DNA synthesis. This process is typically repeated for about 30 cycles, resulting in amplification of the target sequence.

The "intelligent primers" define the target sequence region to be amplified and analyzed. In one embodiment, the target sequence is a ribosomal RNA (rRNA) gene sequence. With the complete sequences of many of the smallest microbial genomes now available, it is possible to identify a set of genes that defines "minimal life" and identify composition signatures that uniquely identify each gene and organism. Genes that encode core life functions such as DNA replication, transcription, ribosome structure, translation, and transport are distributed broadly in the bacterial genome and are preferred regions for BCS analysis. Ribosomal RNA (rRNA) genes comprise regions that provide useful base composition signatures. Like many genes involved in core life functions, rRNA genes contain sequences that are extraordinarily conserved across bacterial domains interspersed with regions of high variability that are more specific to each species. The variable regions can be utilized to build a database of base composition signatures. The strategy involves creating a structure-based alignment of sequences of the small (16S) and the large (23S) subunits of the rRNA genes. For example, there are currently over 13,000 sequences in the ribosomal RNA database that has been created and maintained by Robin Gutell, University of Texas at Austin, and is publicly available on the Institute for Cellular and Molecular Biology web page on the world wide web of the Internet at, for example, "rna-.icmb.utexas.edu/." There is also a publicly available rRNA database created and maintained by the University of Antwerp, Belgium on the world wide web of the Internet at, for example, "rrna.uia.ac.be."

These databases have been analyzed to determine regions that are useful as base composition signatures. The characteristics of such regions include: a) between about 80 and 100%, preferably >about 95% identity among species of the particular bioagent of interest, of upstream and downstream nucleotide sequences which serve as sequence amplification primer sites; b) an intervening variable region which exhibits no greater than about 5% identity among species; and c) a separation of between about 30 and 1000 nucleotides, preferably no more than about 50-250 nucleotides, and more preferably no more than about 60-100 nucleotides, between the conserved regions.

Due to their overall conservation, the flanking rRNA primer sequences serve as good "universal" primer binding sites to amplify the region of interest for most, if not all, bacterial species. The intervening region between the sets of primers varies in length and/or composition, and thus provides a unique base composition signature.

It is advantageous to design the "intelligent primers" to be as universal as possible to minimize the number of primers which need to be synthesized, and to allow detection of multiple species using a single pair of primers. These primer pairs can be used to amplify variable regions in these species. Because any variation (due to codon wobble in the $3^{rd}$ position) in these conserved regions among species is likely to occur in the third position of a DNA triplet, oligonucleotide primers can be designed such that the nucleotide corresponding to this position is a base which can bind to more than one nucleotide, referred to herein as a "universal base." For example, under this "wobble" pairing, inosine (I) binds to U, C or A; guanine (G) binds to U or C, and uridine (U) binds to U or C. Other examples of universal bases include nitroindoles such as 5-nitroindole or 3-nitropyrrole (Loakes et al., *Nucleosides and Nucleotides,* 1995, 14, 1001-1003), the degenerate nucleotides dP or dK (Hill et al.), an acyclic nucleoside analog containing 5-nitroindazole (Van Aerschot et al., *Nucleosides and Nucleotides,* 1995, 14, 1053-1056) or the purine analog 1-(2-deoxy-∃-D-ribofuranosyl)-imidazole-4-carboxamide (Sala et al., *Nucl. Acids Res.,* 1996, 24, 3302-3306).

In another embodiment of the invention, to compensate for the somewhat weaker binding by the "wobble" base, the oligonucleotide primers are designed such that the first and second positions of each triplet are occupied by nucleotide analogs which bind with greater affinity than the unmodified nucleotide. Examples of these analogs include, but are not limited to, 2,6-diaminopurine which binds to thymine, propyne T which binds to adenine and propyne C and phenoxazines, including G-clamp, which binds to G. Propynes are described in U.S. Pat. Nos. 5,645,985, 5,830.653 and 5,484,908, each of which is incorporated herein by reference in its entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

Bacterial biological warfare agents capable of being detected by the present methods include, but are not limited to, *Bacillus anthracis* (anthrax), *Yersinia pestis* (pneumonic plague), *Franciscella tularensis* (tularemia), *Brucella suis, Brucella abortus, Brucella melitensis* (undulant fever), *Burkholderia mallei* (glanders), *Burkholderia pseudomalleii* (melioidosis), *Salmonella typhi* (typhoid fever), *Rickettsia typhii* (epidemic typhus), *Rickettsia prowasekii* (endemic typhus) and *Coxiella burnetii* (Q fever), *Rhodobacter capsulatus, Chlamydia pneumoniae, Escherichia coli, Shigella dysenteriae, Shigella flexneri, Bacillus cereus, Clostridium botulinum, Coxiella burnetti, Pseudomonas aeruginosa, Legionella pneumophila*, and *Vibrio cholerae.*

Besides 16S and 23S rRNA, other target regions suitable for use in the present invention for detection of bacteria include, but are not limited to, 5S rRNA and RNase P (FIG. 3).

Biological warfare fungus biowarfare agents include, but are not limited to, *coccidioides immitis* (Coccidioidomycosis).

Biological warfare toxin genes capable of being detected by the methods of the present invention include, but are not limited to, botulism, T-2 mycotoxins, ricin, staph enterotoxin B, shigatoxin, abrin, aflatoxin, *Clostridium perfringens* epsilon toxin, conotoxins, diacetoxyscirpenol, tetrodotoxin and saxitoxin.

Biological warfare viral threat agents are mostly RNA viruses (positive-strand and negative-strand), with the exception of smallpox. Every RNA virus is a family of related viruses (quasispecies). These viruses mutate rapidly and the potential for engineered strains (natural or deliberate) is very high. RNA viruses cluster into families that have conserved RNA structural domains on the viral genome (e.g., virion components, accessory proteins) and conserved housekeeping genes that encode core viral proteins including, for single strand positive strand RNA viruses, RNA-dependent RNA polymerase, double stranded RNA helicase, chymotrypsin-like and papain-like proteases and methyltransferases.

Examples of (−)-strand RNA viruses include, but are not limited to, arenaviruses (e.g., sabia virus, lassa fever, Machupo, Argentine hemorrhagic fever, flexal virus), bunyaviruses (e.g., hantavirus, nairovirus, phlebovirus, hantaan virus, Congo-crimean hemorrhagic fever, rift valley fever), and mononegavirales (e.g., filovirus, paramyxovirus, ebola virus, Marburg, equine morbillivirus).

Examples of (+)-strand RNA viruses include, but are not limited to, picornaviruses (e.g., coxsackievirus, echovirus, human coxsackievirus A, human echovirus, human enterovirus, human poliovirus, hepatitis A virus, human parechovirus, human rhinovirus), astroviruses (e.g., human astrovirus), calciviruses (e.g., chiba virus, chitta virus, human calcivirus, norwalk virus), nidovirales (e.g., human coronavirus, human torovirus), flaviviruses (e.g., dengue virus 1-4, Japanese encephalitis virus, Kyanasur forest disease virus, Murray Valley encephalitis virus, Rocio virus, St. Louis encephalitis virus, West Nile virus, yellow fever virus, hepatitis c virus) and togaviruses (e.g., Chikugunya virus, Eastern equine encephalitis virus, Mayaro virus, O' nyong-nyong virus, Ross River virus, Venezuelan equine encephalitis virus, Rubella virus, hepatitis E virus). The hepatitis C virus has a 5'-untranslated region of 340 nucleotides, an open reading frame encoding 9 proteins having 3010 amino acids and a 3'-untranslated region of 240 nucleotides. The 5'-UTR and 3'-UTR are 99% conserved in hepatitis C viruses.

In one embodiment, the target gene is an RNA-dependent RNA polymerase or a helicase encoded by (+)-strand RNA viruses, or RNA polymerase from a (−)-strand RNA virus. (+)-strand RNA viruses are double stranded RNA and replicate by RNA-directed RNA synthesis using RNA-dependent RNA polymerase and the positive strand as a template. Helicase unwinds the RNA duplex to allow replication of the single stranded RNA. These viruses include viruses from the family picornaviridae (e.g., poliovirus, coxsackievirus, echovirus), togaviridae (e.g., alphavirus, flavivirus, rubivirus), arenaviridae (e.g., lymphocytic choriomeningitis virus, lassa fever virus), cononaviridae (e.g., human respiratory virus) and Hepatitis A virus. The genes encoding these proteins comprise variable and highly conserved regions which flank the variable regions.

In another embodiment, the detection scheme for the PCR products generated from the bioagent(s) incorporates at least three features. First, the technique simultaneously detects and differentiates multiple (generally about 6-10) PCR products. Second, the technique provides a BCS that uniquely identifies the bioagent from the possible primer sites. Finally, the detection technique is rapid, allowing multiple PCR reactions to be run in parallel.

In one embodiment, the method can be used to detect the presence of antibiotic resistance and/or toxin genes in a bacterial species. For example, *Bacillus anthracis* comprising a tetracycline resistance plasmid and plasmids encoding one or both anthracis toxins (px01 and/or px02) can be detected by using antibiotic resistance primer sets and toxin gene primer sets. If the *B. anthracis* is positive for tetracycline resistance, then a different antibiotic, for example quinalone, is used.

Mass spectrometry (MS)-based detection of PCR products provides all of these features with additional advantages. MS is intrinsically a parallel detection scheme without the need for radioactive or fluorescent labels, since every amplification product with a unique base composition is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons. Intact molecular ions can be generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). For example, MALDI of nucleic acids, along with examples of matrices for use in MALDI of nucleic acids, are described in WO 98/54751 (Genetrace, Inc.).

Upon ionization, several peaks are observed from one sample due to the formation of ions with different charges. Averaging the multiple readings of molecular mass obtained from a single mass spectrum affords an estimate of molecular mass of the bioagent. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), ion trap, quadrupole, magnetic sector, time of flight (TOF), Q-TOF, and triple quadrupole.

In general, the mass spectrometric techniques which can be used in the present invention include, but are not limited to, tandem mass spectrometry, infrared multiphoton dissociation and pyrolytic gas chromatography mass spectrometry (PGC-MS). In one embodiment of the invention, the bioagent detection system operates continually in bioagent detection mode using pyrolytic GC-MS without PCR for rapid detection of increases in biomass (for example, increases in fecal contamination of drinking water or of germ warfare agents). To achieve minimal latency, a continuous sample stream flows directly into the PGC-MS combustion chamber. When an increase in biomass is detected, a PCR process is automatically initiated. Bioagent presence produces elevated levels of large molecular fragments from, for example, about 100-7,000 Da which are observed in the PGC-MS spectrum. The observed mass spectrum is compared to a threshold level and when levels of biomass are determined to exceed a predetermined threshold, the bioagent classification process described hereinabove (combining PCR and MS, preferably FT-ICR MS) is initiated. Optionally, alarms or other processes (halting ventilation flow, physical isolation) are also initiated by this detected biomass level.

The accurate measurement of molecular mass for large DNAs is limited by the adduction of cations from the PCR reaction to each strand, resolution of the isotopic peaks from natural abundance $^{13}C$ and $^{15}N$ isotopes, and assignment of the charge state for any ion. The cations are removed by in-line dialysis using a flow-through chip that brings the solution containing the PCR products into contact with a solution containing ammonium acetate in the presence of an electric field gradient orthogonal to the flow. The latter two problems are addressed by operating with a resolving power of >100,000 and by incorporating isotopically depleted nucleotide triphosphates into the DNA. The resolving power of the instrument is also a consideration. At a resolving power of 10,000, the modeled signal from the $[M-14H+]^{14-}$ charge state of an 84mer PCR product is poorly characterized and assignment of the charge state or exact mass is impossible. At a resolving power of 33,000, the peaks from the individual isotopic components are visible. At a resolving power of 100,000, the isotopic peaks are resolved to the baseline and assignment of the charge state for the ion is straightforward. The [$^{13}$C, $^{15}$N]-depleted triphosphates are obtained, for example, by growing microorganisms on depleted media and harvesting the nucleotides (Batey et al., *Nucl. Acids Res.*, 1992, 20, 4515-4523).

While mass measurements of intact nucleic acid regions are believed to be adequate to determine most bioagents, tandem mass spectrometry (MS") techniques may provide more definitive information pertaining to molecular identity or sequence. Tandem MS involves the coupled use of two or more stages of mass analysis where both the separation and detection steps are based on mass spectrometry. The first stage is used to select an ion or component of a sample from which further structural information is to be obtained. The selected ion is then fragmented using, e.g., blackbody irradiation, infrared multiphoton dissociation, or collisional activation. For example, ions generated by electrospray ionization (ESI) can be fragmented using IR multiphoton dissociation. This activation leads to dissociation of glycosidic bonds and the phosphate backbone, producing two series of fragment ions, called the w-series (having an intact 3' terminus and a 5' phosphate following internal cleavage) and the a-Base series (having an intact 5' terminus and a 3' furan).

The second stage of mass analysis is then used to detect and measure the mass of these resulting fragments of product ions. Such ion selection followed by fragmentation routines can be performed multiple times so as to essentially completely dissect the molecular sequence of a sample.

If there are two or more targets of similar base composition or mass, or if a single amplification reaction results in a product which has the same mass as two or more bioagent reference standards, they can be distinguished by using mass-modifying "tags." In this embodiment of the invention, a nucleotide analog or "tag" is incorporated during amplification (e.g., a 5-(trifluoromethyl) deoxythymidine triphosphate) which has a different molecular weight than the unmodified base so as to improve distinction of masses. Such tags are described in, for example, PCT WO97/33000, which is incorporated herein by reference in its entirety. This further limits the number of possible base compositions consistent with any mass. For example, 5-(trifluoromethyl)deoxythymidine triphosphate can be used in place of dTTP in a separate nucleic acid amplification reaction. Measurement of the mass shift between a conventional amplification product and the tagged product is used to quantitate the number of thymidine nucleotides in each of the single strands. Because the strands are complementary, the number of adenosine nucleotides in each strand is also determined.

In another amplification reaction, the number of G and C residues in each strand is determined using, for example, the cytidine analog 5-methylcytosine (5-meC) or propyne C. The combination of the A/T reaction and G/C reaction, followed by molecular weight determination, provides a unique base composition. This method is summarized in FIG. 4 and Table 1.

TABLE 1

| Mass tag | Double strand sequence | Single strand sequence | Total mass this strand | Base info this strand | Base info other strand | Total base comp. Top strand | Total base comp. Bottom strand |
|---|---|---|---|---|---|---|---|
| T* · mass (T* - T) = x | T*ACGT*ACGT* AT*GCAT*GCA | T*ACGT*ACGT* | 3x | 3T | 3A | 3T 2A 2C 2G | 3A 2T 2G 2C |
| | | AT*GCAT*GCA | 2x | 2T | 2A | | |
| C* · mass (C* - C) = y | TAC*GTAC*GT ATGC*ATGC*A | TAC*GTAC*GT | 2x | 2C | 2G | | |
| | | ATGC*ATGC*A | 2x | 2C | 2G | | |

The mass tag phosphorothioate A (A*) was used to distinguish a *Bacillus anthracis* cluster. The *B. anthracis* ($A_{14}G_9C_{14}T_9$) had an average MW of 14072.26, and the *B. anthracis* ($A_1A^*_{13}G_9C_{14}T_9$) had an average molecular weight of 14281.11 and the phosphorothioate A had an average molecular weight of +16.06 as determined by ESI-TOF MS. The deconvoluted spectra are shown in FIG. 5.

In another example, assume the measured molecular masses of each strand are 30,000.115Da and 31,000.115 Da respectively, and the measured number of dT and dA residues are (30,28) and (28,30). If the molecular mass is accurate to 100 ppm, there are 7 possible combinations of dG+dC possible for each strand. However, if the measured molecular mass is accurate to 10 ppm, there are only 2 combinations of dG+dC, and at 1 ppm accuracy there is only one possible base composition for each strand.

Signals from the mass spectrometer may be input to a maximum-likelihood detection and classification algorithm such as is widely used in radar signal processing. The detection processing uses matched filtering of BCS observed in mass-basecount space and allows for detection and subtraction of signatures from known, harmless organisms, and for detection of unknown bioagent threats. Comparison of newly observed bioagents to known bioagents is also possible, for estimation of threat level, by comparing their BCS to those of known organisms and to known forms of pathogenicity enhancement, such as insertion of antibiotic resistance genes or toxin genes.

Processing may end with a Bayesian classifier using log likelihood ratios developed from the observed signals and average background levels. The program emphasizes performance predictions culminating in probability-of-detection versus probability-of-false-alarm plots for conditions involving complex backgrounds of naturally occurring organisms and environmental contaminants. Matched filters consist of a priori expectations of signal values given the set of primers used for each of the bioagents. A genomic sequence database (e.g. GenBank) is used to define the mass basecount matched filters. The database contains known threat agents and benign background organisms. The latter is used to estimate and subtract the signature produced by the background organisms. A maximum likelihood detection of known background organisms is implemented using matched filters and a running-sum estimate of the noise covariance. Background signal strengths are estimated and used along with the matched filters to form signatures which are then subtracted. the maximum likelihood process is applied to this "cleaned up" data in a similar manner employing matched filters for the organisms and a running-sum estimate of the noise-covariance for the cleaned up data.

In one embodiment, a strategy to "triangulate" each organism by measuring signals from multiple core genes is used to reduce false negative and false positive signals, and enable reconstruction of the origin or hybrid or otherwise engineered bioagents. After identification of multiple core genes, alignments are created from nucleic acid sequence databases. The alignments are then analyzed for regions of conservation and variation, and potential primer binding sites flanking variable regions are identified. Next, amplification target regions for signature analysis are selected which distinguishes organisms based on specific genomic differences (i.e., base composition). For example, detection of signatures for the three part toxin genes typical of B. anthracis (Bowen et al., J. Appl. Microbiol., 1999, 87, 270-278) in the absence of the expected signatures from the B. anthracis genome would suggest a genetic engineering event.

The present method can also be used to detect single nucleotide polymorphisms (SNPs), or multiple nucleotide polymorphisms, rapidly and accurately. A SNP is defined as a single base pair site in the genome that is different from one individual to another. The difference can be expressed either as a deletion, an insertion or a substitution, and is frequently linked to a disease state. Because they occur every 100-1000 base pairs, SNPs are the most frequently bound type of genetic marker in the human genome.

For example, sickle cell anemia results from an A-T transition, which encodes a valine rather than a glutamic acid residue. Oligonucleotide primers may be designed such that they bind to sequences which flank a SNP site, followed by nucleotide amplification and mass determination of the amplified product. Because the molecular masses of the resulting product from an individual who does not have sickle cell anemia is different from that of the product from an individual who has the disease, the method can be used to distinguish the two individuals. Thus, the method can be used to detect any known SNP in an individual and thus diagnose or determine increased susceptibility to a disease or condition.

In one embodiment, blood is drawn from an individual and peripheral blood mononuclear cells (PBMC) are isolated and simultaneously tested, preferably in a high-throughput screening method, for one or more SNPs using appropriate primers based on the known sequences which flank the SNP region. The National Center for Biotechnology Information maintains a publicly available database of SNPs on the world wide web of the Internet at, for example, "ncbi.nlm.nih.gov/SNP/."

The method of the present invention can also be used for blood typing. The gene encoding A, B or O blood type can differ by four single nucleotide polymorphisms. If the gene contains the sequence CGTGGTGACCCTT (SEQ ID NO:1), antigen A results. If the gene contains the sequence CGTCGTCACCGCTA (SEQ ID NO:2) antigen B results. If the gene contains the sequence CGTGGT-ACCCCTT (SEQ ID NO:3), blood group O results ("-" indicates a deletion). These sequences can be distinguished by designing a single primer pair which flanks these regions, followed by amplification and mass determination.

Figure 18A:
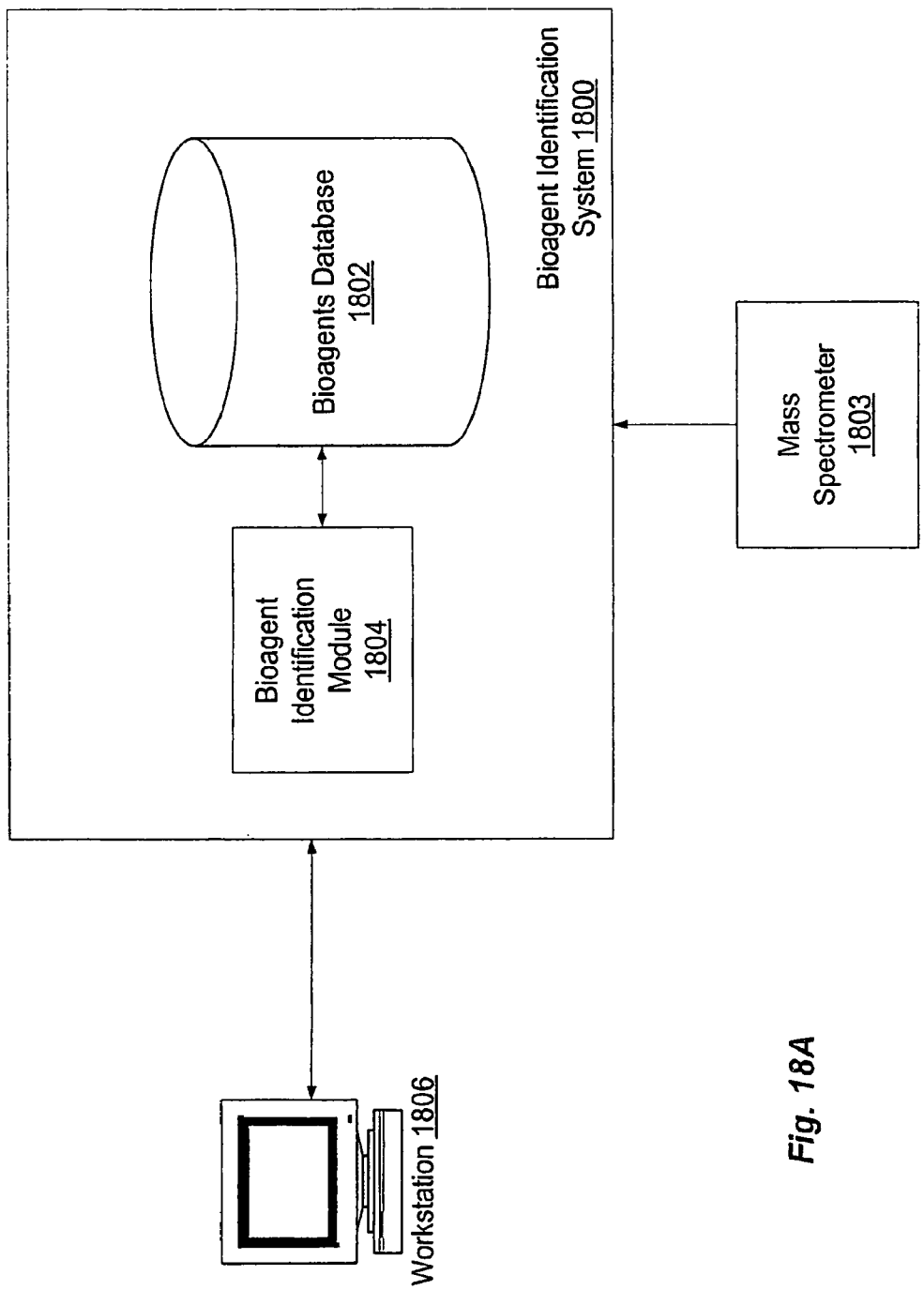
Figure 18B:
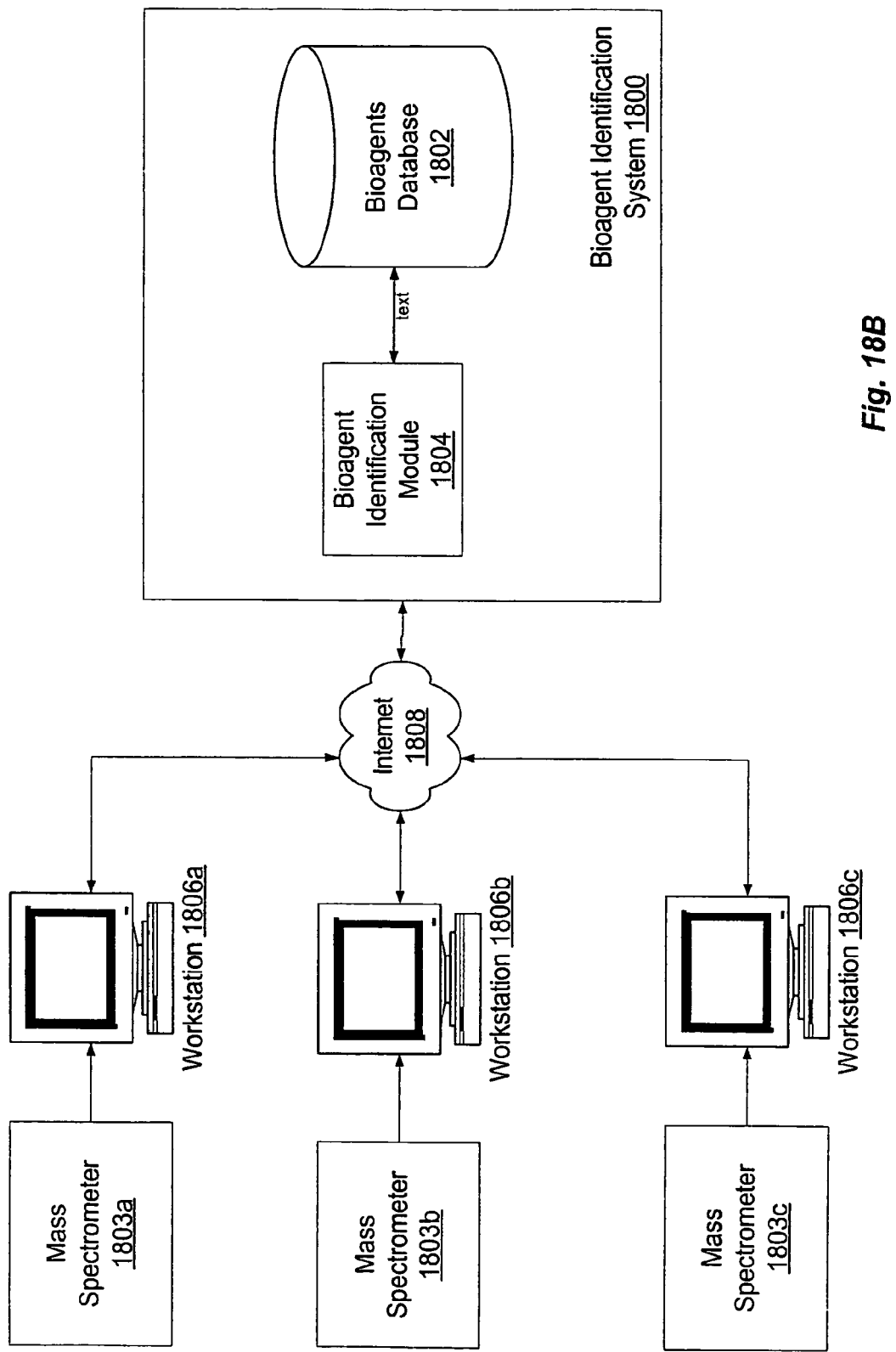
Figure 18C:
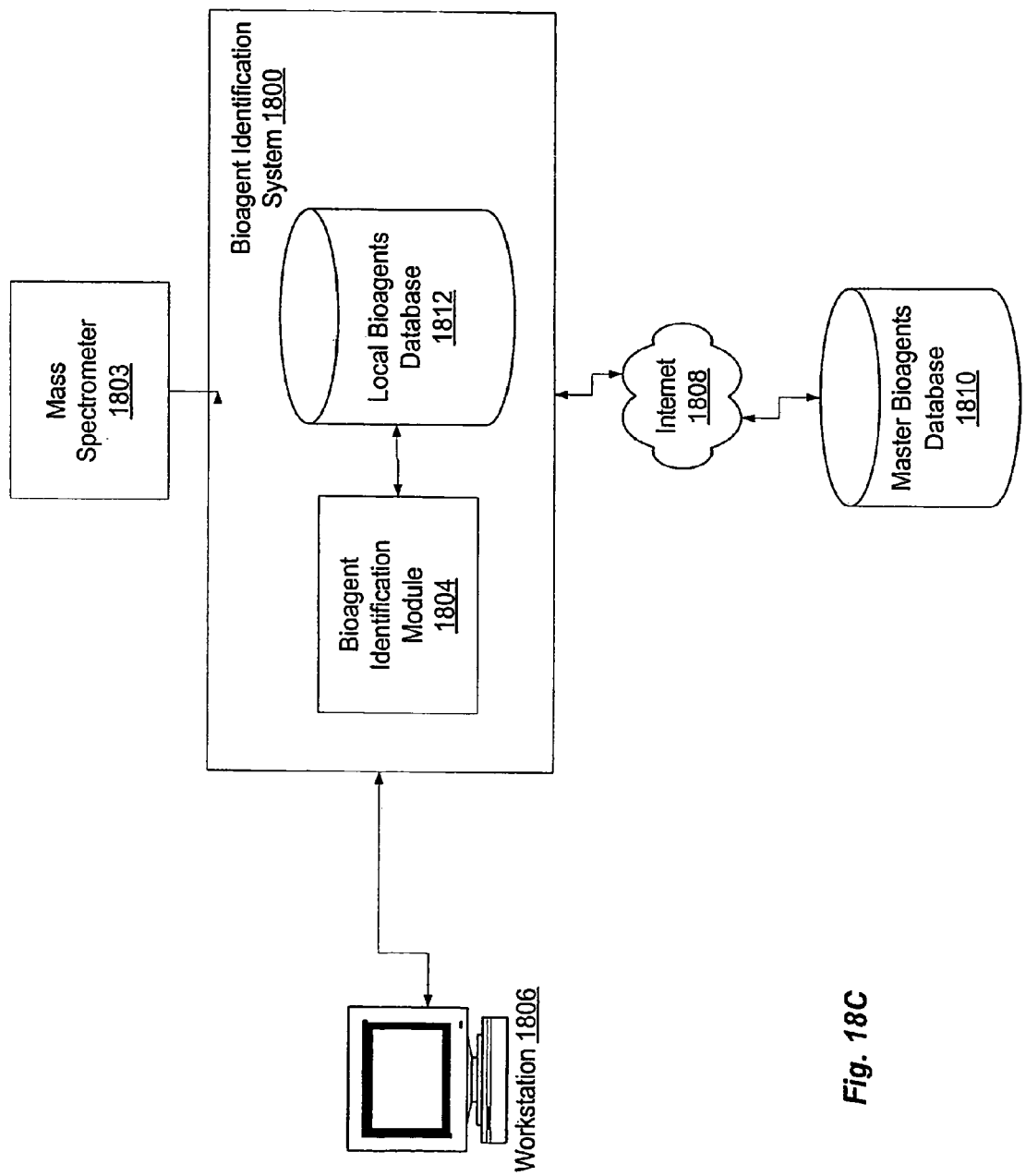

FIGS. 18A, 18B and 18C illustrate block diagrams of three embodiments of a bioagent identification system 1800 in accordance with embodiments of the present invention. Referring to FIG. 18A, Bioagent identification system 1800 includes a bioagent identification module 1804 and a bioagents database 1802. Also shown in FIG. 18A are a workstation 1806 and a mass spectrometer 1803. Bioagents database 1802, as described above, contains records of masses for various previously-identified bioagents—that is, bioagents that have been previously discovered and which have known amplicon masses. As one of ordinary skill will recognize, these known amplicons masses may comprise empirically-determined and/or calculated masses. Bioagent identification module 1804 receives mass data associated with amplification products derived, e.g., using mass spectrometer 1803, from a nucleic acid obtained from an unknown bioagent—that is, a bioagent having an identification not yet determined at the time of the assay—and returns an identifier of a bioagent that matches or corresponds to the received mass data, or alternatively, derived nucleic acid composition obtained from the received mass data, in accordance with the methods set forth above, if one can be found in the database. In fact, throughout this specification, as will be apparent to one of ordinary skill in the art, mass data may be substituted with base composition information. The operation of bioagent identification module 1804 is described further below with respect to FIG. 19. Workstation 1806 sends and receives data to system 1800, either through operator intervention, or automatically upon the occurrence of certain events, such as receipt of a new bioagent to be identified. Referring now to FIG. 18B, there is shown an alternative embodiment of a bioagent identification system 1800 in which workstations 1806a, 1806b, 1806c are located at diverse locations, and send requests for identification to system 1800 via a network such as the Internet 1808. FIG. 18C illustrates an example of a system 1800 that includes a local bioagents database 1812, as well as a master bioagents database 1810. In this embodiment, master bioagents database 1810 is located at a remote location and is accessible over a network such as the Internet 1808. In addition, system 1800 includes a local database 1812 that is preferably a mirrored version of master database 1810. This architecture allows for data queries to be executed locally, resulting in both increased efficiency and security, while at the same time ensuring that local database 1812 is kept up to date with the most current bioagent information.

The logic of the query is always available to the user and can be branched out from any point to create alternate search paths. Queries of user-defined complexity and depth can be annotated, saved as XML files and re-run or edited at a later time. The lists of results can be manually manipulated or combined with other lists using set logic (union, intersection, difference, etc.). Result lists can display any level of depth for a query from a single result to an entire history for the query that produced those results. Individual items in the list will display further detail when selected, and the display may be simple text output, more complex HTML or even graphical in nature. Our automatically generated interfaces use HTML as the default detail display, but the methods can be manually replaced with more complex visualization code. We use HTML not only for display formatting, but for the ability to embed URLs to other public data sources, allowing us to link from within the system to externally available information.

Figure 19:
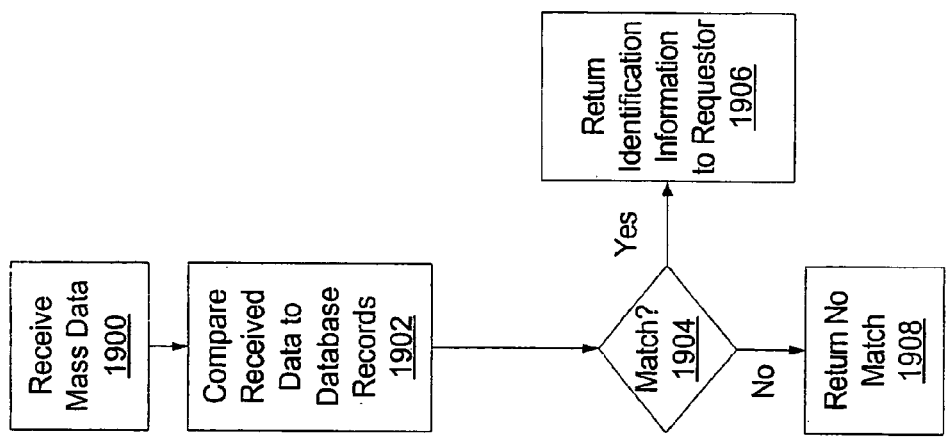

Referring now to FIG. 19, bioagent identification module 1804 is preferably configured to receive data including a mass of an amplification product or a base composition determined in accordance with the manner described above. Those of skill in the art will appreciate that bioagent identification module 1804 can be implemented in a variety of ways, including through the use of a maximum likelihood detector. Upon receiving 1900 the mass data, module 1804 compares 1902 the mass data or nucleic acid composition to mass data or nucleic acid composition present in database 1802 to determine whether a match exists in the database. If 1904 a match exists, module 1804 returns 1906 the identification information to the requestor 1806. In one embodiment, module 1804 is configured to return only those matches that are identical to data found in the database. In an alternative embodiment, module 1804 first determines a list of most likely matches according to the heuristics described above, and returns the list, preferably including confidence levels associated with each bioagent on the list. If 1904 a match does not exist, module 1804 returns 1908 an indication that no match was found. The process of matching optionally may include a base composition probability cloud analysis, used to aid identification of natural variants of individual bioagents. Base composition probability cloud analyses are described in U.S. Publication No. US2004-0209260, filed Apr. 18, 2003 and in the application "Methods For Rapid Identification of Pathogens in Humans and Animals," Ser. No. 10/728,486, filed Dec. 5, 2003, both of which are commonly owned and incorporated herein by reference in their entirety.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by real time network operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description above. In addition, the present invention is not described with reference to any particular programming language.

EXAMPLES

Example 1

Nucleic Acid Isolation and PCR

In one embodiment, nucleic acid is isolated from the organisms and amplified by PCR using standard methods prior to BCS determination by mass spectrometry. Nucleic acid is isolated, for example, by detergent lysis of bacterial cells, centrifugation and ethanol precipitation. Nucleic acid isolation methods are described in, for example, *Current Protocols in Molecular Biology* (Ausubel et al.) and *Molecular Cloning; A Laboratory Manual* (Sambrook et al.). The nucleic acid is then amplified using standard methodology, such as PCR, with primers which bind to conserved regions of the nucleic acid which contain an intervening variable sequence as described below.

Example 2

Mass Spectrometry

FTICR Instrumentation: The FTICR instrument is based on a 7 tesla actively shielded superconducting magnet and modified Bruker Daltonics Apex II 70e ion optics and vacuum chamber. The spectrometer is interfaced to a LEAP PAL autosampler and a custom fluidics control system for high throughput screening applications. Samples are analyzed directly from 96-well or 384-well microtiter plates at a rate of about 1 sample/minute. The Bruker data-acquisition platform is supplemented with a lab-built ancillary NT datastation which controls the autosampler and contains an arbitrary waveform generator capable of generating complex rf-excite waveforms (frequency sweeps, filtered noise, stored waveform inverse Fourier transform (SWIFT), etc.) for sophisticated tandem MS experiments. For oligonucleotides in the 20-30-mer regime typical performance characteristics include mass resolving power in excess of 100,000 (FWHM), low ppm mass measurement errors, and an operable m/z range between 50 and 5000 m/z.

Modified ESI Source: In sample-limited analyses, analyte solutions are delivered at 150 nL/minute to a 30 mm i.d. fused-silica ESI emitter mounted on a 3-D micromanipulator. The ESI ion optics consist of a heated metal capillary, an rf-only hexapole, a skimmer cone, and an auxiliary gate electrode. The 6.2 cm rf-only hexapole is comprised of 1 mm diameter rods and is operated at a voltage of 380 Vpp at a frequency of 5 MHz. A lab-built electro-mechanical shutter can be employed to prevent the electrospray plume from entering the inlet capillary unless triggered to the "open" position via a TTL pulse from the data station. When in the "closed" position, a stable electrospray plume is maintained between the ESI emitter and the face of the shutter. The back face of the shutter arm contains an elastomeric seal which can be positioned to form a vacuum seal with the inlet capillary. When the seal is removed, a 1 mm gap between the shutter blade and the capillary inlet allows constant pressure in the external ion reservoir regardless of whether the shutter is in the open or closed position. When the shutter is triggered, a "time slice" of ions is allowed to, enter the inlet capillary and is subsequently accumulated in the external ion reservoir. The rapid response time of the ion shutter (<25 ms) provides reproducible, user defined intervals during which ions can be injected into and accumulated in the external ion reservoir.

Apparatus for Infrared Multiphoton Dissociation: A 25 watt CW $CO_2$ laser operating at 10.6 μm has been interfaced to the spectrometer to enable infrared multiphoton dissociation (IRMPD) for oligonucleotide sequencing and other tandem MS applications. An aluminum optical bench is positioned approximately 1.5 m from the actively shielded superconducting magnet such that the laser beam is aligned with the central axis of the magnet. Using standard IR-compatible mirrors and kinematic mirror mounts, the unfocused 3 mm laser beam is aligned to traverse directly through the 3.5 mm holes in the trapping electrodes of the FTICR trapped ion cell and longitudinally traverse the hexapole region of the external ion guide finally impinging on the skimmer cone. This scheme allows IRMPD to be conducted in an m/z selective manner in the trapped ion cell (e.g. following a SWIFT isolation of the species of interest), or in a broadband mode in the high pressure region of the external ion reservoir where collisions with neutral molecules stabilize IRMPD-generated metastable fragment ions resulting in increased fragment ion yield and sequence coverage.

Example 3

Identification of Bioagents

Figures 1, 1B:
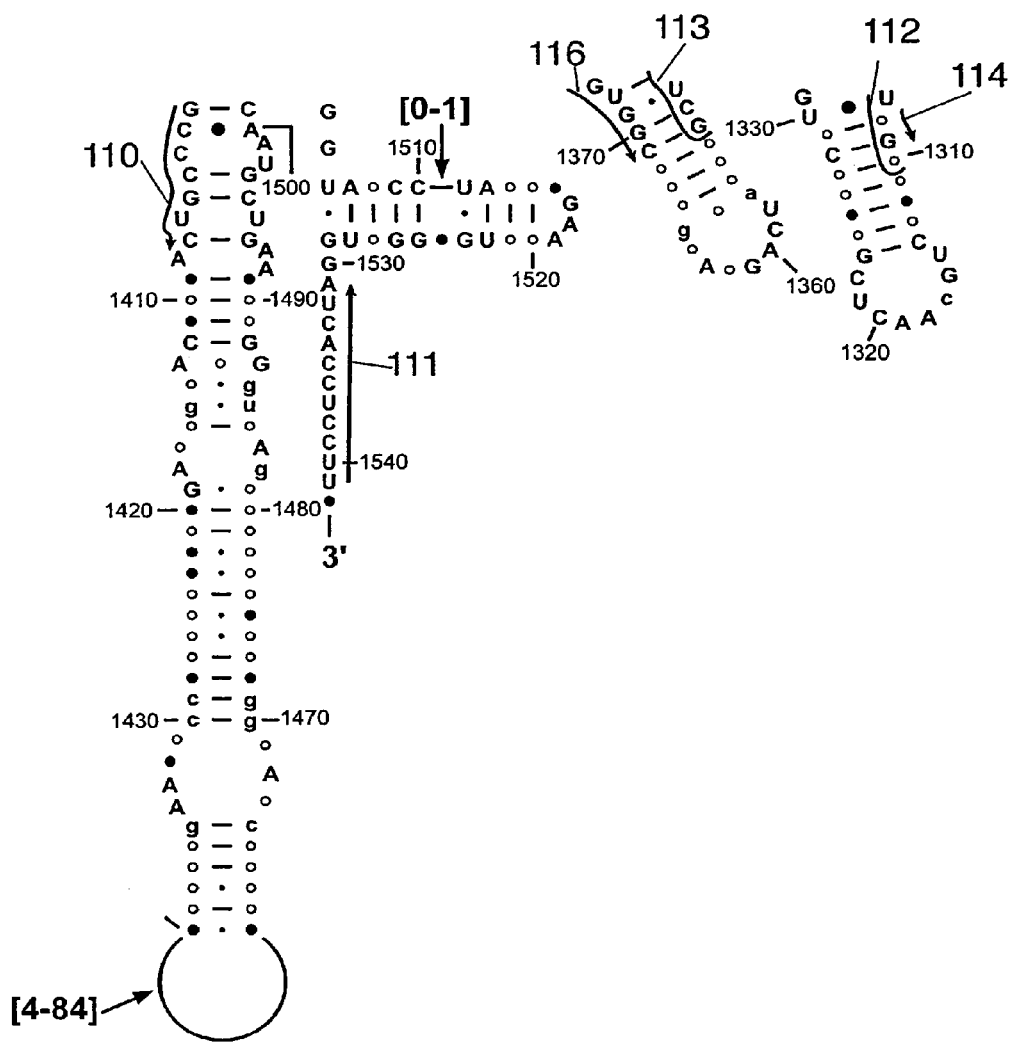
Figures 1, 1B, 2:
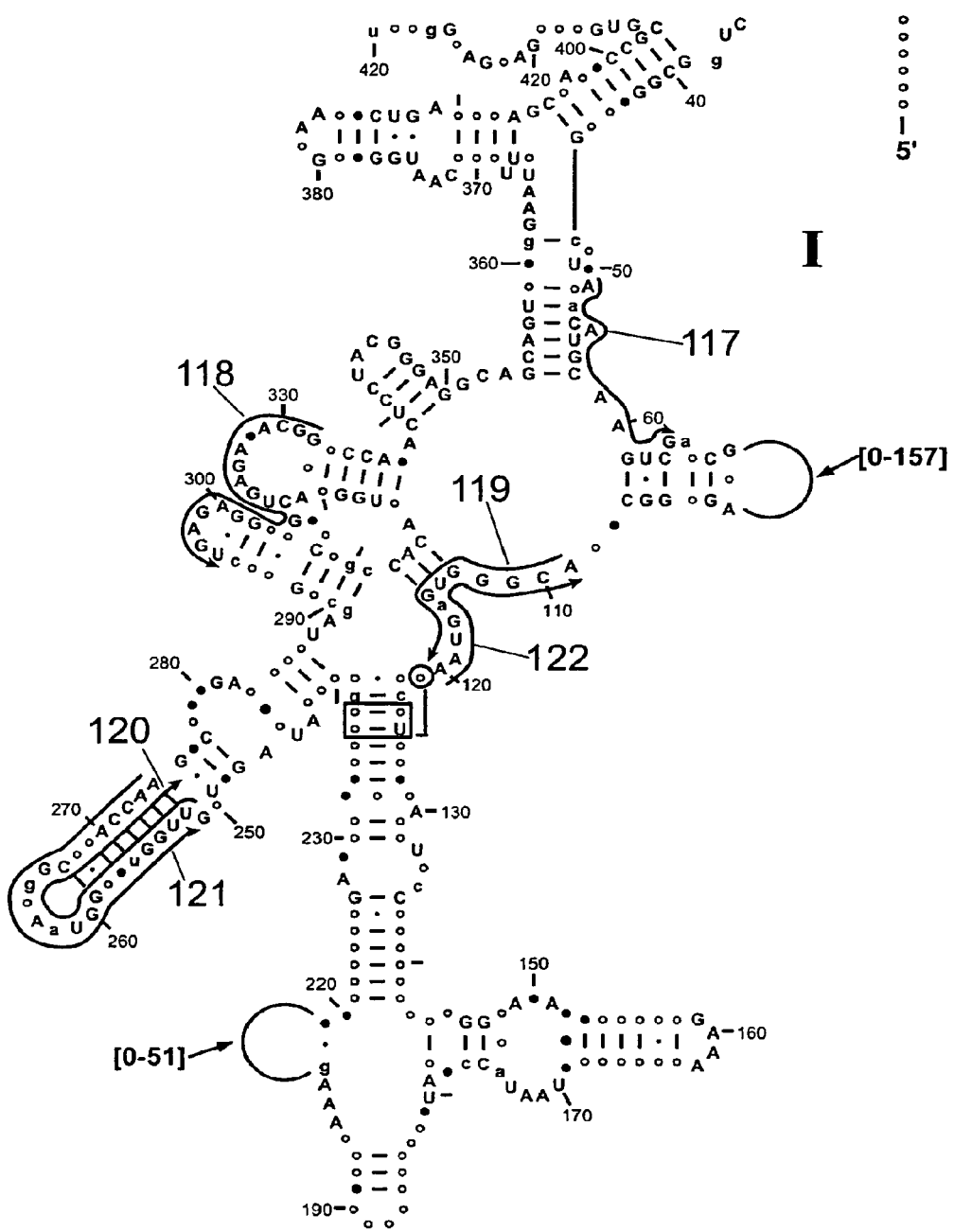
Figures 1, 1C:
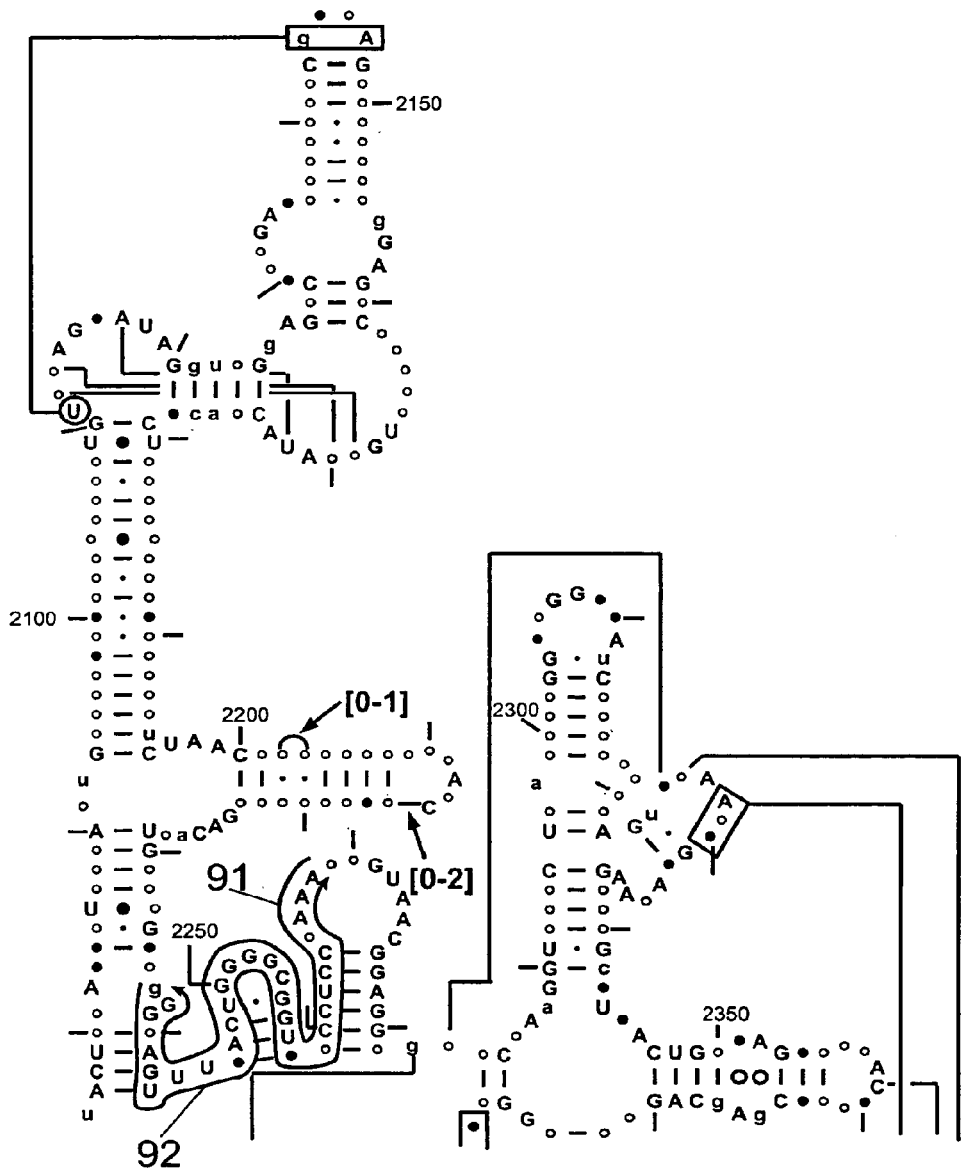
Figures 1, 1C, 2:
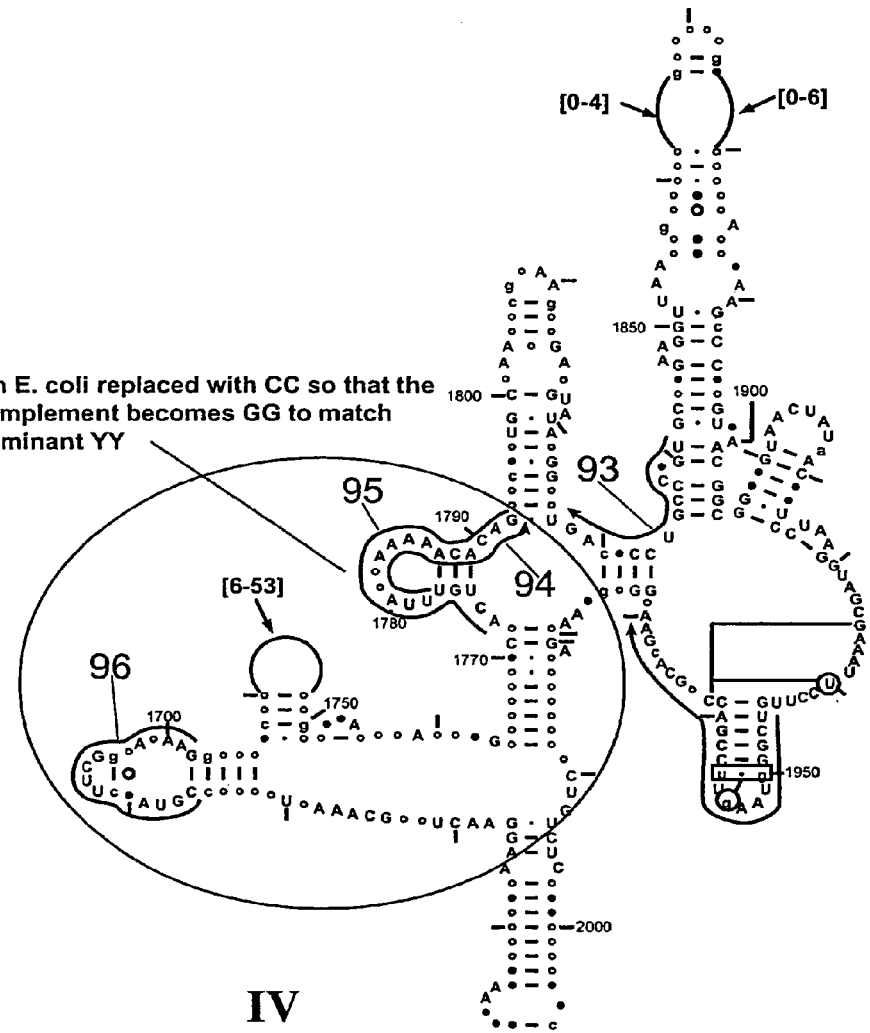
Figure 1D:
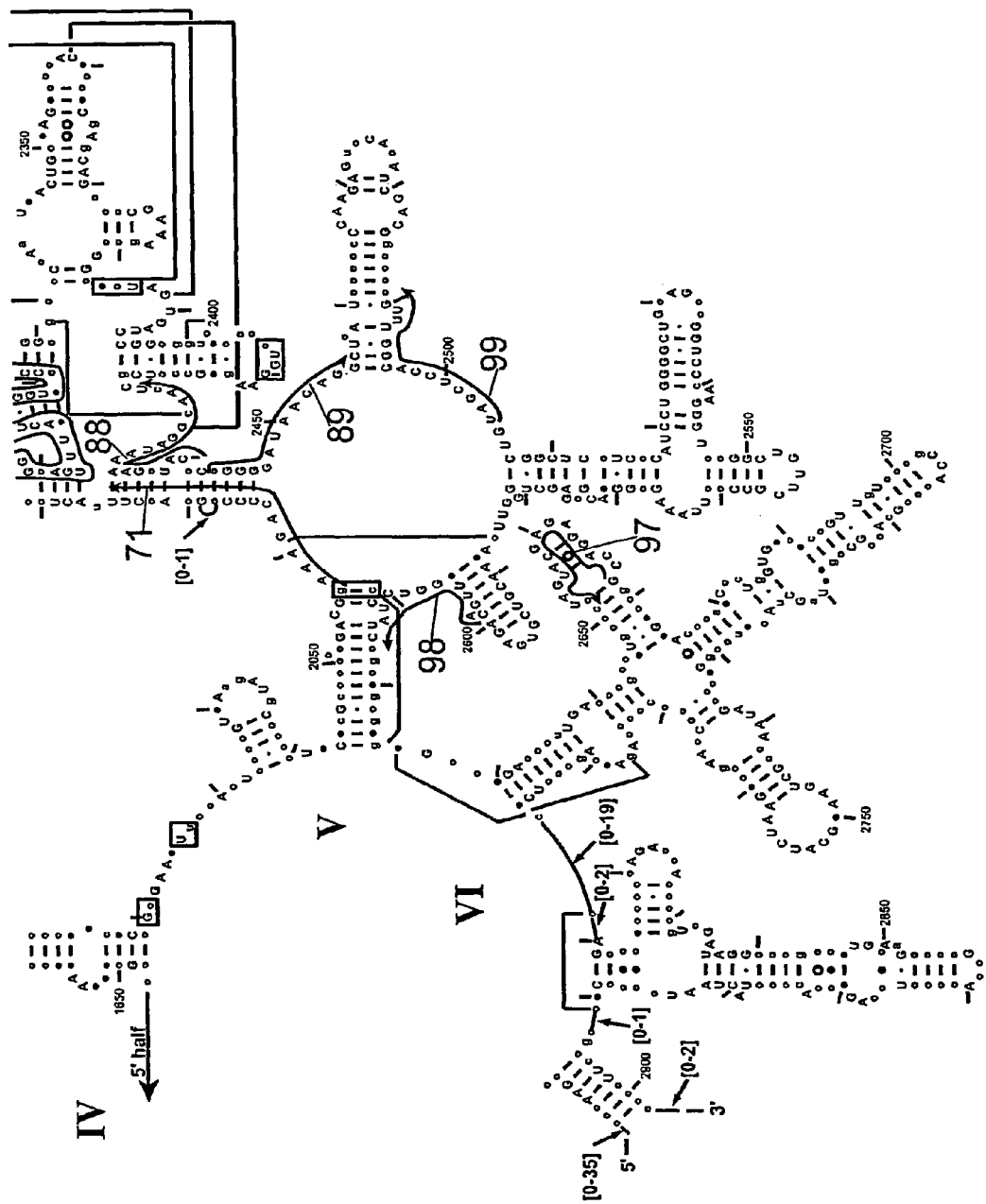
Figure 1E:
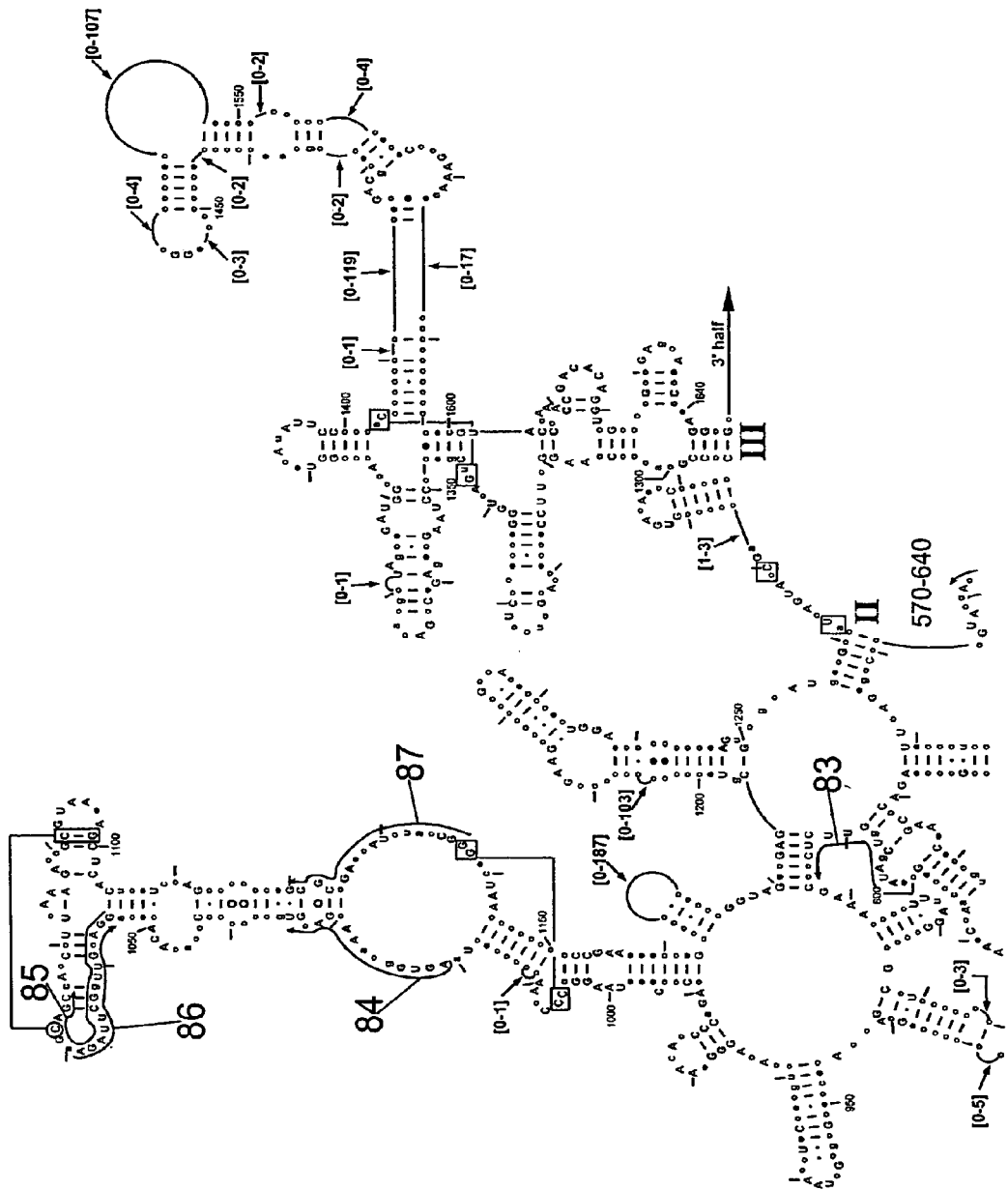
Figure 1F:
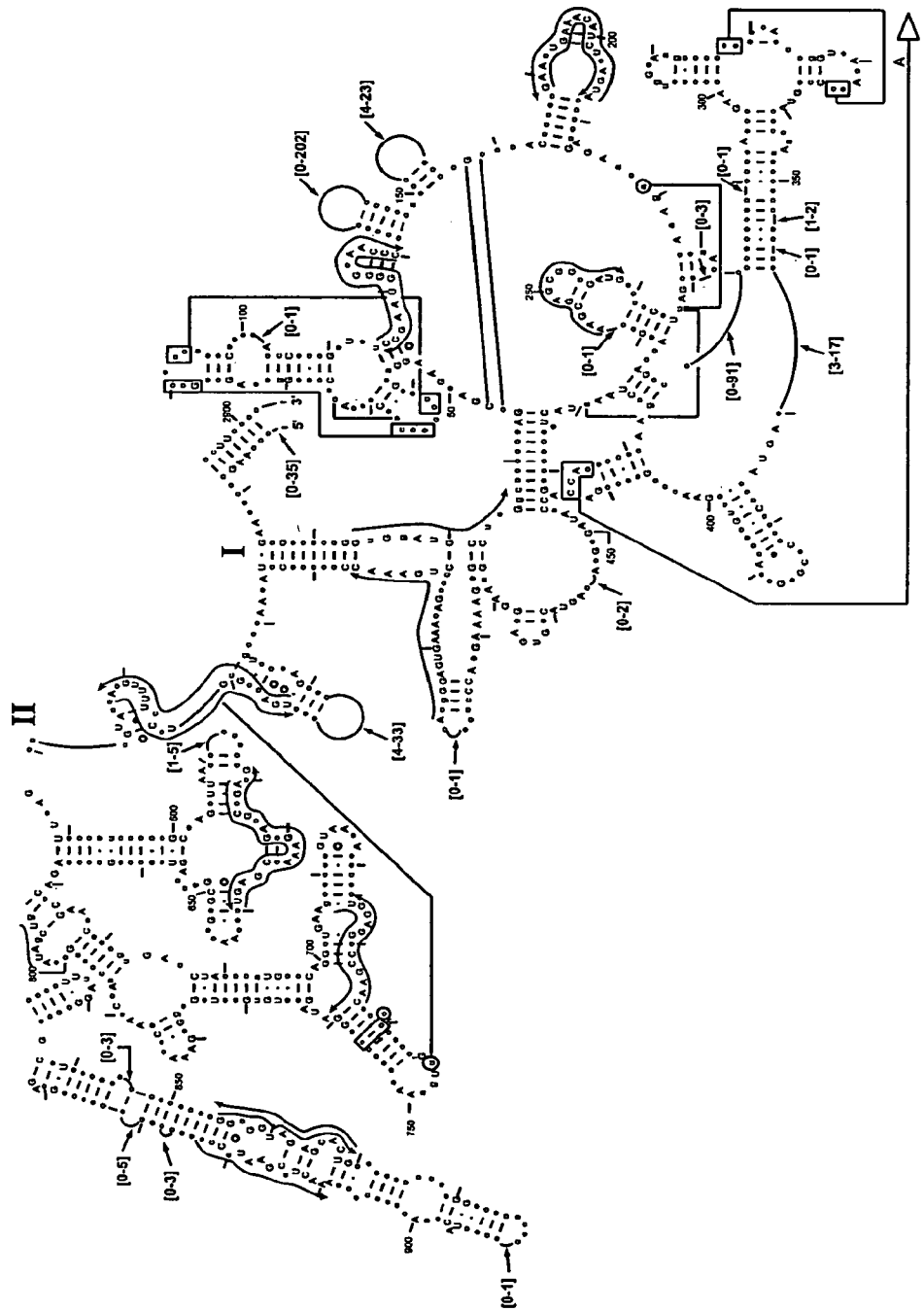
Figure 1G:
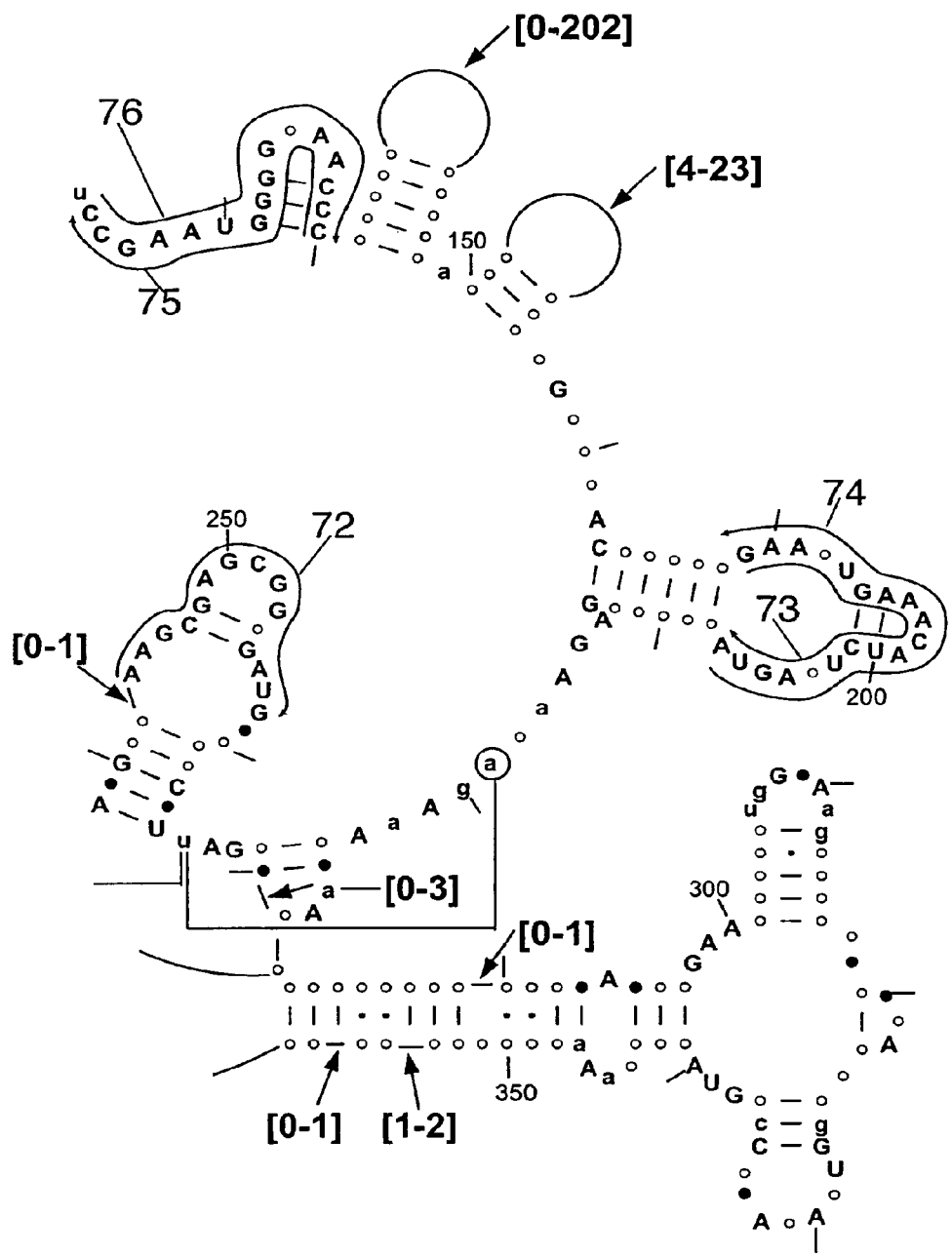
Figure 1H:
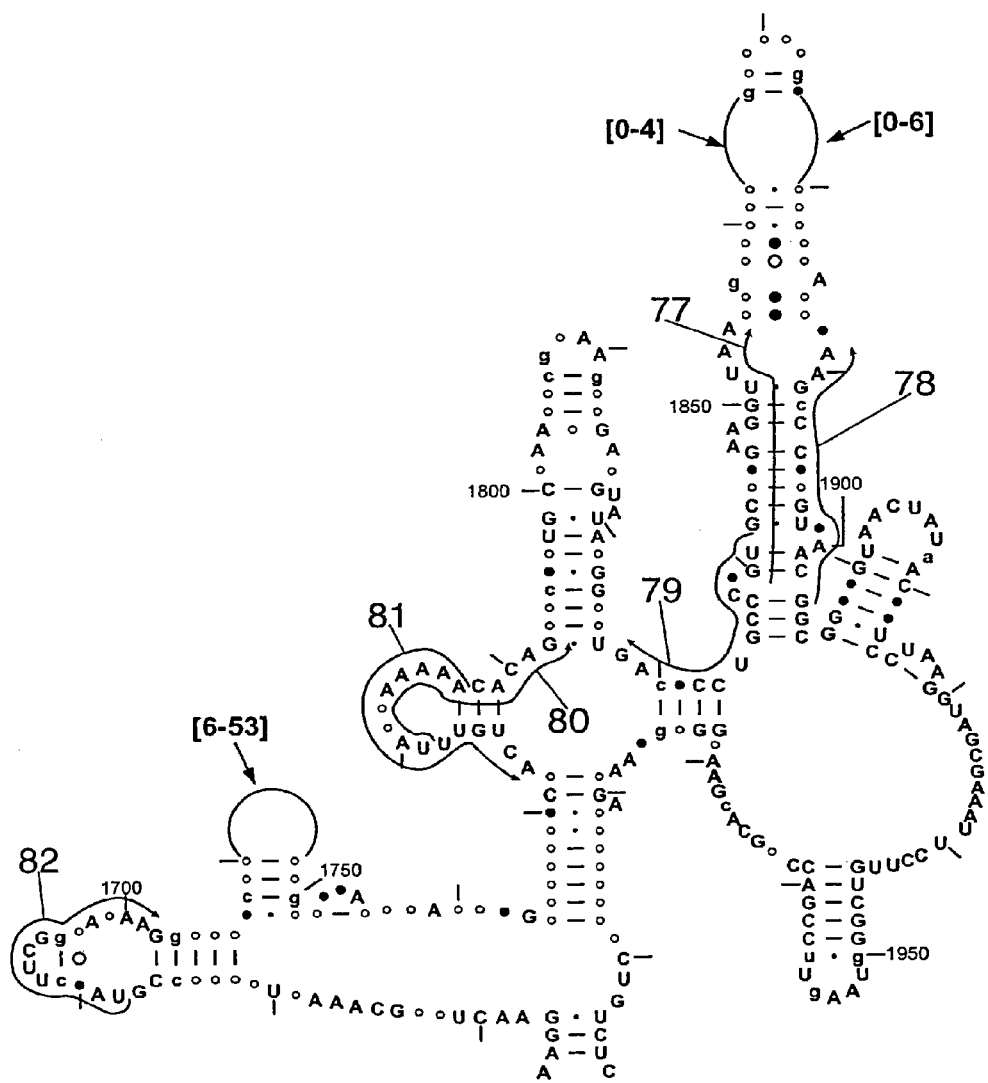
Figure 1I:
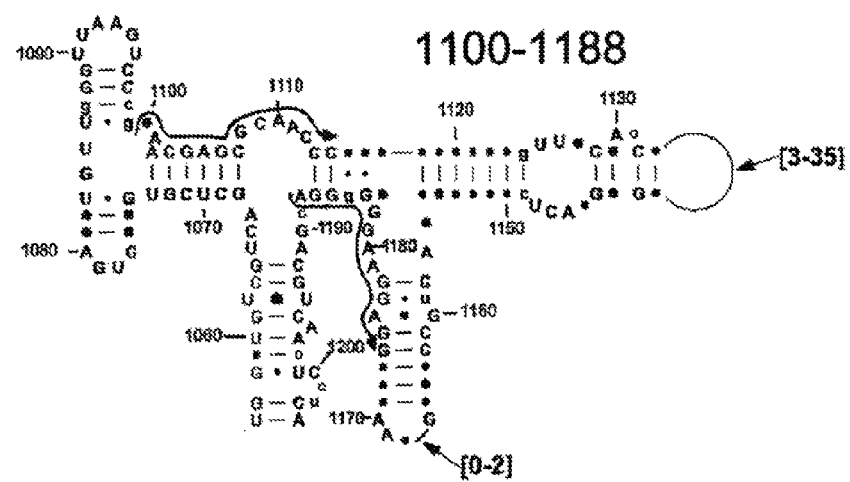
Figure 2:
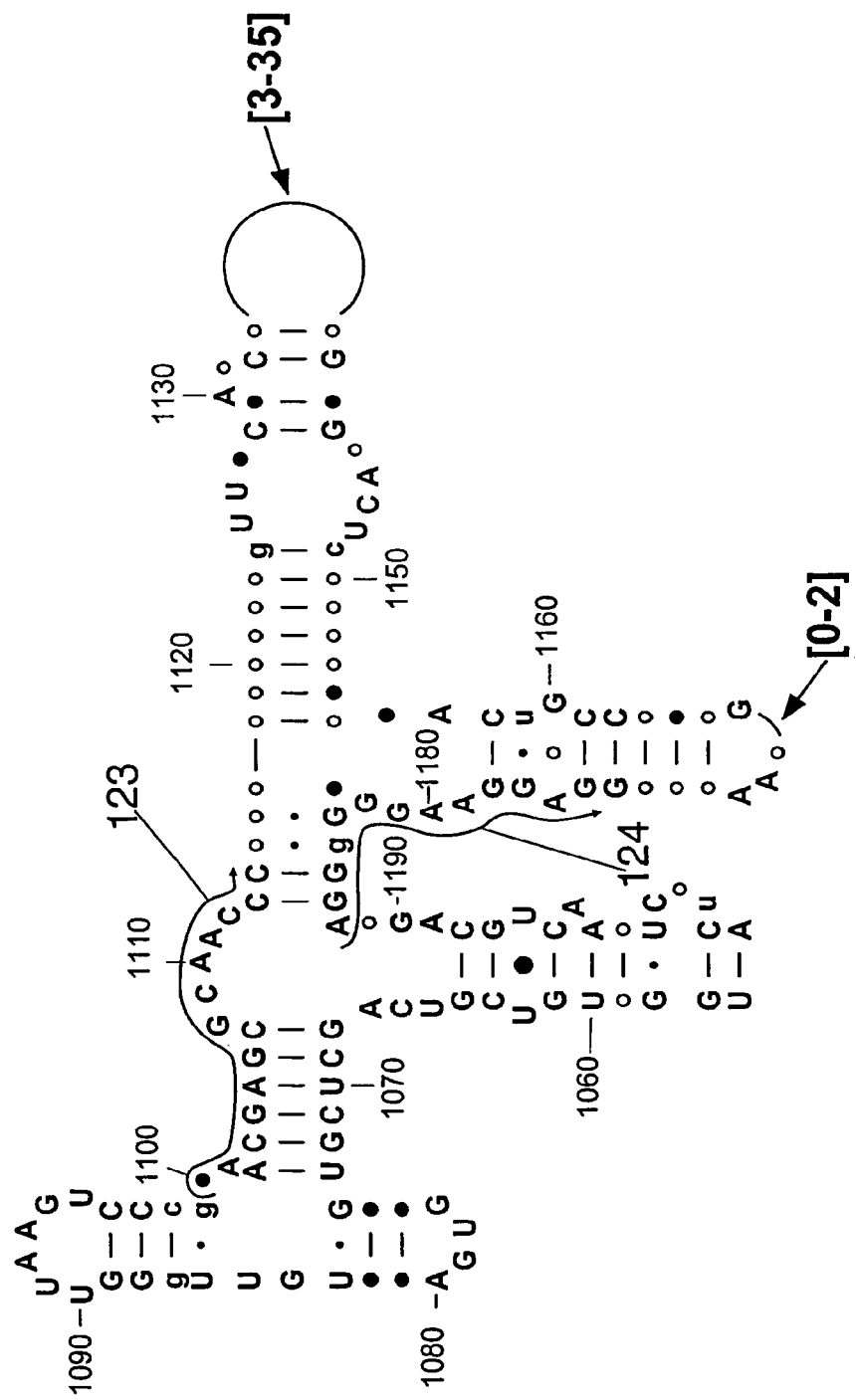
Figure 3:
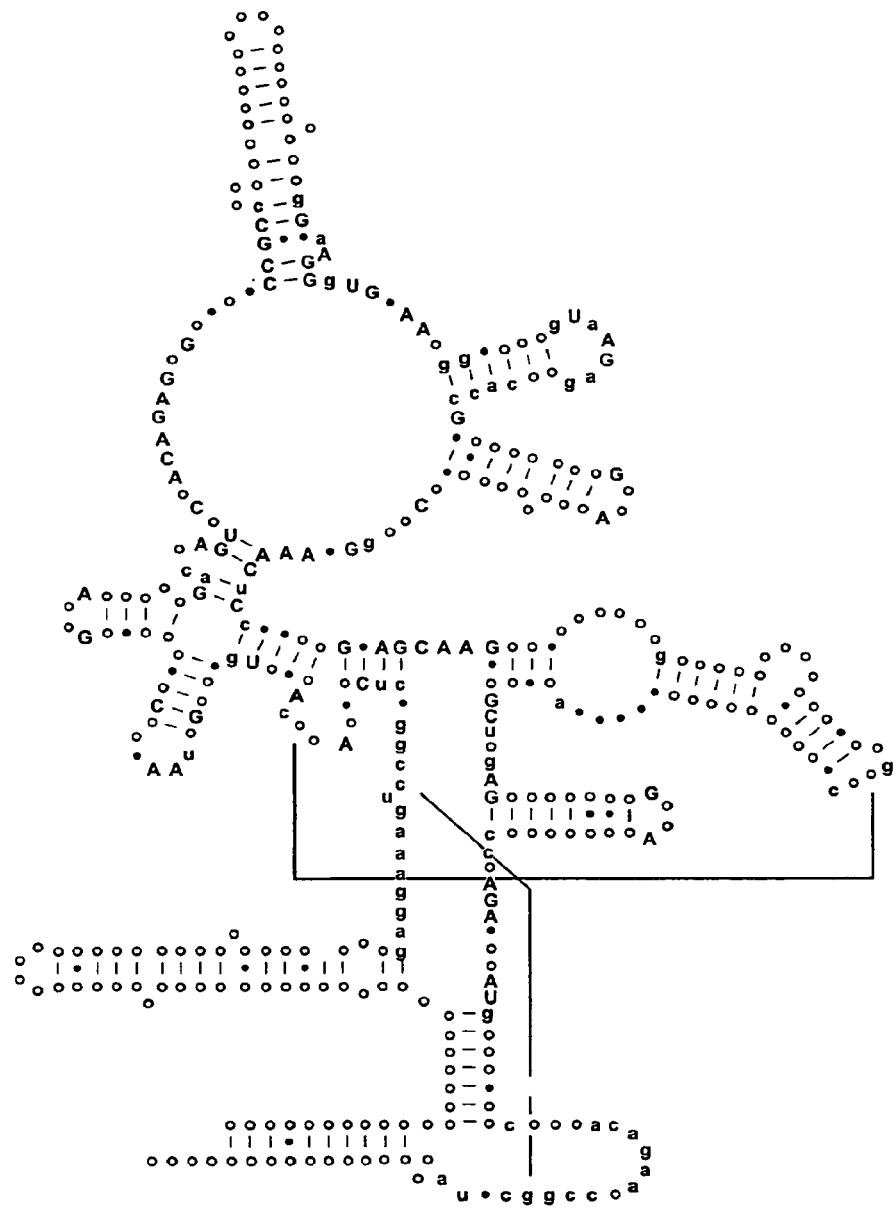

Table 2 shows a small cross section of a database of calculated molecular masses for over 9 primer sets and approximately 30 organisms. The primer sets were derived from rRNA alignment. Examples of regions from rRNA consensus alignments are shown in FIGS. 1A-1C. Lines with arrows are examples of regions to which intelligent primer pairs for PCR are designed. The primer pairs are >95% conserved in the bacterial sequence database (currently over 10,000 organisms). The intervening regions are variable in length and/or composition, thus providing the base composition "signature" (BCS) for each organism. Primer pairs were chosen so the total length of the amplified region is less than about 80-90 nucleotides. The label for each primer pair represents the starting and ending base number of the amplified region on the consensus diagram.

Included in the short bacterial database cross-section in Table 2 are many well known pathogens/biowarfare agents (shown in bold/red typeface) such as *Bacillus anthracis* or *Yersinia pestis* as well as some of the bacterial organisms found commonly in the natural environment such as *Streptomyces*. Even closely related organisms can be distinguished from each other by the appropriate choice of primers. For instance, two low G+C organisms, *Bacillus anthracis* and *Staph aureus*, can be distinguished from each other by using the primer pair defined by 16S_1337 or 23S_855 (ΔM of 4 Da).

TABLE 2

Cross Section Of A Database Of Calculated Molecular Masses[1]

| Primer Regions → <br> Bug Name | 16S_971 | 16S_1100 | 16S_1337 | 16S_1294 | 16S_1228 | 23S_1021 | 23S_855 | 23S_193 | 23S_115 |
|---|---|---|---|---|---|---|---|---|---|
| *Acinetobacter calcoaceticus* | 55619.1 | 55004 | 28446.7 | 35854.9 | 51295.4 | 30299 | 42654 | 39557.5 | 54999 |
| Bacillus anthracis | 55005 | 54388 | 28448 | 35238 | 51296 | 30295 | 42651 | 39560 | 56850 |
| *Bacillus cereus* | 55622.1 | 54387.9 | 28447.6 | 35854.9 | 51296.4 | 30295 | 42651 | 39560.5 | 56850.3 |
| *Bordetella bronchiseptica* | 56857.3 | 51300.4 | 28446.7 | 35857.9 | 51307.4 | 30299 | 42653 | 39559.5 | 51920.5 |
| *Borrelia burgdorferi* | 56231.2 | 55621.1 | 28440.7 | 35852.9 | 51295.4 | 30297 | 42029.9 | 38941.4 | 52524.6 |
| Brucella Abortus | 58098 | 55011 | 28448 | 35854 | 50683 | | | | |
| *Campylobacter jejuni* | 58088.5 | 54386.9 | 29061.8 | 35856.9 | 50674.3 | 30294 | 42032.9 | 39558.5 | 45732.5 |
| Chlamydia Pnuemoniae | 55000 | 55007 | 29063 | 35855 | 50676 | 30295 | 42036 | 38941 | 56230 |
| Clostridium botulinum | 55006 | 53767 | 28445 | 35855 | 51291 | 30300 | 42656 | 39562 | 54999 |
| *Clostridium difficile* | 56855.3 | 54386.9 | 28444.7 | 35853.9 | 51296.4 | 30294 | 41417.8 | 39556.5 | 55612.2 |
| *Enterococcus faecalis* | 55620.1 | 54387.9 | 28447.6 | 35858.9 | 51296.4 | 30297 | 42652 | 39559.5 | 56849.3 |
| Escherichia coli | 55622 | 55009 | 28445 | 35857 | 51301 | 30301 | 42656 | 39562 | 54999 |
| Francisella tularensis | 53769 | 54385 | 28445 | 35856 | 51298 | | | | |
| *Haemophilus influenzae* | 55620.1 | 55006 | 28444.7 | 35855.9 | 51298.4 | 30298 | 42656 | 39560.5 | 55613.1 |
| *Klebsiella pneumoniae* | 55622.1 | 55008 | 28442.7 | 35856.9 | 51297.4 | 30300 | 42655 | 39562.5 | 55000 |
| Legionella pneumophila | 55618 | 55626 | 28446 | 35857 | 51303 | | | | |
| *Mycobacterium avium* | 54390.9 | 55631.1 | 29064.8 | 35858.9 | 51915.5 | 30298 | 42656 | 38942.4 | 56241.2 |
| *Mycobacterium leprae* | 54389.9 | 55629.1 | 29064.8 | 35860.9 | 51917.5 | 30298 | 42656 | 39559.5 | 56240.2 |
| *Mycobacterium tuberculosis* | 54390.9 | 55629.1 | 29064.8 | 35860.9 | 51301.4 | 30299 | 42656 | 39560.5 | 56243.2 |
| *Mycoplasma genitalium* | 53143.7 | 45115.4 | 29061.8 | 35854.9 | 50671.3 | 30294 | 43264.1 | 39558.5 | 56842.4 |
| *Mycoplasma pneumoniae* | 53143.7 | 45115.4 | 29061.8 | 35854.9 | 50673.3 | 30294 | 43264.1 | 39559.5 | 56843.4 |
| *Neisseria gonorrhoeae* | 55627.1 | 54389.9 | 28445.7 | 35855.9 | 51302.4 | 30300 | 42649 | 39561.5 | 55000 |
| Pseudomonas aeruginosa | 55623 | 55010 | 28443 | 35858 | 51301 | 30298 | 43272 | 39558 | 55619 |
| Rickettsia prowazekii | 58093 | 55621 | 28448 | 35853 | 50677 | 30293 | 42650 | 39559 | 53139 |
| Rickettsia rickettsii | 58094 | 55623 | 28448 | 35853 | 50679 | 30293 | 42648 | 39559 | 53755 |
| Salmonella typhimurium | 55622 | 55005 | 28445 | 35857 | 51301 | 30301 | 42658 | | |
| Shigella dysenteriae | 55623 | 55009 | 28444 | 35857 | 51301 | | | | |
| *Staphylococcus aureus* | 56854.3 | 54386.9 | 28443.7 | 35852.9 | 51294.4 | 30298 | 42655 | 39559.5 | 57466.4 |
| *Streptomyces* | 54389.9 | 59341.6 | 29063.8 | 35858.9 | 51300.4 | | | 39563.5 | 56864.3 |
| *Treponema pallidum* | 56245.2 | 55631.1 | 28445.7 | 35851.9 | 51297.4 | 30299 | 42034.9 | 38939.4 | 57473.4 |

TABLE 2-continued

Cross Section Of A Database Of Calculated Molecular Masses[1]

| Primer Regions →<br>Bug Name | 16S_971 | 16S_1100 | 16S_1337 | 16S_1294 | 16S_1228 | 23S_1021 | 23S_855 | 23S_193 | 23S_115 |
|---|---|---|---|---|---|---|---|---|---|
| Vibrio cholerae | 55625 | 55626 | 28443 | 35857 | 52536 | 29063 | 30303 | 35241 | 50675 |
| Vibrio parahaemolyticus | 54384.9 | 55626.1 | 28444.7 | 34620.7 | 50064.2 | | | | |
| Yersinia pestis | 55620 | 55626 | 28443 | 35857 | 51299 | | | | |

[1]Molecular mass distribution of PCR amplified regions for a selection of organisms (rows) across various primer pairs (columns).
Pathogens are shown in bold.
Empty cells indicate presently incomplete or missing data.

Figure 6:
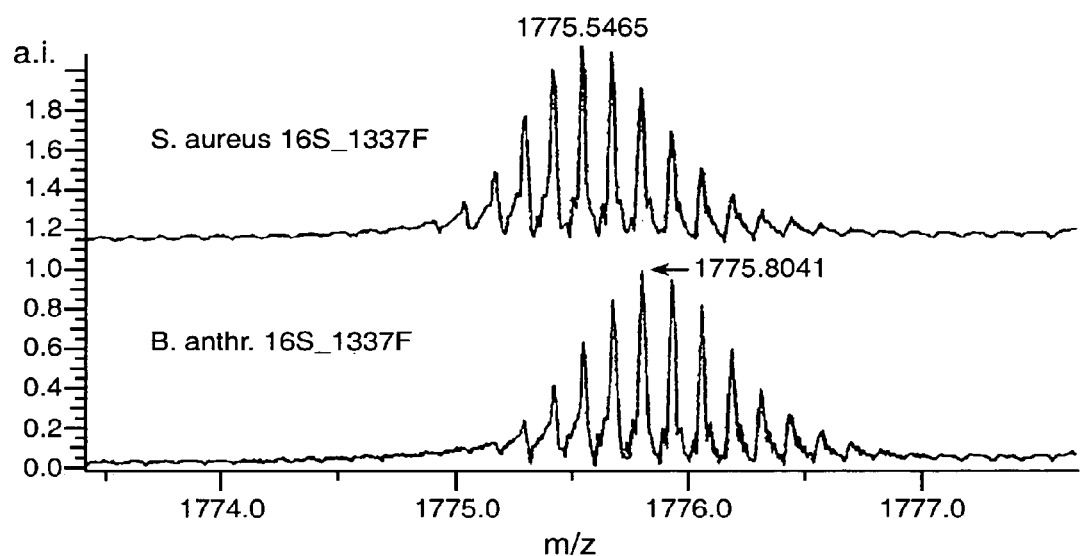

FIG. 6 shows the use of ESI-FT-ICR MS for measurement of exact mass. The spectra from 46mer PCR products originating at position 1337 of the 16S rRNA from *S. aureus* (upper) and *B. anthracis* (lower) are shown. These data are from the region of the spectrum containing signals from the $[M-8H+]^{8-}$ charge states of the respective 5'-3' strands. The two strands differ by two (AT→SCG) substitutions, and have measured masses of 14206.396 and 14208.373±0.010 Da, respectively. The possible base compositions derived from the masses of the forward and reverse strands for the *B. anthracis* products are listed in Table 3.

TABLE 3

Possible base composition for *B. anthracis* products

| Calc. Mass | Error | Base Comp. |
|---|---|---|
| 14208.2935 | 0.079520 | A1 G17 C10 T18 |
| 14208.3160 | 0.056980 | A1 G20 C15 T10 |
| 14208.3386 | 0.034440 | A1 G23 C20 T2 |
| 14208.3074 | 0.065560 | A6 G11 C3 T26 |
| 14208.3300 | 0.043020 | A6 G14 C8 T18 |
| 14208.3525 | 0.020480 | A6 G17 C13 T10 |
| 14208.3751 | 0.002060 | A6 G20 C18 T2 |
| 14208.3439 | 0.029060 | A11 G8 C1 T26 |
| 14208.3665 | 0.006520 | A11 G11 C6 T18 |
| 14208.3890 | 0.016020 | A11 G14 C11 T10 |
| 14208.4116 | 0.038560 | A11 G17 C16 T2 |
| 14208.4030 | 0.029980 | A16 G8 C4 T18 |
| 14208.4255 | 0.052520 | A16 G11 C9 T10 |
| 14208.4481 | 0.075060 | A16 G14 C14 T2 |
| 14208.4395 | 0.066480 | A21 G5 C2 T18 |
| 14208.4620 | 0.089020 | A21 G8 C7 T10 |
| 14079.2624 | 0.080600 | A0 G14 C13 T19 |
| 14079.2849 | 0.058060 | A0 G17 C18 T11 |
| 14079.3075 | 0.035520 | A0 G20 C23 T3 |
| 14079.2538 | 0.089180 | A5 G5 C1 T35 |
| 14079.2764 | 0.066640 | A5 G8 C6 T27 |
| 14079.2989 | 0.044100 | A5 G11 C11 T19 |
| 14079.3214 | 0.021560 | A5 G14 C16 T11 |
| 14079.3440 | 0.000980 | A5 G17 C21 T3 |
| 14079.3129 | 0.030140 | A10 G5 C4 T27 |
| 14079.3354 | 0.007600 | A10 G8 C9 T19 |
| 14079.3579 | 0.014940 | A10 G11 C14 T11 |
| 14079.3805 | 0.037480 | A10 G14 C19 T3 |
| 14079.3494 | 0.006360 | A15 G2 C2 T27 |
| 14079.3719 | 0.028900 | A15 G5 C7 T19 |
| 14079.3944 | 0.051440 | A15 G8 C12 T11 |
| 14079.4170 | 0.073980 | A15 G11 C17 T3 |
| 14079.4084 | 0.065400 | A20 G2 C5 T19 |
| 14079.4309 | 0.087940 | A20 G5 C10 T13 |

Among the 16 compositions for the forward strand and the 18 compositions for the reverse strand that were calculated, only one pair (shown in bold) are complementary, corresponding to the actual base compositions of the *B. anthracis* PCR products.

Example 4

BCS of Region from *Bacillus anthracis* and *Bacillus cereus*

Figure 7:
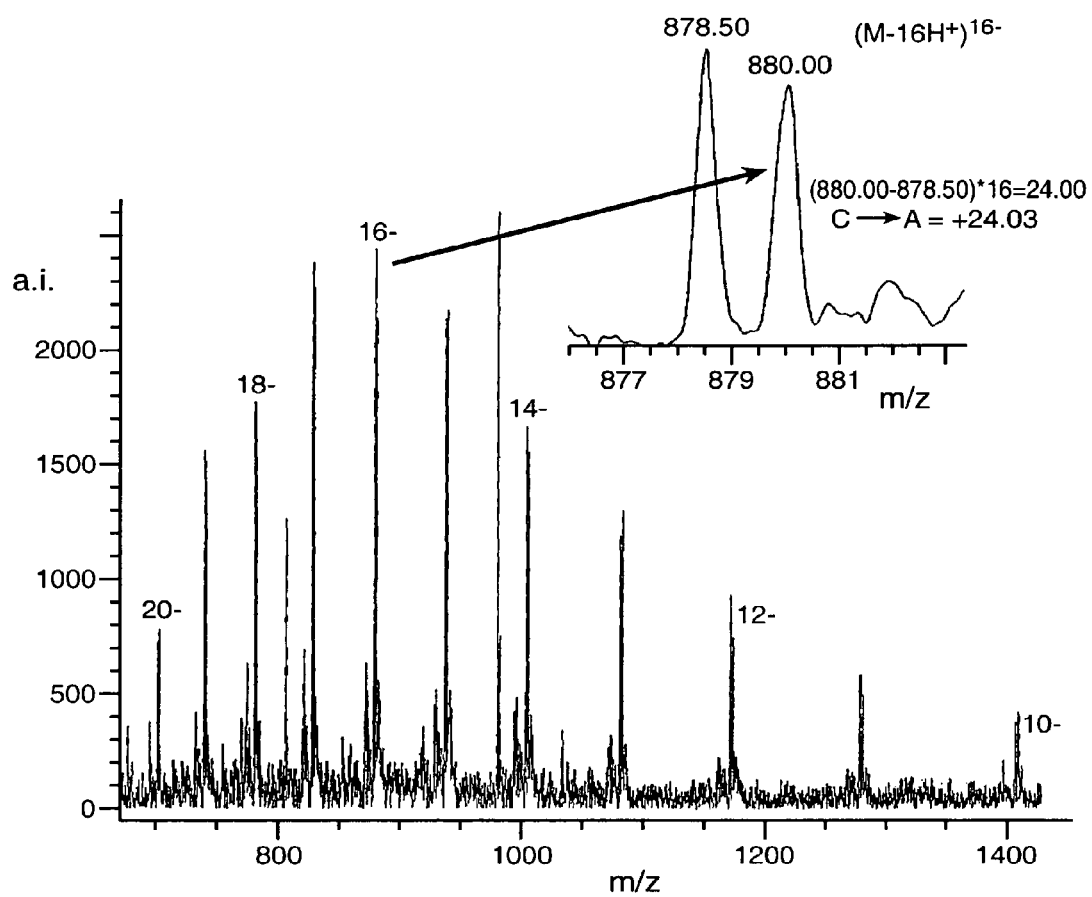

A conserved *Bacillus* region from *B. anthracis* ($A_{14}G_9C_{14}T_9$) and *B. cereus* ($A_{15}G_9C_{13}T_9$) having a C to A base change was synthesized and subjected to ESI-TOF MS. The results are shown in FIG. 7 in which the two regions are clearly distinguished using the method of the present invention (MW=14072.26 vs. 14096.29).

Example 5

Identification of Additional Bioagents

In other examples of the present invention, the pathogen *Vibrio cholera* can be distinguished from *Vibrio parahemolyticus* with ΔM>600 Da using one of three 16S primer sets shown in Table 2 (16S_971, 16S_1228 or 16S_1294) as shown in Table 4. The two mycoplasma species in the list (*M. genitalium* and *M. pneumoniae*) can also be distinguished from each other, as can the three mycobacteriae. While the direct mass measurements of amplified products can identify and distinguish a large number of organisms, measurement of the base composition signature provides dramatically enhanced resolving power for closely related organisms. In cases such as *Bacillus anthracis* and *Bacillus cereus* that are virtually indistinguishable from each other based solely on mass differences, compositional analysis or fragmentation patterns are used to resolve the differences. The single base difference between the two organisms yields different fragmentation patterns, and despite the presence of the ambiguous/unidentified base N at position 20 in *B. anthracis*, the two organisms can be identified.

Tables 4a-b show examples of primer pairs from Table 1 which distinguish pathogens from background.

TABLE 4a

| Organism name | 23S_855 | 16S_1337 | 23S_1021 |
|---|---|---|---|
| *Bacillus anthracis* | 42650.98 | 28447.65 | 30294.98 |
| *Staphylococcus aureus* | 42654.97 | 28443.67 | 30297.96 |

TABLE 4b

| Organism name | 16S_971 | 16S_1294 | 16S_1228 |
|---|---|---|---|
| *Vibrio cholerae* | 55625.09 | 35856.87 | 52535.59 |
| *Vibrio parahaemolyticus* | 54384.91 | 34620.67 | 50064.19 |

Table 4 shows the expected molecular weight and base composition of region 16S_1100-1188 in *Mycobacterium avium* and *Streptomyces* sp.

TABLE 5

| Region | Organism name | Length | Molecular weight | Base comp. |
|---|---|---|---|---|
| 16S_1100-1188 | *Mycobacterium avium* | 82 | 25624.1728 | $A_{16}G_{32}C_{18}T_{16}$ |
| 16S_1100-1188 | *Streptomyces* sp. | 96 | 29904.871 | $A_{17}G_{38}C_{27}T_{14}$ |

Table 5 shows base composition (single strand) results for 16S_1100-1188 primer amplification reactions different species of bacteria. Species which are repeated in the table (e.g., *Clostridium botulinum*) are different strains which have different base compositions in the 16S_1100-1188 region.

TABLE 6

| Organism name | Base comp. |
|---|---|
| *Mycobacterium avium* | $A_{16}G_{32}C_{18}T_{16}$ |
| *Streptomyces* sp. | $A_{17}G_{38}C_{27}T_{14}$ |
| *Ureaplasma urealyticum* | $A_{18}G_{30}C_{17}T_{17}$ |
| *Streptomyces* sp. | $A_{19}G_{36}C_{24}T_{18}$ |
| *Mycobacterium leprae* | $A_{20}G_{32}C_{22}T_{16}$ |
| *M. tuberculosis* | $A_{20}G_{33}C_{21}T_{16}$ |
| *Nocardia asteroides* | $A_{20}G_{33}C_{21}T_{16}$ |
| *Fusobacterium necroforum* | $A_{21}G_{26}C_{22}T_{18}$ |
| *Listeria monocytogenes* | $A_{21}G_{27}C_{19}T_{19}$ |
| *Clostridium botulinum* | $A_{21}G_{27}C_{19}T_{21}$ |
| *Neisseria gonorrhoeae* | $A_{21}G_{28}C_{21}T_{18}$ |
| *Bartonella quintana* | $A_{21}G_{30}C_{22}T_{16}$ |
| *Enterococcus faecalis* | $A_{22}G_{27}C_{20}T_{19}$ |
| *Bacillus megaterium* | $A_{22}G_{28}C_{20}T_{18}$ |
| *Bacillus subtilis* | $A_{22}G_{28}C_{21}T_{17}$ |
| *Pseudomonas aeruginosa* | $A_{22}G_{29}C_{23}T_{15}$ |
| *Legionella pneumophila* | $A_{22}G_{32}C_{20}T_{16}$ |
| *Mycoplasma pneumoniae* | $A_{23}G_{26}C_{14}T_{16}$ |
| *Clostridium botulinum* | $A_{23}G_{26}C_{20}T_{19}$ |
| *Enterococcus faecium* | $A_{23}G_{26}C_{21}T_{18}$ |
| *Acinetobacter calcoaceti* | $A_{23}G_{26}C_{21}T_{19}$ |
| *Leptospira borgpeterseni* | $A_{23}G_{26}C_{24}T_{15}$ |
| *Leptospira interrogans* | $A_{23}G_{26}C_{24}T_{15}$ |
| *Clostridium perfringens* | $A_{23}G_{27}C_{19}T_{19}$ |
| *Bacillus anthracis* | $A_{23}G_{27}C_{20}T_{18}$ |
| *Bacillus cereus* | $A_{23}G_{27}C_{20}T_{18}$ |
| *Bacillus thuringiensis* | $A_{23}G_{27}C_{20}T_{18}$ |
| *Aeromonas hydrophila* | $A_{23}G_{29}C_{21}T_{16}$ |
| *Escherichia coli* | $A_{23}G_{29}C_{21}T_{16}$ |
| *Pseudomonas putida* | $A_{23}G_{29}C_{21}T_{17}$ |
| *Escherichia coli* | $A_{23}G_{29}C_{22}T_{15}$ |
| *Shigella dysenteriae* | $A_{23}G_{29}C_{22}T_{15}$ |
| *Vibrio cholerae* | $A_{23}G_{30}C_{21}T_{16}$ |
| *Aeromonas hydrophila* | $A_{23}G_{31}C_{21}T_{15}$ |
| *Aeromonas salmonicida* | $A_{23}G_{31}C_{21}T_{15}$ |
| *Mycoplasma genitalium* | $A_{24}G_{19}C_{12}T_{18}$ |
| *Clostridium botulinum* | $A_{24}G_{25}C_{18}T_{20}$ |
| *Bordetella bronchiseptica* | $A_{24}G_{26}C_{19}T_{14}$ |
| *Francisella tularensis* | $A_{24}G_{26}C_{19}T_{19}$ |
| *Bacillus anthracis* | $A_{24}G_{26}C_{20}T_{18}$ |
| *Campylobacter jejuni* | $A_{24}G_{26}C_{20}T_{18}$ |
| *Staphylococcus aureus* | $A_{24}G_{26}C_{20}T_{18}$ |
| *Helicobacter pylori* | $A_{24}G_{26}C_{20}T_{19}$ |
| *Helicobacter pylori* | $A_{24}G_{26}C_{21}T_{18}$ |
| *Moraxella catarrhalis* | $A_{24}G_{26}C_{23}T_{16}$ |
| *Haemophilus influenzae Rd* | $A_{24}G_{28}C_{20}T_{17}$ |
| *Chlamydia trachomatis* | $A_{24}G_{28}C_{21}T_{16}$ |
| *Chlamydophila pneumoniae* | $A_{24}G_{28}C_{21}T_{16}$ |
| *C. pneumonia AR39* | $A_{24}G_{28}C_{21}T_{16}$ |
| *Pseudomonas putida* | $A_{24}G_{29}C_{21}T_{16}$ |
| *Proteus vulgaris* | $A_{24}G_{30}C_{21}T_{15}$ |
| *Yersinia pestis* | $A_{24}G_{30}C_{21}T_{15}$ |
| *Yersinia pseudotuberculos* | $A_{24}G_{30}C_{21}T_{15}$ |
| *Clostridium botulinum* | $A_{25}G_{24}C_{18}T_{21}$ |
| *Clostridium tetani* | $A_{25}G_{25}C_{18}T_{20}$ |

TABLE 6-continued

| Organism name | Base comp. |
|---|---|
| *Francisella tularensis* | $A_{25}G_{25}C_{19}T_{19}$ |
| *Acinetobacter calcoacetic* | $A_{25}G_{26}C_{20}T_{19}$ |
| *Bacteriodes fragilis* | $A_{25}G_{27}C_{16}T_{22}$ |
| *Chlamydophila psittaci* | $A_{25}G_{27}C_{21}T_{16}$ |
| *Borrelia burgdorferi* | $A_{25}G_{29}C_{17}T_{19}$ |
| *Streptobacillus monilifor* | $A_{26}G_{26}C_{20}T_{16}$ |
| *Rickettsia prowazekii* | $A_{26}G_{28}C_{18}T_{18}$ |
| *Rickettsia rickettsii* | $A_{26}G_{28}C_{20}T_{16}$ |
| *Mycoplasma mycoides* | $A_{28}G_{23}C_{16}T_{20}$ |

The same organism having different base compositions are different strains. Groups of organisms which are highlighted or in italics have the same base compositions in the amplified region. Some of these organisms can be distinguished using multiple primers. For example, *Bacillus anthracis* can be distinguished from *Bacillus cereus* and *Bacillus thuringiensis* using the primer 16S_971-1062 (Table 6). Other primer pairs which produce unique base composition signatures are shown in Table 6 (bold). Clusters containing very similar threat and ubiquitous non-threat organisms (e.g. anthracis cluster) are distinguished at high resolution with focused sets of primer pairs. The known biowarfare agents in Table 6 are *Bacillus anthracis, Yersinia pestis, Francisella tularensis* and *Rickettsia prowazekii*.

TABLE 7

| Organism | 16S_971-1062 | 16S_1228-1310 | 16S_1100-1188 |
|---|---|---|---|
| *Aeromonas hydrophila* | $A_{21}G_{29}C_{22}T_{20}$ | $A_{22}G_{27}C_{21}T_{13}$ | $A_{23}G_{31}C_{21}T_{15}$ |
| *Aeromonas salmonicida* | $A_{21}G_{29}C_{22}T_{20}$ | $A_{22}G_{27}C_{21}T_{13}$ | $A_{23}G_{31}C_{21}T_{15}$ |
| *Bacillus anthracis* | $A_{21}G_{27}C_{22}T_{22}$ | $A_{24}G_{22}C_{19}T_{18}$ | $A_{23}G_{27}C_{20}T_{18}$ |
| *Bacillus cereus* | $A_{22}G_{27}C_{21}T_{22}$ | $A_{24}G_{22}C_{19}T_{18}$ | $A_{23}G_{27}C_{20}T_{18}$ |
| *Bacillus thuringiensis* | $A_{22}G_{27}C_{21}T_{22}$ | $A_{24}G_{22}C_{19}T_{18}$ | $A_{23}G_{27}C_{20}T_{18}$ |
| *Chlamydia trachomatis* | $A_{22}G_{26}C_{20}T_{23}$ | $A_{24}G_{23}C_{19}T_{16}$ | $A_{24}G_{28}C_{21}T_{16}$ |
| *Chlamydia pneumoniae AR39* | $A_{26}G_{23}C_{20}T_{22}$ | $A_{26}G_{22}C_{16}T_{18}$ | $A_{24}G_{28}C_{21}T_{16}$ |
| *Leptospira borgpetersenii* | $A_{22}G_{26}C_{20}T_{21}$ | $A_{22}G_{25}C_{21}T_{15}$ | $A_{23}G_{26}C_{24}T_{15}$ |
| *Leptospira interrogans* | $A_{22}G_{26}C_{20}T_{21}$ | $A_{22}G_{25}C_{21}T_{15}$ | $A_{23}G_{26}C_{24}T_{15}$ |
| *Mycoplasma genitalium* | $A_{28}G_{23}C_{15}T_{22}$ | $A_{30}G_{18}C_{15}T_{19}$ | $A_{24}G_{19}C_{12}T_{18}$ |
| *Mycoplasma pneumoniae* | $A_{28}G_{23}C_{15}T_{22}$ | $A_{27}G_{19}C_{16}T_{20}$ | $A_{23}G_{20}C_{14}T_{16}$ |
| *Escherichia coli* | $A_{22}G_{28}C_{20}T_{22}$ | $A_{24}G_{25}C_{21}T_{13}$ | $A_{23}G_{29}C_{22}T_{15}$ |
| *Shigella dysenteriae* | $A_{22}G_{28}C_{21}T_{21}$ | $A_{24}G_{25}C_{21}T_{13}$ | $A_{23}G_{29}C_{22}T_{15}$ |
| *Proteus vulgaris* | $A_{23}G_{26}C_{22}T_{21}$ | $A_{26}G_{24}C_{19}T_{14}$ | $A_{24}G_{30}C_{21}T_{15}$ |
| *Yersinia pestis* | $A_{24}G_{25}C_{21}T_{22}$ | $A_{25}G_{24}C_{20}T_{14}$ | $A_{24}G_{30}C_{21}T_{15}$ |
| *Yersinia pseudotuberculosis* | $A_{24}G_{25}C_{21}T_{22}$ | $A_{25}G_{24}C_{20}T_{14}$ | $A_{24}G_{30}C_{21}T_{15}$ |
| *Francisella tularensis* | $A_{26}G_{25}C_{21}T_{23}$ | $A_{23}G_{26}C_{17}T_{17}$ | $A_{24}G_{26}C_{19}T_{19}$ |
| *Rickettsia prowazekii* | $A_{21}G_{26}C_{24}T_{25}$ | $A_{24}G_{23}C_{16}T_{19}$ | $A_{26}G_{28}C_{18}T_{18}$ |
| *Rickettsia rickettsii* | $A_{21}G_{26}C_{25}T_{24}$ | $A_{24}G_{24}C_{17}T_{17}$ | $A_{26}G_{28}C_{20}T_{16}$ |

The sequence of *B. anthracis* and *B. cereus* in region 16S_971 is shown below. Shown in bold is the single base difference between the two species which can be detected using the methods of the present invention. *B. anthracis* has an ambiguous base at position 20.

*B. anthracis*_16S_971 GCGAAGAACCUUACCAG-GUNUUGACAUCCUCUGACAACCCUAGAGAUA GGGCUUCUCCUUCGGGAGCAGAGUGA-CAGGUGGUGCAUGGUU (SEQ ID NO:4)

*B. cereus*_16S_971 GCGAAGAACCUUACCAGGUCU-UGACAUCCUCUGAAAACCCUAGAGAUA GGGCU-UCUCCUUCGGGAGCAGAGUGACAGGUG-GUGCAUGGUU (SEQ ID NO:5)

Example 6

ESI-TOF MS of sspE 56-mer Plus Calibrant

Figure 8:
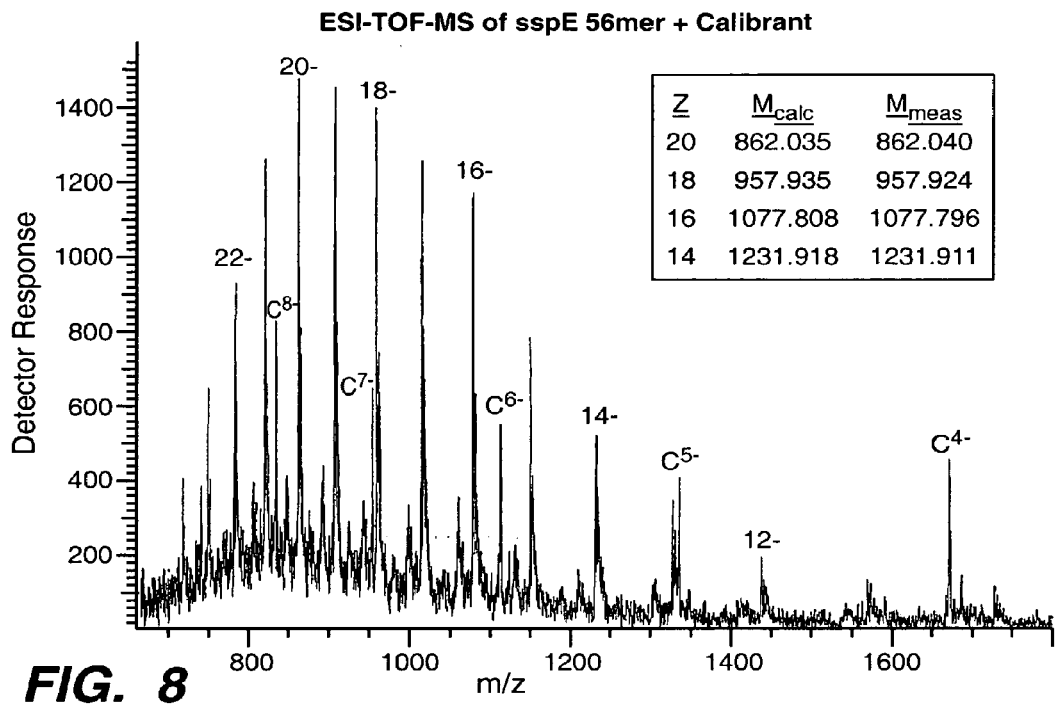

The mass measurement accuracy that can be obtained using an internal mass standard in the ESI-MS study of PCR products is shown in FIG. 8. The mass standard was a 20-mer phosphorothioate oligonucleotide added to a solution containing a 56-mer PCR product from the *B. anthracis* spore coat protein sspE. The mass of the expected PCR product distinguishes. *B. anthracis* from other species of *Bacillus* such as *B. thuringiensis* and *B. cereus*.

Example 7

*B. anthracis* ESI-TOF Synthetic 16S_1228 Duplex

Figure 9:
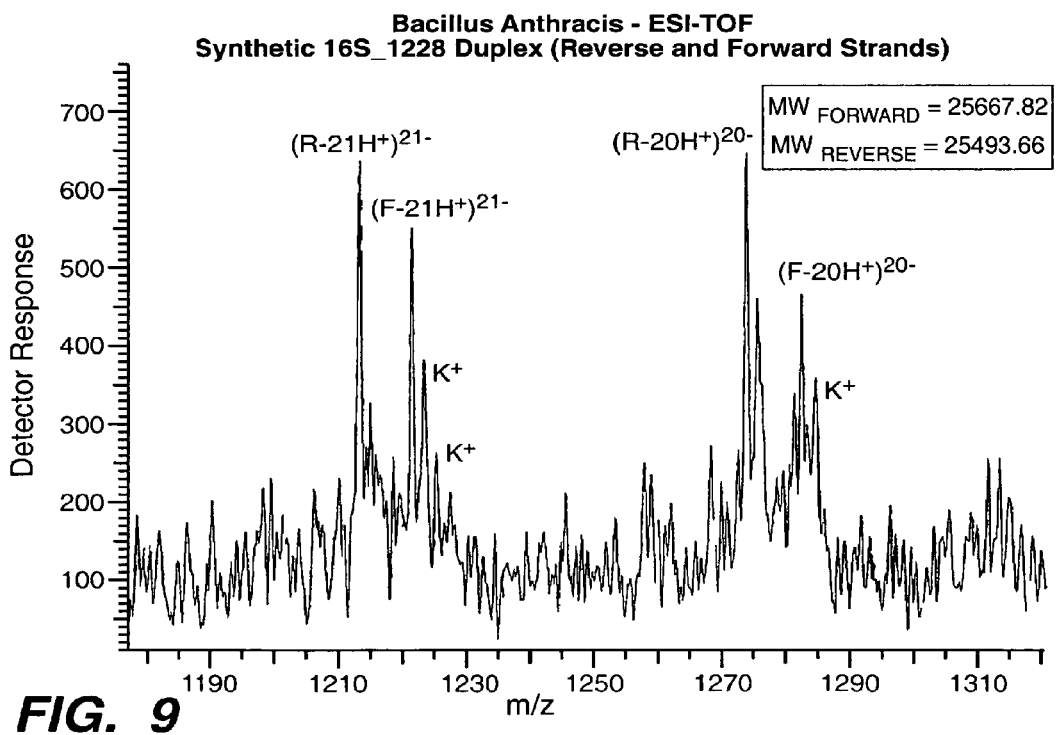

An ESI-TOF MS spectrum was obtained from an aqueous solution containing 5 μM each of synthetic analogs of the expected forward and reverse PCR products from the nucleotide 1228 region of the *B. anthracis* 16S rRNA gene. The results (FIG. 9) show that the molecular weights of the forward and reverse strands can be accurately determined and easily distinguish the two strands. The $[M-21H^+]^{21-}$ and $[M-20H^+]^{20-}$ charge states are shown.

Example 8

ESI-FTICR-MS of Synthetic *B. anthracis* 16S_1337 46 Base Pair Duplex

An ESI-FTICR-MS spectrum was obtained from an aqueous solution containing 5 μM each of synthetic analogs of the expected forward and reverse PCR products from the nucleotide 1337 region of the *B. anthracis* 16S rRNA gene. The results (FIG. 10) show that the molecular weights of the strands can be distinguished by this method. The $[M-16H^+]^{16-}$ through $[M-10H^+]^{10-}$ charge states are shown. The insert highlights the resolution that can be realized on the FTICR-MS instrument, which allows the charge state of the ion to be determined from the mass difference between peaks differing by a single 13C substitution.

Example 9

Figure 11:
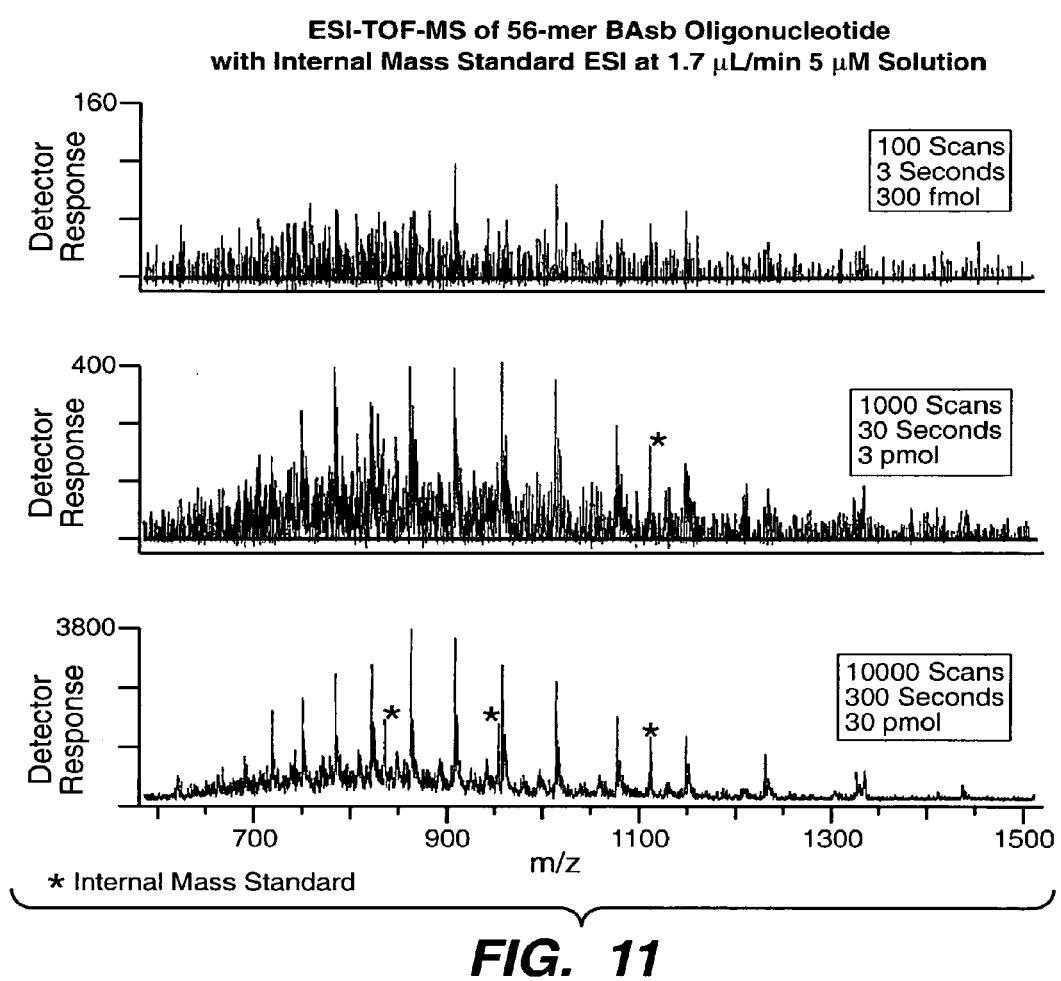

ESI-TOF MS of 56-mer Oligonucleotide from saspB Gene of *B. anthracis* with Internal Mass Standard ESI-TOF MS spectra were obtained on a synthetic 56-mer oligonucleotide (5 μM) from the saspB gene of *B. anthracis* containing an internal mass standard at an ESI of 1.7 μL/min as a function of sample consumption. The results (FIG. 11) show that the signal to noise is improved as more scans are summed, and that the standard and the product are visible after only 100 scans.

Example 10

Figure 12:
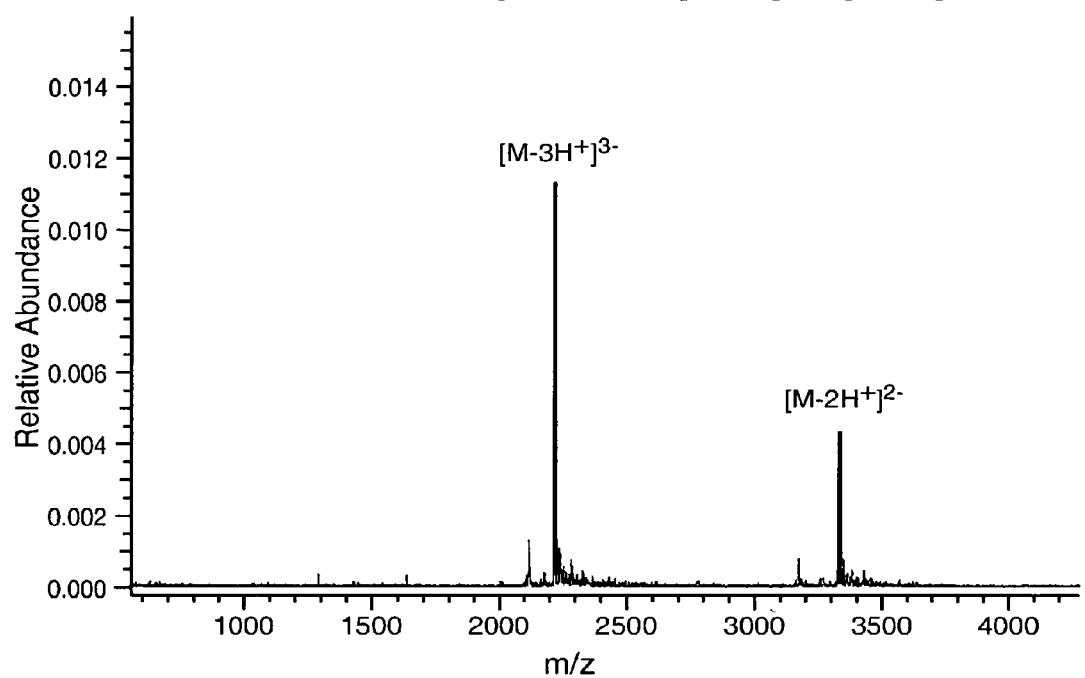
Figure 13:
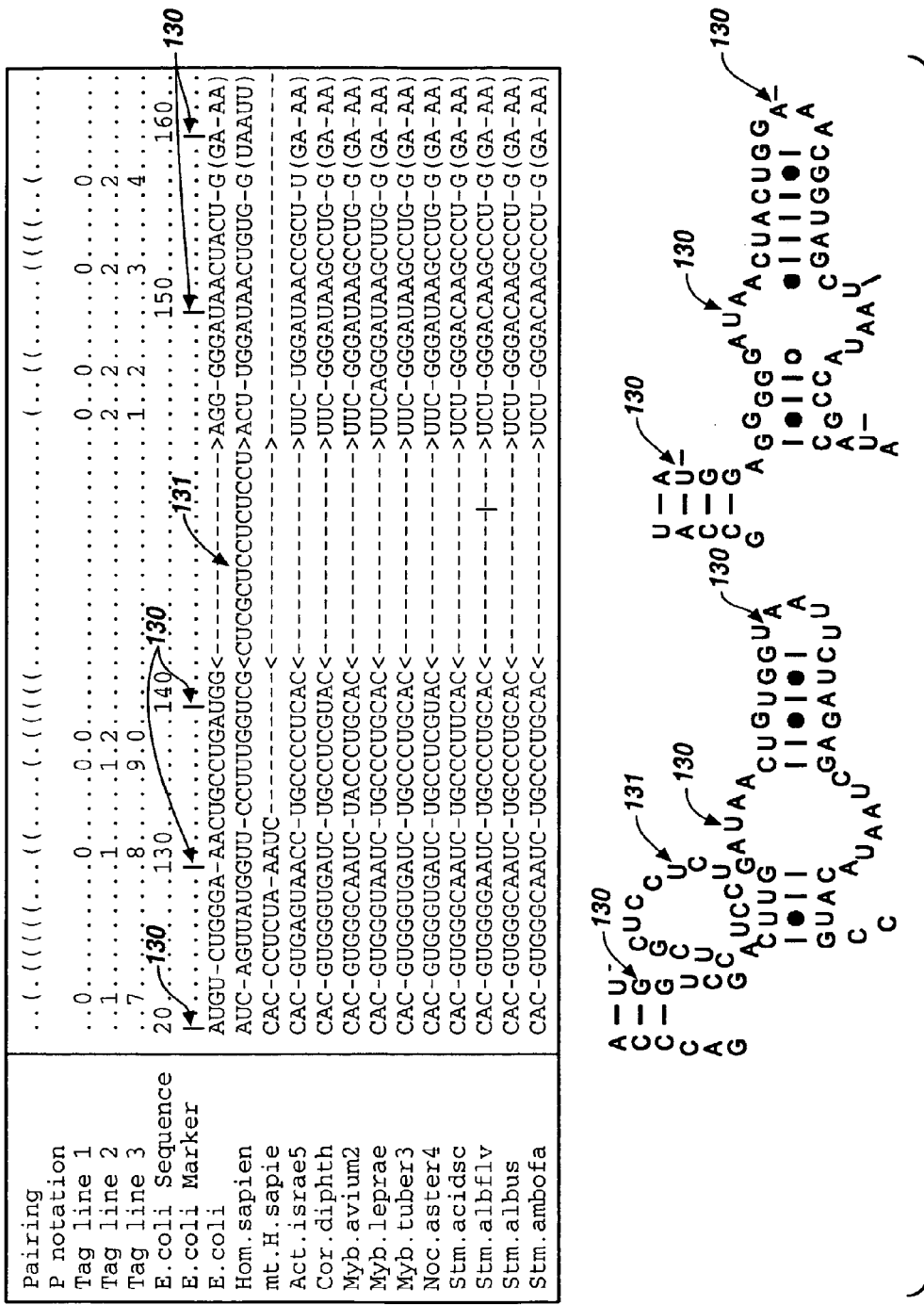
Figure 14:
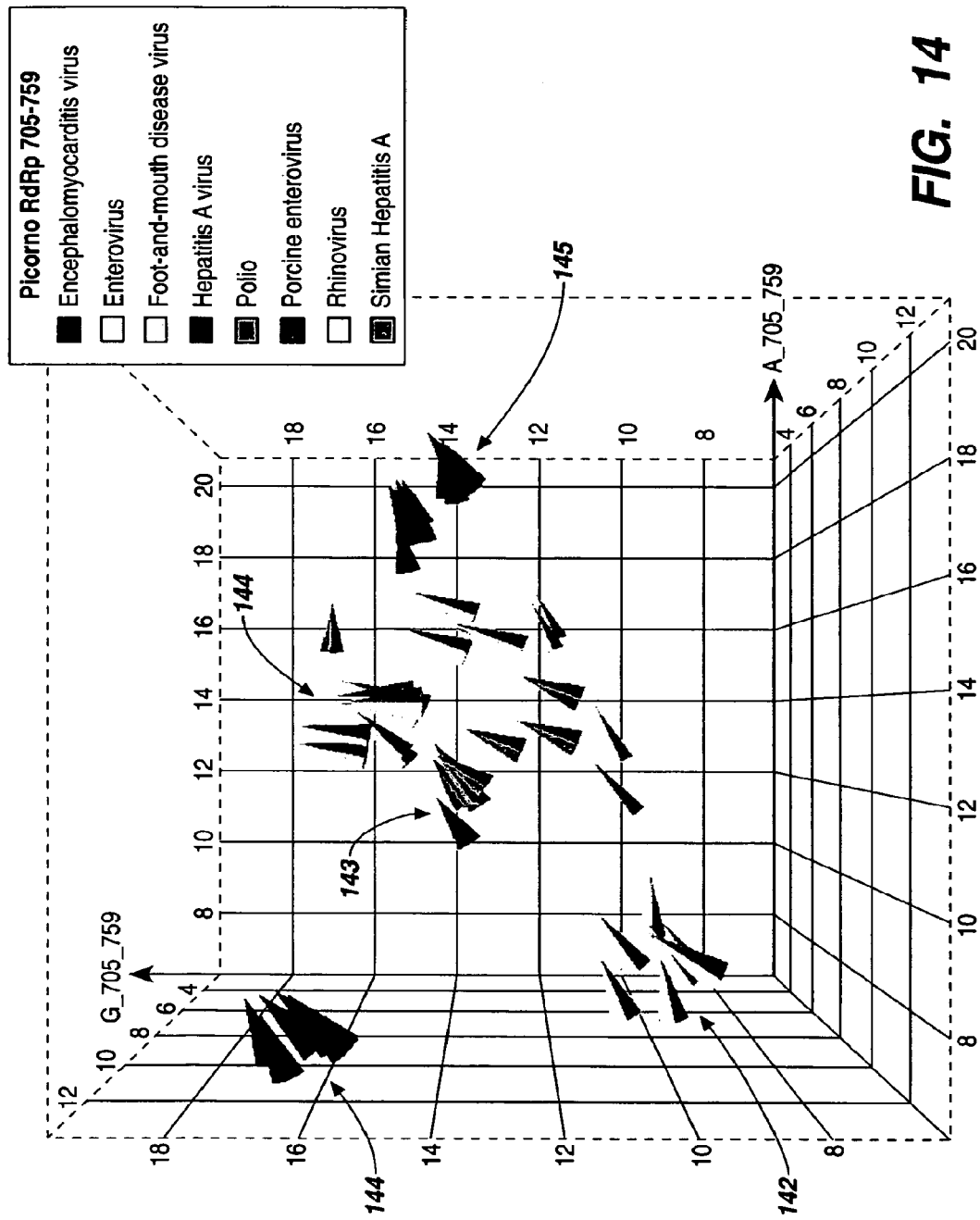
Figure 15:
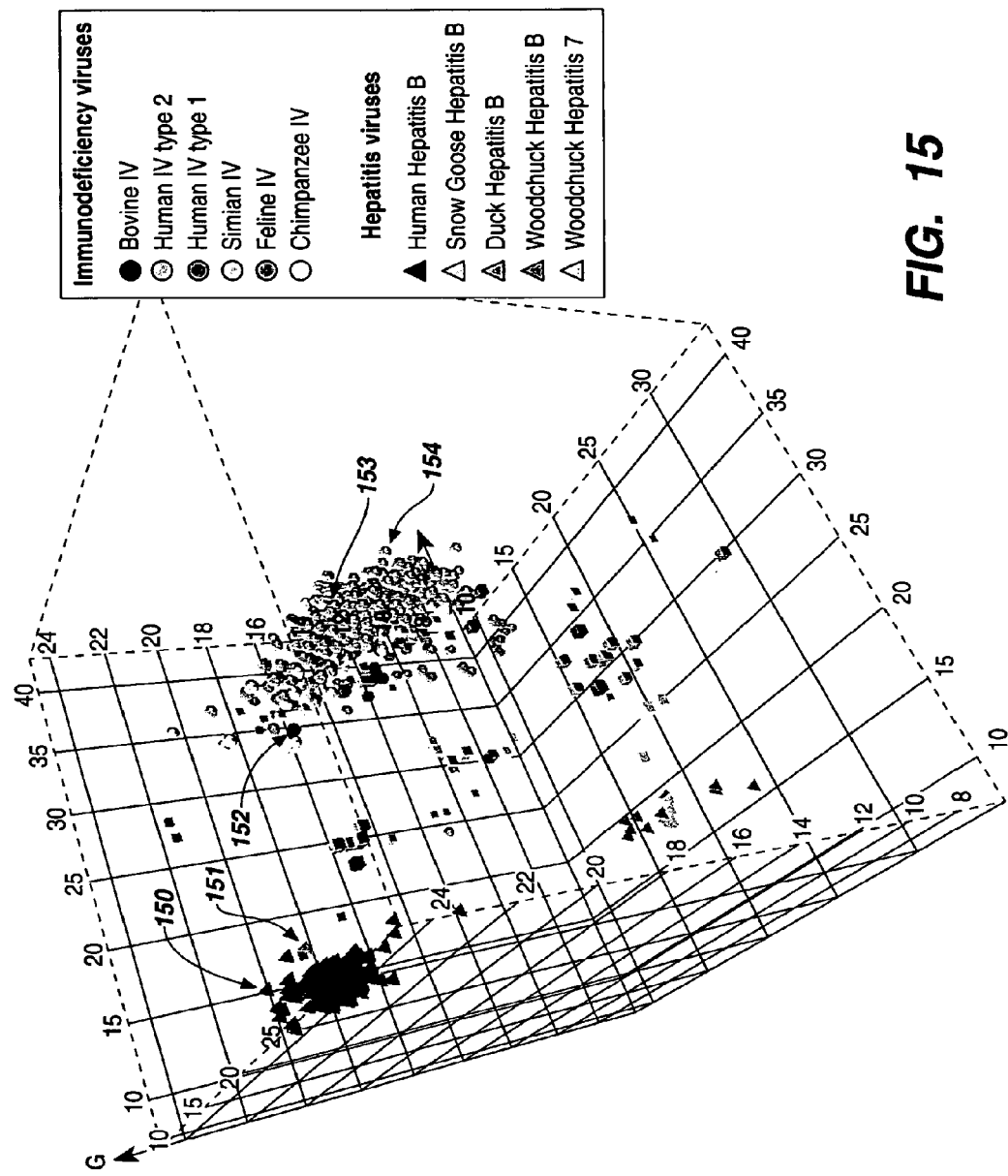
Figure 16:
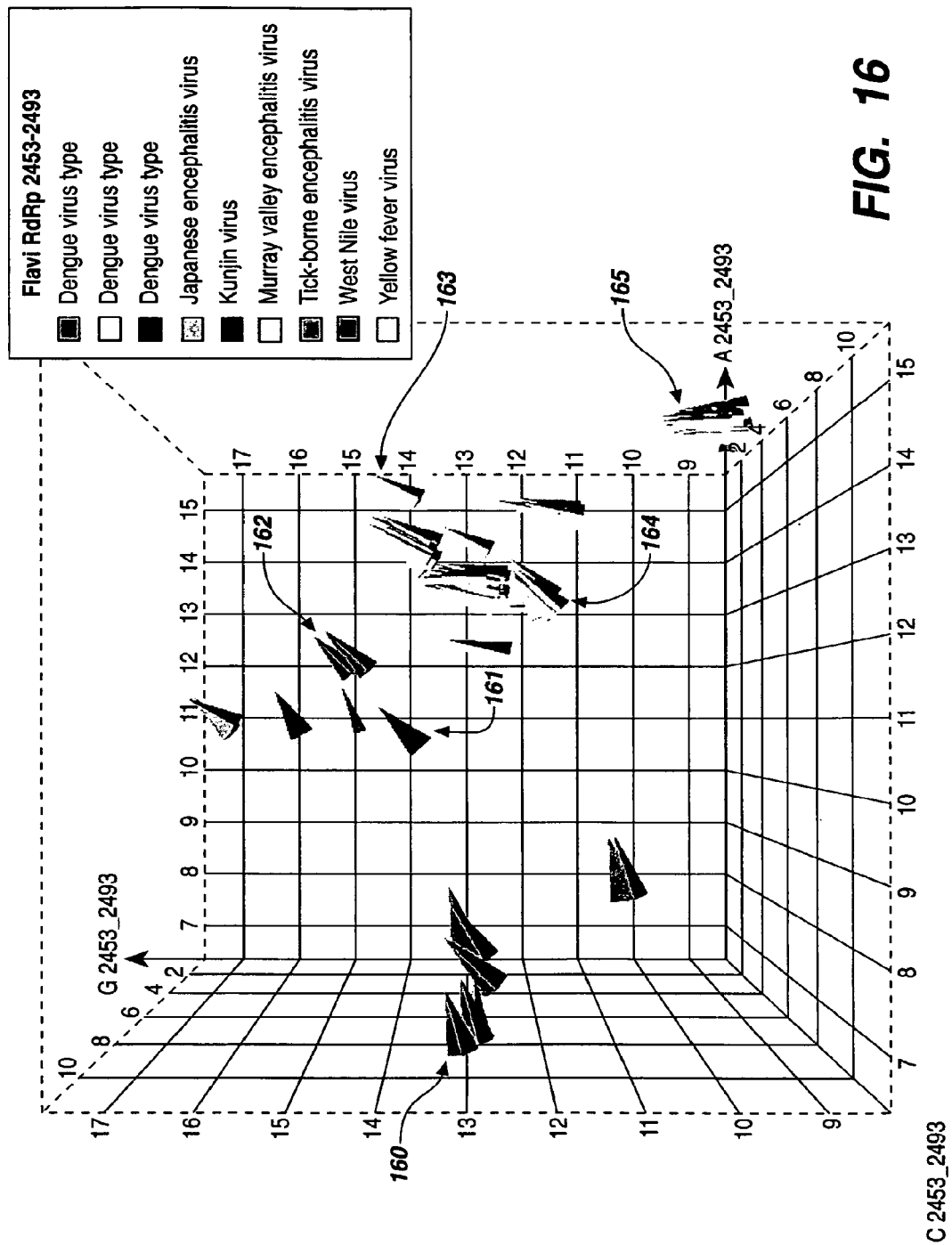
Figure 17:
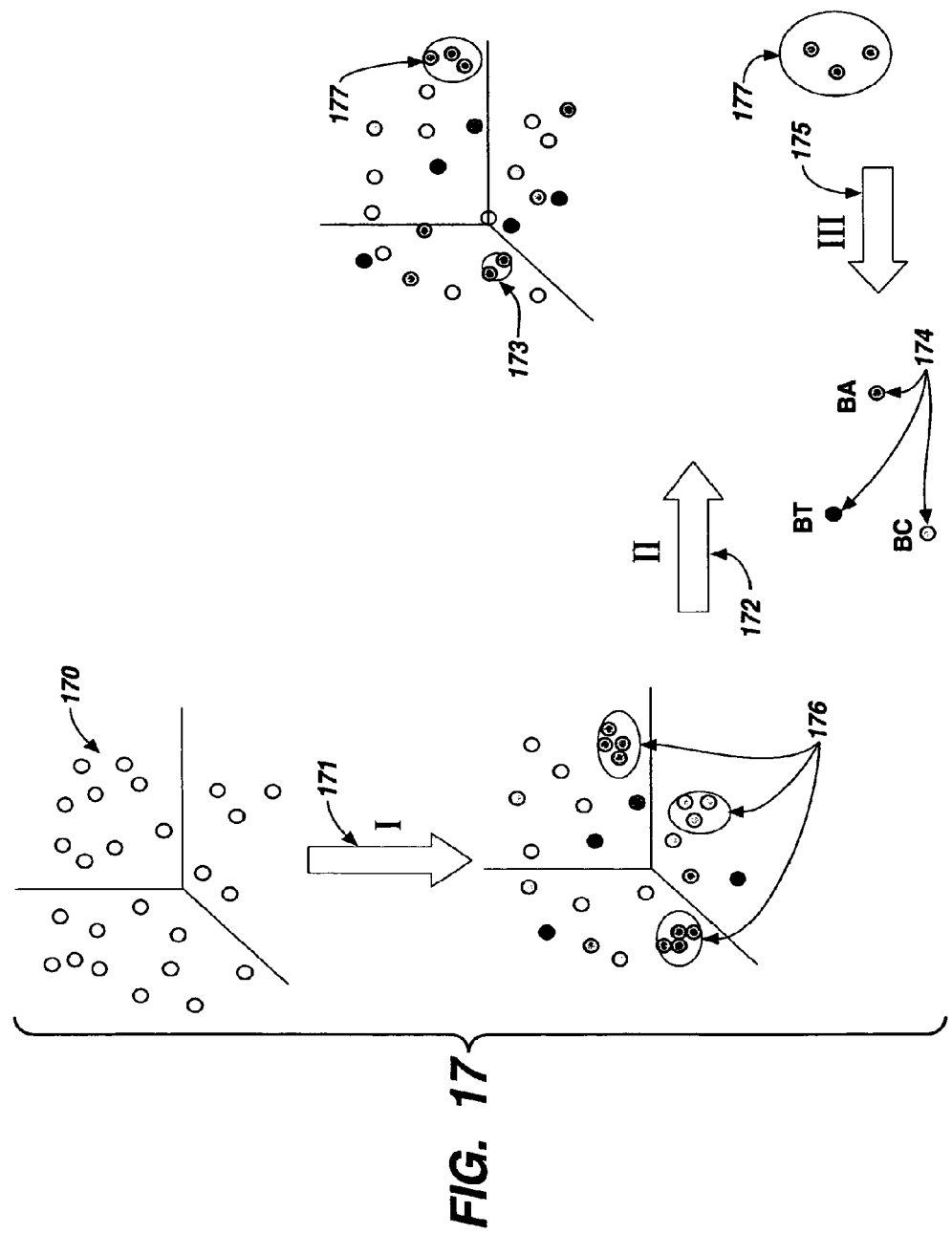

ESI-TOF MS of an Internal Standard with Tributylammonium (TBA)-trifluoroacetate (TFA) Buffer An ESI-TOF-MS spectrum of a 20-mer phosphorothioate mass standard was obtained following addition of 5 mM TBA-TFA buffer to the solution. This buffer strips charge from the oligonucleotide and shifts the most abundant charge state from $[M-8H]^{8-}$ to $[M-3H^+]^{3-}$ (FIG. 12).

Example 11

Master Database Comparison

The molecular masses obtained through Examples 1-10 are compared to molecular masses of known bioagents stored in a master database to obtain a high probability matching molecular mass.

Example 12

Master Data Base Interrogation Over the Internet

The same procedure as in Example 11 is followed except that the local computer did not store the Master database. The Master database is interrogated over an interne connection, searching for a molecular mass match.

Example 13

Master Database Updating

The same procedure as in example 11 is followed except the local computer is connected to the internet and has the ability to store a master database locally. The local computer system periodically, or at the user's discretion, interrogates the Master database, synchronizing the local master database with the global Master database. This provides the current molecular mass information to both the local database as well as to the global Master database. This further provides more of a globalized knowledge base.

Example 14

Global Database Updating

The same procedure as in example 13 is followed except there are numerous such local stations throughout the world. The synchronization of each database adds to the diversity of information and diversity of the molecular masses of known bioagents.

Various modifications of the invention, in addition to those described herein, will be apparent to those skilled in the art from the foregoing description. Such modifications are also intended to fall within the scope of the appended claims.

---

We claim:

1. A system for identifying a pathogen, said system comprising:
   a.) an automatic fluidics control system configured to receive two or more amplification products of nucleic acid of said pathogen, said two or more amplification products produced with two or more primer pairs wherein at least one of said two or more primer pairs hybridizes to conserved coding regions of a nucleic acid gene sequence wherein said conserved regions flank at least one variable coding region of said nucleic acid gene sequence of said pathogen;
   b.) a mass spectrometer configured to directly receive said two or more amplification products from said fluidics control system and configured to provide two or more molecular masses of said two or more amplification products;
   c.) a computer program stored on a computer readable medium configured to receive and convert said two or more molecular masses to two or more base compositions wherein said base compositions identify the number but not the nucleic acid gene sequence order of A residues, C residues, T residues, G residues, U residues, analogues thereof or mass tag residues thereof in said two or more amplification products without sequencing said two or more amplification products;
   d.) a database stored on a computer readable medium, said database comprising, for at least 19 known pathogens, base compositions of amplification products each indexed to a corresponding primer pair and a pathogen, wherein said amplification products have a variable region flanked by conserved coding regions and wherein at least one of said two or more primer pairs hybridizes to said conserved coding region; and,
   e.) a pathogen identification module configured to receive said two or more base compositions from said computer program, and configured to query said received two or more base compositions against said database and configured to determine a match between said two or more base compositions and a member of said at least nineteen base compositions of said database.

2. A method for identifying a pathogen comprising:
   a.) providing a system, said system comprising:
      i.) an automatic fluidics control system configured to receive two or more amplification products of nucleic acid of said pathogen, said two or more amplification products produced with two or more primer pairs;
      ii.) a mass spectrometer configured to directly receive said two or more amplification products from said fluidics control system and configured to provide two or more molecular masses of said two or more amplification products;
      iii.) a computer program stored on a computer readable medium configured to receive and convert said two or more molecular masses to two or more base compositions wherein said base compositions identify the number but not the nucleic acid gene sequence order of A residues, C residues, T residues, G residues, U residues, analogues thereof or mass tag residues thereof in said two or more amplification products without sequencing said two or more amplification products;
      iv.) a database stored on a computer readable medium, said database comprising, for at least 19 known pathogens, base compositions of amplification products each indexed to a corresponding primer pair and a pathogen, wherein said amplification products have a variable region flanked by conserved coding regions and wherein at least one of said two or more primer pairs hybridizes to said conserved coding region;
      v.) a pathogen identification module configured to receive said two or more base compositions from said computer program, and configured to query said received two or more base compositions against said database and configured to determine a match between said two or more base compositions and a member of said at least nineteen base compositions of said database; and
      vii.) a display interface configured to produce a pathogen identification report from said match;
   b.) obtaining nucleic acid of said pathogen;
   c.) amplifying said nucleic acid with said two or more primer pairs to obtain two or more amplification products, wherein at least one of said two or more primer pairs hybridizes to conserved coding regions of a nucleic acid gene sequence wherein said conserved regions flank at least one variable coding region of said nucleic acid gene sequence of said pathogen;
   d.) transferring said two or more amplification products to said mass spectrometer using said automated fluidics control system;
   e.) measuring two or more molecular masses of said two or more amplification products using said mass spectrometer;
   f.) converting said two or more molecular masses to two or more base compositions using said computer program without sequencing said two or more amplification products; and
   g.) determining a match between said two or more base compositions and a member of said plurality of base compositions of said database using said pathogen identification module, wherein said member of said at least nineteen base compositions is a known amplification product of a known pathogen produced with said two or more primer pairs, and wherein said match identifies said pathogen.

3. The method of claim 2 wherein said pathogen is a virus.

4. The method of claim 2 wherein said pathogen is a fungus.

5. The method of claim 2 wherein said determining step identifies said pathogen at the genus level.

6. The method of claim 2 wherein said determining step identifies said pathogen at the species level.

7. The method of claim 2 wherein said determining step identifies said pathogen at the sub-species level.

8. The method of claim 2 wherein said system further comprises:
- vii.) a thermocycler configured to:
  - provide said two or more amplification products to said fluidics control system.

9. The method of claim 2 wherein said pathogen is a bacterium.

10. The method of claim 9 wherein said bacterium is a pathogen selected from the group consisting of: *Acinetobacter, Aeromonas, Bacillus, Bacteriodes, Bartonella, Bordetella, Borrelia, Brucella, Burkholderia, Campylobacter, Chlamydia, Chlamydophila, Clostridium, Coxiella, Enterococcus, Escherichia, Francisella, Fusobacterium, Haemophilus, Helicobacter, Klebsiella, Legionella, Leptospira, Listeria, Moraxella, Mycobacterium, Mycoplasma, Neisseria, Proteus, Pseudomonas, Rhodobacter, Rickettsia, Salmonella, Shigella, Staphylococcus, Streptobacillus, Streptomyces, Treponema, Ureaplasma, Vibrio,* or *Yersinia*.

11. The method of claim 9 wherein said bacterium is a pathogen selected from the group consisting of: *Acinetobacter calcoaceticus, Bacillus anthracis, Bacillus cereus, Bordetella bronchiseptica, Borrelia burgdorferi, Brucella abortus, Campylobacter jejuni, Chlamydia pnuemoniae, Clostridium botulinum, Clostridium difficile, Enterococcus faecalis, Escherichia coli, Francisella tularensis, Haemophilus influenzae, Klebsiella pneumoniae, Legionella pneumophila, Mycobacterium avium, Mycobacterium leprae, Mycobacterium tuberculosis, Mycoplasma genitalium, Mycoplasma pneumoniae, Neisseria gonorrhoeae, Pseudomonas aeruginosa, Rickettsia prowazekii, Rickettsia rickettsii, Salmonella typhimurium, Shigella dysenteriae, Staphylococcus aureus, Streptomyces, Treponema pallidum, Vibrio cholerae, Vibrio parahaemolyticus, Yersinia pestis.*

12. The method of claim 9 wherein said bacterium is a biowarfare agent.

13. The method of claim 12 wherein said biowarfare agent is selected from the group consisting of: *Bacillus anthracis, Yersinia pestis, Franciscella tularensis, Brucella suis, Brucella abortus, Brucella melitensis, Burkholderia mallei, Burkholderia pseudomalleii, Salmonella typhii, Salmonella typhimurium, Rickettsia typhii, Rickettsia rickettsii, Rickettsia prowasekii, Coxiella burnetii, Rhodobacter capsulatus, Chlamydia pneumoniae, Escherichia coli, Shigella dysenteriae, Shigella flexneri, Bacillus cereus, Clostridium botulinum, Coxiella burnetti, Pseudomonas aeruginosa, Legionella pneumophila,* or *Vibrio cholerae.*

14. A system for identifying a pathogen, said system comprising:
- a.) an automatic fluidics control system configured to receive two or more amplification products of nucleic acid of said pathogen, said two or more amplification products produced with two or more primer pairs wherein at least one of said two or more primer pairs hybridizes to conserved coding regions of a nucleic acid gene sequence wherein said conserved regions flank at least one variable coding region of said nucleic acid gene sequence of said pathogen;
- b.) a mass spectrometer configured to directly receive said two or more amplification products from said fluidics control system and configured to provide two or more molecular masses of said two or more amplification products;
- c.) a computer program stored on a computer readable medium configured to receive and convert said two or more molecular masses to two or more base compositions wherein said base compositions identify the number but not the nucleic acid gene sequence order of A residues, C residues, T residues, G residues, U residues, analogues thereof or mass tag residues thereof in said two or more amplification products without sequencing said two or more amplification products;
- d.) a database stored on a computer readable medium, said database comprising, for at least 19 known pathogens, base compositions of amplification products each indexed to a corresponding primer pair and a pathogen, wherein said amplification products have a variable region flanked by conserved coding regions and wherein at least one of said two or more primer pairs hybridizes to said conserved coding region;
- e.) a pathogen identification module configured to receive said two or more base compositions from said computer program, and configured to query said received two or more base compositions against said database and configured to determine a match between said two or more base compositions and a member of said at least nineteen base compositions of said database; and
- f.) a display interface configured to produce a pathogen identification report from said match.

15. The system of claim 14 wherein said mass spectrometer is an electrospray time-of-flight mass spectrometer.

16. The system of claim 14 wherein said mass spectrometer comprises a signal processor configured to analyze mass spectral peaks and provide said two or more molecular masses.

17. The system of claim 14 wherein said automated fluidics control system is configured for high throughput mass spectrometry analysis of a plurality of amplification products at a rate of about one sample per minute.

18. The system of claim 14 further comprising: g.) a thermocycler configured to:
- provide said two or more amplification products to said fluidics control system.

19. The system of claim 18 further comprising: h.) a reaction vessel wherein said reaction vessel comprises a 96-well or a 384-well microtiter plate.

20. The system of claim 14 wherein said database is a local database.

21. The system of claim 20 wherein said local database is updated by inclusion of additional base compositions of amplification products of additional pathogens from a master database at a remote location.

22. The system of claim 20 wherein said local database is updated by inclusion of additional base compositions of amplification products of additional pathogens from a transferable computer formatted medium.

23. The system of claim 14 wherein said at least nineteen base compositions are base compositions from amplification products of at least one essential gene or at least one nucleic acid encoding ribosomal RNA.

24. The system of claim 23 wherein said at least one essential gene is selected from the group consisting of genes that express polypeptides involved in translation, replication, recombination, repair, transcription, nucleotide metabolism, amino acid metabolism, lipid metabolism, energy generation, secretion, uptake and combinations thereof.

25. The system of claim 23 wherein said at least one essential gene is selected from the group consisting of genes that encode DNA polymerase, elongation factor TU, heat shock protein, groEL, RNA polymerase, phosphoglycerate kinase, NADH dehydrogenase, DNA ligase, DNA topoisomerase, elongation factor G and combinations thereof.

* * * * *

UNITED STATES PATENT AND TRADEMARK OFFICE
CERTIFICATE OF CORRECTION

| | | |
|---|---|---|
| PATENT NO. | : 8,073,627 B2 | Page 1 of 1 |
| APPLICATION NO. | : 10/754415 | |
| DATED | : December 6, 2011 | |
| INVENTOR(S) | : Ecker et al. | |

It is certified that error appears in the above-identified patent and that said Letters Patent is hereby corrected as shown below:

The Title page of the patent reads:

Item (54) SYSTEM FOR INDENTIFICATION OF PATHOGENS [[incorrect]]

when in fact it should read:

Item (54) SYSTEM FOR IDENTIFICATION OF PATHOGENS [[correct]]

Signed and Sealed this
Tenth Day of January, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,073,627 B2 | Page 1 of 1 |
| APPLICATION NO. | : 10/754415 | |
| DATED | : December 6, 2011 | |
| INVENTOR(S) | : Ecker et al. | |

It is certified that error appears in the above-identified patent and that said Letters Patent is hereby corrected as shown below:

Title page, Item (54) and at Column 1, lines 1 and 2, Title:

"SYSTEM FOR INDENTIFICATION OF PATHOGENS"

should read:

-- SYSTEM FOR IDENTIFICATION OF PATHOGENS --

This certificate supersedes the Certificate of Correction issued January 10, 2012.

Signed and Sealed this
Fourteenth Day of February, 2012

David J. Kappos
*Director of the United States Patent and Trademark Office*